(12) United States Patent
Forest

(10) Patent No.: US 9,535,494 B2
(45) Date of Patent: Jan. 3, 2017

(54) APPARATUS AND METHOD FOR SELECTING FROM A DISPLAY

(71) Applicant: Donald K. Forest, Bryn Mawr, PA (US)

(72) Inventor: Donald K. Forest, Bryn Mawr, PA (US)

( * ) Notice: Subject to any disclaimer, the term of this patent is extended or adjusted under 35 U.S.C. 154(b) by 375 days.

(21) Appl. No.: 13/827,216

(22) Filed: Mar. 14, 2013

(65) Prior Publication Data

US 2013/0239015 A1    Sep. 12, 2013

Related U.S. Application Data

(60) Division of application No. 11/890,355, filed on Aug. 6, 2007, now abandoned, which is a division of
(Continued)

(51) Int. Cl.
*G06F 3/00* (2006.01)
*G06F 3/01* (2006.01)
(Continued)

(52) U.S. Cl.
CPC ............... *G06F 3/011* (2013.01); *A61F 4/00* (2013.01); *G06F 3/012* (2013.01); *G06F 3/017* (2013.01);
(Continued)

(58) Field of Classification Search
CPC ...... G06F 3/0488; G06F 3/011; G06F 3/0487; G06F 3/023; G06F 3/0482; G06F 3/0219; G06F 3/167; G06F 3/017; G06F 3/012; Y10S 345/902; A61F 4/00
See application file for complete search history.

(56) References Cited

U.S. PATENT DOCUMENTS 3,541,521 A    11/1970    Koster
4,109,145 A     8/1978    Graf
(Continued)

FOREIGN PATENT DOCUMENTS

DE    U 93 00 231         8/1993
DE    U9300231      *     8/1993
(Continued)

OTHER PUBLICATIONS

Barnett, C.J.; Dynche, M.P.; Golding, V.G.; Ng, Y.H.; Taylor, G.D.; "Speech Output Display Terminal," IBM Technical Disclosure Bulletin, vol. 26, No. 10A, Mar. 1984, pp. 4950-4951.*
(Continued)

*Primary Examiner* — Kieu Vu
*Assistant Examiner* — Asteway T Gattew

(57) ABSTRACT

The apparatus and method of the disclosure relate to data entry and menu selection. Applications include: (a) data entry for ideographic languages, including Chinese, Japanese and Korean; (b) fast food ordering; (c) correction of documents generated by optical character recognition; and (d) computer access and speech synthesis by persons temporarily or permanently lacking normal motor capabilities. In a preferred embodiment, each option of a menu is associated respectively with a selectable region displayed adjacent an edge of a display, forming a perimeter menu and leaving a region in the center of the perimeter menu for the output of an application program. Selectable regions may be on the display, outside the display, or both. A menu option may be selected by clicking on the associated selectable region, by dwelling on it for a selection threshold period or by a cursor path toward the selectable region, or by a combination thereof. Remaining dwell time required to select a selectable region is preferably indicated by the brightness of the selectable region. Submenus of a perimeter menu may also be perimeter menus and the location of a
(Continued)

submenu option may be foretold by the appearance of its parent menu option. Menu options may be ideographs sharing a sound, a structure or another characteristic. Ideographs, which may be homophones of one another, may be associated with colored indicating regions and selection of an ideograph may be made by speaking the name of the associated color.

93 Claims, 67 Drawing Sheets

Related U.S. Application Data application No. 11/124,563, filed on May 6, 2005, now abandoned, which is a division of application No. 08/506,032, filed on Jul. 24, 1995, now Pat. No. 6,903,723, which is a continuation-in-part of application No. PCT/US95/03591, filed on Mar. 27, 1995.

(51) Int. Cl.
  *A61F 4/00*      (2006.01)
  *G06F 3/02*      (2006.01)
  *G06F 3/023*     (2006.01)
  *G06F 3/0482*    (2013.01)
  *G06F 3/16*      (2006.01)
  *G06F 3/0487*    (2013.01)
  *G06F 3/0488*    (2013.01)

(52) U.S. Cl.
  CPC ............. *G06F 3/023* (2013.01); *G06F 3/0219* (2013.01); *G06F 3/0482* (2013.01); *G06F 3/0487* (2013.01); *G06F 3/0488* (2013.01); *G06F 3/167* (2013.01); *Y10S 345/902* (2013.01)

(56) References Cited

U.S. PATENT DOCUMENTS

| | | | |
|---|---|---|---|
| 4,149,716 A | 4/1979 | Scudder | |
| 4,181,813 A | 1/1980 | Marley | |
| 4,291,198 A | 9/1981 | Anderson et al. | |
| 4,310,839 A | 1/1982 | Schwerdt | |
| 4,336,421 A | 6/1982 | Welch et al. | |
| 4,345,313 A | 8/1982 | Knox | |
| 4,354,184 A | 10/1982 | Woborschil | |
| 4,354,185 A | 10/1982 | Worborschil | |
| 4,386,346 A | 5/1983 | Levine | |
| 4,393,271 A | 7/1983 | Fujinami et al. | |
| 4,531,119 A | 7/1985 | Nakayama et al. | |
| 4,555,193 A | 11/1985 | Stone | |
| 4,559,598 A | 12/1985 | Goldwasser et al. | |
| 4,586,035 A | 4/1986 | Baker et al. | |
| 4,587,520 A | 5/1986 | Astle | |
| 4,591,841 A | 5/1986 | Gunderson et al. | |
| 4,595,990 A | 6/1986 | Garwin et al. | |
| 4,638,312 A | 1/1987 | Quinn et al. | |
| 4,648,028 A | 3/1987 | DeKlotz et al. | |
| 4,651,145 A | 3/1987 | Sutter | |
| 4,665,402 A | 5/1987 | Young | |
| 4,679,951 A | 7/1987 | King et al. | |
| 4,720,189 A | 1/1988 | Heynen et al. | |
| RE32,632 E | 3/1988 | Atkinson | |
| 4,731,769 A * | 3/1988 | Schaefer | B60K 35/00 360/12 |
| 4,748,502 A | 5/1988 | Friedman et al. | |
| 4,751,503 A | 6/1988 | Kermisch | |
| 4,763,356 A | 8/1988 | Day, Jr. et al. | |
| 4,788,649 A | 11/1988 | Shea et al. | |
| 4,829,576 A | 5/1989 | Porter | |
| 4,836,670 A * | 6/1989 | Hutchinson | A61B 3/113 351/210 |
| 4,885,580 A * | 12/1989 | Noto | H04M 1/247 341/23 |
| 4,891,630 A | 1/1990 | Friedman et al. | |
| 4,931,783 A | 6/1990 | Atkinson | |
| 4,950,069 A | 8/1990 | Hutchinson | |
| 4,973,149 A | 11/1990 | Hutchinson | |
| 4,977,520 A * | 12/1990 | McGaughey, III | G06Q 10/109 345/156 |
| 4,979,094 A | 12/1990 | Gemmell et al. | |
| 4,987,411 A | 1/1991 | Ishigami | |
| 5,012,231 A | 4/1991 | Felsenstein | |
| 5,020,107 A | 5/1991 | Rohani et al. | |
| 5,027,109 A | 6/1991 | Donovan et al. | |
| 5,027,406 A | 6/1991 | Roberts et al. | |
| 5,045,843 A | 9/1991 | Hansen | |
| 5,119,075 A * | 6/1992 | Smith | G06F 3/0386 345/173 |
| 5,122,951 A | 6/1992 | Kamiya | |
| 5,124,940 A * | 6/1992 | Lapeyre | B41J 5/10 708/145 |
| 5,146,210 A | 9/1992 | Heberle | |
| 5,164,900 A | 11/1992 | Bernath | |
| 5,175,688 A | 12/1992 | Sasaki et al. | |
| 5,177,328 A | 1/1993 | Ito et al. | |
| 5,195,179 A | 3/1993 | Tokunaga | |
| 5,204,703 A | 4/1993 | Hutchinson et al. | |
| 5,220,361 A | 6/1993 | Lehmer et al. | |
| 5,223,828 A | 6/1993 | McKiel, Jr. | |
| 5,231,674 A | 7/1993 | Cleveland et al. | |
| 5,233,662 A | 8/1993 | Christensen | |
| 5,249,121 A * | 9/1993 | Baum | A61F 9/007 345/4 |
| 5,254,983 A | 10/1993 | Long et al. | |
| 5,257,314 A | 10/1993 | Kimura | |
| 5,266,931 A | 11/1993 | Tanaka | |
| 5,285,265 A | 2/1994 | Choi | |
| 5,287,119 A | 2/1994 | Drumm | |
| 5,289,168 A | 2/1994 | Freeman | |
| 5,300,943 A | 4/1994 | Jakobs et al. | |
| 5,305,435 A | 4/1994 | Bronson | |
| 5,329,609 A | 7/1994 | Sanada et al. | |
| 5,373,857 A | 12/1994 | Travers et al. | |
| 5,376,946 A * | 12/1994 | Mikan | G06F 3/0488 345/157 |
| 5,387,896 A | 2/1995 | Alappat et al. | |
| 5,396,264 A | 3/1995 | Falcone et al. | |
| 5,408,582 A | 4/1995 | Colier | |
| 5,428,355 A | 6/1995 | Jondrow et al. | |
| 5,428,707 A | 6/1995 | Gould et al. | |
| 5,429,513 A | 7/1995 | Diaz-Plaza | |
| 5,454,062 A | 9/1995 | LaRue | |
| 5,471,542 A | 11/1995 | Ragland | |
| 5,473,347 A | 12/1995 | Collas et al. | |
| 5,543,818 A * | 8/1996 | Scott | G06F 3/0489 345/160 |
| 5,546,527 A | 8/1996 | Fitzpatrick et al. | |
| 5,583,795 A | 12/1996 | Smyth | |
| 5,586,198 A | 12/1996 | Lakritz | |
| 5,617,515 A | 4/1997 | MacLaren et al. | |
| 5,625,380 A | 4/1997 | Hansen | |
| 5,737,540 A * | 4/1998 | Ogawa | H04L 51/28 710/300 |
| 5,767,919 A * | 6/1998 | Lee | H04N 5/44513 345/157 |
| 5,802,516 A * | 9/1998 | Shwarts | G06F 3/0483 |
| 5,828,360 A | 10/1998 | Anderson et al. | |
| 5,844,544 A | 12/1998 | Kahn et al. | |
| 6,005,549 A | 12/1999 | Forest | |
| 6,160,536 A | 12/2000 | Forest | |
| 6,903,723 B1 | 6/2005 | Forest | |
| 2005/0231520 A1 | 10/2005 | Forest | |
| 2008/0030463 A1 | 2/2008 | Forest | |

FOREIGN PATENT DOCUMENTS

| | | |
|---|---|---|
| EP | 0 026 381 A2 | 4/1981 |
| EP | 0 026 382 A2 | 4/1981 |
| EP | 0026381 A2 * | 4/1981 |

(56) References Cited

FOREIGN PATENT DOCUMENTS

| | | | |
|---|---|---|---|
| EP | 0026382 A2 | * | 4/1981 |
| EP | 0 159 400 A1 | | 10/1985 |
| EP | 0159400 A1 | * | 10/1985 |
| EP | 0 324 306 A2 | | 7/1989 |
| EP | 0324306 A2 | * | 7/1989 |
| EP | 0 513 694 A2 | | 11/1992 |
| EP | 0513694 A2 | * | 11/1992 |
| EP | 0 538 166 A2 | | 4/1993 |
| EP | 0538166 A2 | * | 4/1993 |
| EP | 0 613 080 A2 | | 8/1994 |
| EP | 0613080 A2 | * | 8/1994 |
| EP | 0 684 541 A2 | | 11/1995 |
| EP | 0684541 A2 | * | 11/1995 |
| GB | 2116341 A | | 9/1983 |
| GB | 2116341 A | * | 9/1983 |
| GB | 2173023 A | * | 10/1986 |
| GB | 2173023 A | | 10/1986 |
| GB | 2290400 A | * | 12/1995 |
| GB | 2290400 A | | 12/1995 |
| GB | 9906822.3 | * | 4/1999 |
| JP | 54-19618 | | 2/1979 |
| JP | 54019618 | * | 2/1979 |
| JP | 57-059241 | | 4/1982 |
| JP | 57-073453 | | 5/1982 |
| JP | 61-121185 | | 6/1986 |
| JP | 61121185 | * | 6/1986 |
| JP | 06-149338 | | 5/1994 |
| JP | 06-149534 | | 5/1994 |
| JP | 06149338 | * | 5/1994 |
| JP | 06149534 | * | 5/1994 |
| JP | 07-295784 | | 11/1995 |
| JP | 07295784 | * | 11/1995 |
| WO | PCT/AU85/00324 | | 7/1986 |
| WO | PCTAU8500324 | * | 7/1986 |
| WO | PCT/US93/07233 | | 2/1994 |
| WO | PCTUS9307233 | * | 2/1994 |
| WO | WO 94/03887 | | 2/1994 |
| WO | WO9403887 A1 | * | 2/1994 |
| WO | PCT/US95/03591 | | 3/1996 |

OTHER PUBLICATIONS

Bryan, R.E.; Chang, F.C.; Hempel, B.C.; Iida, Y.; "Pre-Selection Highlighting," IBM Technical Disclosure Bulletin, vol. 32, No. 8b, Jan. 1990, New York, NY, XP 000082441, pp. 231 & 232.*

Callahan, Jack; Hopkins, Don; Weiser, Mark; Schneiderman, Ben, "An Empirical Comparison of Pie vs. Linear Menus," Computer Science Technical Report Series CS-TR- 1919, College Park, MD: University of Maryland, Sep. 1987.*

Downing, Andrew; Martin, Byron; Stern, Loon, "Methods for Measuring the Characteristics of Movements of Motor-Impaired Children", Assistive Technology, vol. 2, pp. 131-141, RESNA Press, Washington, DC, 1990.*

Fitts, P.M., "The information capacity of the human motor system in controlling the amplitude of movement", Journal of Experimental Psychology, 1954, vol. 47, pp. 15 381-391.*

Fitts, P.M and Peterson, J.R., "Information capacity of discrete motor responses", Journal of Experimental Psychology, 1964, vol. 67, pp. 103-112.*

Goosens, Carol; Crain, Sharon Sapp, "Overview of Currently Used Eye-Gaze Communication Approaches," In Augmentative Communication Intervention Resources, 1986.*

Hamann, Gil, "Two Switchless Selection Techniques Using a Headpointing Device for Graphical User Interfaces" in Proceedings of the 13th Annual RESNA Conference, pp. 439-440, RESNA Press, Washington, DC, 1990.*

Hopkins, Don, "Directional Selection is Easy as Pie Menus!" in Fourth USENIX Computer Graphics Workshop, Cambridge, MA, Oct. 8-9, 1987, published by University of Maryland, p. 103.*

Jacob, Robert J. K., "What you look at is what you get," Computer, vol. 26, No. 7, Jul. 15, 1993, Los Alamitos, California. pp. 65 & 66.*

Lin, Mei Li; Radwin, Robert G.; Vanderheiden, Gregg C., Gain Effects on Performance Using a Head-Controlled Computer Input Device, Ergonomics, vol. 35, No. 2, pp. 159-175, 1992.*

Perricos, Costi; Jackson, Robin D., "A Head Gesture Recognition System for Computer Access" in Proceedings of the RESNA '94 Annual Conference, RESNA Press, Washington, DC, pp. 92-94, 1994.*

Treviranus, Jutta, "Quartering, Halving, Gesturing: Computer Access Using Imprecise Pointing" in Proceedings of the RESNA International Conference '92, RESNA Press, Washington, DC, pp. 374-376, 1992.*

Vanderheiden, Gregg C.; Kelso, D.P., "Comparative Analysis of Fixed-Vocabulary Communication Techniques", Trace Center, University of Wisconsin, Madison, WI, 1987.*

Video of Video Tape No. 032-27, submitted in parent U.S. Appl. No. 08/506,032, https://vimeo.com/176067557/c8a29b05cb.*

Becker, Joseph D., "User Friendly Design for Japanese Typing," Xerox Office Systems Division Publication No. T8301, Xerox Corp., Palo Alto, CA, Aug. 1983.

CTI Electronics Corporation, "Model M80XX Industrial Mouse" product flyer, Stratford, CT: CTI Electronics Corporation.

CTI Electronics Corporation, "Joysticks, Touchscreens, & Trackballs", product flyer, Stratford, CT: CTI Electronics Corporation.

Darci Too Product Description, WesTest Engineering Corp., Bountiful, UT: WesTest Engineering Corp., 1992.

Don Johnston Developmental Equipment, Inc., "CO:WRITER" product brochure, Wauconda, IL: Don Johnston Developmental Equipment, Inc.

DragonDictate, The Premier PC Dictation System, Dragon Systems, Inc., Newton, MA, 1994.

Drawing Gallery, In The Graphics Gallery Release 3.0 User Manual, Hewlett-Packard Co., Boise, ID: Hewlett-Packard Co., 1988.

Johnson, Frank, "Communications system for speechless quadriplegics", Design Product News, Jan. 1994.

LC Technologies, Inc. "The Eyegaze System" product brochure, Fairfax, VA: LC Technologies, Inc.

Mayer-Johnson Company, "Non-Speech Communication Products 1992" catalog, Mayer-Johnson Company, Solana, Beach, CA.

Origin Instruments Corporation, "HeadMouse Manual", Grand Prairie, TX: Origin Instruments Corporation.

Pointer Systems '92/'93 Catalog, Pointer Systems, Inc., Burlington, VT: Pointer Systems, Inc., 1992.

Prentke Romich Company, "1994-1995 Catalog", Wooster, OH: Prentke Romich Company.

Prentke Romich Company, "AlphaTalker™" product brochure, Wooster, OH: Prentke Romich Company.

Prentke Romich Company, "DeltaTalker™" product brochure, Wooster, OH: Prentke Romich Company.

Prentke Romich Company, "Liberator™" reference manual, version 1.03, Wooster, OH: Prentke Romich Company, 1992.

Prentke Romich Company, "Operator's Manual for Remote HeadMaster Mouse Emulator", Wooster, OH: Prentke Romich Company.

Quartet Technologies, Inc., "Mouse/Keyboard Controller", product flyer, Chelmsford, MA: Quartet Technology, Inc.

Quartet Technologies, Inc., "Switch Activated Environmental Control Units, Simplicity Series 7 and Series 7M" product flyer, Chelmsford, MA: Quartet Technology, Inc.

Quartet Technologies, Inc., "Voice Activated Environmental Control Units, Simplicity Series 5,6, & 6 Plus!" product flyer, Chelmsford, MA: Quartet Technology, Inc.

Quartet Technologies, Inc., "Voice and Switch Activated All-In-One Environmental Control Unit" product flyer, Chelmsford, MA: Quartet Technology, Inc.

Sentient Systems Technology, Inc., "DigiVox" product brochure, Pittsburgh, PA: Sentient Systems Technology, Inc.

Sentient Systems Technology, Inc., "DynaVox" product brochure, Pittsburgh, PA: Sentient Systems Technology, Inc.

WiViK2, Visual Keyboard for Windows 3.1 User's Guide, Prentke Romich Co., Wooster, OH: Prentke Romich Co., 1992.

(56) References Cited

OTHER PUBLICATIONS

Becker, Joseph D., "User Friendly Design for Japanese Typing," Xerox Office Systems Division Publication No. T8301, Xerox Corp., Palo Alto, CA, Aug. 1983. See pp. 14 & 15.

Callahan, Jack; Hopkins, Don; Weiser, Mark; Schneiderman, Ben, "An Empirical Comparison of Pie vs. Linear Menus," Computer Science Technical Report Series CS-TR-1919, College Park, MD: University of Maryland, Sep. 1987.

Callahan, Jack; Hopkins, Don; Weiser, Mark; Shneiderman, Ben; "An Empirical Comparison of Pie vs. Linear Menus," Human Factors in Computing Systems: CHI '88, Conference Proceedings, pp. 95-100.

"Discrete and continuous control using stable speech sounds", IBM Technical Disclosure Bulletin, vol. 33, No. 10a, Mar. 1991, New York, NY, XP 000110092, p. 378.

DragonDictate, The Premier PC Dictation System, Dragon Systems, Inc., Newton, MA, 1994. See p. 4.

Fitts, P.M., "The information capacity of the human motor system in controlling the amplitude of movement", Journal of Experimental Psychology, 1954, vol. 47, pp. 381-391.

Golding, V.G.; Heneghan, M.J.; "Audio Response Terminal," IBM Technical Disclosure Bulletin, vol. 26, No. 10B, Mar. 1984, pp. 5633-5636.

Heynen, J.; Kahn, D.A., "An Eye Transducer for Keyboard Emulation" in IEEE Global Telecommunications Conference, Dec. 2-5, 1985, Institute of Electrical and Electronics Engineers, New York, NY, pp. 1063-1065.

Heynen, J.; Kahn, D.A.; Lukas, H., "An Eye Transducer for Actuating a Typewriter" in Proceedings of the Second International Conference on Rehabilitation Engineering, Jun. 17-22, 1984, Rehabilitation Engineering Society of North America, Bethesda, MD, pp. 448-449.

Jacob, Robert J. K., "What you look at is what you get," Computer, vol. 26, No. 7, Jul. 1993, Los Alamitos, California. pp. 65 & 66.

Johnson, Frank, "Communications system for speechless quadriplegics", Design Product News, Jan. 1994. See the entire document which consists of one page.

Lazzaro, Joseph J., "Computers for the Disabled," Byte, Jun. 1993, pp. 59-64.

Video Tape, Tape No. 032-27, submitted and considered in parent U.S. Appl. No. 08/506,032.

Yamada, Mitsuho; Fukada, Tadahiko, "Eye word processor (EWP) and peripheral controller for the ALS patient", I.E.E.E. Proceedings a Physical Science, Measurement & Instrumentation, Management & Education, Apr. 1987, vol. 134, No. 4, Part A, Stevenage.

\* cited by examiner

PRIOR ART

FIG. 11

| Meaning | Picture Communication Symbols | Rebus | Pic Sym | Blissymbol |
|---------|------------------------------|-------|---------|------------|
| want | | | | |
| eat | | | | |
| think | | | | |
| where | | | | |
| friend | | | | |
| wheelchair | | | | |
| television | | | | |
| yesterday | | | | |
| no | | | | |
| not, un | | | | | go garden wagon sad pretzel potato stick m & m tidbit gumdrop cereal peanut fizzie butterscotch Frito

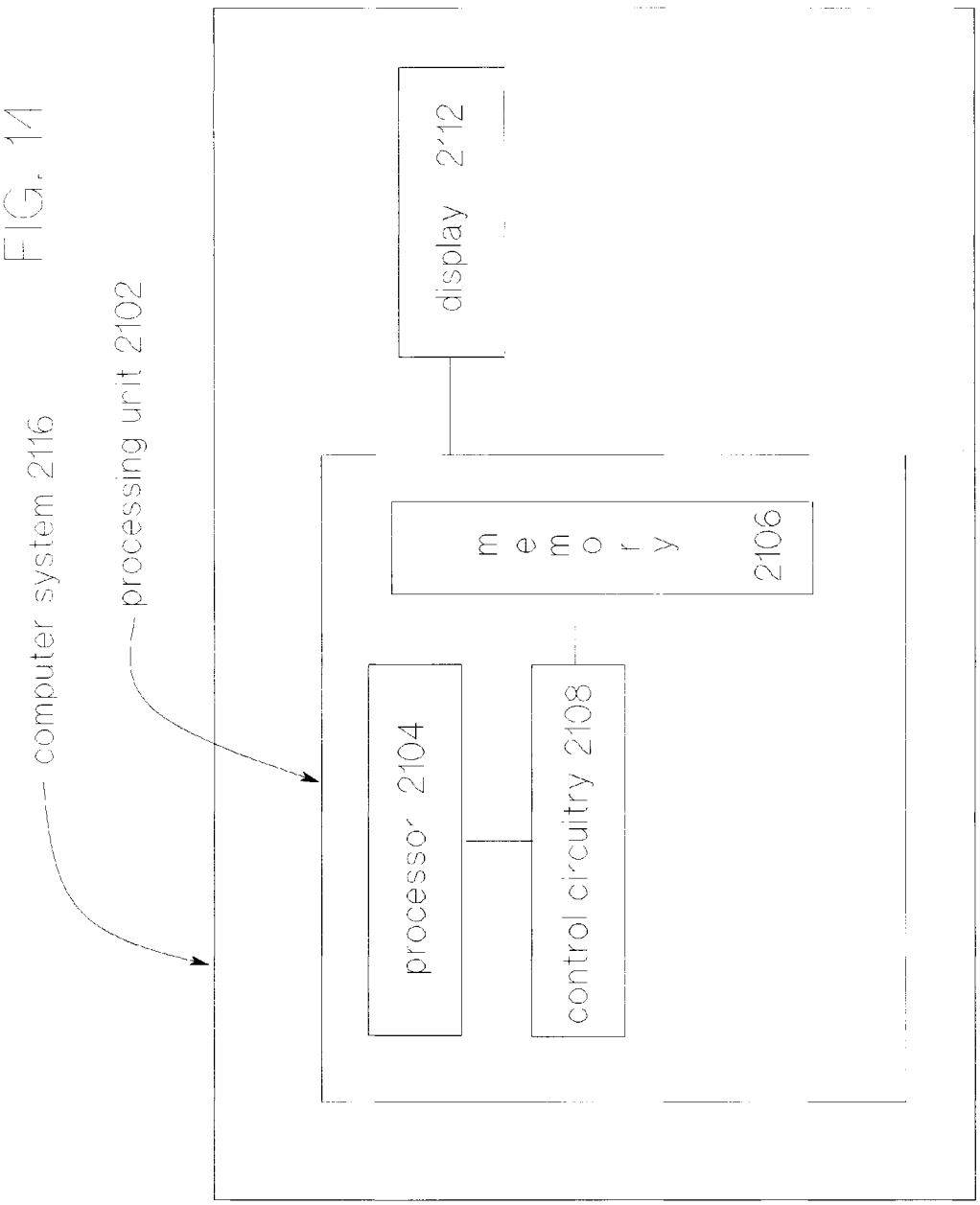

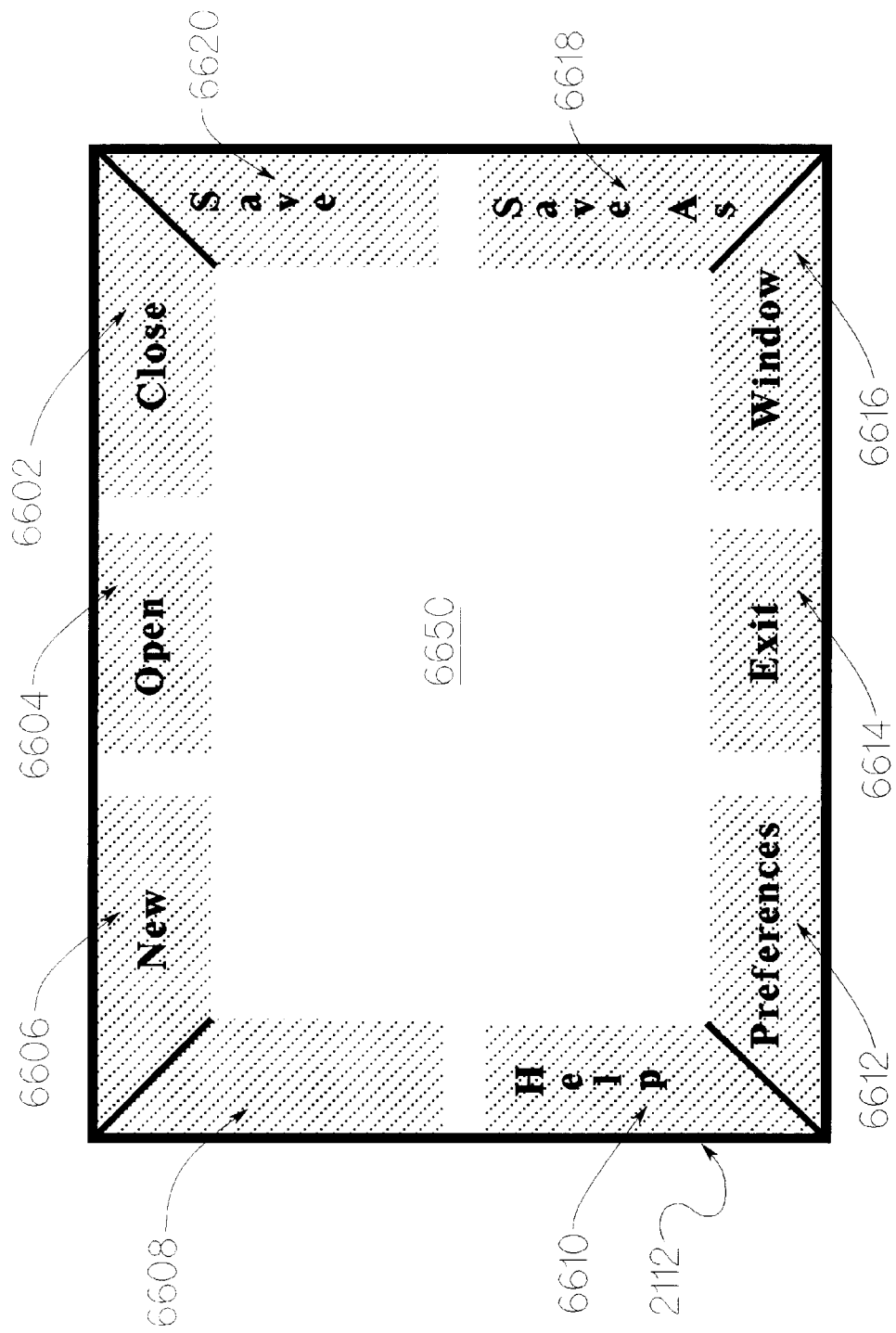

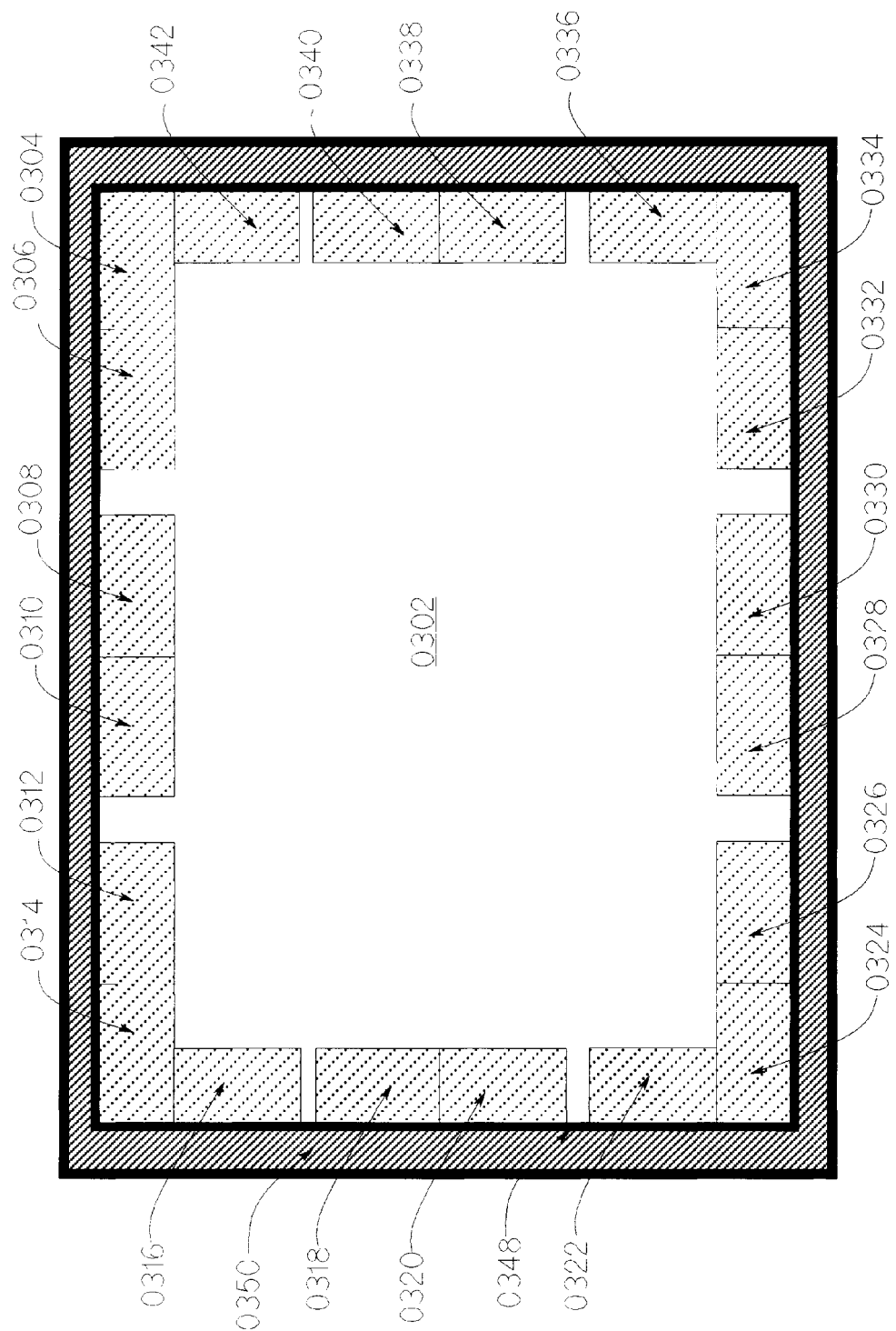

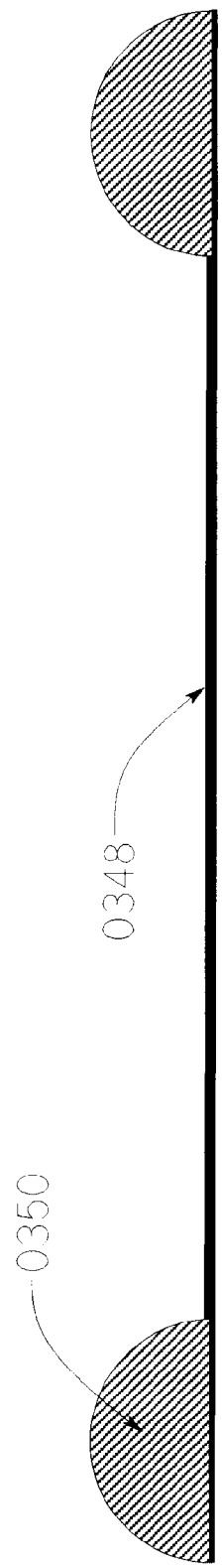

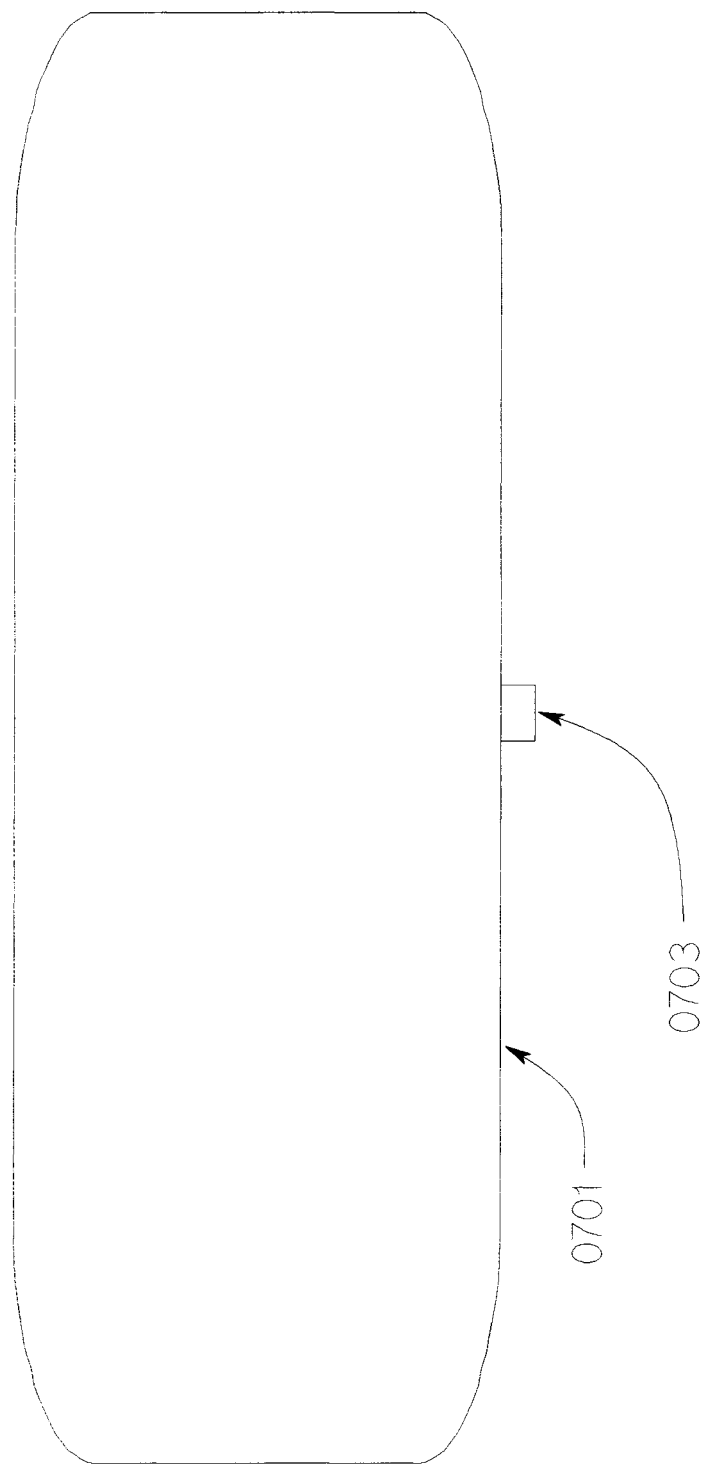

| | FIG. 29 | | | | | | | | | |
|---|---|---|---|---|---|---|---|---|---|---|
| | | Event | | | | | | | | |
| | | 0 | 1 | 2 | 3 | 4 | 5 | 6 | 7 | 8 | 9 |
| | State | EV_NULL | EV_RESET | EV_DECAY | EV_DWELL | EV_CROSS_OUT | EV_STEP_DOWN | EV_STEP_UP | EV_MOVEMENT | EV_IDLE_TIMEOUT | EV_CEILING |
| 0 | ST_ILLEGAL_STATE | 0 | 0 | 0 | 0 | 0 | 0 | 0 | 0 | 0 | 0 |
| 1 | ST_ERROR | 0 | 0 | 0 | 0 | 0 | 0 | 0 | 0 | 0 | 0 |
| 2 | ST_INITIAL | 0 | 3 | 2 | 2 | 2 | 2 | 2 | 2 | 2 | 0 |
| 3 | ST_RESET | 0 | 3 | 3 | 3 | 12 | 0 | 0 | 12 | 3 | 0 |
| 4 | ST_LOW_TIDE | 4 | 3 | 8 | 9 | 4 | 0 | 5 | 8 | 10 | 0 |
| 5 | ST_SELECTED | 6 | 3 | 0 | 0 | 0 | 0 | 0 | 0 | 0 | 0 |
| 6 | ST_CREST_TIDE | 6 | 3 | 8 | 9 | 7 | 4 | 0 | 8 | 10 | 9 |
| 7 | ST_SELECT_AND_OUT | 0 | 3 | 0 | 0 | 0 | 0 | 0 | 0 | 0 | 0 |
| 8 | ST_DECAY | 0 | 0 | 0 | 0 | 0 | 0 | 0 | 0 | 0 | 0 |
| 9 | ST_DWELL | 0 | 0 | 0 | 0 | 0 | 0 | 0 | 0 | 0 | 0 |

FIG. 30

| | | Event | | | | | | | | | |
|---|---|---|---|---|---|---|---|---|---|---|---|
| | | 0 | 1 | 2 | 3 | 4 | 5 | 6 | 7 | 8 | 9 |
| | State | EV_NULL | EV_RESET | EV_DECAY | EV_DWELL | EV_CROSS_OUT | EV_STEP_DOWN | EV_STEP_UP | EV_MOVEMENT | EV_IDLE_TIMEOUT | EV_CEILING |
| 10 | ST_IDLE | 3 | 0 | 0 | 0 | 0 | 0 | 0 | 0 | 0 | 0 |
| 11 | ST_SELECTED_SEQ_ON | 0 | 3 | 0 | 0 | 0 | 0 | 0 | 0 | 0 | 0 |
| 12 | ST_EBB_TIDE | 12 | 3 | 8 | 13 | 12 | 0 | 5 | 8 | 10 | 0 |
| 13 | ST_ENTRY | 1 | 0 | 0 | 0 | 0 | 0 | 0 | 0 | 0 | 0 |
| 14 | ST_BEGIN_TO_LOCK | 0 | 3 | 15 | 15 | 15 | 0 | 0 | 15 | 10 | 15 |
| 15 | ST_LOCK | 16 | 3 | 15 | 15 | 15 | 0 | 0 | 15 | 10 | 15 |
| 16 | ST_END_LOCK | 0 | 3 | 17 | 17 | 7 | 0 | 0 | 17 | 10 | 17 |
| 17 | ST_DISCARD | 0 | 0 | 0 | 0 | 0 | 0 | 0 | 0 | 0 | 0 |

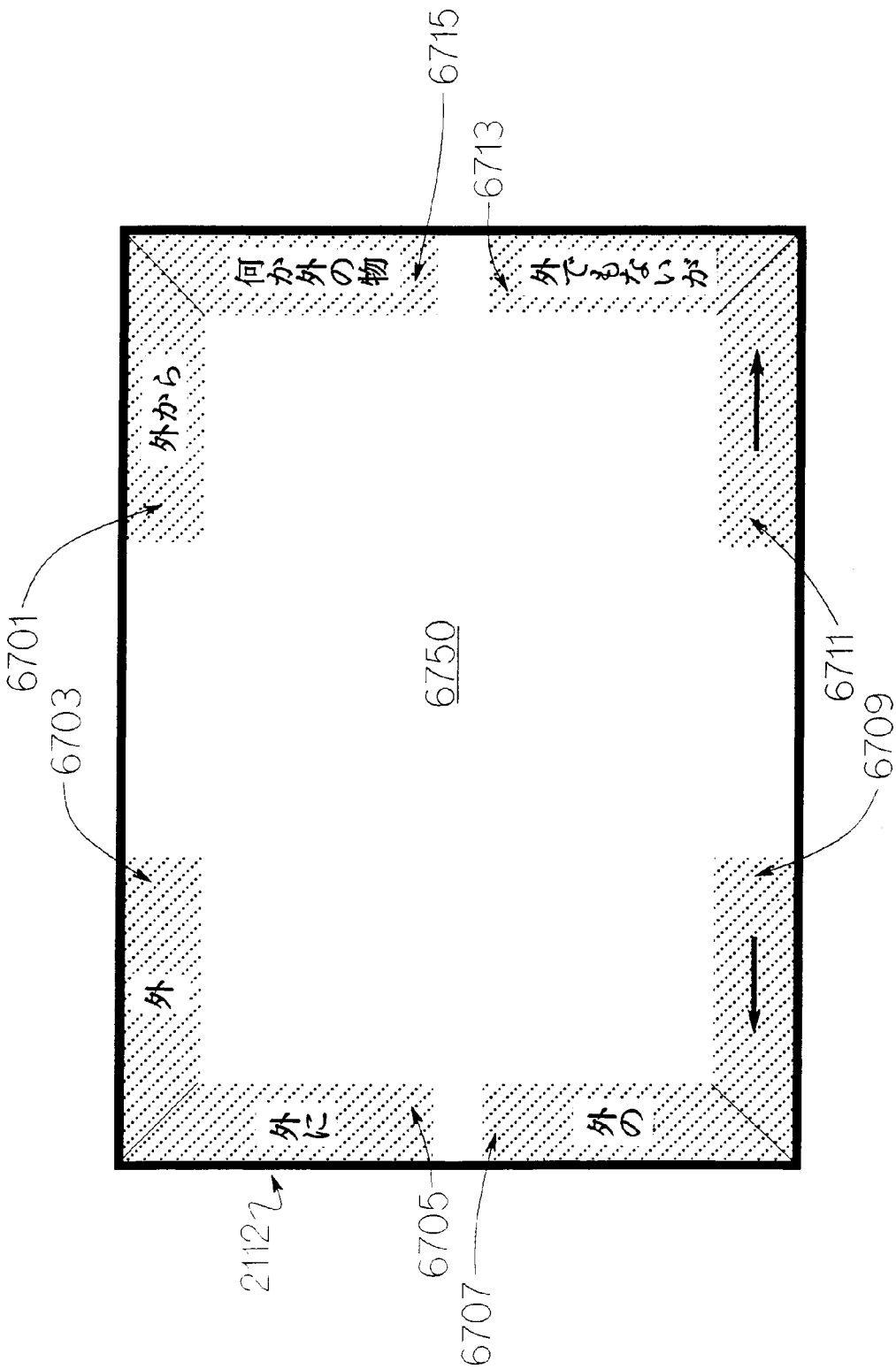

APPARATUS AND METHOD FOR SELECTING FROM A DISPLAY

This is a divisional application of pending application Ser. No. 11/890,355, filed 6 Aug. 2007, published application number 20080030463, published 7 Feb. 2008, now abandoned, which in turn is a divisional application of application Ser. No. 11/124,563, filed 6 May 2005, published application number 20050231520, published 20 Oct. 2005, now abandoned, which in turn is a divisional application of application Ser. No. 08/506,032, filed 24 Jul. 1995, which in turn is a continuation-in-part application of international application number PCT/US95/03591, International Publication Number WO 96/30822, filed 27 Mar. 1995, as amended 25 Apr. 1995 and 26 May 1995, which designated the United States. The international application issued as U.S. Pat. No. 6,160,536 on 12 Dec. 2000. Application Ser. No. 08/506,032 issued as U.S. Pat. No. 6,903,723 on 7 Jun. 2005. Each of the international application, U.S. Pat. No. 6,903,723, published application number 20050231520, and published application number 20080030463 is incorporated herein by reference.

TECHNICAL FIELD

The present disclosure relates generally to interactive displays and interactive display methods, and more particularly to interactive displays and interactive display methods for use by persons temporarily or permanently lacking normal motor capabilities. It also relates to systems and methods for the assessment of the motor capabilities of persons lacking normal motor capabilities. It further relates to interactive displays and interactive display methods for use in speech synthesis for persons having impaired speech. It also relates to systems and methods for the control of devices, including appliances, by persons lacking normal motor capabilities. It further relates to interactive displays and interactive display methods for selecting one menu option from a menu. It further relates to systems and methods utilizing sound recognition for selecting a menu option from a menu. It further relates to data and order entry systems including, and data and order entry methods utilizing, an interactive display terminal. It also relates to interactive displays and interactive display methods for displaying and selecting ideographic characters, such as are used in the Chinese, Japanese and Korean languages. It also relates to interactive displays and interactive display methods for producing an indication of progress toward and/or away from selection of a menu option.

A portion of the disclosure of this patent document contains material which is subject to copyright protection. The copyright owner has no objection to the facsimile reproduction by anyone of the patent document or the patent disclosure, as it appears in the World Intellectual Property Organization or United States Patent and Trademark Office patent file or records, but otherwise reserves all copyright rights whatsoever.

BACKGROUND ART

Many persons suffer from various neurogenic muscular disorders, such as Cerebral Palsy ("CP"), Traumatic Brain Injury, Spinal Cord Injury, Muscular Dystrophy, Amyotrophic Lateral Sclerosis and Multiple Sclerosis. These conditions can result in a reduced ability to voluntarily control or prevent the movement of parts of the body, including the head, limbs and digits, muscle stiffness, weakness, limited range of motion, abnormal posture, involuntary muscle tremors, involuntary muscle activity causing involuntary motion, impaired ability to voluntarily stop motion, impaired ability to coordinate muscle activity, and/or impaired ability to sense the position of a part of the body. Any one of these symptoms may impair an affected individual's fine motor control. Moreover, while some individuals affected by a neuromuscular disorder may be able to exercise fine motor control with enormous effort, the struggle to do so often fatigues the individual, limiting the period of time the individual is capable or comfortable performing the fine motor control task.

Neuromuscular disorders are often systemic in effect, impairing an individual's ability to operate prosthetic devices, such as a wheelchair, and to perform the activities of daily life, such as speaking, walking and operating household appliances. Speech is frequently affected since the mechanics of producing speech require coordination of many muscle groups—the muscles of the diaphragm which push air over the vocal cords, the muscles of the larynx, jaws, tongue and lips. The inability to use or coordinate these muscle groups may result in impaired speech. Depending upon the degree of impairment, speech may be totally absent, present but impaired to the point of unintelligibility, or intelligible on the whole but with occasional unintelligible words. The ability to walk is often affected since walking requires coordination and voluntary control of many muscle groups. Furthermore, impaired fine motor control may prevent or impede an individuals from effectively operating household appliances or computer input devices.

Devices are available which produce speech, control appliances and facilitate computer access for some persons having neuromuscular disorders ("NMD operators"). Devices which produce speech for individuals whose own speech is impaired, called Augmentative and Alternative Communication ("AAC") devices, allow the operator to select words or phrases by spelling the words, by specifying an abbreviation for the phrase or by selecting a sequence of symbols, and then speak the selected words or phrases using an electronic speech synthesizer. However, due to the systemic nature of neuromuscular disorders, NMD operators are often unable to efficiently use a standard keyboard and mouse. For example, an NMD operator who is unable to stop the movement of a limb with precision, when attempting to use a keyboard or mouse, may move his arm toward the target key or move the cursor toward the target object on the display but overshoot the target. If he has involuntary tremors and cannot hold a limb still, then, when attempting to use a keyboard, he may hit keys adjacent to his target key. If he has involuntary motion moving left to right, then, when attempting to use a keyboard, he may have difficulty accessing an intended key on the right side of the keyboard.

The benefits of interfacing an NMD operator to a general purpose computer so that he may control the computer and devices attached to it ("computer access") are both numerous, because many of the problems faced by the disabled are susceptible to a computer-driven solution, and profound, because of the psychological deprivation occasioned by a severe physical disability. The benefits potentially obtained through computer access for individuals affected by neuromuscular disorders include:

a. Speech synthesis. A computer connected to a speech synthesizer enables an NMD operator with impaired speech to direct the computer to speak for him b. Device control. A user who is physically unable to operate a household appliance, for example, a television, video cassette recorder, compact disc player, radio, alarm clock, telephone, light, thermostat, dimmer or power switch, may be able to control the appliance via a computer equipped with an interface he can control.

c. Access to general purpose computer applications. NMD operators may make use of the same general purpose computer application programs ("applications") as able-bodied users, including applications for word processing, database, computer-aided instruction, access to literature accessible via computer, spreadsheet, time management and computer utilities.

d. Enhanced self-esteem and peer approval. Adolescents with CP are obviously different from their peers. They are often surrounded by non-normative assistive technology, e.g. wheelchair or walker, special school bus equipped with a chair lift, stair lift, standing aid, AAC device, feeding apparatus, bath seat, toiletting apparatus, etc. In addition, they may drool, lacking the ability to coordinate lip closure with swallowing. Nonetheless they are adolescents and need peer approval to support them in their maturation from dependent children to independent adults. Today, demonstrated facility with a computer is an emblem of intelligence among adolescents, so computer use provides adolescents the opportunity to prove their intelligence and thus potentially rewards NMD operators with both self-esteem and peer approval.

e. Privacy. Some severely disabled school-aged children require nearly constant physical assistance to transfer them to and from bed, to feed them, help them with toiletting and personal hygiene, etc. Because they are constantly attended, all their mistakes in class or when doing homework are known to their attendant, often a family member. They do not have the opportunity to make mistakes in private. Computer use, if it can be done without assistance, affords the NMD operator the opportunity to avoid the embarrassment of showing their failings to their attendant.

f. Expanded personal interaction. Some severely disabled individuals, e.g. quadriplegics, are essentially incarcerated by their disability. They interact with their family or their caretakers, depending upon whether they live at home or in an institution. Their circle of friends is often very small. Using a computer and a modem, they can expand their circle of friends to include the tens of thousands of people who periodically connect to worldwide electronic networks to trade information on topics of mutual interest. Moreover, the interaction via present computer networks is mostly textual; there is no voice or visual interaction between users. Since messages are customarily composed and read off-line to minimize connect time charges, no one even knows how long it took the sender to enter the text. Electronic networks thus afford the disabled user an opportunity to relate to others on an equal footing, not as a disabled person to his able-bodied peers, something many NMD operators dearly want to do but were never able to.

NMD operators vary widely in their motor capabilities. Even individuals having the same medical diagnosis may require completely different technologies for computer access. Many NMD operators are able to use an oversize keyboard, a device having a pressure-sensitive surface divided into squares, each square associated with a letter of the alphabet. The squares may be sized to match the operator's abilities, but typically each square is two inches on either side. NMD operators who are unable to efficiently use an oversize keyboard may use another conventional computer access solution, called an "on-screen keyboard", which, as illustrated in FIG. 1, is a picture of keyboard drawn on a computer display (1101). The operator selects a letter by pointing to that letter's key image on the display with a pointing device ("pointer"), then indicating that he has reached his target either by operating a switch, a process called selection by click, or by maintaining the location indicated by the pointer ("dwelling") on the key image for a predetermined period of time (the "selection threshold"), a process called selection by dwell. Switch operation includes, but is not limited to, each of the following: opening the switch, closing the switch, opening the switch multiple times within a predetermined period, and closing the switch multiple times within a predetermined period. A program executing on the computer determines which letter the operator has selected and processes the letter or passes it to some other application program which processes the letter as if it came from a true keyboard.

Conventional pointing devices include a mouse, trackball, joystick (which may be integrated into a keyboard, e.g. TrackPoint II®), stylus and graphics tablet, lightpen, thumb wheel, touch screen, touch panel, head pointer, occulometer, intraoral pointer and eye tracker. They may be active, e.g. a lightpen that emits an infrared beam, or passive, e.g. an eye tracker that uses images of an individual's eyes to determine where his eyes are focusing. Conventional switches include a button on the mouse, a switch in the tip of the stylus actuated by pressure or the release of pressure, a switch mounted on the user's wheelchair operated by a turn of the head to or the switch below a keyboard key.

Dwell time may be continuous or discontinuous depending upon the operator's motor capabilities. In continuous dwelling, if the operator moves the cursor from one key image to another region of the display, the time accumulated on the key image is discarded so that if the operator returns to that key image he must dwell on it for the full selection threshold to select it. Discontinuous dwelling, by contrast, compensates for involuntary tremors which pull the operator off the desired key image. Accumulated dwell time on a key image is remembered, so that on return to a key image, the operator need only dwell for a period equal to the difference between the selection threshold and the previously accumulated dwell time for that key image. Accumulated dwell time is reset to zero for all key images following the selection of any one key image. Conventional on-screen keyboards do not indicate to the operator the dwell time associated with any key image.

There may be a single selection threshold period for all key images or each key image may be associated with its own selection threshold period. In the latter case, keys associated with shorter selection threshold periods are easier to select than keys associated with longer selection threshold periods.

As was mentioned earlier, computer access permits an NMD operator to run a variety of applications. One such application is speech synthesis. In a computer-based speech synthesis system, a computer system displaying an on-screen keyboard is connected to a speech synthesizer. The operator spells the desired word or words using the on-screen keyboard. These are then spoken by the speech synthesizer. Another application of the on-screen keyboard is word processing. FIG. 2 illustrates an example of a combined display of an on-screen keyboard and a word processing application program. The on-screen keyboard (0201) is shown on the lower portion of a display connected to a computer system (not shown) which also executes the word processing application program whose output (0203) appears on the upper portion of the display. Letters selected by the operator are input to the word processing application program.

Due to impaired fine motor control, many NMD operators have difficulty selecting a key image by click or by dwell and this difficulty increases as the size of the key image decreases. FIG. 1 shows an on-screen keyboard containing 81 total keys including 26 alphabetic keys, 10 numeric keys, 12 function keys, 4 arrow keys and 29 special purpose keys. Drawing this many key images on a display restricts the size of each key image making each very difficult for many NMD operators to select.

When a display is shared between application program output (0203) and an on-screen keyboard (0201), as is the display shown in FIG. 2, the size of each key image must be reduced from its size in FIG. 1 to allow space for the application program output. Thus, as more display space is allotted to application program output, the key images become more difficult for an NMD operator to select.

Many NMD operators have difficulty using the conventional dwell selectable on-screen keyboard because they cannot maintain a steady pointer position. The body member with which they control the pointer may move slightly ("drift") when they want it to remain still. One approach to this problem is a variation of the on-screen keyboard, depicted in FIGS. 3, 4 and 5 and called a quaternary on-screen keyboard ("quaternary keyboard"). The quaternary keyboard provides for larger key images. The alphabet is divided into four groups of letters, each displayed in one of the four quadrants (1302), (1304), (1306) and (1308) of the display, as shown in FIG. 3. The operator selects one of the four groups by, for example, pointing to and dwelling on one quadrant of the display. The selected group is then exploded into four subgroups, each displayed in one quadrant of the display, as shown in FIG. 4. Once more the operator selects one of the four. The selected group is exploded into four letters and each letter displayed in one quadrant of the display, as shown in FIG. 5. The operator again selects one of the four. This letter is then input to an application program (not shown).

The quaternary keyboard illustrates the use of a menu hierarchy in computer access. Each of the four groups of letters (1302), (1304), (1306) and (1308) is a menu option. Each of these menu options is itself a menu which includes other menu options. A menu hierarchy exists if at least one of a menu's menu options is itself a menu. Hereinafter, a menu accessed from another menu may be called a submenu, and the options of the submenu may be called submenu options. If a menu hierarchy is narrow and deep, many selections are required to make the desired choice. If a menu hierarchy is broad and shallow, each layer is composed of many menu options.

The quaternary keyboard greatly expands the size of a single key image and thus accommodates certain NMD operators with drift or involuntary tremors. The cost of this adjustment is high Instead of selecting a letter with one pointing motion and dwelling for one selection threshold, the quaternary keyboard requires three pointing motions and dwelling for three selection thresholds. Thus the operator's productivity is dramatically reduced from the standard on-screen keyboard depicted in FIG. 1.

The computer access advantage gained from the quaternary keyboard is greatest when the quaternary keyboard occupies the entire display. In this configuration the size of each of the four active display regions is maximized, making them easier to hit and dwell on for the operator. However, this configuration allows no room on the display for the output of the application program being run by the operator, the reason he is sitting at the computer in the first place. This does not prevent the on-screen keyboard from passing letters to the application program since an application program need not be visible to be active, but it does prevent the operator from seeing what the application program has to show him. The more of the application program output that is displayed, the smaller the on-screen keyboard, the smaller each active region of the on-screen keyboard and the more difficult access becomes. FIG. 6 illustrates a display combining a quaternary keyboard and output from two application programs.

Another conventional structure for selecting of a menu option from a menu is a pie menu A pie menu is an opaque region on a display divided into selectable slices, each slice associated with a menu option. The pie menu suffers some of the drawbacks discussed above, particularly that, while displayed the pie menu occupies more space than a linear menu and obscures much of the output of the operator's application program. For illustrations and a discussion of pie menus, see Callahan, Jack et. al., "An Empirical Comparison of Pie vs. Linear Menus", Computer Science Technical Report Series, CS-TR-1919, University of Maryland, College Park, Md., September 1987.

NMD operators who cannot effectively use a conventional keyboard or a pointing device may use a computer access method called "joystick patterns". FIG. 7 depicts a conventional joystick pattern device. The device (1602) is connected to a joystick and to a computer. The operator pushes the joystick to the top, bottom, left, right, top left corner, top right corner, lower left corner or lower right corner, closing one of eight switch contacts within the joystick housing. That switch position is then indicated on the display (1604). A sequence of consecutive of switch closures encodes a letter or other programmed output that the device (1602) displays on an LCD display (1606) and sends to the connected computer, simulating keyboard input.

The conventional joystick pattern device is ill-suited for many NMD operators. The involuntary tremors common some neuromuscular disorders may result in unintended switch closures. In addition, the device does not provide an indication that the operator is moving a body member in an unintended direction until switch closure occurs. For example, an operator with CP who intends to move the joystick the right but actually moves it to the upper right receives no indication from the device, prior to switch closure, that he's not on target. Moreover, the device requires that the operator memorize the encoding of each letter or other output since there's no indication on the display (1606) which sequence encodes which letter. Further, the device provides no support for head pointing, although the head is often the best controlled part of an NMD operator's body.

NMD operators who cannot effectively use either a conventional keyboard or a pointing device but can reliably actuate a switch may use a computer access method called "scanning", which is subdivided by cursor control technique into three types of scanning: automatic, directed and step. In automatic scanning all the operators' options, for example, the letters of the alphabet, appear on either a static or dynamic display (depending upon the implementation), organized in rows and columns. At the scanning interval, usually about one second, a cursor moves from one row to the next. When the cursor indicates the row containing the letter the operator wants, he closes a switch. The machine now moves the cursor from one letter to the next within the selected row until the operator closes the switch again. The operator has now selected one letter. In directed scanning, like automatic scanning, the cursor moves at the frequency determined by the scanning interval, however, it moves only when the switch is closed. To select an option, such as a row or a letter in a row, the operator opens the switch while the cursor indicates the desired option. In step scanning, the cursor moves with each switch activation.

As one can well imagine, writing a sentence via any of these scanning techniques is an extremely slow process, since selecting a single letter may take many seconds.

Problems of computer access cascade and affect the quality of verbal interactions between AAC device operators ("AAC operators") and others. People speak much faster than they type. Not surprisingly, operators who speak with AAC devices, particularly NMD operators whose motor deficits impair their ability to use a keyboard, lag substantially in their conversations. The slow pace of an AAC operator's word production disrupts normal verbal interaction. Speaking persons, accustomed or not to the AAC operator's slow rate, often lose patience in conversations with AAC operators. They may prematurely terminate the conversation, read the AAC device display in an attempt to guess at the AAC operator's intended utterance and so accelerate the interaction, lead the AAC operator, ask predominantly yes/no questions, change the topic of conversation with little input from the AAC operator and otherwise dominate the interaction. The AAC operator often has difficulty participating as an equal partner in the conversation. He may be unable to change the topic, interject a humorous comment in a timely fashion or respond to a question before the speaking person changes the topic. Slow AAC operators may be perceived as mentally slow. Thus the quality of verbal interactions where one party uses an AAC device to speak depends significantly upon the AAC operator's rate of word production.

Increasing an operator's letter or menu option selection rate proportionately increases his word production rate and increases the operator's productivity in data entry generally. Letter or menu option selection time includes the time the operator requires (a) to comprehend the menu options displayed, (b) to move the pointer to the desired menu option on the display, and, in selection by dwell, (c) the selection threshold period, or, in selection by click, (c) the time required to operate the switch. Decreasing any one of these increases the operator's productivity, assuming all other steps in the selection process are unaffected.

Personal interactions are composed of more than speech alone. People in conversation gesture to one another, use facial expressions, change the object of their gaze and make non-speech utterances (e.g. "hmmm-mmmm") to bid for a turn to speak, to grant such a bid made by the other party, to request to continue speaking and to acknowledge, accept or dispute what has been said. Ideally, the production of speech from an AAC devices does not distract the AAC operator from the personal interaction and subject matter of the conversation. This is possible if the operator habituates the AAC device access technique and menu structure, producing speech without focusing on each step of the process, much as automobile drivers habituate mechanical tasks, such as changing gears and switching between foot pedals, and focus their attention on pedestrians or traffic lights while operating their vehicle.

Another consequence of personal interaction during conversation for an AAC device operator is that the operator needs a way to easily enable and disable the AAC device operator interface so that movement the operator makes during personal interaction, for example, nodding his head, is not interpreted by the AAC device.

As noted previously, neurogenic muscular disorders may impair the ability of an individual to sense the position of a body member. An NMD operator thus relies more than his able-bodied peer on the location of a cursor or similar automated indication of body member position. Conventional access methods which use a pointer do not provide additional feedback to the operator of the position of a body member.

Access methods which require the NMD operator to make the same movement for most selections, such as single switch access, mouth sticking (the use of a small rod held in the mouth and used to depress keys on a keyboard) and head sticking (the use of a rod mounted on the head and used to depress keys on a keyboard), may result in repetitive motion injury, particularly after years of use.

The need for quick selection from a menu also arises from the use of optical character recognition ("OCR") systems which attempt to recognize graphic symbols and words based on attributes for optical recognition purposes, for example, the appearance of graphic symbols, the ratio of dark space to light space within part or all of a graphic symbol, the ratio of dark space in one part of a graphic symbol to the dark space in another part of the graphic symbol, and the derivative of darkness over the scan of the graphic symbol. OCR systems convert the contents of a typewritten document into a computer encoding of the same. OCR systems at times are unable to recognize a graphic symbol or word, or may err in selecting a graphic symbol or word from a plurality of candidates. Therefore, following optical character recognition, a human may proofread and correct the computer encoded document. The proofreader may indicate where an error or omission in the computer encoded document occurred and may select from a plurality of menu options, each representing a candidate graphic symbol or word.

There are several aspects of the disclosure, each addressing one or more of the problems described above and/or one or more problems specifically addressed by that aspect of the disclosure. The advantages and description of each aspect, where applicable, is separately described below under one of the headings: (A) Perimeter Menu, (B) Confinement, (C) Dwell, (D) Path Directness, (E) Intersection, (F) Alignment, (G) Length Order, (H) Location Indication, (I) Sound Match, and (J) Ideographic Languages. Where there is background art applicable to an aspect in addition to that described above, the additional background art is described below.

A & B. Perimeter Menu and Confinement

One advantage of the Perimeter Menu and Confinement aspects of the disclosure is to simultaneously display an application program window and a computer access menu which does not obstruct the application program window.

Another advantage of the Perimeter Menu and Confinement aspects of the disclosure is to allow an operator to enable and disable a menu.

Another advantage of the Perimeter Menu and Confinement aspects of the disclosure is to speed data entry.

C. Dwell

Conventional systems allowing selection by dwell do not provide an indication to the operator of either how much dwell time has been accumulated for any selectable region or how much more dwell time is required to select a selectable region. Consequently, an operator of a conventional system who is dwelling on a intended selectable region has no indication, other than his estimation from prior use of the system, that he has nearly made his selection and can plan his next movement to the next selectable region or that he has very nearly made his selection and can begin moving to the next selectable region. Furthermore, an operator of a conventional system who is dwelling on an unintended selectable region, has no indication, other than his estimation from prior use of the system, of how close he is to making an unintended selection and thus how important it is to act quickly. Conventional systems using discontinuous dwell give no indication of the accumulated dwell time associated with a selectable region either when the operator dwells on that region or when the operator ceases dwelling on that region. Some disabled users can dwell relatively easily on their intended targets for short periods of time, but have difficulty dwelling for long periods. If such an operator knows that only a little more dwell time is needed he may be able to satisfy the dwell time required for selection, without preparing himself to dwell for an extended period.

Conventional menu-driven data entry and order entry systems incorporating pointing at intended selections employ a two step selection procedure. In the first step the operator indicates, with a pointer, his intended selection. The system then provides feedback, for example, by highlighting the indicated selection, showing which selection the operator has indicated. In the second step, the operator selects the indicated selection, for example, by operating a switch. Thus, conventional data entry and order entry systems are ill-suited to circumstances where the operator cannot easily operate a switch while maintaining the pointer on the intended selection.

While the two step procedure is not complicated, many operators require some training to learn it, and, if they are infrequent users of the system, these operators may require refresher training. Simplifying the procedure further would lessen the need for initial and refresher training.

One advantage of the Dwell aspect of the disclosure is to facilitate the use of systems allowing selection by dwell.

Yet another advantage of the Dwell aspect of the disclosure is to facilitate the use of a data entry system by an intermittent operator.

D. Path Directness

The on-screen keyboard with dwell selectable key images is ill-suited for use by many NMD operators. Selection by dwell may fatigue NMD operators or may require greater fine motor control than they bring to this task. Operators with impaired ability to stop motion and those having involuntary tremors may have difficulty maintaining the location indicated by a pointer on a key image for a period sufficient to distinguish intentional dwelling from unintentional dwelling. Consequently, some NMD operators who try to use on-screen keyboards often miss their target key images and/or accidentally select unintended key images. Following such an error, the operator must erase his erroneous selection by selecting the backspace or undo key. As the number of erroneous selections increases, the operator's productivity decreases markedly, since each error requires a correction in which there might be another error.

Conventional on-screen keyboards require the ability to select by dwell or by click and thus are limited to operators with these capabilities. Conventional on-screen keyboards do not utilize the relatively intact motor capabilities of some NMD operators to compensate for impaired ability to select by dwell or by click or to speed up the slow process of selecting by dwell. For example, while an NMD operator may overshoot a key image, his directional control may be relatively intact. Conventional on-screen keyboards do not exploit this capability.

The dominant computer operating system for graphic applications on general purpose computer systems today is the Windows® Operating System. Windows® assigns meaning to the cursor location. When the operator moves the cursor on top of a menu item and clicks, Windows® interprets the action as manifesting an intent to choose that menu item. The operator's path to that menu item, whether direct or circuitous, is irrelevant. Operators who can move toward a target accurately but cannot maintain the location indicated by a pointer on the target cannot effectively use standard Windows® applications through the conventional interface to these applications.

Often NMD operators cannot steady a pointer while operating a switch; the act of operating the switch triggers involuntary muscle activity pulling the cursor off target. For these operators, conventional selection by click is not practicable. Conventional selection by dwell also requires greater fine motor control than many NMD operators bring to this task. Operators with impaired ability to stop motion may overshoot their intended target. Operators whose voluntary muscle activity is accompanied by some involuntary muscle activity affecting their directional control often cannot point accurately. Operators with involuntary tremors often cannot maintain the location indicated by a pointer on a key image. Consequently, NMD operators who try to use on-screen keyboards often miss their target key images and accidentally select unintended key images. Following such an error, the operator must erase his erroneous selection by selecting the backspace or undo key. As the number of erroneous selections increases, the operator's productivity decreases markedly, since each error requires a correction in which there might be another error.

F. Alignment

Conventional on-screen keyboards do not compensate for NMD operators' inability to stop motion. Suppose the operator has been fitted with a head pointing device so that his head motion moves the cursor and that he's using the quaternary keyboard shown in FIGS. 3, 4 and 5. Assume further that, as he attempts to point to the quadrant containing the "j" key image (1308) in FIG. 3, he is unable to stop on that quadrant and continues turning 20 more degrees to the left. There are two known ways of responding to this situation: (1) the cursor may continue to track the operator's motion and disappear from the display, leaving no indication to the operator of the location of the cursor and consequently causing some operator disorientation, or (2) the cursor may "stick", i.e. remain confined to the display, at, for example, point (1312). Conventional on-screen keyboards respond in this way. The operator's line of sight is now 20 degrees to the left of the cursor location. After the dwell period, the quadrant (1308) is selected and FIG. 4 is displayed. The cursor hasn't moved. It is now at point (1320). Assume that again the operator attempts to point to the quadrant containing the "j" key image (1324) in FIG. 4. As the operator turns his head to the right, the cursor immediately moves with him Thus, the operator's line of sight remains 20 degrees to the left of the cursor location as the cursor moves to the right across the display. The operator must watch the cursor out of his right eye. The problem is aggravated if either the operator cannot cleanly stop or if he drifts as he dwells. Assume that while attempting to dwell on quadrant (1324) the operator drifts 25 degrees past the bottom of the screen. His line of sight is now 25 degrees below and 20 degrees to the left of the cursor. To correct this misalignment in the conventional quaternary keyboard, the operator must turn his head to the right, "stick" the cursor against the right edge of the display, and continue turning 20 degrees until he has the cursor in his line of sight. Then he must lift his head until he sticks the cursor against the top edge and continue lifting 25 degrees more. Alternatively, in this scenario, the operator could stick the cursor in the upper right corner of the display and simultaneously rotate his head up and to the right until he brought the cursor into his line of sight.

Alignment is also a problematic for NMD operators who use a pointer, such as a mouse, with which the operator indicates a location on a surface, e.g. a desk top, which corresponds to a desired location on the display, and achieves alignment by removing the pointer from the surface, e.g. lifting the mouse, moving the mouse, then replacing it on the surface. Due to impaired fine motor control, many NMD operators cannot remove a pointer from the surface and replace it on the surface at a desired location without unintentional movement or extraordinary effort. For these operators, alignment cannot be effectively achieved through conventional means.

In summary, misalignment interferes with accurate pointing and the process of correcting for misalignment may result in the selection of unintended key images.

G. Length Order

As noted previously, one of the elements determining the menu option selection time is the time the operator requires to comprehend the menu options displayed. This time may be reduced if the operator can limit the number of menu options he searches in looking for his desired menu option. Conventional word prediction systems attempt to reduce this operator search time. The operator of a conventional word prediction system may, for example, select the letter "p". The system displays some number, say six, of the most frequently used words beginning with the letter "p". Conventionally these six words are displayed either in alphabetic order or in order of frequency of use. Assuming the operator does not see his desired word on the display, he selects another letter, say "r". The system then displays the six most frequently used words beginning with the letters "pr".

Searching a displayed list of words in alphabetic order requires that the operator focus his attention on the selection task, as opposed to the information content of the conversation or other task the operator is engaged in. Further, determining whether a given word is alphabetically greater or lesser than a desired word takes substantial time, slowing the selection process. An alphabetically ordered list is of limited use to an individual who has below normal spelling ability, a frequent problem among individuals with impaired speech. Ordering words by frequency of use often does not limit the number of words the operator must search. The word at the bottom of the displayed list, for example, the sixth most frequently used word beginning with the letters "pr" may be a very common word, even though it is less frequently used than the other five displayed words.

H. Location Indication

The difficulties experienced by NMD operators in pointing to relatively small selectable regions have already been described. One approach to these difficulties is to enlarge the on-screen selectable region, illustrated by the quaternary expansion on-screen keyboard already described. Another approach is the conventional eye gaze system for a speech impaired individual, depicted in FIG. 8. The system consists of a plexiglass frame (6352) having a centrally located aperture (6354). The eye gaze system is positioned between the speech impaired individual and person with whom the speech impaired individual is communicating. There are eight groups of five squares each on the plexiglass frame. Each square within each group of five squares is color coded, e.g. red, blue, green, yellow and clear, matching the color on each of the four corners of the plexiglass frame. The clear square matches the aperture (6354). All squares are labeled with symbols representing items to be communicated. These labels are not shown in FIG. 8. The person with whom the speech impaired individual is communicating observes the eyes of the speech impaired individual to determine the target of the speech impaired individual's eye gaze. To communicate an item, the speech impaired individual gazes first toward the one of the eight groups of five squares, indicating that he wants to communicate one of the symbols in that group, and gazes second toward one of the four corners and aperture (6354) matching the color of the square labeled with the item to be communicated in the previously indicated group.

Two types of selectable regions are conventionally used in a point and click menu interface in a graphical user interface. The first, shown in FIG. 9, depicts a menu having three menu options, labeled "High", "Medium" and "Low", each displayed on a display (4807), each associated respectively with selectable regions (4801), (4803) and (4805), and each located adjacent the associated selectable region. FIG. 10 depicts a menu having the same three menu options, each displayed on a display (4807), each associated respectively with selectable regions (4901), (4903) and (4905), and each intersecting the associated selectable region. In both these conventional menus, a menu option is selected by pointing to and clicking on the associated selectable region.

Conventional menu hierarchies in automated systems, built from menus of the type shown in FIG. 9 or FIG. 10, require that the operator proceed sequentially through the steps of searching menu options, selecting one of them, and, assuming a menu option including a submenu was selected, searching the submenu options, and selecting one of them. Where selection from menu hierarchies constitutes a substantial component of the operator's activities, the slowness of the selection process diminishes productivity.

Locating selectable regions or parts thereof outside the display, in accordance with the Perimeter Menu aspect of the disclosure, allows the large areas outside the display to be used, a major advantage for operators having impaired fine motor control who are unable to maintain a pointer on a small selectable region while selecting by click or by dwell. However, if menu options are displayed on the display near the perimeter of display and near their associated selectable region, the operator has an indication of the location of each selectable region but may not be able to see all the displayed menu options in a glance. Because an operator usually searches a displayed menu for his intended menu option, placing the menu only near the perimeter of the display may increase menu search time, thus increasing menu option selection time.

I. Sound Match

Conventional speech recognition systems facilitate computer access for individuals unable to use a standard keyboard whose speech is relatively unimpaired, for example, an individual with quadriplegia, and hands-free computer access for able-bodied individuals. The operator of such a speech recognition system reads a menu option out loud, for example, "open file", and the system, which includes sound receiving means, for example, a microphone coupled to a sound board having a Digital Signal Processor ("DSP"), receives the sound of the read menu option, digitizes the sound of the read menu option, and then provides the digitized sound to another component of the speech recognition system, sound matching means which includes an application program for matching the digitized sound to one of a plurality of sounds, each representing respectively the sound of a spoken menu option. The system determines which sound best matches the sound of the read menu option and selects the menu option associated with this best matched sound.

Individuals whose speech is impaired are often unable to effectively use conventional speech recognition systems because they often cannot produce a large distinct variety of sounds characteristic of phonetic languages. For example, such an individual may produce similar sounds for the two consonants "t" and "d" so that these sound are indistinguishable to a conventional speech recognition system, or such an individual may not be able to consistently produce sounds distinguishable by a speech recognition system, resulting in false matches. Other symptoms of impaired speech, for example, similarities among certain phonemes and impaired ability to start or stop sound production appropriately, may substantially limit the variety of sounds distinguishable to a conventional speech recognition system an individual may consistently produce.

Conventional speech recognition systems provide limited capabilities in languages rich in homophones, for example, Chinese, because in such languages, a distinct sound is often insufficient to specify a word, as is described in the Background Art section of the Ideographic Languages aspect of the disclosure. The problem may be briefly illustrated by an example. Suppose a Chinese data entry operator using a conventional speech recognition system speaks the phonetic unit "fu" with a particular intonation. This distinct sound may well have over 15 homophones. Although the operator could use the keyboard to select one of these 15 homophones, this defeats the purpose of speech recognition, which is to facilitate hands-free computer access.

J. Ideographic Language

The use of ideographs as the graphic symbols in written languages is found in many parts of the world. An ideograph, as used herein, is a graphic symbol used to represent an object, an idea or a word, without expressing, as in a phonetic system, the specific sounds forming the verbal expression of the object, idea or word. Ideographic languages include Chinese, Japanese and Korean. A graphic symbol, as used herein, includes, but is not limited to, each of the following: a letter of an alphabet, a Japanese kava, and an ideograph. For purposes of illustrating the concepts of the present disclosure specific reference will be made herein to a preferred embodiment of the system and method as it applies to the Chinese language.

In modern Chinese, a repertoire of between 2500 and 3000 ideographs is necessary to achieve normal business adequacy in reading and writing, while the language itself has approximately 50,000 ideographs that have been identified historically, with about 10,000 ideographs in current use. The conventional keyboard, with approximately 100 keys, is designed for languages with phonetic scripts, such languages having a small set of graphic symbols, i.e. letters. If such a keyboard were to be used in a corresponding manner for the direct input of Chinese ideographs, it would require many thousands of keys since, unlike western phonetic languages, Chinese has many thousands of ideographs. Selection of an ideograph from such a keyboard would require the operator to search a great many keys for the desired key, and thus be impracticably slow.

Prior art methods for selecting Chinese ideographs make use of various ideograph classification systems known to Chinese speakers. The operator first specifies a class of ideograph, based on a first characteristic common to many ideographs. Ideographs having that common characteristic are displayed and the operator selects from among them, either directly, by selecting an individual ideograph, or indirectly, by specifying a second common characteristic usually dependent upon the first characteristic, thus further limiting the displayed ideographs to those having both the first and second common characteristics. In some prior art methods, the operator may continue to specify characteristics until he has specified a unique ideograph.

One ideograph classification system is called the Pin Yin System. This classification system uses the phonetic structure of the Chinese language. In spoken Chinese there are approximately 412 basic phonetic units, each having a monosyllabic sound, for example, "nee", "how" and "ma". Four intonations can potentially be applied to each phonetic unit, resulting in approximately 1280 distinct sounds. With 10,000 ideographs in current use, each represented by one of approximately 1280 distinct sounds, it is evident that many Chinese ideographs are homophones, i.e. have the same sound. Over 80% of Chinese ideographs have homophones. The Pin Yin System uses this limited number of phonetic units as the basis for its classification. Ideographs which are homophones are classified together; the common characteristic of the Pin Yin System is the distinct sound.

According to the Pin Yin and Zhu Yin coding methods, known in the prior art, the operator specifies a distinct sound using a keyboard labeled with symbols representing the Latin alphabet (Pin Yin method) or Chinese phonetic units (Zhu Yin method). The first key operation or sequence of key operations specifies the phonetic unit. The second key operation specifies the intonation. In general, less than 15 ideographs have this sound, though in some cases there are many more homophones. These are displayed and the user selects from among them. In such cases, the operator, depending upon the system, may page through matching ideographs or specify another common characteristic to further limit the number of ideographs displayed. A common characteristic which may be used at this stage exploits another feature of the Chinese language. The majority of Chinese words are expressed by a combination of two ideographs, the meaning of the paired ideographs has its own meaning which may or may not be related to that of the constituent ideographs. Assuming the operator has specified a first distinct sound matching 40 ideographs, he may specify a second distinct sound which alone may match, for example, 20 ideographs, but there may be only two ideograph pairs having the specified first and second distinct sounds in that order. Thus, a second common characteristic may limit matching ideograph pairs to a number sufficiently small for the operator to efficiently search and select from, or may uniquely specify an ideograph pair. Another common characteristic the operator may specify to limit the number of matching ideographs is a meaning or meaning class to which one or more sequences of one or more ideographs belong.

Yet another feature of the Chinese language which may be exploited to limit the number of matching sequences of ideographs is the ideograph block. An ideograph block is a sequence of four ideographs which together has its own meaning which may or may not be related to that of the constituent ideographs. As above, where the operator specified a distinct sound for the second of two ideographs of an ideograph pair, so may the operator specify a distinct sound for the second, third and/or fourth ideograph of an ideograph block, to limit the number of matching ideograph blocks.

Another conventional ideograph classification system makes use of a classification of parts of ideographs. Ideographs are built from a set of 214 components, called radicals. Different radicals, perhaps placed within different locations within an ideograph, are combined to create an ideograph. According to the Chan Jie coding method, known in the prior art, the operator specifies one or more radicals appearing in the ideograph he wishes to enter. He may, for example, use a keyboard having at least 214 keys, each corresponding to a radical, or may actuate a sequence of keys, the sequence corresponding to a radical. Other common characteristics the operator may specify to limit the number of matching ideographs include a phonetic unit, the first brush stroke, and the last brush stroke used to draw the ideograph.

Another conventional ideograph classification system makes use of a classification of parts of ideographs. According to the Four Corner coding method, known in the prior art, the operator specifies the classification of the four corners of the ideograph he wishes to enter. Other common characteristics the operator may specify to further limit the number of matching ideographs include the number of horizontal strokes used to draw the ideograph, and the classification of a certain part of the ideograph above the lower right corner.

Yet another conventional ideograph classification system makes use of a classification ideographs based on the basic strokes from which each ideograph is built. In Chinese, there are a limited number of basic strokes, each ideograph being composed of between 1 and 33 such strokes. Ideographs may be classified by a small number of basic strokes, preferably according to strict rules regarding the order of stroke entry. In one conventional application of this coding method, the operator specifies only the first and last basic strokes of the desired ideograph, then selects from a display of all ideographs sharing this first-last basic stroke combination.

Japanese is somewhat more complicated than Chinese. In addition to ideographs, the Japanese language uses graphic symbols called kana, which includes hiragana and katakana. In written Japanese, ideographs are frequently combined with kana. Kana may be may specified phonetically, for example, to designate the hiragana pronounced "ko" an operator of a Japanese word processing system may type "k" and then "o" on a Latin alphabetic keyboard or may type a single key associated with this hiragana. Kana has multiple uses in a Japanese word processing system. Kana may represent itself, since kana may stand alone in Japanese text. Alternatively, kana may be used to specify Japanese ideographs, either by specifying the radicals which compose Japanese ideographs or by specifying the pronunciation of Japanese ideographs. A sequence of phonetic units specified by kana may represent that sequence of kana, a single Japanese ideograph, multiple Japanese ideographs, or a combination of one or more Japanese ideographs and one or more kana. In addition, a single Japanese ideograph may have multiple pronunciations, including a Japanese pronunciation and a Chinese pronunciation, and may have multiple kana spellings.

Conventional word processing systems for ideographic languages suffer from certain deficiencies. First, in systems where the operator specifies common characteristics until he has uniquely specified an ideograph, the operator must be extensively trained in the particular classification system. Depending upon the system, the operator may need to know, for example, how may horizontal brush strokes are required to draw a desired ideograph, or each of the 214 radicals and the encoding of each of them on a keyboard having less than 214 keys. Second, in systems where the operator uses both hands on the keyboard to specify a common characteristic, then selects from among ideographs, ideograph pairs or ideograph blocks by operating a function key or by pointing to one of the options with a mouse or other hand operated pointer and then operating a switch, the operator lifts one of his hands from the keyboard, makes the selection and then moves his hand back to the keyboard to specify another common characteristic. This sequence occurs often and contributes to the slow average rate of word entry (approximately 20 words per minute) for Chinese relative to alphabetic languages. Another problem in these systems is that the display of ideographs for selection may obscure part of the image of the previously entered ideographs or other information on the display.

Another drawback of many word processing systems for ideographic languages relates to the ease of copying a document. Ideally, the operator concentrates on the document to be copied, only occasionally scanning text he has input. For those word processing systems that display ideographs on a display for the operator's selection, the operator must frequently shift his gaze from the document to the display and back again. The operator cannot concentrate on both the document and the display simultaneously.

Ideographs, as used herein, also include the symbols of symbol sets used for communication by individuals who have hearing, speech or language impairments, for teaching literacy skills to those lacking them, including pre-literate children and individuals with intellectual disabilities, and for international written communication. These symbol sets include, but are not limited to, each of the following: Picture Communication Symbols, Rebus, Picsym, Pictogram Ideogram Communication Symbols, Yerkish, Blissymbolics and depictions of the signs of a manual sign language. Examples of symbols of the Picture Communication Symbols, Rebus, Picsyms, and Blissymbolics symbol sets are shown in FIG. 11, Pictogram Ideogram Communication Symbols in FIGS. 12(a)-12(d) and Yerkish in FIGS. 13(a)-13 (j). Picture Communication Symbols, Rebus, Picsyms, Pictogram Ideogram Communication Symbols, Yerkish, and Blissymbolics are each described in Beukelman, David R. & Mirenda, Pat, *Augmentative and Alternative Communication, Management of Severe Communication Disorders in Children and Adults*, Paul H. Brookes Publishing Co., 1992, pp. 22-29.

Individuals who have not acquired or who have lost their literacy skills may use symbolic symbol sets in learning to read. If the individual lacks fine motor control, for example, due to cerebral palsy, the individual's disability may inhibit the acquisition of literacy skills by, for example, inhibiting repetition of an exercise by the individual, by limiting the individual's ability to participate in the classroom, or by making skill assessment by a teacher difficult so that the teacher may incorrectly believe that remediation is necessary or that a particular skill has been mastered. If the individual also has impaired speech, literacy acquisition is more difficult still.

Conventional literacy training systems for individuals who are unable to use a standard keyboard or mouse may use switch access, often in combination with scanning. As already described, scanning is an extremely slow process. Moreover, as the number of symbols in the symbol set increases, the time required to select a symbol also increases. Of the symbol sets mentioned above, Picture Communication Symbols contains approximately 1800 symbols, Rebus contains approximately 800 symbols, Picsyms contains approximately 1800 symbols, Pictogram Ideogram Communication Symbols contains approximately 400 symbols and Blissymbolics contains approximately 1400 symbols. When using a system with a static display, the operator may expend considerable time and effort finding the desired symbol; when using a system with a dynamic display, the operator may expend considerable time effort memorizing and recalling where a particular symbol is located within a hierarchy of symbols. This time and effort generally does not contribute to the acquisition of literacy skills.

One advantage of the Ideographic Languages aspect of the disclosure is to display a menu of sequences of one or more ideographs on a display so that a large contiguous area on the display is not obstructed by the menu.

Another advantage of the Ideographic Languages aspect of the disclosure is to facilitate ideograph entry in word processing systems for the Chinese, Japanese and Korean languages.

Still another advantage of the Ideographic Languages aspect of the disclosure is to speed selection of sequences of graphics including one or more ideographs.

Yet another advantage of the Ideographic Languages aspect of the disclosure is to allow an operator of a word processing system for an ideographic language to select a sequence of one or more ideographs without lifting either hand from the keyboard.

A further advantage of the Ideographic Languages aspect of the disclosure is to indicate to an operator the progress toward selection of a dwell-selectable sequence of one or more ideographic characters.

Additional advantages and features of the disclosure will be set forth in part in the description which follows, and in part will become apparent to those skilled in the art upon examination of the following or may be learned by practice of the disclosure. Each of the advantages of the disclosure may be realized by at least one embodiment of at least one of the appended claims.

Still other advantages of the present disclosure will become readily apparent to those skilled in this art from the following detailed descriptions, wherein I have shown and described the preferred embodiment of each aspect of the disclosure, simply by way of illustration of the best mode contemplated by me of carrying out each aspect of my disclosure. As will be realized, each aspect of the disclosure is capable of other and different embodiments, and its several details are capable of modifications in various obvious respects, all without departing from the disclosure. Accordingly, the drawings and descriptions are to be regarded as illustrative in nature, and not as restrictive.

BRIEF DESCRIPTION OF DRAWINGS

FIG. 11 depicts examples of symbols from the Picture Communication Symbols, Rebus, PicSym and Blissymbols symbol sets.

FIG. 14 is a block diagram of a computer which may be utilized in accordance with the disclosure.

FIGS. 24 and 25 are each illustrations of a display and structures in accordance with another embodiment of the Perimeter Menu aspect of the disclosure.

FIGS. 26 and 27 illustrate an apparatus in accordance with still another embodiment of the Perimeter Menu aspect of the disclosure. FIG. 26 depicts a front view of the apparatus. FIG. 27 depicts a cut away view from the top of the apparatus.

FIG. 28 is a top view of a headrest in accordance with an embodiment of the Perimeter Menu aspect disclosure.

FIGS. 29 and 30 illustrate the state table aPocketFsm in accordance with the preferred embodiment of the Perimeter Menu aspect of the disclosure.

FIG. 67 is an illustration of a display and structures in accordance with yet another embodiment of the Ideographic Language aspect of the disclosure.

DESCRIPTION

The hardware and software operating environment of the preferred embodiment of all aspects of the disclosure will now be described with reference to a particular embodiment of the disclosure, hereinafter "prototype". The prototype of the disclosure illustrates the best mode of practicing each aspect of the disclosure known by me except where a preferred mode is described.

Figure 1:
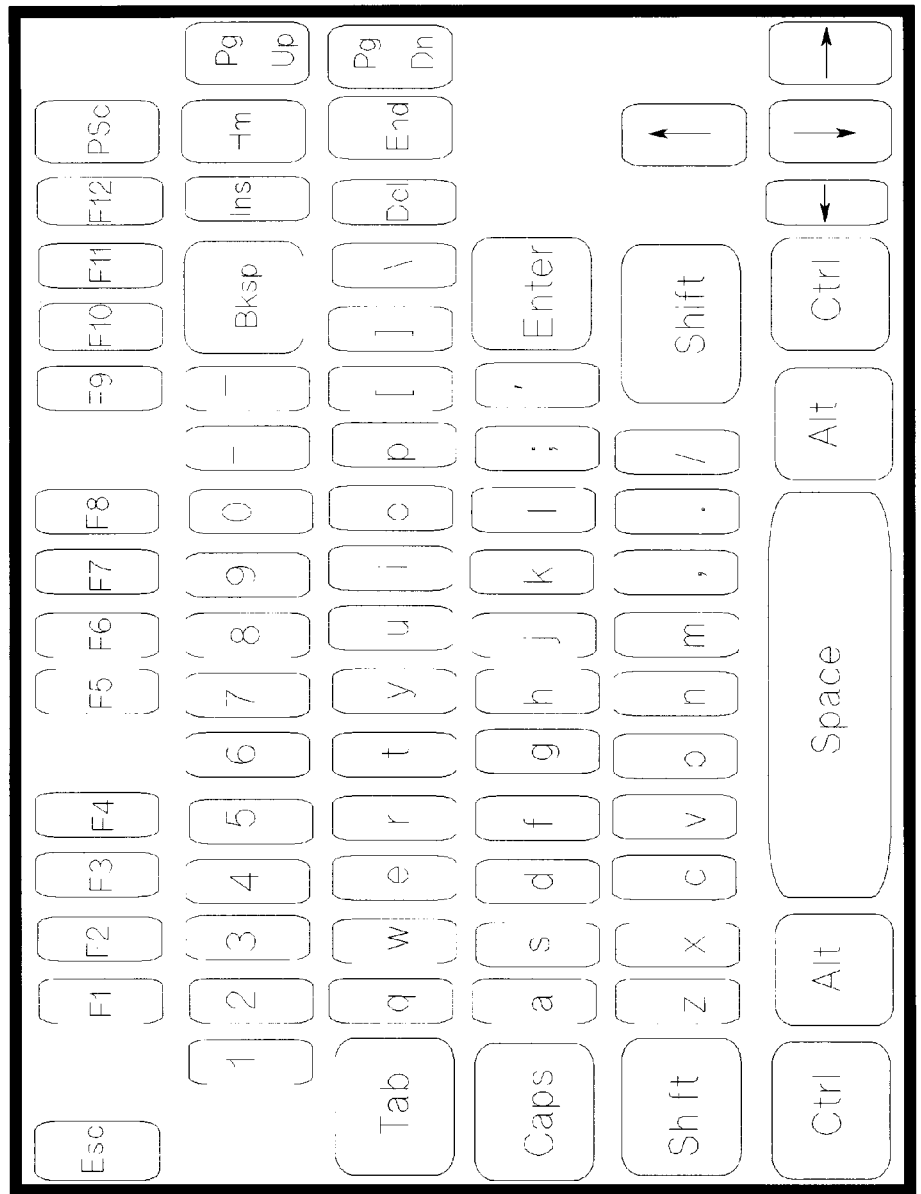
FIG. 1 is an illustration of a display showing a conventional on-screen keyboard.
Figure 2:
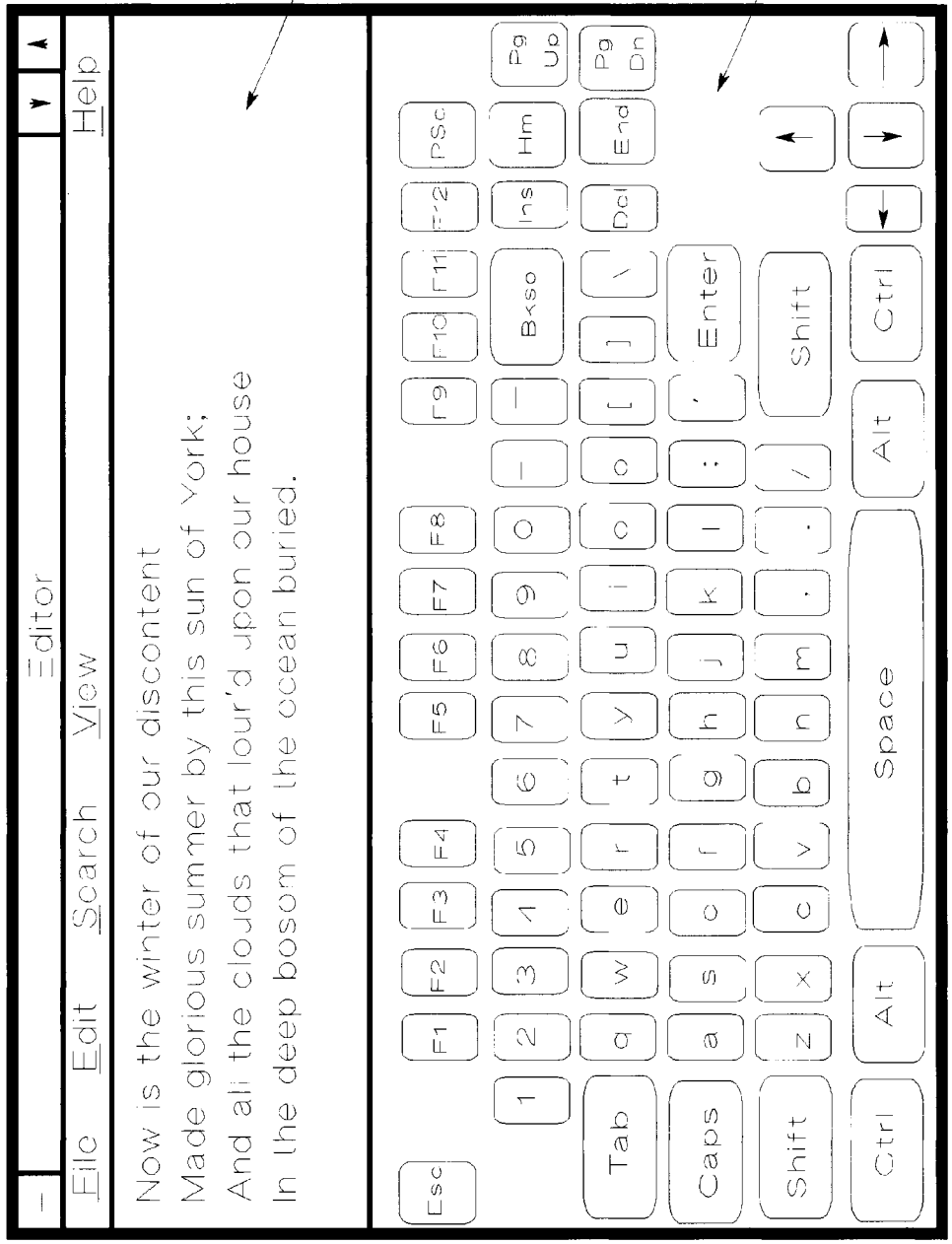
FIG. 2 is an illustration of a display showing a conventional on-screen keyboard and output from a word processing application program.
Figure 3:
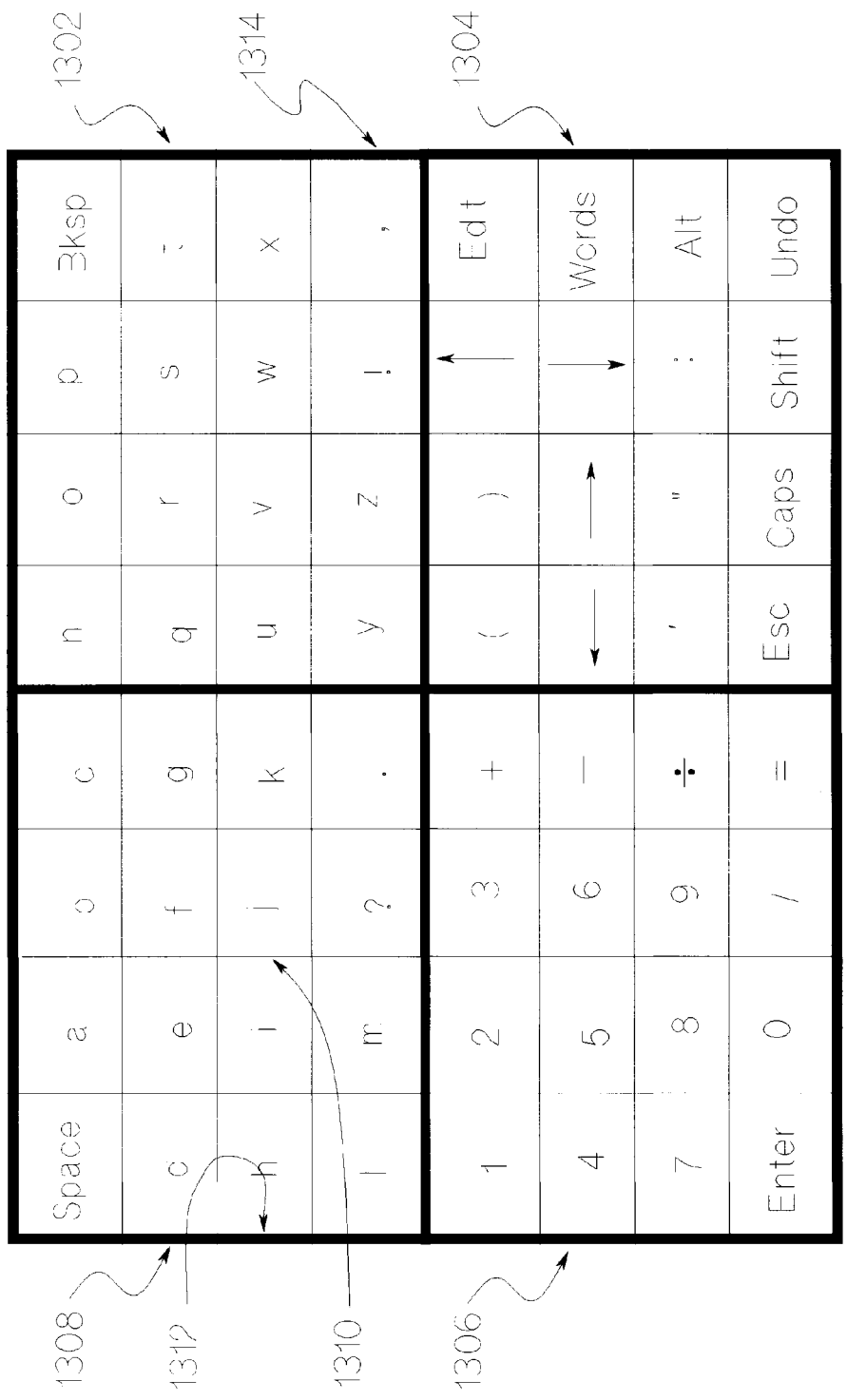
FIGS. 3, 4 and 5 are each illustrations of the display of each step of letter selection using a conventional quaternary on-screen keyboard.
Figure 4:
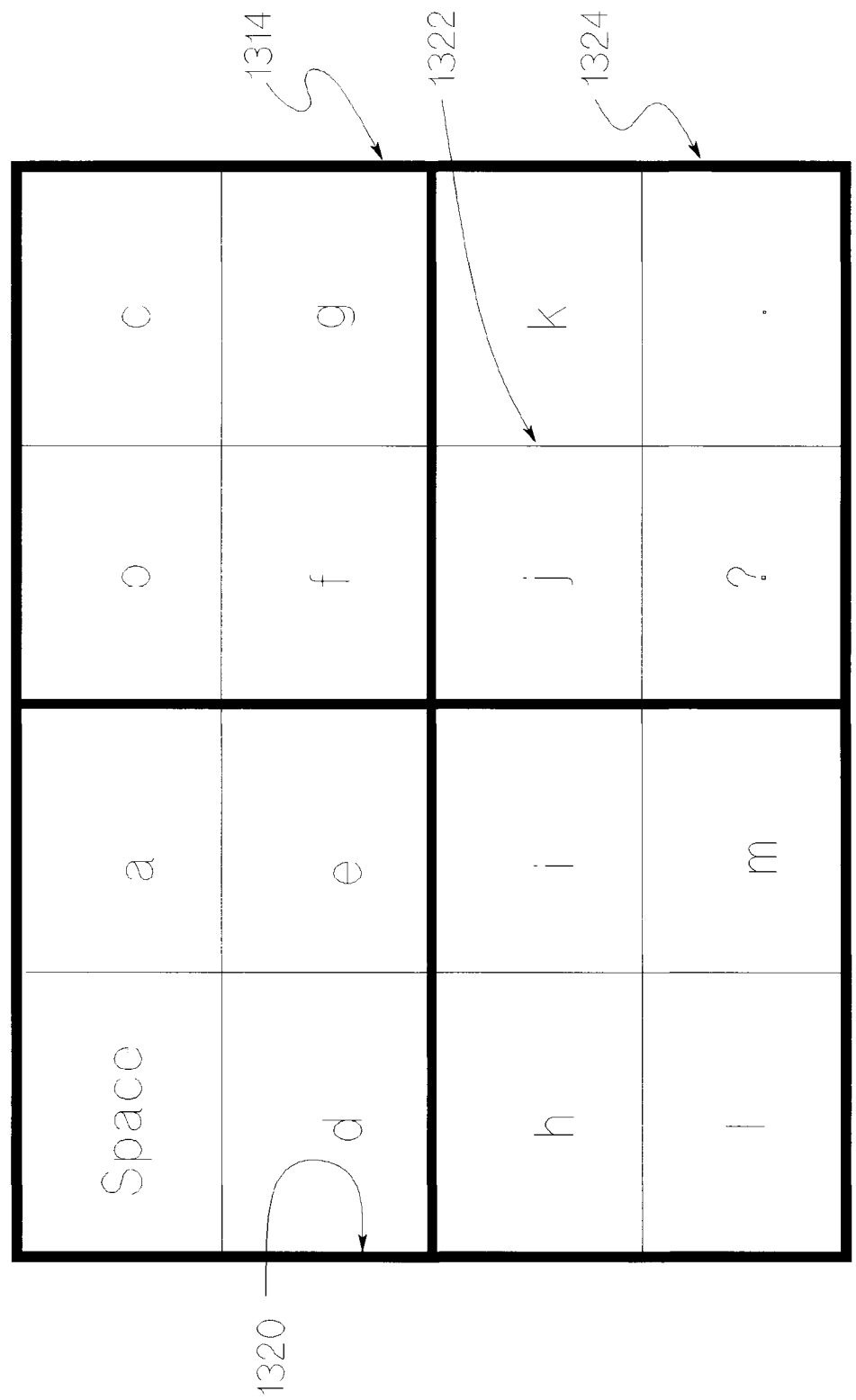
Figure 5:
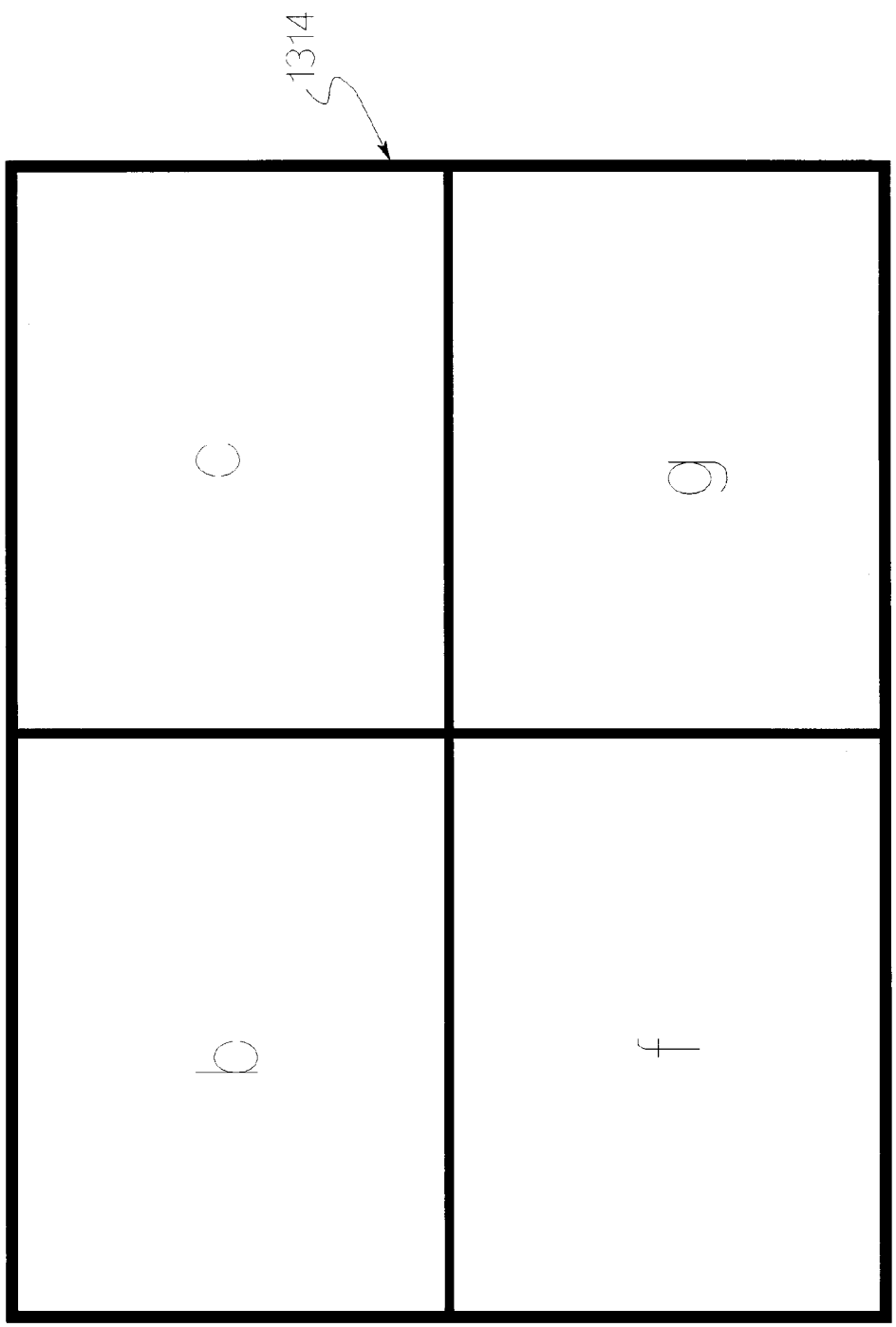
Figure 6:
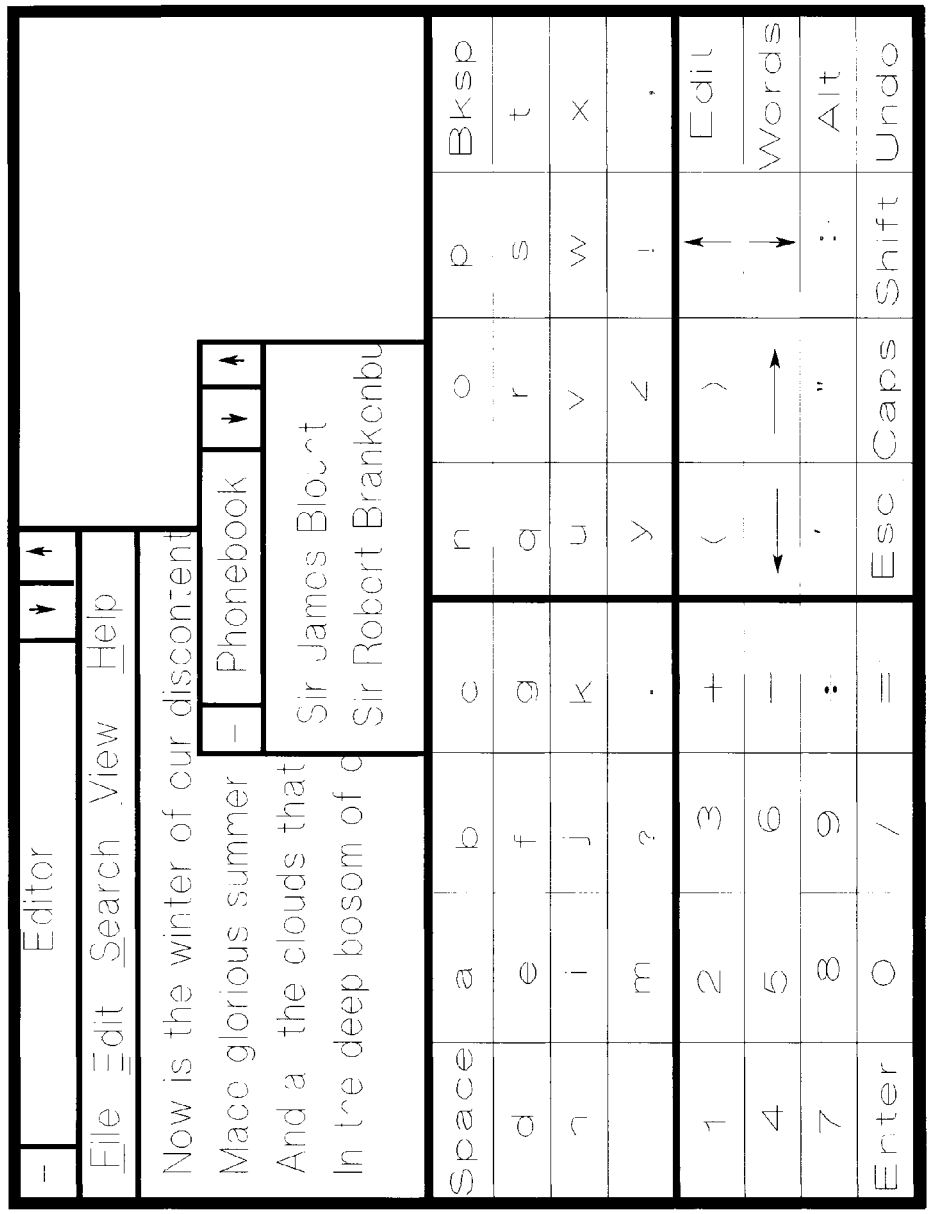
FIG. 6 is an illustration of a display showing a conventional quaternary on-screen keyboard and output from two application programs.
Figure 7:
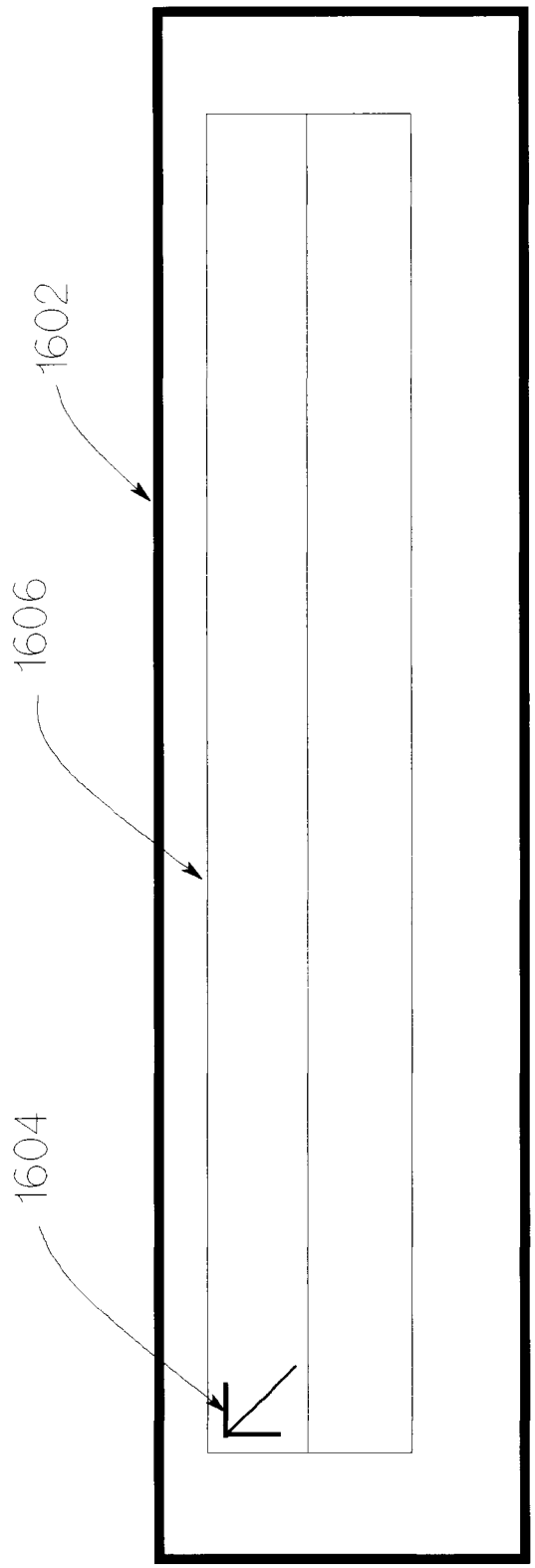
FIG. 7 is an illustration of a conventional device implementing joystick patterns.
Figure 8:
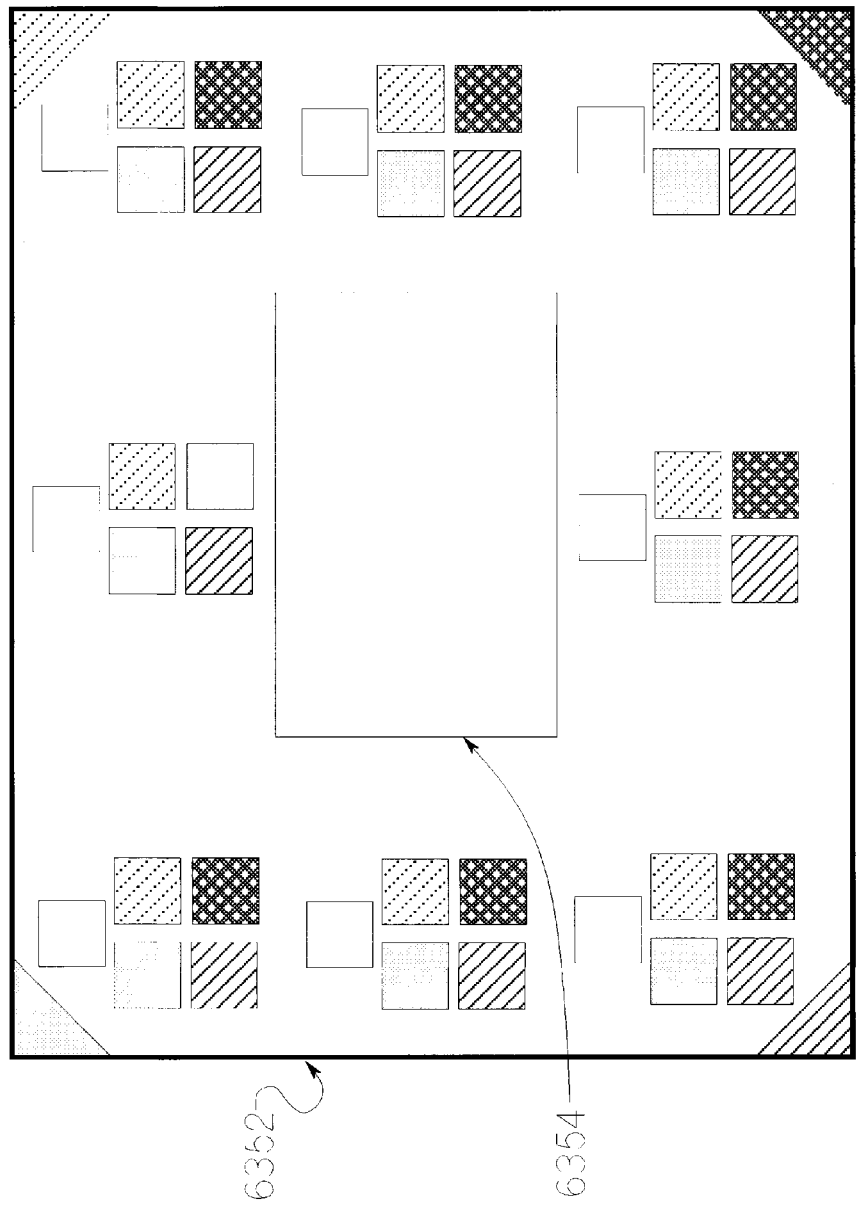
FIG. 8 is an illustration of a display of a conventional eye gaze system.
Figure 9:
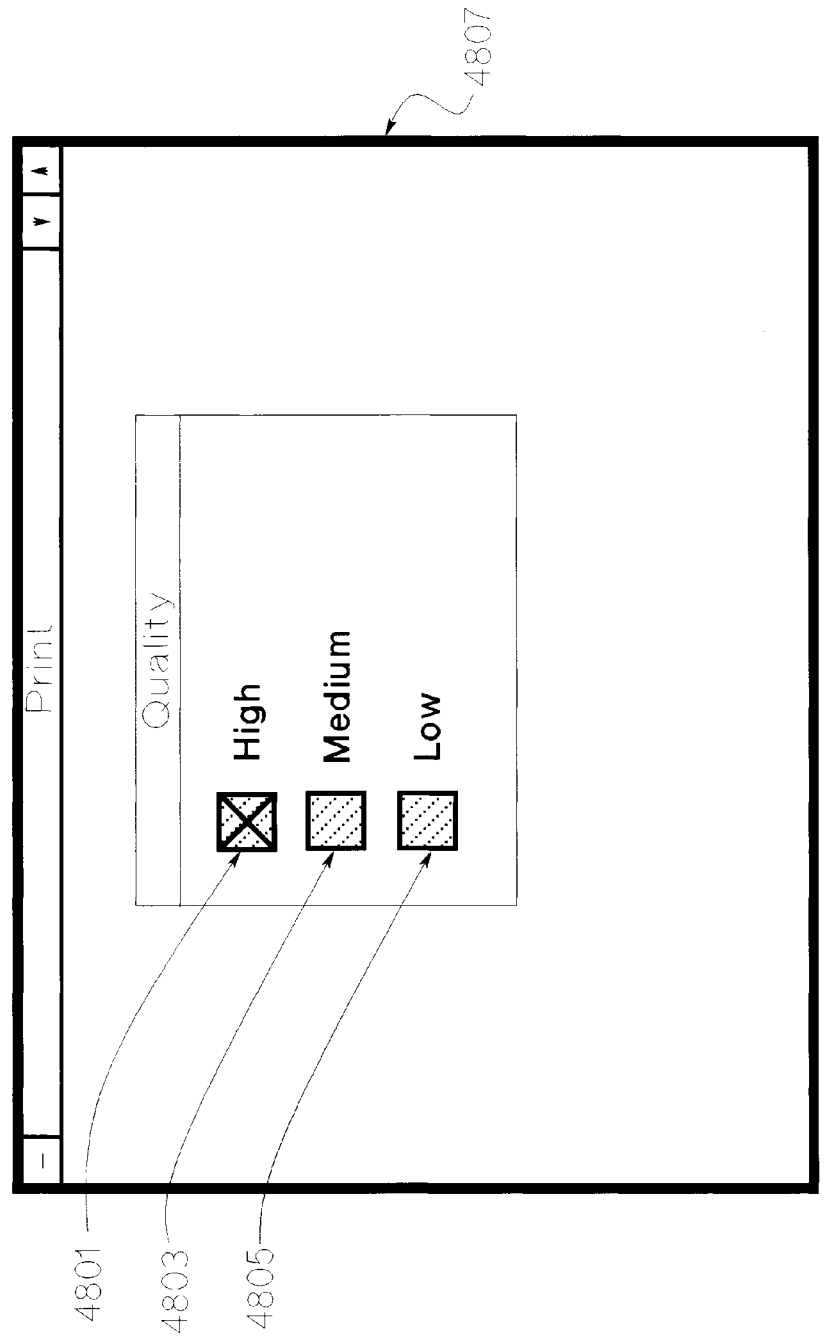
FIGS. 9 and 10 are each illustrations of a display showing a conventional menu.
Figure 10:
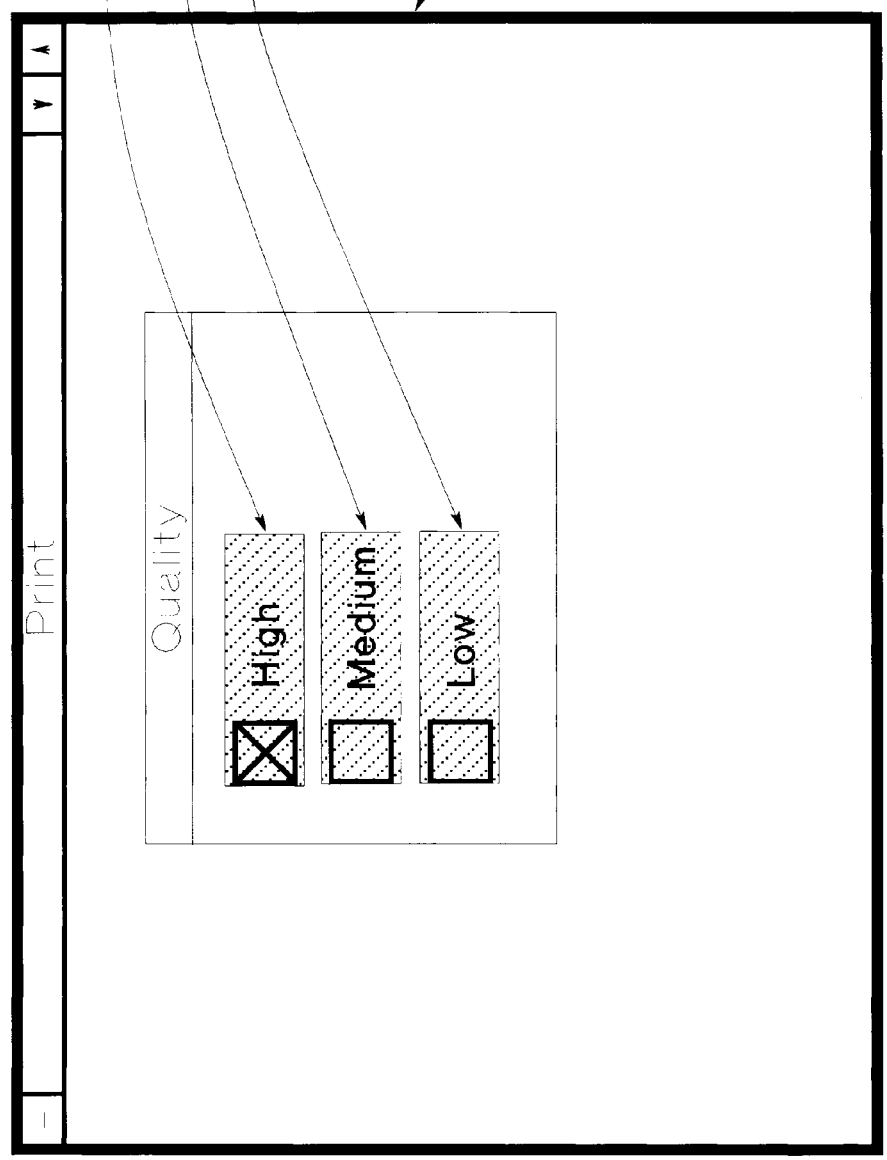
Figure 12A:
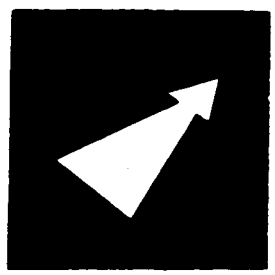
FIG. 12(a)-FIG. 12(d) depict examples of symbols from the Pictogram Ideogram Communication Symbols symbol set.
Figure 12B:
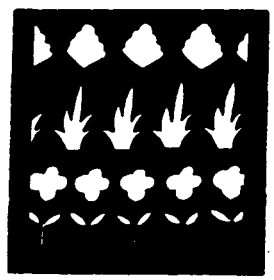
Figure 12C:
Figure 12D:
Figure 13A:
FIG. 13(a)-FIG. 13(j) depict examples of symbols from the Yerkish symbol set.
Figure 13B:
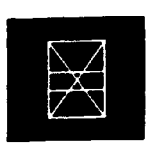
Figure 13C:
Figure 13D:
Figure 13E:
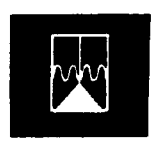
Figure 13F:
Figure 13G:
Figure 13H:
Figure 13I:
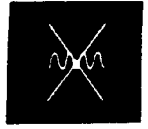
Figure 13J:
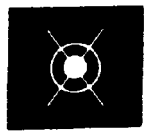
Figure 15:
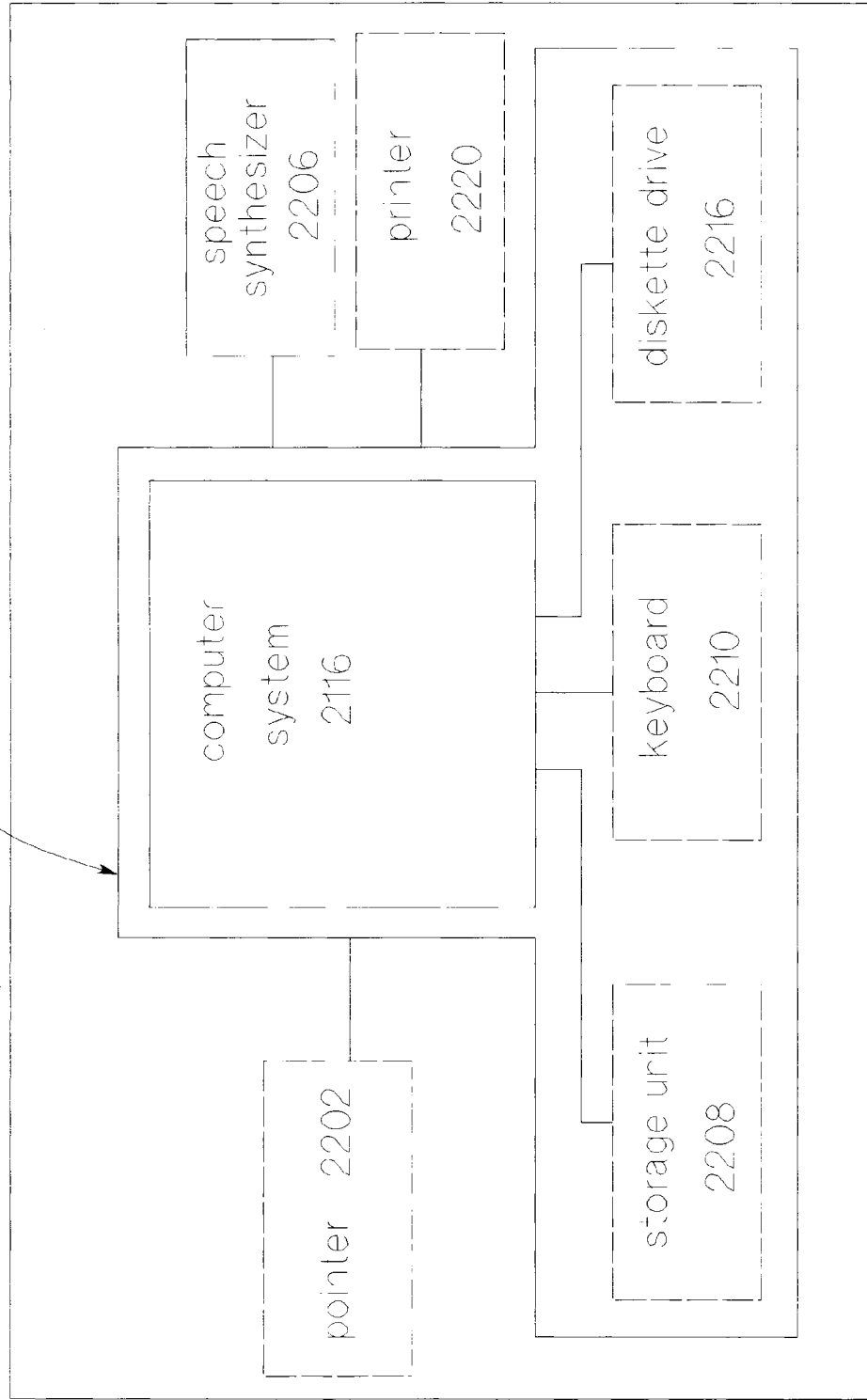
FIG. 15 is a block diagram of a speech synthesis system which may be utilized in accordance with the disclosure.

FIG. 15 depicts a block diagram of the hardware components of the prototype (2214), including a conventional general purpose computer system (2218), an optional pointer (2202), an optional printer (2220) and a speech synthesizer (2206). The general purpose computer system (2218) includes a conventional computer system (2116), a storage unit (2208), a keyboard (2210), and a diskette drive (2216). FIG. 14 depicts a block diagram of the conventional computer system (2116), including a processing unit (2102) and a display (2112). The processing unit (2102) includes a processor (2104), a memory (2106) and control circuitry (2108). The prototype employs the Toshiba T6400DXC general purpose computer system manufactured by Toshiba Corporation, Kawasaki, Japan. However, the T6400DXC is preferably substituted with the IBM ThinkPad 755C computer system, part number 9545F0C, manufactured by IBM Corporation, Armonk, N.Y., USA, because the former requires a 110 VAC power source while the latter is powered by an integral battery. An integral battery allows an NMD operator to use the system when a 100 VAC source is not available or when attaching to a 110 VAC power source is inconvenient. The prototype further includes a head mounted pointer communicating via an infrared link with the computer system so that there are no cables tethering the operator to the computer system. Any cable between the operator and the computer system would have to be connected, probably by an attendant since the operator may lack the fine motor skills required to make such a connection. Preferably computer access can be accomplished independently by the operator. The choice of a pointing device is primarily dictated by the particular capabilities of the operator. Usually the best pointing device for a particular operator is the one drawing on that operator's best motor control. For example, if an operator's foot control is superior to his head control, a pointing device using his foot is preferably to a head pointer.

The prototype employs the Remote Headmaster® manufactured by the Prentke Romich Company, Wooster, Ohio, USA. However, the combination of the HeadMaster® Plus, part number HM-1P, HeadMaster® Plus Remote Adapter, part number HM-RA, and HeadMaster® Plus Laptop Adapter, part number HM-LA, all available from the Prentke Romich Company, is preferable because the headset is more comfortable and the HeadMaster® Plus ultrasonic transmitter mounts more easily on a laptop computer system than the Remote Headmaster ultrasonic transmitter.

The preferred embodiment further includes a battery powered printer, the MobileWriter®, part number 730879, manufactured by Mannessmann Tally Corporation, Kent, Wash., USA and a speech synthesizer, the Multivoice Speech Synthesizer, part number MV2-SS, manufactured by The Institute on Applied Technology, Children's Hospital, Boston, Mass., USA.

The pointer (2202) is a device which provides data concerning the relative or absolute position of the operator or any body member of the operator. The display (2112) and pointer (2202) together provide for the interactive nature of the general purpose computer system (2218) in that, in accord with the various aspects of the disclosure, the interpretation that the processor (2104) gives to a certain pointer action made by the operator depends, in the majority of situations, upon what is being displayed to the operator at that time.

The prototype (2214) shown in FIG. 15 further includes a keyboard (2210), which functions to provide input from an able-bodied operator to the general purpose computer system (2218). The keyboard (2210) is useful for configuration, diagnostic and backup purposes, functions which are performed relatively infrequently and usually require an able-bodied person for ancillary activities, for example, loading backup media into the general purpose computer system. The prototype (2214) also optionally includes a printer (2220) which functions to provide hard copy output of data developed or stored in the general purpose computer system, and a speech synthesizer (2206), which functions to provide speech output for utterances and words composed using or retrieved from the general purpose computer system (2218).

The couplings between the devices depicted in FIG. 15 may be made by any means which permits the orderly and timely exchange of data across the interface. In the preferred embodiment, the interfaces between the pointer (2202) and the general purpose computer system (2218) and between the general purpose computer system (2218) and the speech synthesizer (2206) conform to the Electronic Industries Association RS-232 interface specification. The interface between the general purpose computer system (2218) and the printer (2220) conform to the Centronix 50 pin parallel interface specification.

Figure 16:
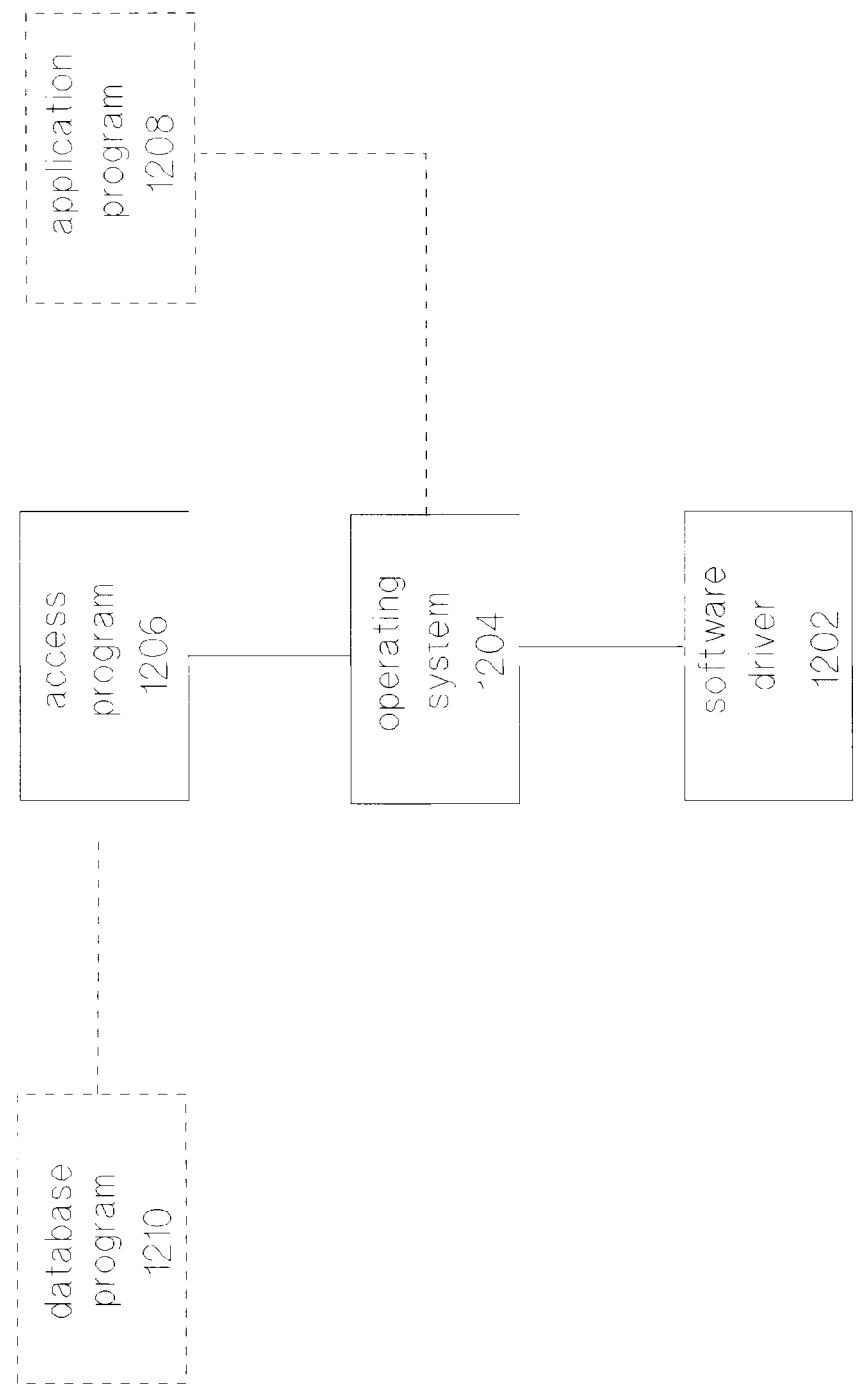
FIG. 16 is an illustration of software components of an apparatus in accordance with an embodiment of the Perimeter Menu aspect of the disclosure.

The software component of the prototype are stored in memory (2106) and executed on the processing unit (2102). The software component of the prototype, depicted in FIG. 16, include a software driver (1202), an operating system (1204), an optional database program (1210), and the prototype access program code and data, hereinafter collectively referred to as the "access program" (1206). In the preferred embodiment, one or more application programs (1208) may also execute on the processing unit (2102) and accept control and data from the access program (1206) via the operating system (1204). The software driver (1202) of the prototype is the Logitech Mouse Driver included with Windows® version 3.1. The operating system (1204) of the prototype is Windows® version 3.1 in combination with MS-DOS® version 6.2. Hereinafter, the operating system is referred to simply as "Windows®", available from Microsoft Corporation, Redmond, Wash., USA.

The optional database program (1210) is described in the detailed description of the Length Order aspect of the disclosure. The prototype access program (1206) is described in detail below.

As stated earlier, the software components of the prototype are stored in memory (2106). Depending on the capacity of memory (2106) and the size of the application programs, portions of these programs may be transferred as needed between memory (2106) and the storage unit (2206) or between memory (2106) and a diskette in the diskette drive (2216) depicted in FIG. 15. The basic function of the storage unit (2206) and the diskette drive (2216) is to store programs and data that are employed by the general purpose computer system (2218) and which may readily be transferred to the memory (2106) when needed.

It is to be understood that components others than those used in the prototype may be utilized in accordance with the disclosure. It is only necessary that the substitute component or components have the capacity to carry out the functions described. For example, the processing unit of the general purpose computer system may be substituted with a microprocessor coupled to custom electronics for performing the functions of the various aspects of the disclosure, or the color display of the prototype may be substituted with a monochrome display.

A. Perimeter Menu

The preferred embodiment of the Perimeter Menu aspect of the disclosure will now be described in detail from a functional perspective using an example. This description refers to selectable regions which include one or more subregions. A selectable region is a region, delimited with respect to a display or a surface, and associated with a menu option which may be selected, usually by a selection event. A subregion is a selectable region that is included within another selectable region. Thus a subregion is, by itself, a selectable region. Assuming that a certain selectable region includes subregions A and B, dwell time on subregions A and B may be combined, for example, by summing, so that dwelling on either subregion A or B or a combination of both for the selection threshold period selects the menu option associated with the selectable region.

Figure 17:
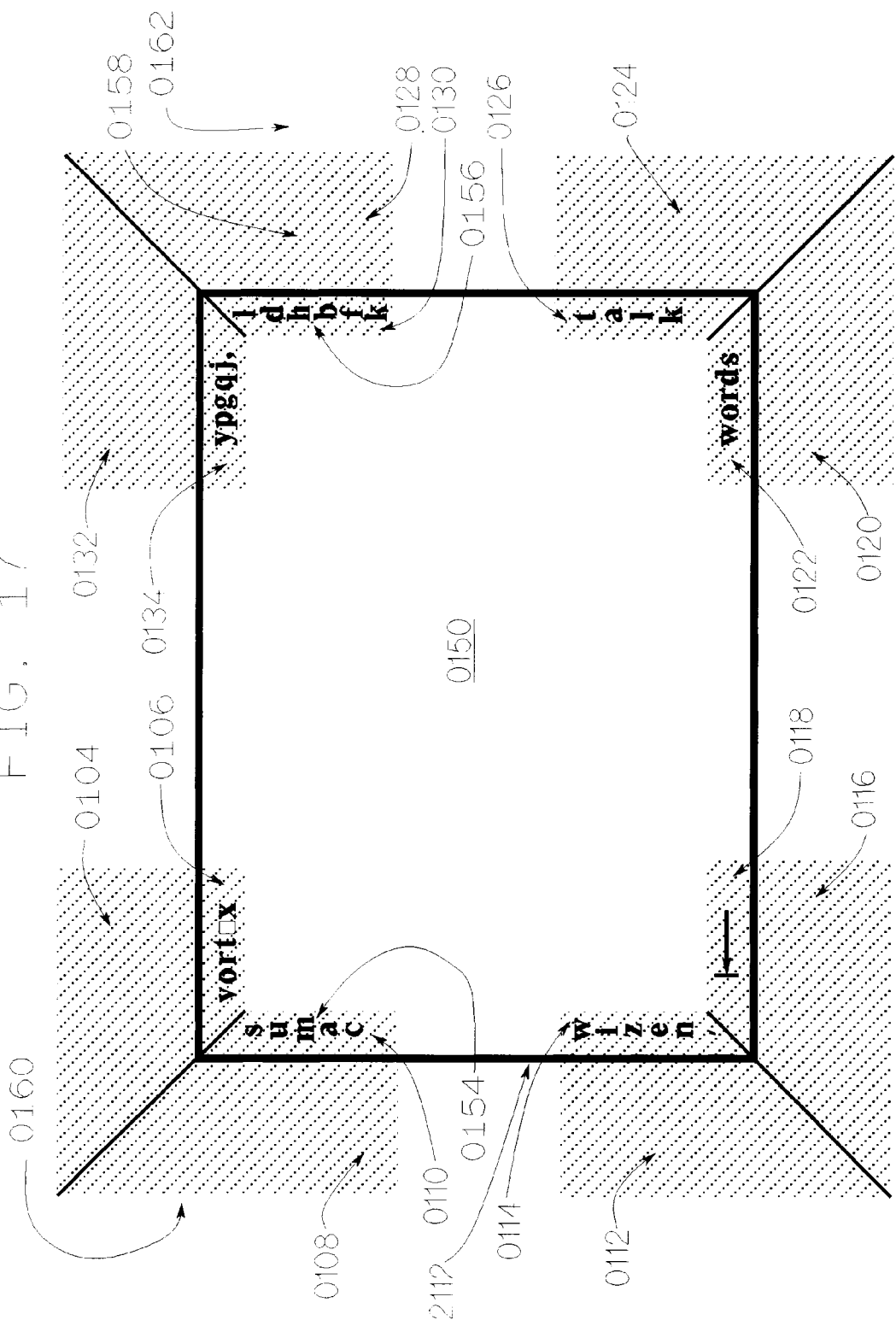
FIGS. 17 and 18 are each illustrations of a display and structures in accordance with an embodiment of the Perimeter Menu aspect of the disclosure.
Figure 18:
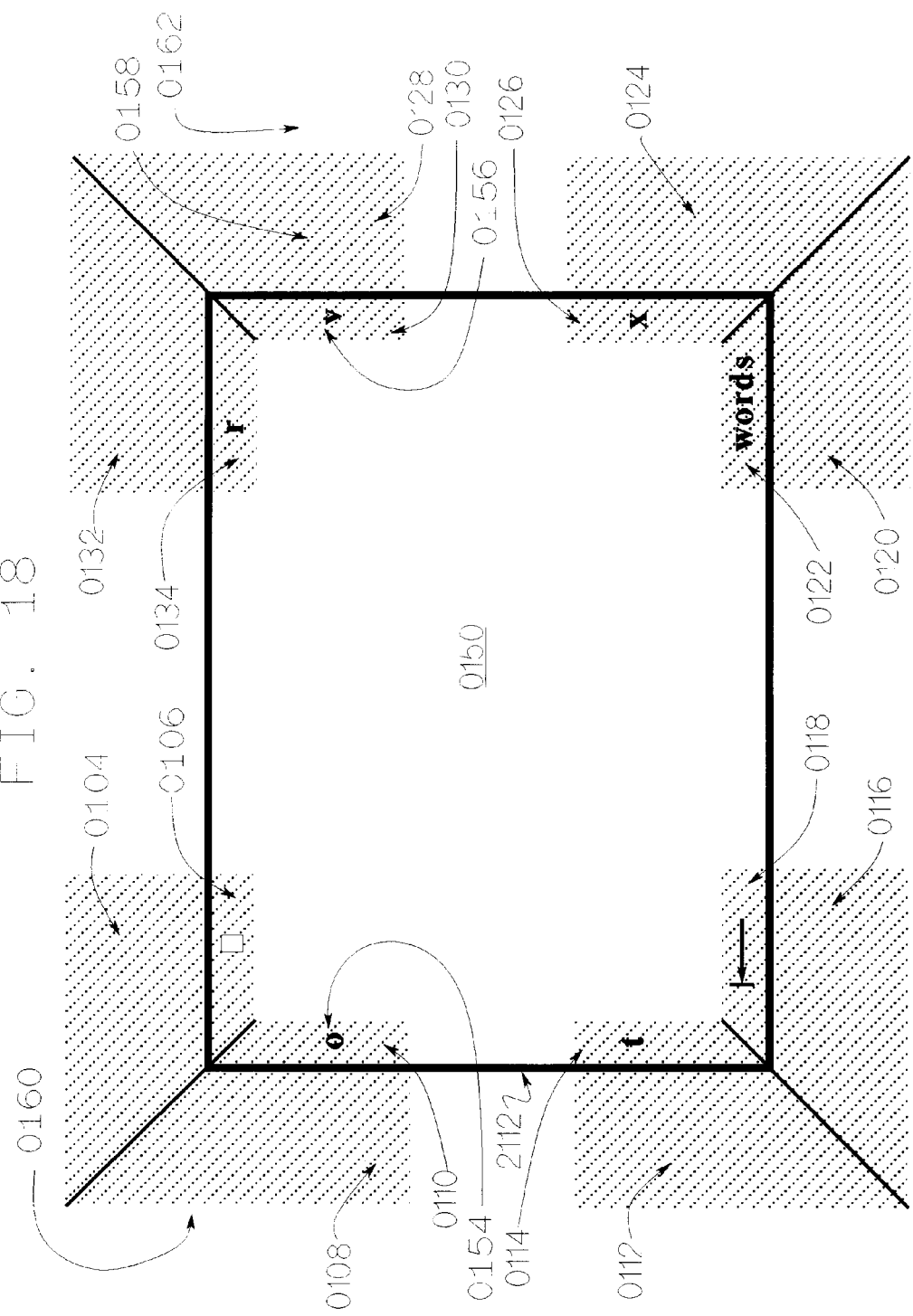

Reference will now be made to FIGS. 17 and 18 which depict an example of the preferred embodiment of the Perimeter Menu aspect of the disclosure. FIG. 17 shows the display (2112) of a general purpose computer system (2218 in FIG. 15) and eight selectable regions. Each of the eight selectable regions consists of the union of a visible subregion on the display (2112) and an invisible subregion located outside the display (2112) and adjacent the visible subregion. For example, the selectable region at 11 o'clock in FIG. 17 labeled with menu option "vort<space>x" consists of invisible subregion (0104) and visible subregion (0106), and within this description of the Perimeter Menu aspect of the disclosure is referred to as selectable region (0104/0106). The other selectable regions shown in FIG. 17, proceeding counter clockwise from selectable region (0104/0106) are (0108/0110), (0112/0114), (0116/0118), (0120/0122), (0124/0126), (0128/0130) and (0132/0134). Each subregion may be sized to suit the operator's preferences and abilities. Each selectable region is associated respectively with a menu option. In FIG. 17, selectable region (0104/0106) is associated with menu option vort<space>x, selectable region (0108/0110) with menu option "sumac", selectable region (0112/0114) with menu option "wizen", selectable region (0116/0118) with the menu option undo indicated by an icon on visible subregion (0118) representing an undo function, selectable region (0120/0122) with menu option "words", selectable region (0124/0126) with menu option "talk", selectable region (0128/0130) with menu option "ldhbfk" and selectable region (0132/0134) with menu option "ypgqj, ". Together, the eight visible subregions circumscribe region (0150) on the display.

Selectable regions may be delimited by data indicative of one or more boundaries of the selectable region. Equivalently, the delimit means may be detectors operative to determine when the location indicated by the movement related signal has crossed one of those boundaries or intersects a selectable region. A partially delimited region or subregion is one which is unbounded on at least one side.

Resuming, now, with the example, to select a menu option associated with a selectable region the operator moves a pointer (2202 in FIG. 15) coupled to the general purpose computer system (2218 in FIG. 15) to indicate a location on the selectable region, including either subregion, associated with the desired menu option and maintains the indicated location on the selectable region for the selection threshold period. The period of time required for selection may vary responsive to the proximity of the indicated location to the location of a cursor on the display or to the proximity of the indicated location to a point within the intersected selectable region. Dwell time may be continuous, discontinuous or dynamic (described below) for either or both subregions of the selectable region.

Selection in the above example is in response to a dwell event. A dwell event includes, but is not limited to, each of the following: (a) the durations of one or more periods of intersection of locations indicated by a movement related signal, a body member or a cursor (including any part of the cursor) and a selectable region equalling or exceeding a predetermined period; (b) a first quantity responsive to the durations of the periods referred to in (a) equalling or exceeding a predetermined quantity; (c) dwell event (a) or (b) followed by a location indicated by the movement related signal, the body member or the cursor no longer intersecting the intersected selectable region; and (d) dwell event (a) or (b) wherein the period of intersection required for selection of a selectable region increases in response to a non-intersection or a period of non-intersection of locations indicated by the movement related signal, the body member or the cursor and the selectable region ("dynamic dwell event"). The use of non-intersection or a period of non-intersection in determining the duration of a period of intersection required for selection is called dynamic dwell. Associated with each type of dwell event is an intersected selectable region. This is the selectable region intersected by the location indicated by the movement related signal, body member or cursor which triggers the dwell event by causing the period or the first quantity to equal or exceed the predetermined period or the predetermined quantity, respectively.

Selection may also be in response to a selection event. A selection event includes, but is not limited to: (a) a dwell event; (b) a switch operation at or near the time of an intersection of a location indicated by a movement related signal, a body member or a cursor and a selectable region; (c) an intersection of a location indicated by a movement related signal, a body member or a cursor and a selectable region; and (d) selection event (c) followed by a location indicated by the movement related signal, the body member or the cursor no longer intersecting the selectable region it previously intersected. Associated with each type of selection event is an intersected selectable region. This is the selectable region intersected by the location indicated by the movement related signal, body member or cursor. The fact that a selection event has occurred may be indicated to the operator, for example, visually by changing the cursor appearance or location, by changing location, size, shape, hue, brightness, contrast, tone, dithering, pattern, hatching, font or fill of an object on the surface, or by displaying a graphic or a point distinguishable from its immediate surroundings on a surface or removing a graphic or point distinguishable from its immediate surroundings from a surface; auditively by generating a sound or changing the pitch or volume of an extant sound; tactilely by changing the surface or temperature of a contact area or the pressure exerted by a contact area; or by other means. In the prototype, following selection, the hue of the visible subregion of the selected selectable region is changed from green to magenta.

As used herein, a cursor includes a temporary marking on a display which emphasizes to an operator, in an optical manner, a momentarily important location or object. As used herein, body member means any part of the body including, but not limited to, each of the following: the shoulder, arm, elbow, wrist, hand, finger, thumb, leg, knee, ankle, foot, toe, hip, trunk, neck, tongue, lip, eye and head. The received movement related signal includes, but is not limited to, a signal indicative of movement or from which movement can be derived, such as a plurality of relative or absolute positions or a difference between two relative or absolute positions. Movement related signal receiving means includes, but is not limited to, each of the following: (a) pointer interface circuitry found in a general purpose computer system; (b) one or more detectors operative to detect movement of a pointer; and (c) one or more detectors operative to detect movement of a body member of an operator. In the prototype, the movement related signal receiving includes electronic circuitry in the general purpose computer system (2218) operative to receive the movement related signal generated in part by the movement of the pointer (2202).

In the prototype subregions are displayed on the display (2112). However, other means for displaying may be substituted for the means used in the prototype, for example, a projector for projecting an image, a surface having a static display thereon, or other suitable means.

Resuming, now, with the example of FIG. 17, and assuming that the operator has selected menu option "vort<space>x", the display is changed to that shown in FIG. 18. In FIG. 18, each of six selectable regions is now associated with a submenu option of the selected menu option "vort<space>x". Selectable region (0104/0106) is now associated with submenu option "<space>", selectable region (0108/0110) with submenu option "o", selectable region (0112/0114) with submenu option "t", selectable region (0124/0126) with submenu option "x", selectable region (0128/0130) with submenu option "v", and selectable region (0132/0134) with submenu option "r". Selectable regions (0116/0118) and (0120/0122) remains associated with the same menu options with which each was associated in FIG. 17. The operator may now select one of these submenu options.

Assuming that the selected submenu option is one of v, o, r, t, x and space, the selected character, or a corresponding computer encoding of that character, may be input to an apparatus coupled to the general purpose computer system (2218 in FIG. 15), or input to an application program (1208) executing on the general purpose computer system (2218) coupled to the display (2112). Inputting, as used herein, includes, but is not limited to, generating or passing signals representative of the selected menu option along a path toward the destination apparatus or program. Preferably, the computer program displays at least some of its output in the circumscribed region (0150).

Given a display having eight selectable regions, an operator may, with a single selection indicate one of eight menu options, with two selections indicate one of up to 64 different menu options, with three selections indicate one of up to 256 menu options, etc. Each of these menu options may represent a sequence of one or more characters, a sequence of one or more data or control inputs to an application program (1208), or a control function for one or more devices or speech synthesizers coupled to the general purpose computer system (2218). As used herein, a character includes a space, a control character as defined by the American National Standards Institute (ANSI) or the American Standard Code for Information Exchange (ASCII), and a letter from one of the Afrikaans, Albanian, Amharic, Arabic, Armenian, Assamese, Assyrian, Avar, Azerbaijani, Balinese, Bamara, Bantu, Bashkir, Basque, Bengali, Birhari, Bulgarian, Buluba-Lulua, Burmese, Buryat, Byelorussian, Caddoan, Catalan, Chechen, Chikaranga, Chippewa, Choctaw, Church Slavik, Chuvash, Coptic, Cree, Croatian, Cyrillic, Czech, Dakota, Danish, Dari, Devanagari, Dutch, Dzongkha, English, Eskimo, Esperanto, Estonian, Ewe, Farsi, Fijian, Filipino, Finnish, Flemish, French, Fulani, Gaelic, Galician, Georgian, German, Greek, Gujarati, Gurmakhi, Harari, Hausa, Hawaiian, Hebrew, Hindi, Hiragana, Ibo, Icelandic, Indonesian, Irish, Irogquoian, Italian, Kabardian, Kalmyk, Kannada, Kanuri, Kashmiri, Katakana, Kazakh, Khasi, Khmer, Kirghiz, Kishmiri, Komi, Kongo, Kurdish, Lao, Latin, Latvian, Lithuanian, Lu-Guanda, Macedonian, Magahi, Maithili, Makua, Malagasy, Malay, Malayalam, Maltese, Mandingo, Manipuri, Marathi, Masai, Mizo, Moldavian, Mongolian, Munda, Naga, Navaho, Nyanja, Nepalese, Norwegian, Oriya, Oromo, Ossetian, Pashto, Polish, Portugese, Punjabi, Rajasthani, Rhaeto-Romanic, Rumanian, Russian, Samoan, Sangs, Serbian, Serbo-Croatian, Sinhalese, Sinhi, Sioux, Slovak, Slovenia, Spanish, Sundanese, Swahili, Swedish, Syriac, Tadzhik, Tagalog, Tajik, Tamil, Tatar, Telugu, Thai, Tibetan, Turkish, Turkmen, Udmurt, Uighur, Ukranian, Umbundu, Urdu, Uzbek, Vietnamese, Visayan, Welsh, Yakut, Yoruba and phonetic alphabets. As used herein, each of a character, ideograph, control input and control function includes a computer encoding of the same. As used herein, a device includes, but is not limited to, each of a wheelchair, a household appliance, an appliance for use in an office, a workstation, a robot, and a computer peripheral. Thus, by selecting from a menu, the operator may, for example, increase the volume of an external speech synthesizer, or turn a wheelchair to the left.

The selectable regions organized as described above help an NMD operator make the menu selection he intends. Referring to FIG. 17, suppose, for example, an NMD operator intends to move a pointer (2202) that is indicating point (0154) to indicate point (0156), a location in subregion (0130), but who is unable to quickly stop motion, so that the location indicated by the pointer (2202) moves from point (0154) past point (0156) to point (0158). Because point (0158) lies within the same selectable region (0128/0130) as the overshot subregion (0130), dwelling at point (0158) operates to select the intended selectable region (0128/0130). Invisible subregions, in accordance with the Perimeter Menu aspect of the disclosure, may extend outward from the edge of the display (2112) to infinity. In such an embodiment, dwelling at point (0162) would operate to select selectable region (0128/0130). Preferably, invisible subregions extend a finite distance from the edge of the display (2112). In such an embodiment, dwelling at point (0162) would not operate to select selectable region (0128/0130). The sizes of the invisible subregions shown in FIGS. 17 and 18 are illustrative only. Preferably the size of each invisible subregion is large enough to encompass overshoot but small enough to avoid unintentional selections when the NMD operator turns to see someone or something.

The prototype utilizes the area outside the display to facilitate menu selection by a disabled operator. If an operator has impaired ability to maintain a steady position, he can point to a relatively large invisible subregion outside the display which is more forgiving of the operator's involuntary motion than the relatively small selectable regions on the display in conventional on-screen keyboards. Thus, the effective area of a selectable region is expanded beyond the region's visible subregion shown on a display. If an operator has impaired ability to stop motion he may, starting from the center of the screen, point to any selectable region. His impaired ability to stop will not impair his ability to select his intended target, assuming his directional control is relatively unimpaired, since, in the prototype, each selectable region is unbounded on its side furthest from the center of the display. Although the selectable regions of the prototype are large, only the visible subregion of each selectable region uses space on the display. Thus a large rectangular region remains available on the display for the output of an application program. The Perimeter Menu aspect of the disclosure is preferably implemented on a general purpose computer system. If the general purpose computer system is coupled to a speech synthesizer and the menu hierarchy allows the selection of letters and/or words, an operator having impaired speech may speak using the speech synthesizer. If a word processing or data entry application program is run on the general purpose computer system, the operator may enter words or data, respectively, for input to the application program. If the general purpose computer system is coupled to a devices capable of executing commands and the menu hierarchy allows the selection of commands, a disabled operator may select and issue commands to control these devices.

Since the cognitive demand for scanning is greater than that for direct selection, the prototype places less cognitive demand on the operator than a scanning system for selecting options from a menu.

Figure 19:
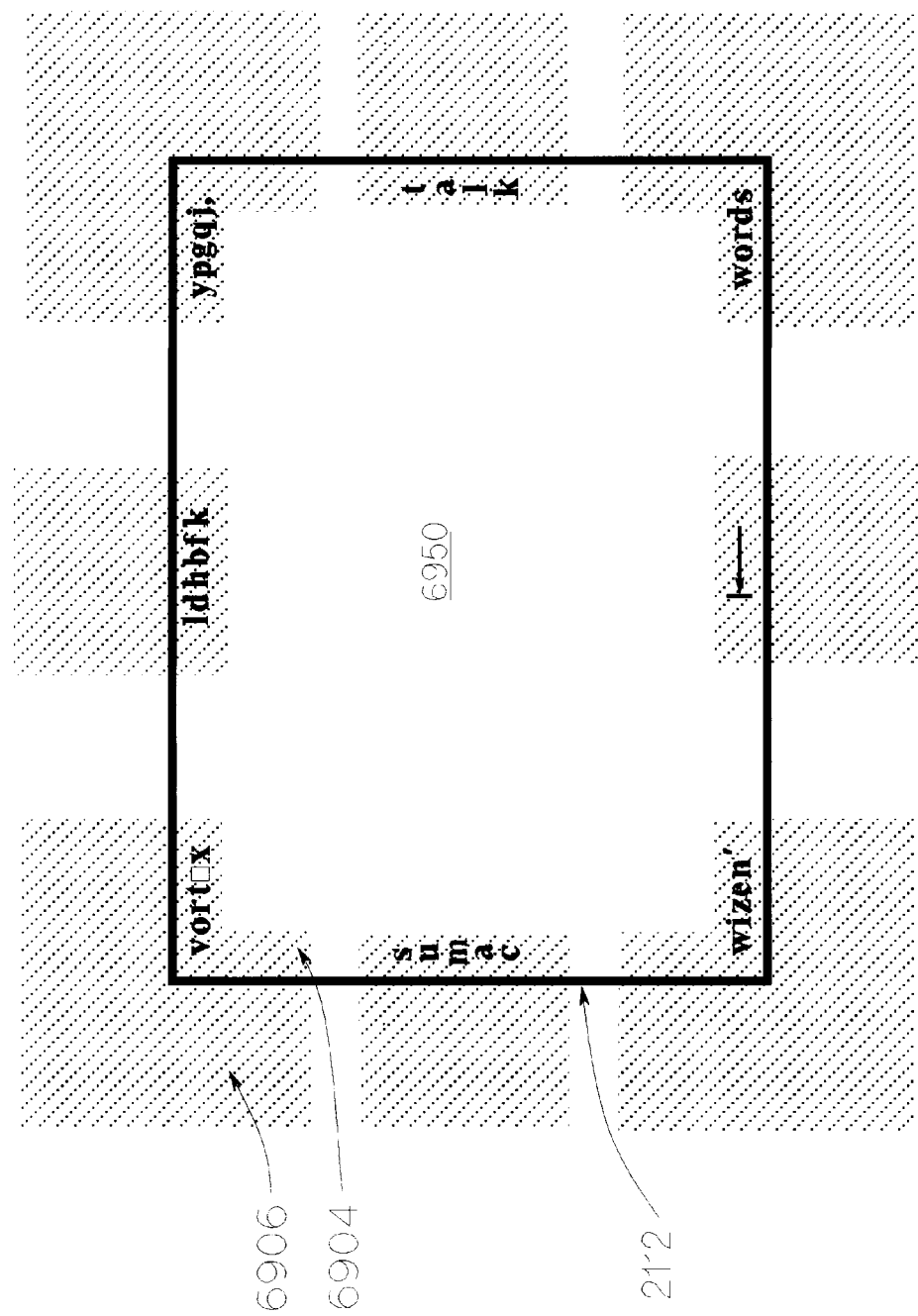
FIG. 19 is an illustration of a display and structures in accordance with another embodiment of the Perimeter Menu aspect of the disclosure.

FIG. 19 illustrates a display in accordance with an alternative embodiment of the Perimeter Menu aspect of the disclosure having eight selectable regions circumscribing a central region (6950) on the display.

Figure 20:
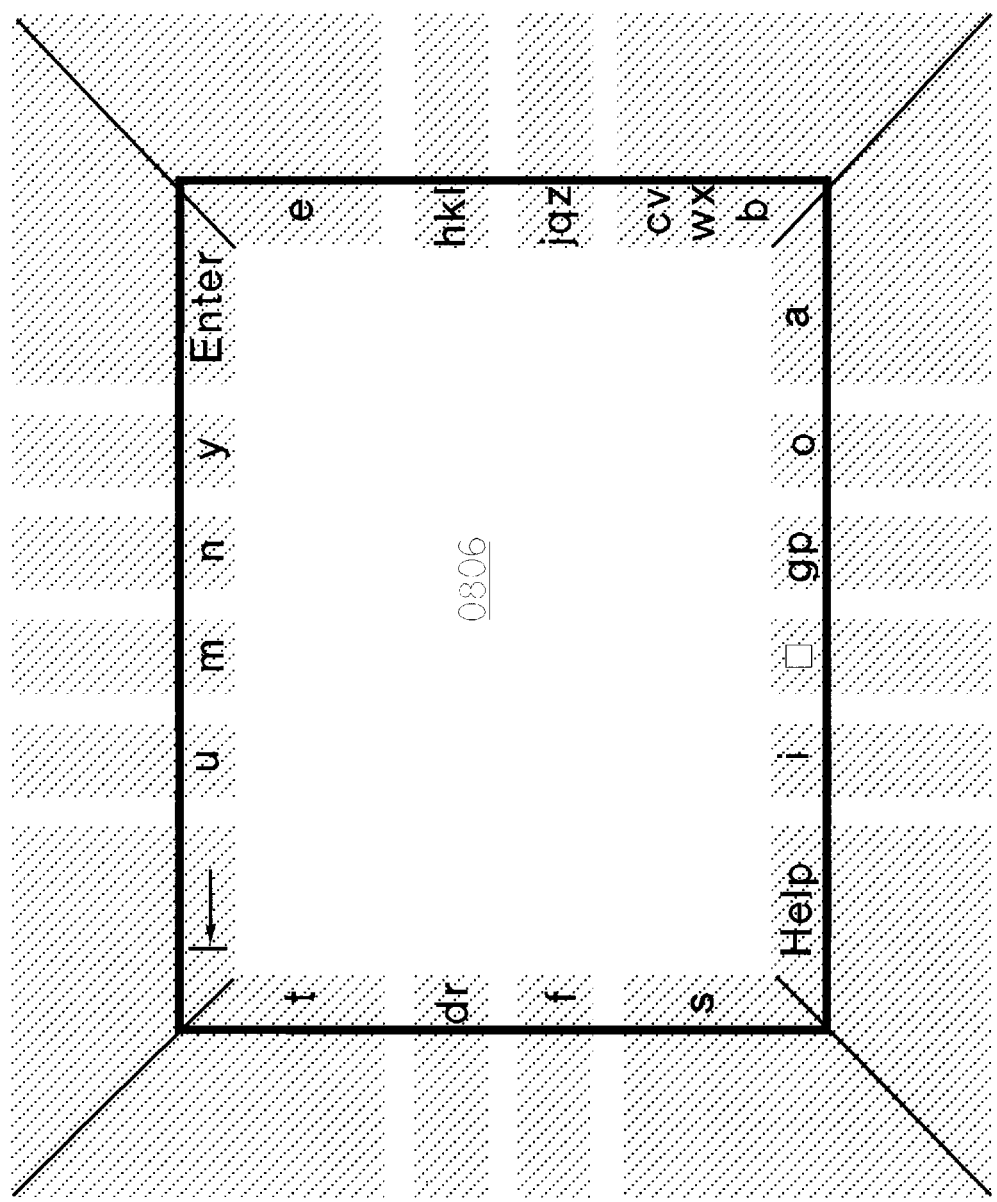
FIG. 20 is an illustration of a display and structures in accordance with still another embodiment of the Perimeter Menu aspect of the disclosure.

FIG. 20 illustrates a display in accordance with an embodiment of the Perimeter Menu aspect of the disclosure having twenty selectable regions circumscribing a central region (0806) on the display.

Figure 21:
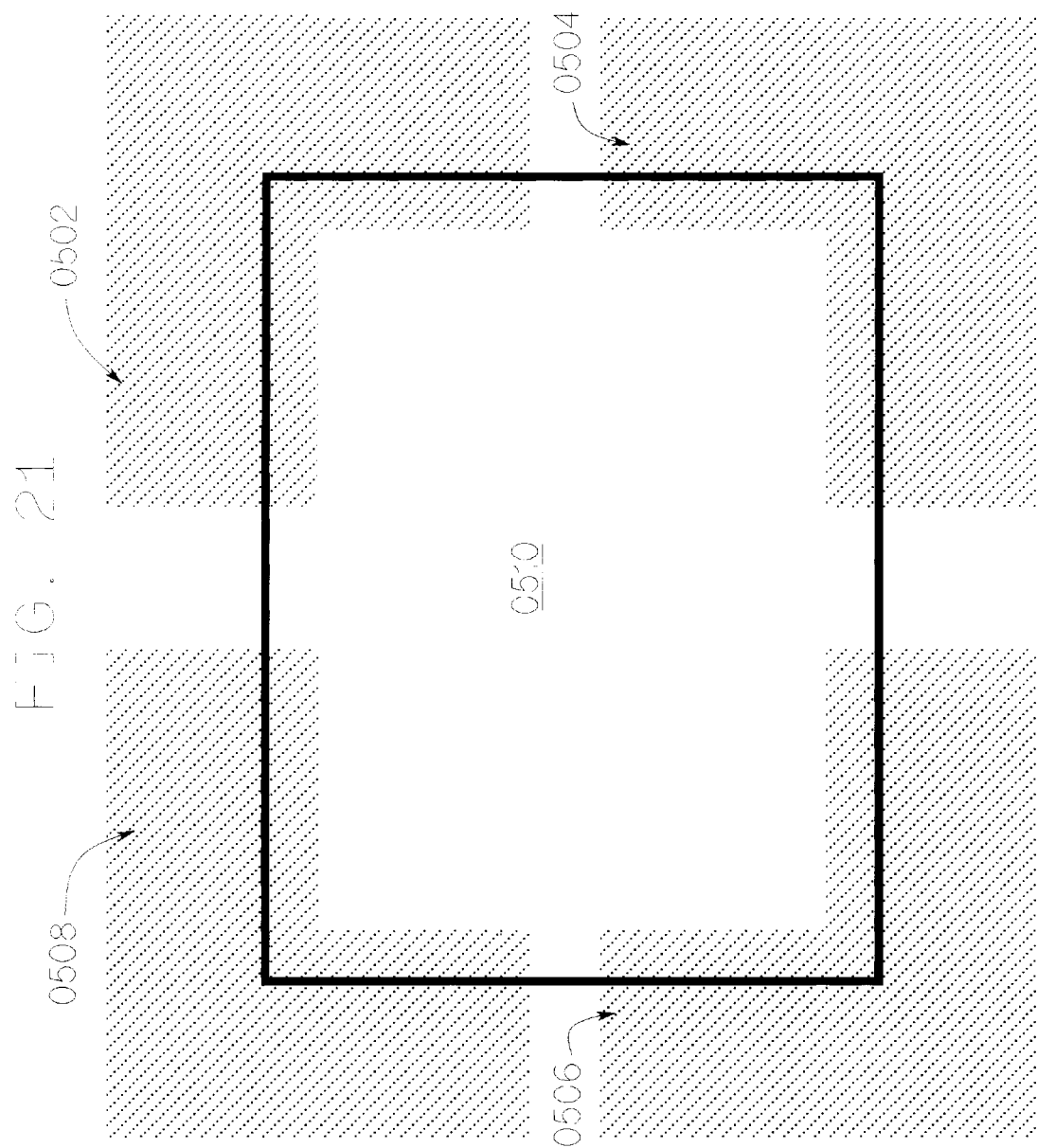
FIG. 21 is an illustration of a display and structures in accordance with another embodiment of the Perimeter Menu aspect of the disclosure.

FIG. 21 illustrates a display in accordance with an embodiment of the Perimeter Menu aspect of the disclosure having four selectable regions (0508), (0506), (0504) and (0502) circumscribing a central region (0510) on the display.

Figure 22:
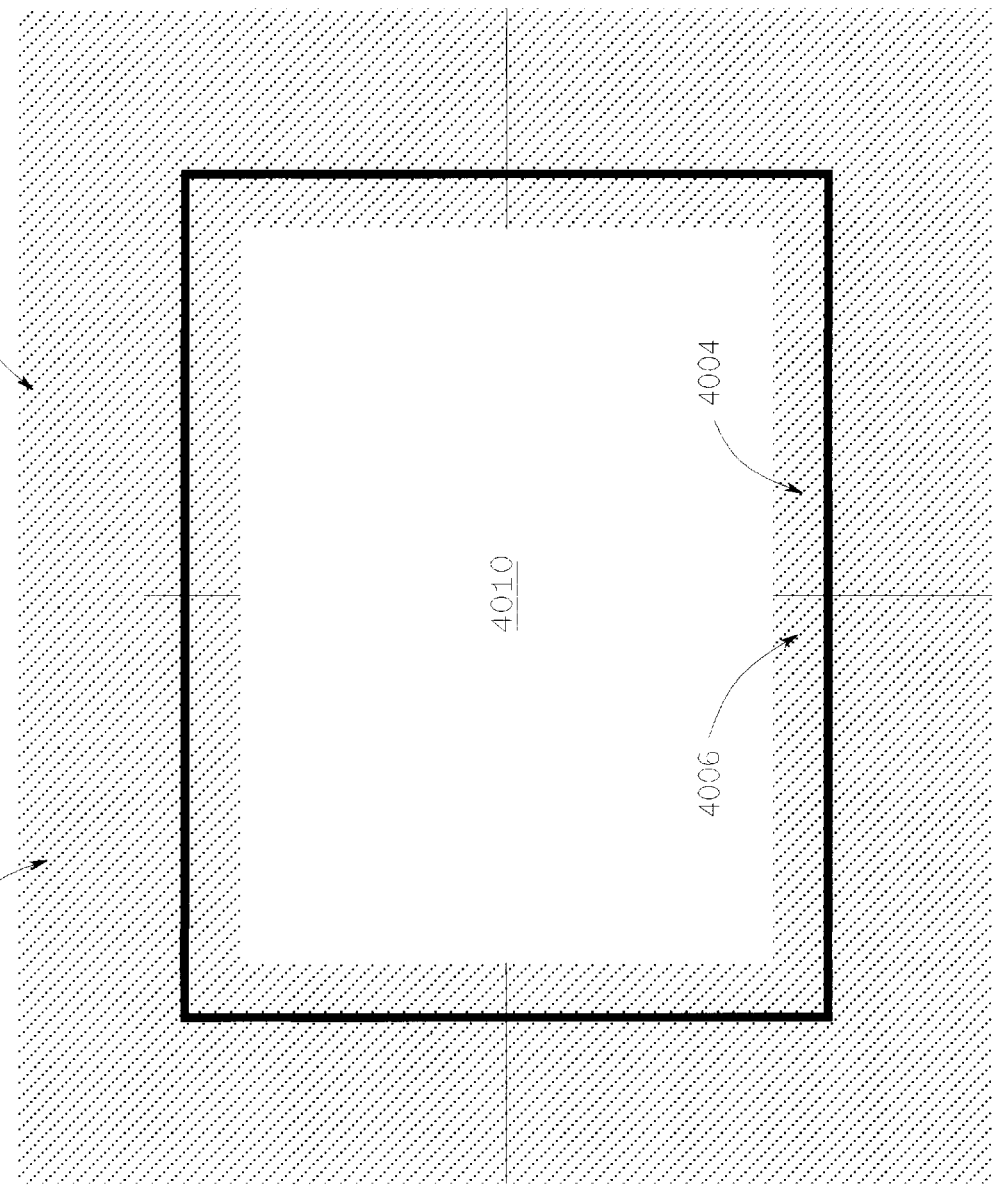
FIG. 22 is an illustration of a display and structures in accordance with yet another embodiment of the Perimeter Menu aspect of the disclosure.

FIG. 22 illustrates a display in accordance with an embodiment of the Perimeter Menu aspect of the disclosure having four selectable regions (4008), (4006), (4004) and (4002) with no space between them other than a circumscribed region (4010) on the display.

Figure 23:
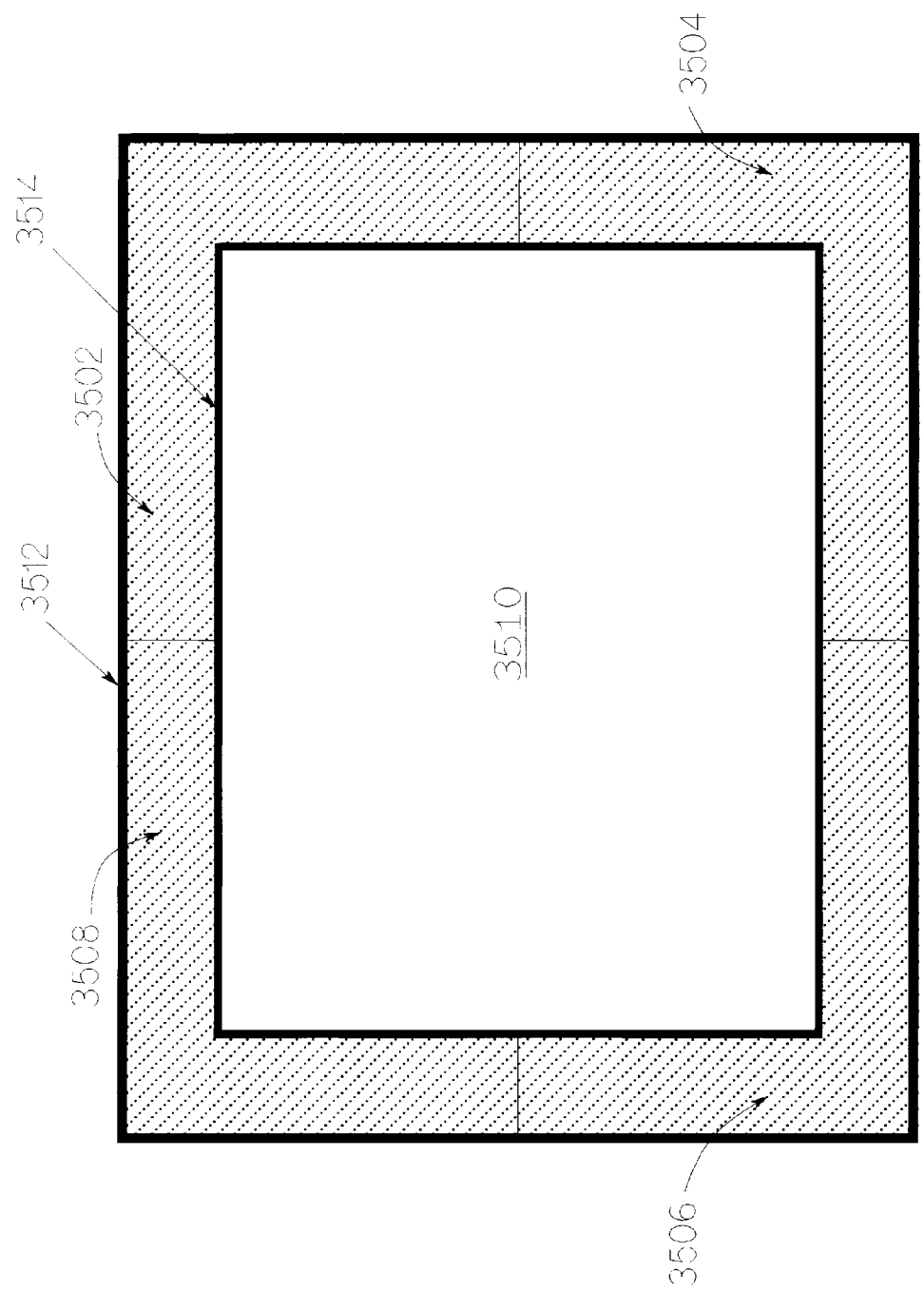
FIG. 23 is an illustration of an apparatus in accordance with a further embodiment of the Perimeter Menu aspect of the disclosure.

FIG. 23 illustrates an apparatus in accordance with of another embodiment of the Perimeter Menu aspect of the disclosure. In FIG. 23, region (3510) is located on interior display (3514) which is circumscribed by peripheral display (3512). Selectable regions (3508), (3535), (3504) and (3502) are located on the peripheral display (3512).

Figure 24:
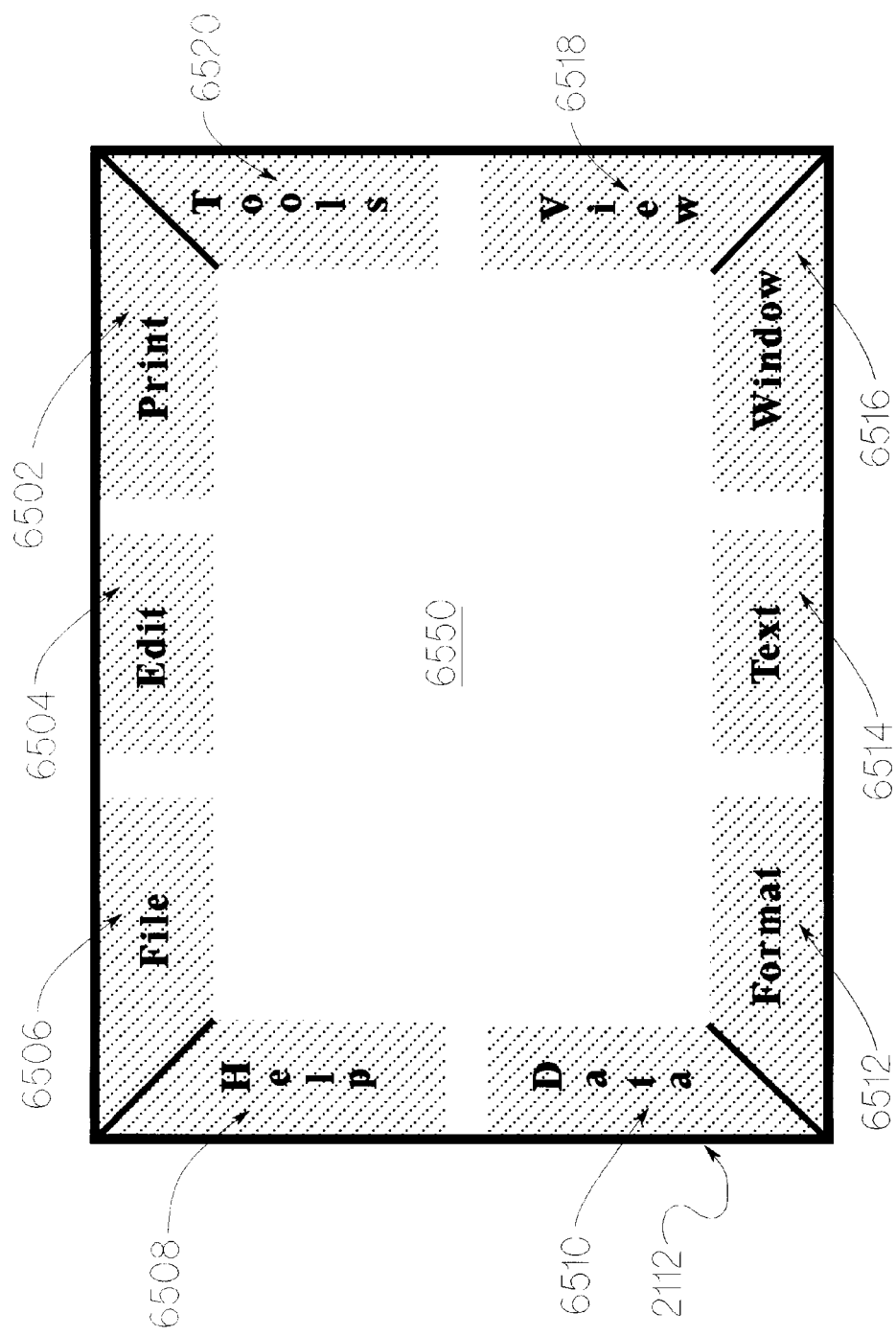

FIGS. 24 and 25 are each illustrations of a display and structures in accordance with another embodiment of the Perimeter Menu aspect of the disclosure. FIG. 24 depicts ten selectable regions (6502), (6504), (6506), (6508), (6510), (6512), (6514), (6514), (6516), (6518), and (6520). Each selectable region is located on the display (2112) adjacent the edge of the display and associated respectively with a menu option. In FIG. 24, the menu options are shown on their associated selectable region. Together the ten selectable region circumscribe region (6550) on the display. In response to only an intersection of a location indicated by a movement related signal and selectable region (6506), the display changes to that shown in FIG. 25, on which are located ten selectable regions each located on the display (2112) adjacent the edge of the display, nine of the ten selectable regions associated respectively with a submenu option. Selectable region (6608) is not associated with a submenu option. Any submenu option may be selected by a selection event.

FIGS. 26 and 27 illustrate an apparatus in accordance with still another embodiment of the Perimeter Menu aspect of the disclosure. FIG. 26 depicts a front view of the apparatus; FIG. 27 a cut away view from the top of the apparatus. FIG. 26 depicts detector area (0348 in FIG. 27) on, in or below which are located a plurality of selectable regions (0304), (0306), (0308), (0310), (0312), (0314), (0316), (0318), (0320), (0322), (0324), (0326), (0328), (0330), (0332), (0334), (0336), (0338), (0340) and (0342). Adjacent the detector area (0348 in FIG. 27) is a berm (0350 in both FIGS. 26 and 27) for confining a body member of the operator or a pointer controlled by the operator to the detector area (0348 in FIG. 27).

Still another apparatus in accordance with the Perimeter Menu aspect of the disclosure is illustrated in FIG. 28 which depicts a headrest for an operator using his head to indicate a location on a display. FIG. 28 shows an irregularity (0703) on the surface (0701) of the headrest. The irregularity is in physical contact with the operator and tactilely indicates to him the position of his head. The tactile indication means may be concave, convex or both or may differ from the surface in temperature. For individuals having impaired ability to sense the position of a body member, e.g. the operator's head, the tactile input thus provided to the operator improves the operator's ability to sense the position of his head.

The prototype of the disclosure will now be described in detail and where the preferred mode of practicing the disclosure differs from the prototype, the preferred mode is described. The description is broken into several parts:
1. A brief overview of how a state table works.
2. A description of the operation of the events, state table and state processing used in the prototype.
3. A general description of each event and one example of the use of that event.
4. An example of state machine processing in the operation of the prototype.

The prototype implements the Perimeter Menu aspect of the disclosure as a state table. A state table is a tool for processing sequential inputs and is most easily understood by analogy. Imagine yourself in a room having a ticket window and three exits, each regulated by a turnstile. You collect a ticket at the ticket window which, when inserted into the appropriate turnstile, allows passage to a connecting room. The turnstile keeps the ticket. Any given ticket operates only one turnstile in a room, though different tickets may operate the same turnstile. You begin in a certain room, collect a ticket, insert it into the appropriate turnstile and pass to a connecting room, where you perform certain tasks associated with the new room. Then you collect another ticket from the ticket window in that room, insert the ticket into the appropriate turnstile in that room, pass to a connecting room, perform certain tasks associated with the new room, and so on.

The state table used in the prototype is depicted in FIGS. 29 and 30. Moving from the analogy above, the rooms are states represented by the rows of the state table; the tickets are events represented by the columns of the state table. Each entry in the state table represents a passage from one state to another. The tasks performed upon entry into a room correspond to the processing performed by the processor (2104) on entry to a new state ("state processing"). For example, state processing may cause a slight lightening of the color of a selectable region. Reentry into that state five times may successively lighten a selectable region five times.

In the prototype, each selectable region is directly controlled by one associated state machine. Each state machine directly controls only its associated selectable region. Each state machine includes data uniquely associated with its associated selectable region, the shared state table shown in FIGS. 29 and 30, and the shared code for state processing, described below. This embodiment means that the state machine associated with selectable region (1614) may be in state ST_SELECTED while the state machine associated with selectable region (1602) is in state ST_INITIAL. In the prototype, these separate states are reflected only in separate values for data uniquely associated with each state machine. Each state machine has a unique index.

The state table used in the prototype defines 18 states, composed of states zero through seventeen shown in FIGS. 29 and 30. State 1 (ST_ERROR_STATE in FIG. 29) is not used. Preferably, it is omitted. In the prototype, the differences between the several state machines, for example, the state of a particular state machine at any given time, are confined to data structures associated with that state machine. The state machines share the same code and the same state table. In other words, returning to the ticket and turnstile analogy, there are multiple travelers each with his own ticket (event) and his own baggage (data) moving from room to room in the same labyrinth. Each traveler's actions in each room usually affect only his own baggage.

In the prototype, there are two types of sequential inputs processed by the state table: external events and internal events. External events are generated outside the state table, for example, by the operator moving the pointer (2202) or by a timer expiring. Pointer movement may generate an event indicating that the operator has moved the cursor across the selectable region boundary from without the selectable region to within it. This event causes a transition from one state to another ("drives" a state machine to a new state). For example, assuming a state machine is in state ST_CREST_TIDE, row 6 in the state table shown in FIG. 29, when an event EV_CROSS_OUT, column 4 of the state table, occurs. At the intersection of row 6 and column 4 is a 7. This represents the new state, row 7 of the state table, state ST_SELECTED. Thus event EV_CROSS_OUT drives the state machine from state ST_CREST_TIDE to state ST_SELECTED. On entry to the new state, the computer performs the state processing associated with the new state.

Internal events are generated during state processing to handle circumstances where a first state transition is made due to an external event and the processing associated with the new state determines that a second state transition is necessary. The first, external, event has already been used so a second, internal, event is generated by the state. For example, if the operator has a prolonged muscle spasm, common among individuals with CP, or loses his grip on a hand held pointing device, the cursor may sit without moving on a selectable region for a considerable period of time. It is desirable to detect this condition, move the cursor to the center of the screen so the operator can easily find the cursor, and reset all selectable regions to their initial color. Detection is accomplished with a timer. On timer expiration, a state machine transitions to state ST_IDLE which centers the cursor. From there it is desirable to transition to state ST_RESET which, among other processing, initializes selectable region color. The transition from state ST_IDLE to state ST_RESET is driven by an internal event, generated by state ST_IDLE state processing.

Although the preferred embodiment uses only one state to perform certain state processing, that state processing may be equivalently performed in multiple states. Likewise, the state processing of multiple states of the described embodiment may be equivalently performed in a single state.

Although the prototype uses a state table to control the flow of program execution and to select one of a plurality of selectable regions, the same function may be equivalently performed using object oriented software architecture, if-then-else statements or a combination of these. In particular, in accord with object oriented software architecture, each state machine may be equivalently represented as an instantiation of a selectable region class for processing inputs affecting a particular selectable region.

Although the described embodiment uses a single processor, state table and code for state processing for all the selectable regions, each of these may be duplicated. Alternate embodiments may include processors, electronic circuitry, state tables or code for state processing used for processing fewer than all the selectable regions or used to process certain selectable regions at one time and other selectable regions at other times.

In the prototype, each state machine processes events independently of all other state machines, though a state machine may send an event to another state machine. For example, when the operator selects a selectable region, the associated state machine sends the event EV_RESET to all other state machines so that all selectable regions revert to their respective initial colors.

A single operator action may result in the issuance of different events to different state machines. For example, when the operator moves the cursor from without a selectable region to within it, EV_DWELL is sent to the newly indicated state machine. EV_MOVEMENT is sent to all other state machines.

Following is a general description of each event used in the prototype and an example of the use of each event. For all uses of each event, refer to the state table shown in FIGS. 29 and 30 which determines what state transition occurs from every state on occurrence of a given event.

The event EV_RESET is an internal event which drives a state machine to its initial state. For example, when the operator has not moved the pointer (2202) for a predetermined period of time, event EV_RESET is sent to all other selectable regions.

The event EV_DECAY is an external event which indicates that the cursor hotspot does not intersect the selectable region associated with the state machine. EV_DECAY is sent to a state machine periodically when the operator has positioned the cursor hotspot on a selectable region other than the selectable region associated with that state machine.

The event EV_DWELL is an external event which indicates that the cursor hotspot intersects the selectable region associated with the state machine. EV_DWELL is sent to a state machine periodically when the operator has positioned the cursor hotspot on the associated selectable region.

The event EV_CROSS_OUT is an external event which indicates that the cursor hotspot has moved from a location intersecting the selectable region associated with the state machine to a location not intersecting the selectable region. After the operator selects a selectable region, he must move the cursor hotspot out of the selectable region, generating EV_CROSS_OUT, before he can again select that selectable region.

The event EV_STEP_UP is an internal event which indicates that a selectable region's selection threshold has been satisfied.

The event EV_MOVEMENT is an external event which indicates that the cursor hotspot has moved. If the cursor hotspot intersects a selectable region without moving for a predetermined period of time, a timeout occurs, causing all state machines to transition to the reset state. EV_MOVEMENT drives the state machine out of the reset state.

The event EV_IDLE_TIMEOUT is an external event which indicates that the cursor hotspot has intersected a selectable region without moving for a predetermined period of time. EV_IDLE_TIMEOUT causes the state machine to move the cursor hotspot to the center of the display.

The event EV_CEILING is an external event which indicates that the cursor hotspot intersects a selectable region and the color of the selectable region equals the selectable region color ceiling. If the locking feature is enabled, EV_CEILING drives the state machine to the begin lock state where it displays the lock icon.

The null event, EV_NULL, is a multi-purpose internal event used in a variety of situations to drive a state machine to another state. For example, after a timeout has been detected, EV_IDLE_TIMEOUT is generated and sent to the appropriate state machine driving it to the idle state, the receiving state machine sends itself EV_NULL in order to drive itself to the reset state. The use of EV_NULL here allows states to be simpler and the reset state to be reused.

The prototype uses eight partially delimited selectable regions. In the description below, the portion of each selectable region shown on the display is referred to as the visible subregion of the selectable region. The portion of each selectable region outside the display is referred to as the invisible subregion of the selectable region. Because the software driver (1202) confines the cursor hotspot to the Windows® cursor clipping rectangle, a rectangle on the display slightly smaller in area than the display, the access program (1206) of the prototype only reads hotspot cursor locations within the Windows® cursor clipping rectangle, even though the operator may in fact be pointing to a location outside the Windows® cursor clipping rectangle, e.g. within an invisible subregion. Thus the access program (1206) does not distinguish between two locations indicated by the operator, the first at a first location on the edge of the Windows® cursor clipping rectangle and the second outside the Windows® cursor clipping rectangle whose location is reported by the software driver (1202) to be the first location. For example, assuming that the operator moves the location indicated by the pointer (2202) to a location within invisible subregion (0104 in FIG. 17), the software driver (1202) in the prototype reports the cursor hotspot location to be the closest point within the visible subregion (0106). Consequently, in the prototype, all invisible subregions are unbounded on their side furthest from and parallel to the edge of the display. Thus, in the prototype, point (0162) in FIG. 17 lies within selectable region (0128/0130) since the rightmost side of selectable region (0128/0130) is unbounded.

The operation of the prototype will now be described using, as an example, the selection of a menu option associated with selectable region (0104/0106). First described are notation conventions used in the description, then initialization in the prototype, and then the example. The description refers to the procedures PocketFsm and CreateEvent. These procedures are listed in pseudo-code in Appendix I.

Notational conventions used in the description below:
1. pPocket→indicates a set of data associated with a particular state machine, in this example, the state machine associated with selectable region (0104/0106).
2. pPocket→State indicates a particular item of data within the set of data associated with the state machine, in this case, the variable "State".

During initialization:
1. The Windows® cursor clipping rectangle is set so that most of the arrow cursor is always visible on the display.
2. The cursor, indicating on the display (2112) the location indicated by the movement related signal receiving means, is positioned at the center of the display.

3. All data associated with each state machine are initialized. The following variables are included in the set of data associated with each state machine. There are as many independent copies of these variables as there are state machines. For each state machine the following variables are initialized as indicated.

| variable | initial value | meaning |
|---|---|---|
| fInvert | FALSE | if TRUE, display the color complementary to that indicated by this selectable region's Color variable |
| State | ST_INITIAL | state of the state machine |
| Previous State | 0 | previous state of the state machine |
| Color | 0 | RGB encoding of visible subregion color |
| fPaint | FALSE | if TRUE, paint visible subregion on receipt of WM_PAINT message |
| InitialColor | RGB (0, 32, 0) | initial value corresponds to a dark green |
| pLabel | initial menu option for the state machine's selectable region | indicates an element within the aLabel array, described below |
| Decrement | RGB (0, 1, 0) | value subtracted from Color on EV_DECAY |
| Increment | RGB (0, 4, 0) | value added to Color on EV_DWELL |
| Ceiling | RGB (0, 255, 0) | initial value corresponds to a very light, bright green |
| CrestTide | RGB (0, 143, 0) | initial value corresponds to a light green |
| Lockspot.x | a point within the selectable region located two thirds of the length of the selectable region from the closest corner of the display | x coordinate of location for the display of the lock icon |
| Lockspot.y | a point within the selectable region located two thirds of the length of the selectable region from the closest corner of the display | y coordinate of location for the display of the lock icon |
| fInterior | TRUE for interior regions, otherwise FALSE; used for the Intersection aspect of the invention | if TRUE, this is an interior region of adjacent regions |
| iAdjacentPocket | index of state machine associated with the adjacent region; used for the Intersection aspect of the invention | |
| first array of points second array of points | boundaries of the visible subregion boundaries of the region; used for the Intersection aspect of the invention | |
| hRegion | handle to Windows ® region corresponding to the visible subregion; used for the Intersection aspect of the invention | |

4. aLabel, an array of data structures defining the menu and submenu options and the menu hierarchy, is initialized. For example, one of the elements of aLabel defines menu option "vort<space>x". This element includes fields which determine that this menu option is displayed horizontally starting at certain (x,y) coordinates, that on selection certain actions are to be taken, for example, outputting text to a speech synthesizer, and that on selection certain submenu options, in this example, "v", "o", "r", "t", "<space>" and "x", and related data are to be associated with certain state machines. In the prototype, this association is accomplished by modifying pLabel in the set of data of the associated state machine to point to the aLabel element corresponding to the menu option to be associated with that state machine.

5. At least one window is created in the circumscribed region (0150) for the display of selected letters.

6. The state table is initialized to the values shown in FIGS. 29 and 30.

7. EV_RESET is sent to each state machine by a procedure call of the form PocketFsm (pPocket, EV_RESET). As an example, assume pPocket indicates the state machine associated with selectable region (0104/0106). Proceeding through the pseudo-code for the procedure PocketFsm listed in Appendix I, fInternalEvent is set to TRUE and consequently control passes into the while loop. fInternalEvent is now set to FALSE. The current state, pPocket→State, is stored in pPocket→PreviousState. Now a state transition is made. The current state, ST_INITIAL, having a value of 2, and the current event, EV_RESET, having a value of 1, are used as row and column indices respectively into the state table aPocketFsm shown in FIGS. 29 and 30, to determine the value of the new state of the state machine, in this example, the state machine associated with selectable region (0104/0106). aPocketFsm[2][1] equals 3. Thus the new state of the state machine is 3, the value of ST_RESET. Control passes, via the switch statement, to the ST_RESET case and ST_RESET state processing is performed. The time of selectable region selection is set to the current time, the state machine's fInvert flag is set to FALSE and the value of the state machine's color variable, pPocket→Color, is compared to the state machine's initial color, pPocket→InitialColor. pPocket→Color was initialized to zero, which is not the value of pPocket→InitialColor. Consequently, pPocket→Color is set to pPocket→InitialColor and the flag pPocket→fPaint is set to TRUE. Upon reaching the break statement, control passes through the bottom of the switch statement and the value of pPocket→fPaint is tested. Since it is TRUE, the client area rectangle is invalidated. In the prototype, Windows® (1204) responds to invalidating the client rectangle by sending the access program (1206) a WM_PAINT message. On receipt of a WM_PAINT message, the access program (1206) redraws all selectable regions and any menu option located thereon for each state machines having pPocket→fPaint equal to TRUE. Thus, somewhat indirectly, visible subregion (0106) is drawn on the display (2112). Then control returns to Windows® (1204). The other seven state machines, each associated respectively with a selectable region, are similarly initialized so that each state machine transitions from ST_INITIAL to ST_RESET and draws its respective visible subregion and any menu option located thereon on the display (2112). The display shown in FIG. 17 now appears on the display (2112) of the computer system (2116).

8. A periodic timer, called the cursor polling timer, is set. This timer provides the access program (1206) with a WM_TIMER message at frequent intervals, in the prototype every system clock tick which occurs approximately every 54 milliseconds. Following access program (1206) initialization, most state transitions are made on expiration of the cursor polling timer. The access program (1206) calls the procedure CreateEvent to determine the appropriate event for each state machine and to complete the event data structure addressed by pEvent accordingly, then repetitively calls the procedure PocketFsm for each state machine, passing the unique indicator for the state machine and the appropriate event for that state machine. Preferably, the cursor polling timer is more frequent so that color changes to visible subregions are smaller and more frequent, giving a smoother appearance to color change.

An example of the selection of selectable region (0104/0106) in accord with the Perimeter Menu aspect of the disclosure will now be described. Following initialization, assume that the operator now begins to move the pointer (2202). Every 54 milliseconds the cursor polling timer expires, causing Windows® (1204) to send a WM_TIMER message to the access program (1206). Following receipt of WM_TIMER, the access program (1206) calls the procedure CreateEvent. The procedure CreateEvent, among other functions, determines whether the current cursor hotspot location lies within any selectable region. In this example, the operator is moving the cursor from its initial location in the center of the display toward selectable region (0104/0106), but since only 54 milliseconds have elapsed, the cursor hotspot has moved only slightly in that direction. The procedure CreateEvent determines that the cursor hotspot does not lie within any selectable region and that the cursor hotspot has not crossed out of a selectable region in the past 54 milliseconds. Therefore, the procedure CreateEvent determines that each state machine should receive EV_MOVEMENT. The procedure PocketFsm is called with the indicator for the state machine associated with selectable region (0104/0106) and with EV_MOVEMENT. The event EV_MOVEMENT drives this state machine from its current state, ST_RESET, to ST_EBB_TIDE. The pseudo-code for ST_EBB_TIDE in procedure PocketFsm is a break statement, indicating that no state specific action is taken at this time, other than the transition to ST_EBB_TIDE. Control returns to Windows® (1204).

Shortly before or shortly after the state machine associated with selectable region (0104/0106) receives EV_MOVEMENT, all other state machines each receive EV_MOVEMENT and each makes the same transition from ST_RESET to ST_EBB_TIDE.

Another 54 milliseconds elapses and again procedure PocketFsm is called, sending EV_MOVEMENT to the state machine associated with selectable region (0104/0106) and driving state machine from ST_EBB_TIDE to ST_DECAY. Stepping through the pseudo-code for ST_DECAY, the ST_DECAY state sets pPocket→State to the value stored in pPocket→PreviousState and decrements pPocket→Color but not below the value of pPocket→InitialColor. pPocket→Color determines the color and brightness of visible subregion (0106). Decrementing pPocket→Color results in a darkening of visible subregion (0106). Resuming with the pseudo-code for ST_DECAY state processing, the ST_DECAY state sets fInternalEvent to TRUE, and, in this case, sets Event to EV_NULL. Following the break statement, the while fInternalEvent condition is true and another state transition occurs, using the value of pPocket→State which was set by ST_DECAY state processing to ST_EBB_TIDE, the previous state. The new state is found at aPocketFsm [ST_EBB_TIDE][EV_NULL], which equals ST_EBB_TIDE. This state transition is unlike an ordinary state transition because the starting state is set by ST_DECAY. All transitions from ST_DECAY share this distinction. The state machine executes the code for the new state, ST_EBB_TIDE, which is simply a break statement. The procedure PocketFsm determines that fPaint is FALSE and exits. Control returns to Windows® (1204).

Shortly before or shortly after the state machine associated with selectable region (0104/0106) receives EV_MOVEMENT, all other state machines each receive EV_MOVEMENT and each makes the same transitions from ST_EBB_TIDE to ST_DECAY to ST_EBB_TIDE.

Every 54 milliseconds this scenario is repeated for each state machine until the operator moves the cursor hotspot to a point within selectable region (0104/0106). At this time the procedure CreateEvent determines that there is an active selectable region, specifically selectable region (0104/0106), and that consequently EV_DWELL should be sent to the associated state machine. The procedure PocketFsm is called with the indicator for the state machine associated with selectable region (0104/0106) and the event EV_DWELL. EV_DWELL drives this state machine from ST_EBB_TIDE to ST_ENTRY. Following the pseudo-code for ST_ENTRY state processing shown in PocketFsm pseudo-code, fInternalEvent is set to TRUE and Event is set to EV_NULL, resulting in another state transition to aPocketFsm[ST_ENTRY][EV_NULL], which equals ST_LOW_TIDE.

The pseudo-code for ST_LOW_TIDE is only a break statement, so there is no state specific action for ST_LOW_TIDE other than entry into this state. fPaint is FALSE so the selectable region is not redrawn. Control returns to Windows® (1204).

Shortly before or shortly after the state machine associated with selectable region (0104/0106) receives EV_DWELL, all other state machines each receive EV_MOVEMENT and each makes the same transitions from ST_EBB_TIDE to ST_DECAY to ST_EBB_TIDE.

Another 54 milliseconds elapses. The procedure CreateEvent determines that the state machine associated with selectable region (0104/0106) should receive EV_MOVEMENT, which drives it from ST_LOW_TIDE to ST_DWELL. Stepping through the pseudo-code for ST_DWELL, the ST_DWELL state sets pPocket→State to the value stored in pPocket→PreviousState, increments pPocket→Color by pPocket→Increment, but not above the value of pPocket→Ceiling, sets pPocket→fPaint to TRUE, sets fInternalEvent to TRUE, and, in this case, sets Event to EV_NULL. Following the break statement, the while fInternalEvent condition is true and another state transition occurs. The new state is found at aPocketFsm [ST_LOW_TIDE][EV_NULL], which equals ST_LOW_TIDE. This path is unlike an ordinary state transition because the starting state is set by ST_DWELL. All transitions from ST_DWELL share this distinction. The state machine executes the code for the new state, ST_LOW_TIDE, which is simply a break statement. The procedure PocketFsm determines that fPaint is TRUE, invalidates the client rectangle and exits. As a result of invalidating the client rectangle, Windows® (1204) sends a WM_PAINT message to the access program (1206). On receipt of WM_PAINT, the access program (1204) checks the value of fPaint for each state machine, and if TRUE, sets fPaint to FALSE and redraws the visible subregion of the selectable region associated with that state machine and any menu option located thereon. The color of the redrawn visible subregion is determined by the value of the Color variable for that state machine. After redrawing, control returns to Windows® (1204).

Shortly before or shortly after the state machine associated with selectable region (0104/0106) receives EV_DWELL, all other state machines each receive EV_MOVEMENT and each makes the state transitions from ST_EBB_TIDE to ST_DECAY to ST_EBB_TIDE.

Assuming the operator maintains the cursor hotspot in the selectable region (0104/0106), the state machine associated with selectable region (0104/0106) cycles repetitively through the state transitions from ST_LOW_TIDE to ST_DWELL to ST_LOW_TIDE, driven by the cursor polling timer. With each transition to ST_DWELL, visible subregion (0106) is brightened a bit. The polling timer interval is short enough and the increment to pPocket→Color is small enough that visible subregion (0106) appears to gradually brighten although in fact it progresses rapidly through a series of discrete brightness levels. With each iteration through ST_DWELL, pPocket→Color in incremented.

Assuming that the operator maintains the cursor hotspot on selectable region (0104/0106), pPocket→Color will eventually equal or exceed pPocket→CrestTide, a variable set at initialization time and not changed thereafter. At this time, Event is set to EV_STEP_UP, driving a transition to aPocketFsm[ST_LOW_TIDE][EV_STEP_UP], which equals ST_SELECTED. The state processing for ST_SELECTED provides the operator with an audible indication that a selection has just been made, takes the action appropriate upon selection of this selectable region, including selecting the menu option associated with the selected selectable region. In this example, the access program (1206) does not generate output to another program or device at this time. ST_SELECTED next sets pPocket→fInvert to TRUE, and, if appropriate, changes the menu options associated with various selectable regions. In this example, selectable region (0104/0106) is now associated with menu option "<space>", selectable region (0108/0110) with menu option "o", selectable region (0112/0114) with menu option "t", selectable region (0124/0126) with menu option "x", selectable region (0128/0130) with menu option "v", and selectable region (0132/0134) with menu option "r". Selectable regions (0116/0118) and (0120/0122) remains associated with the same menu options with which they were associated in FIG. 17. fPaint is set to TRUE for the state machines associated with the selectable regions having changed menu options. ST_SELECTED next sets Event to EV_NULL and fInternalEvent to TRUE. The state machine now makes the transition to aPocketFsm[ST_SELECTED_TIDE][EV_NULL], which equals ST_CREST_TIDE. There is no state specific action for ST_CREST_TIDE other than entry into this state. The pseudo-code for ST_CREST_TIDE is only a break statement. Control returns to Windows® (1204).

When the access program (1206) later receives the WM_PAINT message resulting from the invalidating of the client rectangle, the setting of fInvert to TRUE causes the visible subregion (0106) to be drawn in the color complementary to the value then indicated by pPocket→Color. The setting of fPaint to TRUE for all selectable regions associated with changed menu options causes those selectable regions and the menu options thereon to be redrawn. The display shown in FIG. 18 now appears on the display (2112) of the computer system (2116).

Assuming the operator maintains the cursor hotspot in the selectable region (0104/0106), the state machine associated with selectable region (0104/0106) cycles repetitively through the state transitions from ST_CREST_TIDE to ST_DWELL to ST_CREST_TIDE, driven by the cursor polling timer. With each transition to ST_DWELL, visible subregion (0106) is brightened a bit, though it is now magenta, the complement of green. The polling timer interval is short enough and the increment to pPocket→Color is small enough that visible subregion (0106) appears to gradually brighten although in fact it progresses rapidly through a series of discrete brightness levels. With each iteration through ST_DWELL, pPocket→Color in incremented. Assuming that the operator maintains the cursor hotspot on selectable region (0104/0106), pPocket→Color will eventually equal pPocket→Ceiling, a variable set at initialization time and not changed thereafter.

Assuming that the operator now moves the cursor so that the hotspot is located outside selectable region (0104/0106), CreateEvent generates the EV_CROSS_OUT for the state machine associated with selectable region (0104/0106), driving the state machine to aPocketFsm[ST_CREST_TIDE][EV_CROSS_OUT], which equals ST_SELECT_AND_OUT. The state processing for ST_SELECT_AND_OUT sends EV_RESET and then EV_MOVEMENT to all state machines, driving each of them from their current state to ST_RESET and then to ST_EBB_TIDE. For each state machine, the transition ST_RESET and then to ST_EBB_TIDE results in actions previously described for those states, except that, unlike before, the value of pPocket→Color for the state machine associated with selectable region (0104/0106) does not equal the value of pPocket→InitialColor for the state machine associated with selectable region (0104/0106). Consequently, pPocket→Color is set to pPocket→InitialColor and fPaint is set to TRUE, subsequently causing visible subregion (0106) to be redrawn in its initial color. Control returns to Windows® (1204).

The prototype continues to sample cursor location at 54 millisecond intervals, determine the appropriate event for each state machine and send that event each state machine, causing state transitions in each state machine according to the state table shown in FIGS. 29 and 30. Assuming that the operator next selects selectable region (0108/0110), the state processing in ST_SELECTED displays the selection, the letter "o", in the circumscribed region (0150), and associates the menu options shown in FIG. 17 with their respective selectable regions. The display shown in FIG. 17 appears on the display (2112) of the computer system (2116).

B. Confinement

Figure 31:
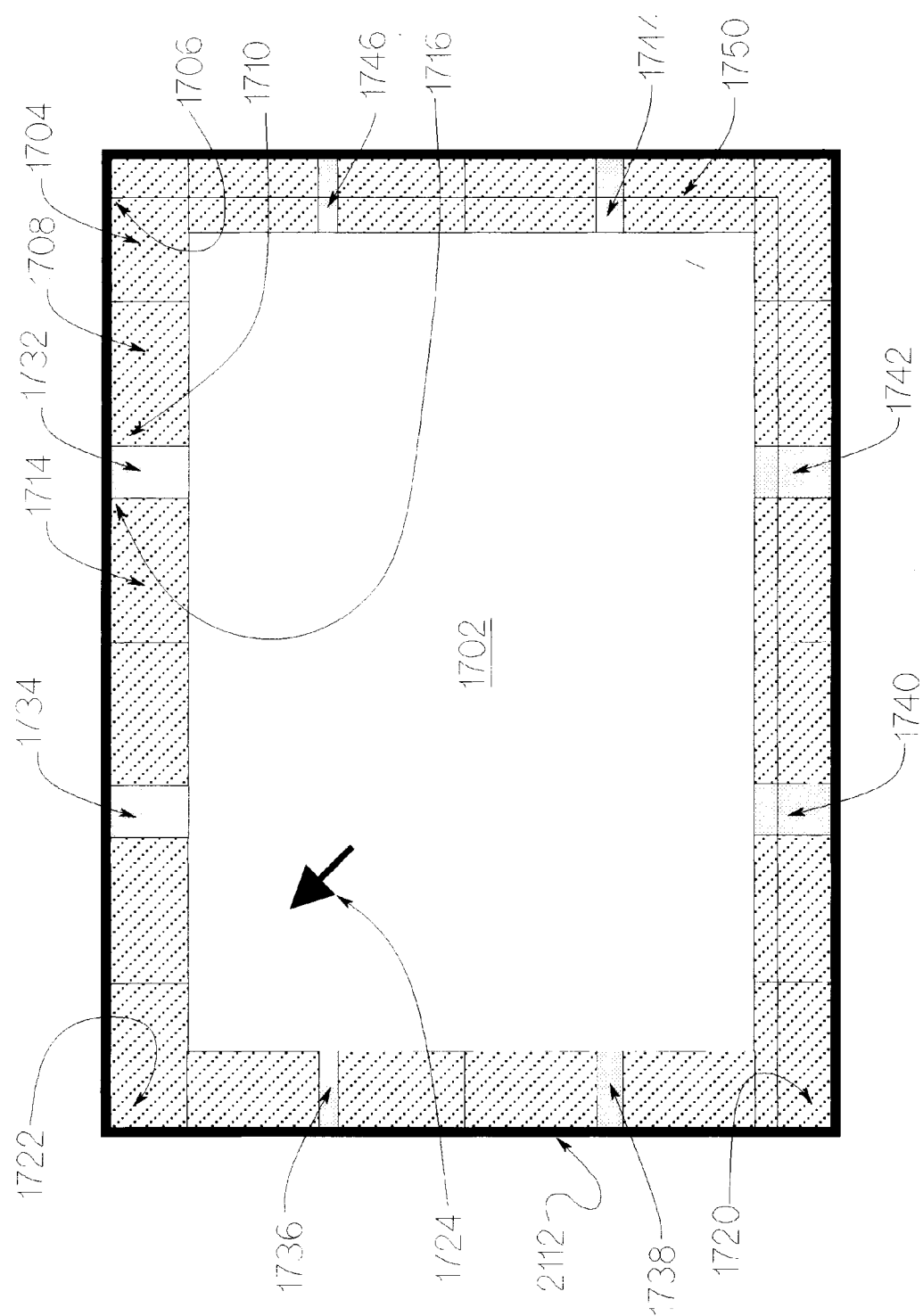
FIG. 31 is an illustration of a display and structures in accordance with the preferred embodiment of the Confinement aspect of the disclosure.

The preferred embodiment of the Confinement aspect of the disclosure will now be described in detail from a functional perspective using an example illustrated in FIG. 31. In FIG. 31, 20 selectable regions, e.g. (1704), (1708) and (1714), are depicted on display (2112). Each of the selectable regions is located on the display (2112) adjacent an edge of the display, and the selectable regions together circumscribe a region (1702) on the display. The top and left edges of the Windows® cursor clipping rectangle (1750) lie on the top and left edges, respectively, of the display (2112). The bottom and right edges of the Windows® cursor clipping rectangle (1750) lie on the display parallel to and slightly indented from the bottom and right edges, respectively, of the display. A confining polygon is delimited on the display. The boundary of the confining polygon, starting from the upper right corner of the Windows® cursor clipping rectangle, follows the top edge of the Windows® cursor clipping rectangle to the left until it reaches region (1732), where the boundary follows the side of region (1732) down, to the left, and back up to the top edge of the Windows® cursor clipping rectangle. The boundary continues left along the top edge of the Windows® cursor clipping rectangle until it reaches region (1734), where the boundary follows the side of region (1734) down, to the left, and back up to the top edge of the Windows® cursor clipping rectangle. The boundary continues left along the top edge of the Windows® cursor clipping rectangle to the upper left corner and then turns down along the left edge of the Windows® cursor clipping rectangle until it reaches region (1736), where the boundary follows the side of region (1736) to the right, down, and to the left to the left edge of the Windows® cursor clipping rectangle. The boundary of the confining polygon continues in this fashion around to the upper right corner of the Windows® cursor clipping rectangle. The confining polygon thus includes all the area of the Windows® cursor clipping rectangle except for the regions (1732), (1734), (1736), (1738), (1740), (1742), (1744), and (1746). An operator controlling a pointer indicating successive locations with respect to the display and attempting to select a target selectable region may overshoot the target so that some of the successive locations lie outside the Windows® cursor clipping rectangle. In the preferred embodiment of the Confinement aspect of the disclosure, the cursor (1724) is confined to the confining polygon. The preferred embodiment is responsive to an intersection of the cursor hotspot and any one selectable region so that an overshot selectable region may be selected by click or by dwell without moving the location presently indicated by the pointer to a location in the overshot selectable region. Thus, the preferred embodiment of the Confinement aspect of the disclosure allows an operator with impaired ability to stop motion to maintain the cursor more easily on a selectable region, and so select the intended selectable region, than do conventional user interface systems.

A selectable region having a single side abutting a confining polygon prevents cursor movement only beyond the abutting side. However, NMD operators who drift may drift in more than one direction. Assume that a certain NMD operator tends to drift both up and to the left and that he is attempting to select selectable region (1704). If he moves the cursor into that selectable region his upward drift will be confined; the drift will not move the cursor beyond the confining polygon. However, the cursor will move to the left, since, in the preferred embodiment of the Confinement aspect of the disclosure, movement in this direction is not affected by the confining polygon, and consequently the cursor may move into selectable region (1708), the selectable region to the left of selectable region (1704). NMD operators having this type of drift may be assisted in selecting by confining corners. For example, such an operator, attempting to select selectable region (1704) could move the cursor to location (1706) in selectable region (1704). As the operator drifts to the left, he can compensate by moving the pointer to the right. Assuming the operator lacks fine motor control, he may overcompensate and indicate a location to the right of the Windows® cursor clipping rectangle (1750). However, since the cursor is confined to the confining polygon, the cursor remains in the intended selectable region.

Confining corners facilitate the selection process for some NMD operators. The preferred embodiment of the Confinement aspect of the disclosure creates a corner or virtual corner in each selectable region. A virtual corner is a corner of a selectable region formed by the intersection of two sides of a selectable region both of which abut a confining polygon. For example, corner (1710) in selectable region (1708) abuts the confining polygon both along the top edge of the Windows® cursor clipping rectangle and along the right side of region (1732). If an NMD operator drifts from selectable region (1708) to the left into region (1732), the cursor remains in selectable region (1708). Thus, drift to the left does not move the cursor out of selectable region (1732). An operator trying to select selectable region (1708) may overcompensate for drift to the right by moving the pointer to indicate a location in region (1732).

Figure 32:
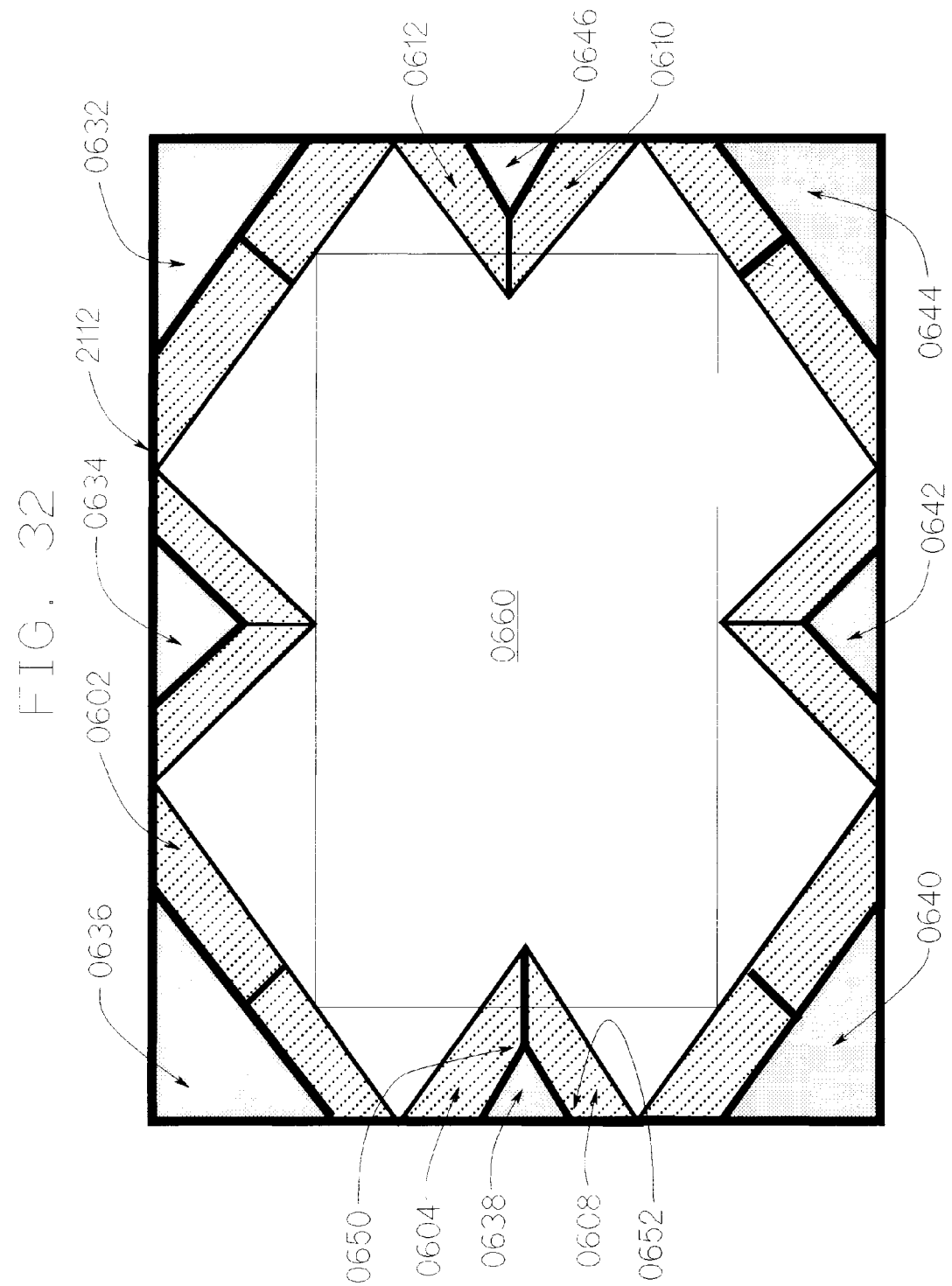
FIG. 32 is an illustration of a display and structures in accordance with another embodiment of the Confinement aspect of the disclosure.

FIG. 32 illustrates a display in accordance with an alternative embodiment of the Confinement aspect of the disclosure. FIG. 32 depicts 16 selectable regions, e.g. selectable region (0602), on a display (2112), the selectable regions together at least partially circumscribing region (0660) on the display. Circumscribed region (0660) intersects four selectable regions, (0604), (0608), (0610), and (0612). Selectable region (0608) includes virtual corner (0652). The confining polygon includes all the area of the Windows® cursor clipping rectangle except for regions (0632), (0634), (0636), (0638), (0640), (0642), (0644), and (0646).

Figure 33:
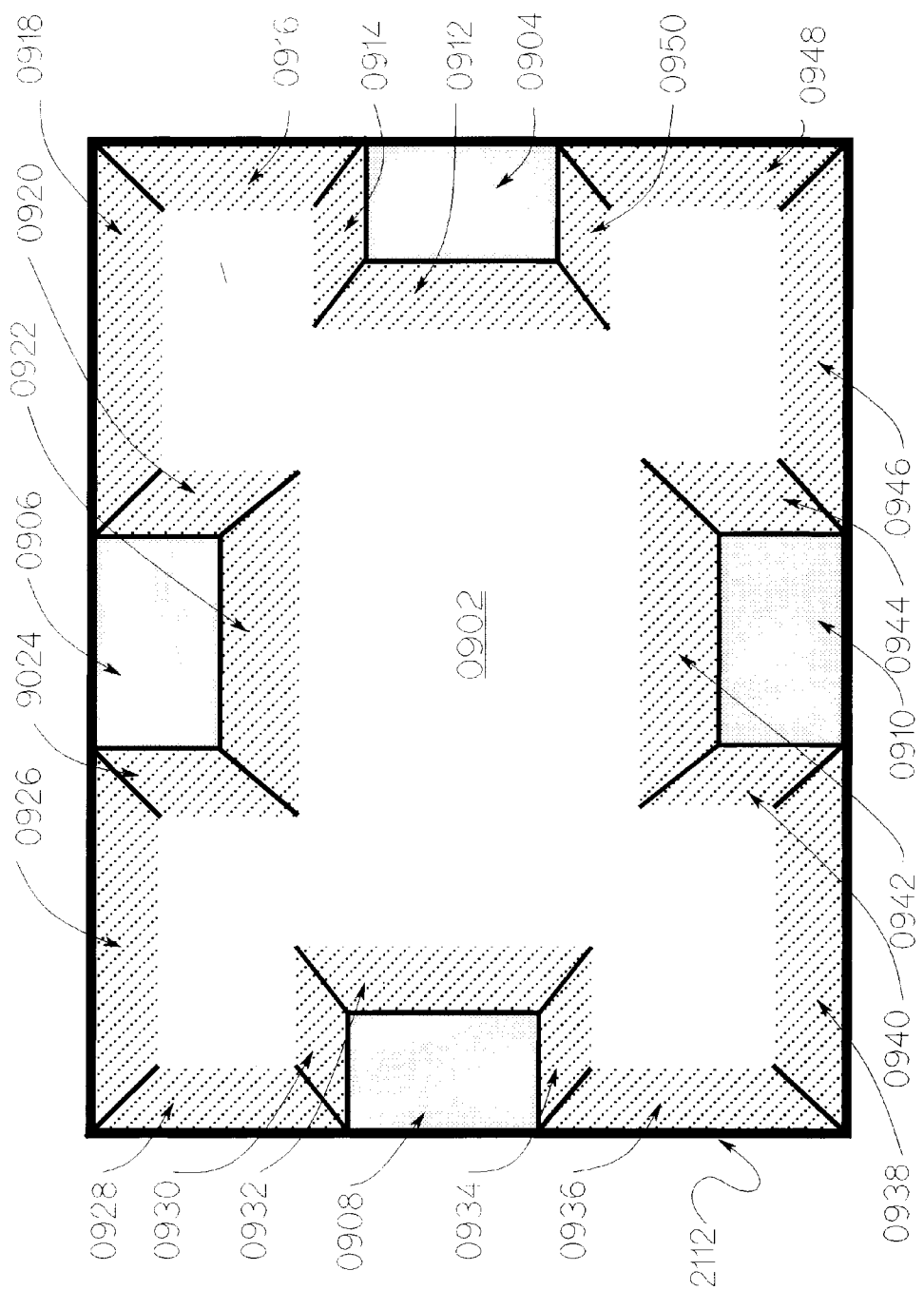
FIG. 33 is an illustration of a display and structures in accordance with another embodiment of the Confinement aspect of the disclosure.

FIG. 33 illustrates a display and structures in accordance with an another embodiment of the Confinement aspect of the disclosure. FIG. 33 depicts 20 selectable regions, e.g. selectable region (0918), on a display (2112), the selectable regions together at least partially circumscribing region (0902) on the display. The confining polygon includes all the area of the Windows® cursor clipping rectangle except for regions (0906), (0908), (0910), and (0904).

The preferred embodiment of the Confinement aspect of the disclosure will now be described in detail from an implementation perspective. Preferably, the Confinement aspect is implemented by modifications to the access program (1206) described in the detailed description of the Perimeter Menu aspect of the disclosure. The modifications required are: (1) define 20 state machines and 20 respectively associated selectable regions located as shown in FIG. 31; (2) at initialization time, create a Windows® region corresponding to the confining polygon described above in the functional description of the preferred embodiment of the Confinement aspect of the disclosure; and (3) modify the procedure CreateEvent so that before generating an EV_CROSS_OUT event, CreateEvent determines whether the current hotspot cursor location intersects the confining polygon, and, if not, set the Windows® hotspot cursor location to the previous hotspot cursor location and transfers control to the code at the beginning of the CreateEvent procedure which gets the current cursor hotspot location from Windows®. If the current hotspot cursor location intersects the confining polygon, CreateEvent takes the same action as in the access program (1206).

C. Dwell

The preferred embodiment of the Dwell aspect of the disclosure will now be described in detail from a functional and implementation perspective. The prototype implements dynamic dwell. The effect of dwelling on a selectable region and its implementation have been described in the detailed description of the Perimeter Menu aspect of the disclosure. Now the effect and implementation of moving the cursor hotspot off a selectable region will be described.

Referring now to FIG. 17, assuming that the state machine associated with the selectable region (0104/0106) is in state ST_LOW_TIDE, that pPocket→Color has been incremented above its initial value, that the cursor hotspot intersected selectable region (0104/0106) at the last expiration of the cursor polling timer, and that the operator initiates movement of the cursor hotspot to the right from selectable region (0104/0106) toward selectable region (0132/0134) so that, when the cursor polling timer next expires, the cursor hotspot is located in area (0150) between visible subregions (0106) and (0134), the procedure CreateEvent determines that the state machine associated with selectable region (0104/0106) should receive EV_CROSS_OUT, which drives it from ST_LOW_TIDE to ST_LOW_TIDE. The state processing for ST_LOW_TIDE has already been described in the detailed description of the Perimeter Menu aspect of the disclosure.

Assuming that the operator continues to move the cursor hotspot toward selectable region (0132/0134), on the next expiration of the cursor polling timer, the procedure CreateEvent determines that the state machine associated with selectable region (0104/0106) should receive EV_MOVEMENT, which drives it from ST_LOW_TIDE to ST_DECAY. Stepping through the pseudo-code for ST_DECAY, the ST_DECAY state sets pPocket→State to the value stored in pPocket→PreviousState, decrements pPocket→Color by pPocket→Decrement, but not below the value of pPocket→InitialColor, sets pPocket→fPaint to TRUE, sets fInternalEvent to TRUE, and, in this case, sets Event to EV_NULL. Following the break statement, the while fInternalEvent condition is true and another state transition occurs. The new state is found at aPocketFsm[ST_LOW_TIDE][EV_NULL], which equals ST_LOW_TIDE. This path is unlike an ordinary state transition because the starting state is set by ST_DECAY. All transitions from ST_DECAY share this distinction. The state machine executes the code for the new state, ST_LOW_TIDE, which is simply a break statement. The procedure PocketFsm determines that fPaint is TRUE, invalidates the client rectangle and exits. As a result of invalidating the client rectangle, Windows® (1204) sends a WM_PAINT message to the access program (1206). On receipt of WM_PAINT, the access program (1204) checks the value of fPaint for each state machine, and if TRUE, sets fPaint to FALSE and redraws the visible subregion of the selectable region associated with that state machine and any menu option located thereon. The color of the redrawn visible subregion is determined by the value of the Color variable for that state machine. After redrawing, control returns to Windows® (1204).

If the movement of the cursor hotspot pause between successive samplings of its location, the procedure Create Event will determine that not EV_MOVEMENT, but EV_DECAY, should be sent to the state machine associated with selectable region (0104/0106). Like EV_DECAY, EV_MOVEMENT drives the state machine associated with selectable region (0104/0106) to ST_DECAY. The same state processing as described above for ST_DECAY takes place, including the transition back to ST_LOW_TIDE.

Assuming the operator maintains the cursor hotspot in area (0150), the state machine associated with selectable region (0104/0106) cycles repetitively through the state transitions from ST_LOW_TIDE to ST_DECAY to ST_LOW_TIDE, driven by the cursor polling timer. With each transition to ST_DECAY, visible subregion (0106) is darkened a bit. The polling timer interval is short enough and the decrement to pPocket→Color is small enough that visible subregion (0106) appears to gradually darken although in fact it progresses rapidly through a series of discrete brightness levels. With each iteration through ST_DECAY, pPocket→Color in decremented until pPocket→Color reaches pPocket→InitialColor.

When the cursor hotspot reaches selectable region (0132/0134), the procedure CreateEvent determines that the state machine associated with selectable region (0104/0106) should receive EV_DECAY, continuing the repetitively cycling through from ST_LOW_TIDE to ST_DECAY to ST_LOW_TIDE, driven by the cursor polling timer. Driven by the same polling timer, the procedure CreateEvent determines that the state machine associated with selectable region (0132/0134) should receive EV_DWELL, driving this state machine through the state transitions described in the detailed description of the Perimeter Menu aspect of the disclosure.

If the operator moves the cursor hotspot from selectable region (0132/0134) back to selectable region (0104/0106), the procedure CreateEvent determines that the state machine associated with selectable region (0104/0106) should receive EV_DWELL, driving this state machine through the state transitions described in the detailed description of the Perimeter Menu aspect of the disclosure.

In the prototype, the selectable regions are shown on a display (2112). Alternatively, the selectable regions may appear on a static display, or they may be projected on a surface.

In the prototype, the brightness of a visible subregion at any time indicates the progress of the selection of the selectable region including the visible subregion. A brightness close to the initial brightness indicates that a relatively long period of dwelling on this selectable region is required for selection. A brightness close to the brightness just prior to selection indicates that relatively short period of dwelling on this selectable region is required for selection. However, means for indicating an intersection of the location indicated by the movement related signal and a selectable region, or the duration of a period of such an intersection includes, but is not limited to, a change in cursor appearance or location, a change in location, size, shape, hue, brightness, contrast, tone, dithering, pattern, hatching, font or fill of an object on the surface, a display of or change in a graphic on the surface or the removal of a graphic from the surface, a generation of a sound or a change in the pitch or volume of an extant sound, a change in the temperature or surface of a contact area, the pressure exerted by a contact area, or frequency of contact by a contact area, or other suitable means. Any of these indications may be continuous or frequent.

Although dwell is implemented in the prototype using a data value, specifically pPocket→Color, it may be implemented using a signal, for example, voltage or current, varying in response to the intersection and subsequent non-intersection of a location indicated by a pointer and a selectable region. For example, a selectable region may include a detector and coupled electronics or electrical circuitry operative to increase the voltage level of a capacitor. Once elevated, the voltage level may decrease over time. Upon reaching a predetermined threshold, the voltage level may trigger selection.

The prototype allows an operator to make selections by dwell more efficiently than in conventional systems. In the prototype, the brightness of a visible subregion indicates the dwell time required for selection. A practiced operator may accurately estimate when he may plan his next pointer movement, when he may begin moving the pointer and may determine when a bit more exertion will select a selectable region and when it will not. Thus a disabled operator who is fatigued by computer access and can maintain a pointer in a steady position for only brief periods, may optimize his energy expenditure, for example, exerting himself to maintain the cursor on a certain selectable region only when doing so will quickly select the selectable region.

The prototype may increase the independence of a disable individual by allowing him to control devices such as a TV, thermostat and other household appliances. As stated earlier, the Perimeter Menu aspect of the disclosure may be implemented on a general purpose computer system. If the general purpose computer system is coupled to a devices capable of executing commands and the menu hierarchy allows the selection of commands, a disabled operator may select and issue commands to control these devices.

Figure 34:
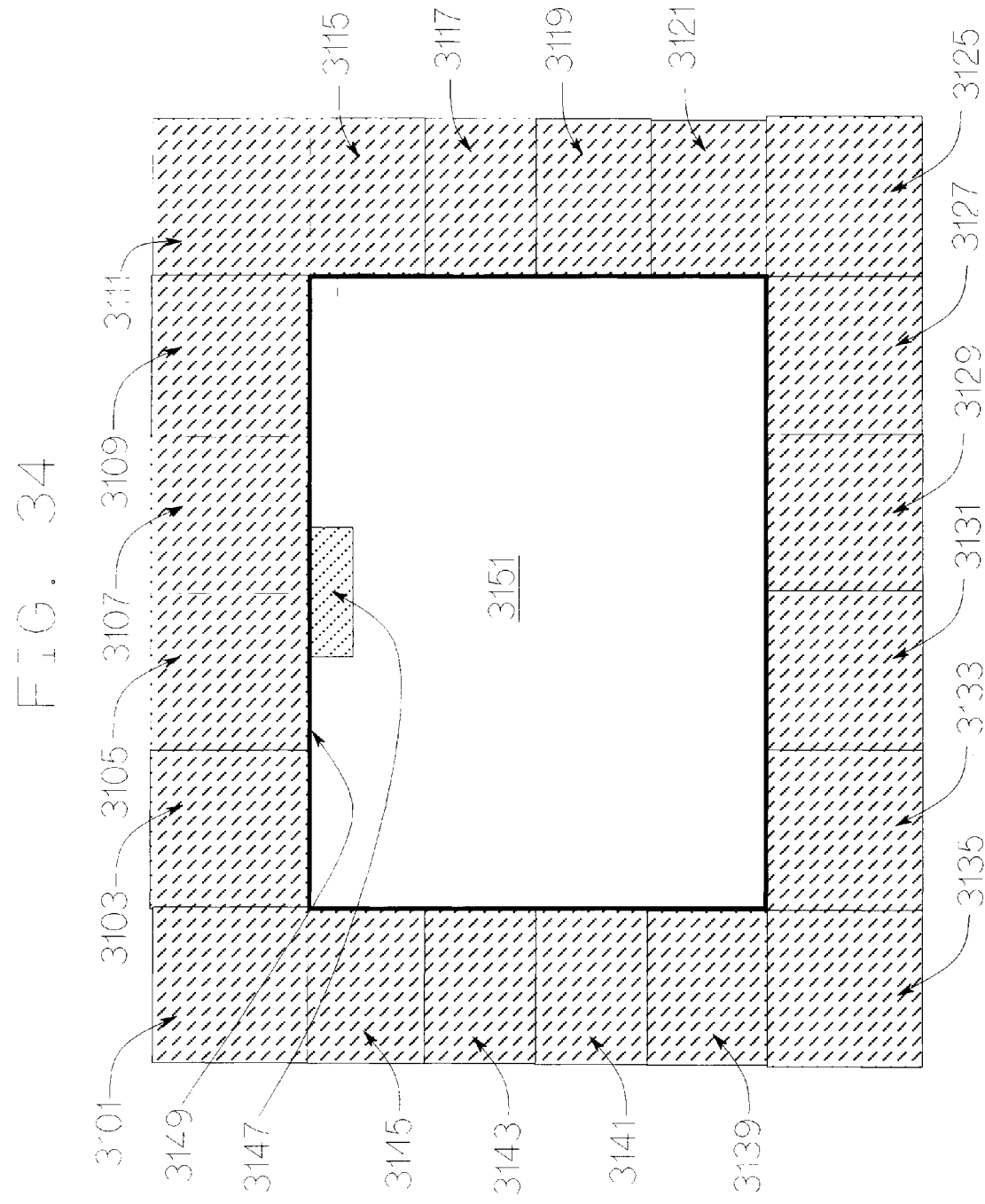
FIG. 34 is an illustration of an apparatus in accordance with the Dwell aspect of the disclosure and with the Path Directness aspect of the disclosure.

FIG. 34 illustrates a display in accordance with of an embodiment of the Dwell aspect of the disclosure having 20 selectable regions (3101), (3103), (3105), (3107), (3109), (3111), (3115), (3117), (3119), (3121), (3125), (3127), (3129), (3131), (3133), (3135), (3139), (3141), (3143), and (3145) circumscribing a surface (3151) having an indicating region (3147) thereon.

Figure 35:
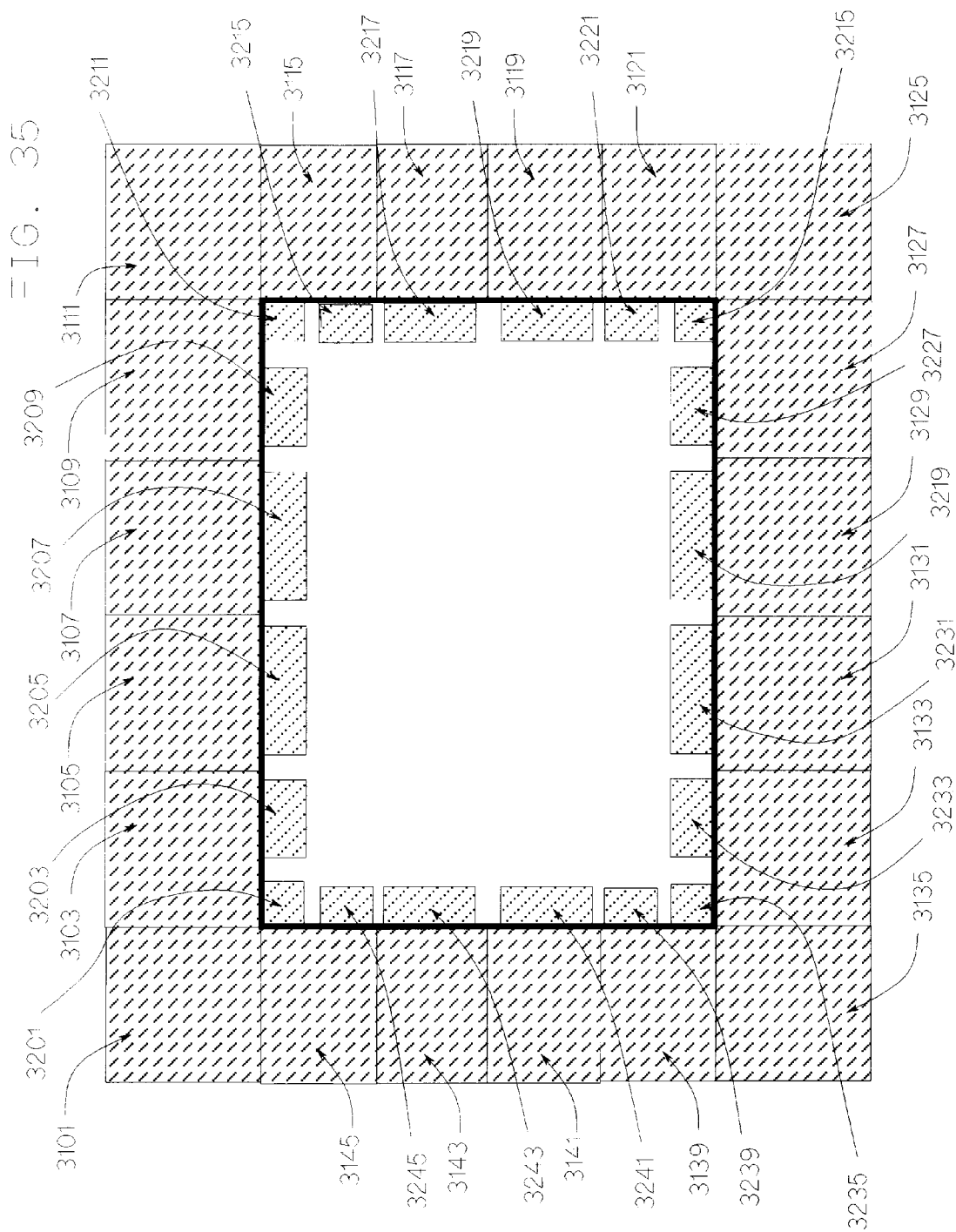
FIG. 35 is an illustration of another apparatus in accordance with the Dwell aspect of the disclosure.

FIG. 35 illustrates an apparatus in accordance with of an embodiment of the Dwell aspect of the disclosure having 20 selectable regions circumscribing a surface, each selectable region associated respectively with an indicating region adjacent its associated selectable region. Selectable region (3101) is associated with indicating region (3201), selectable region (3103) with indicating region (3203), etc.

Figure 36:
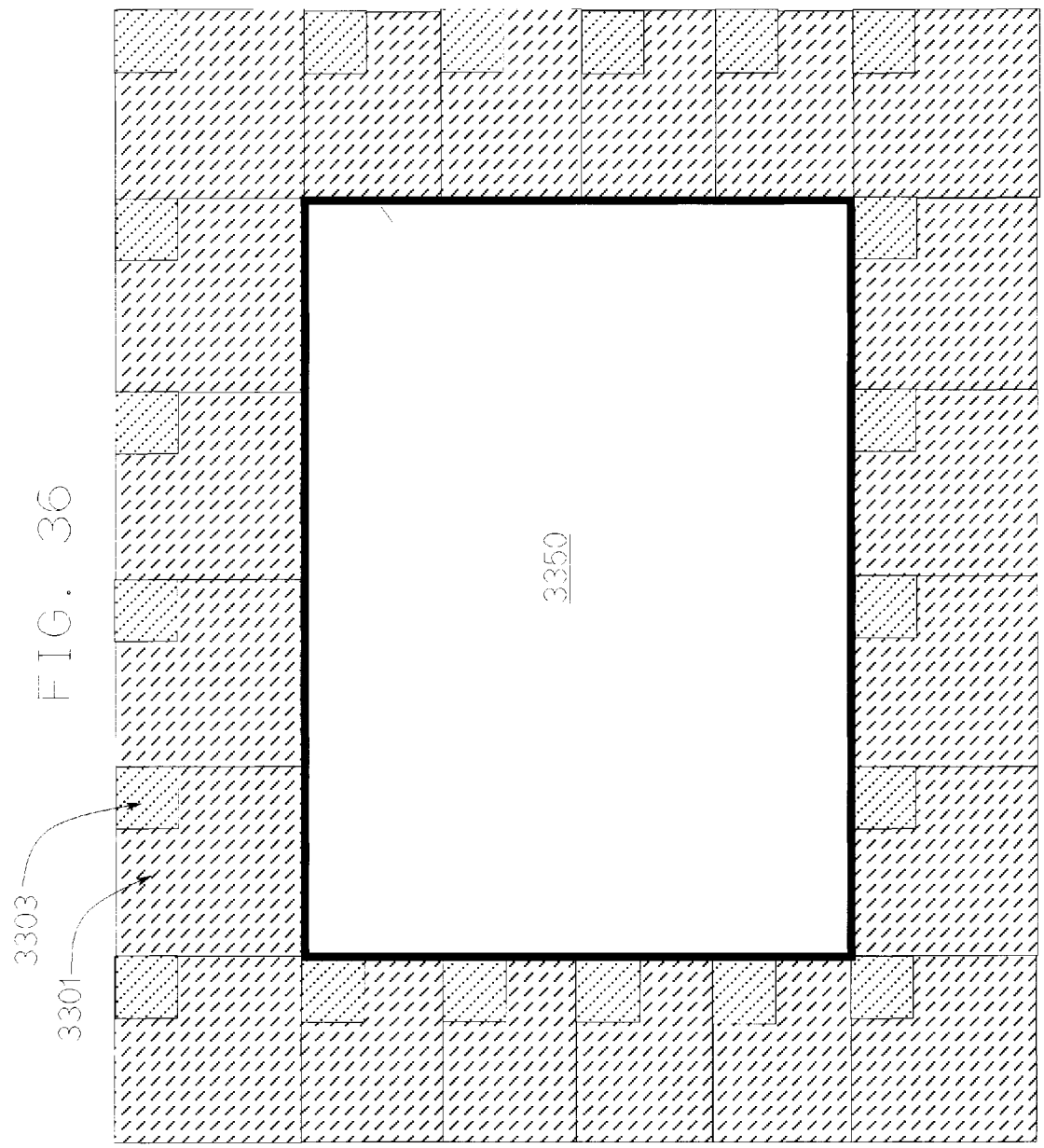
FIG. 36 is an illustration of still another apparatus in accordance with the Dwell aspect of the disclosure.

FIG. 36 illustrates an apparatus in accordance with of an embodiment of the Dwell aspect of the disclosure having 20 detectors circumscribing an aperture (3350), each detector associated respectively with an indicator intersecting its associated detector, e.g. detector (3301) is associated with indicator (3303).

Figure 37:
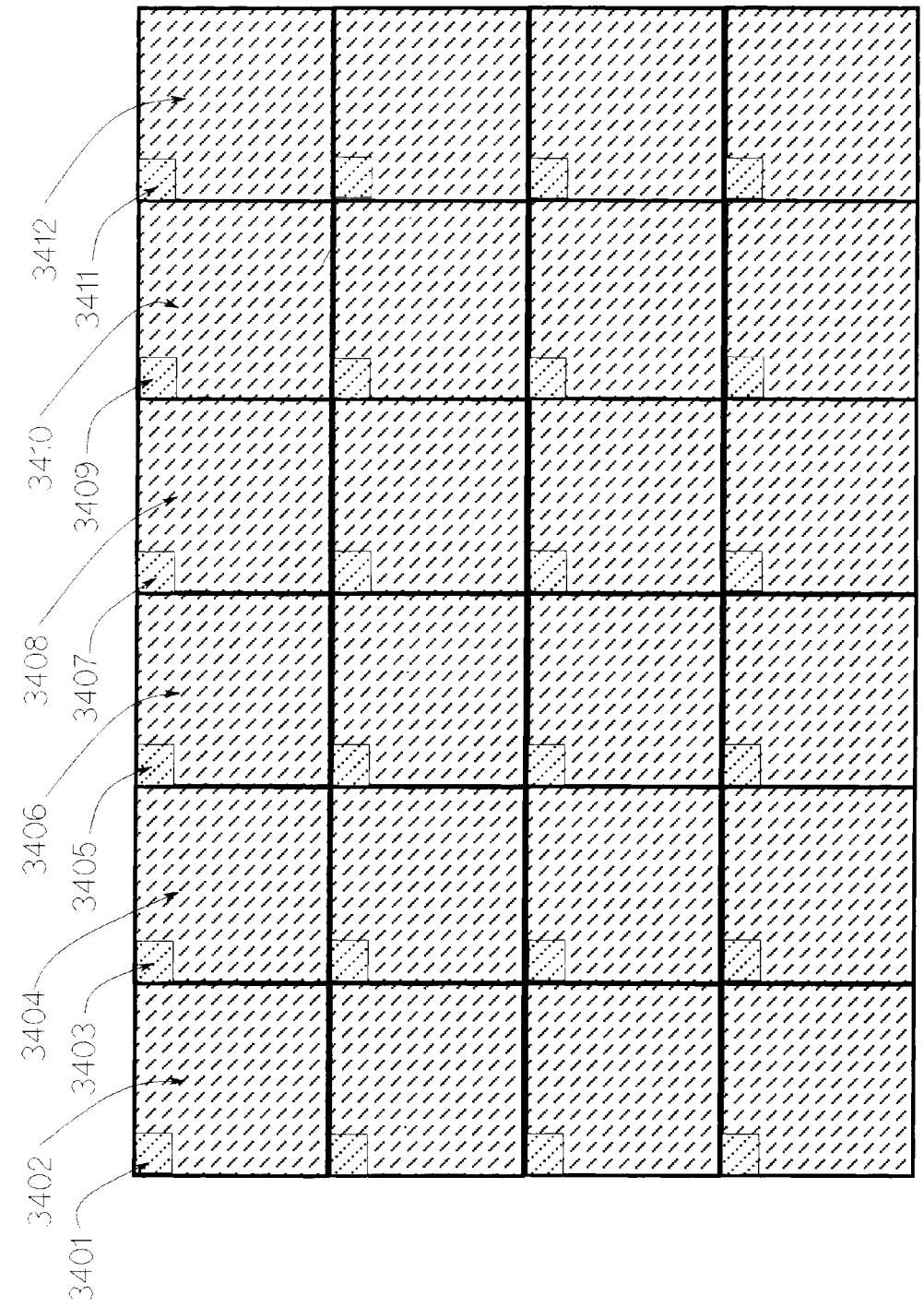
FIG. 37 is an illustration of yet another apparatus in accordance with the Dwell aspect of the disclosure.

FIG. 37 illustrates an apparatus in accordance with of an embodiment of the Dwell aspect of the disclosure having 24 selectable regions arranged in a grid of four rows and six columns, each selectable region associated respectively with an indicating region intersecting its associated selectable region. For example, selectable region (3402) is associated with indicating region (3401).

Figure 38:
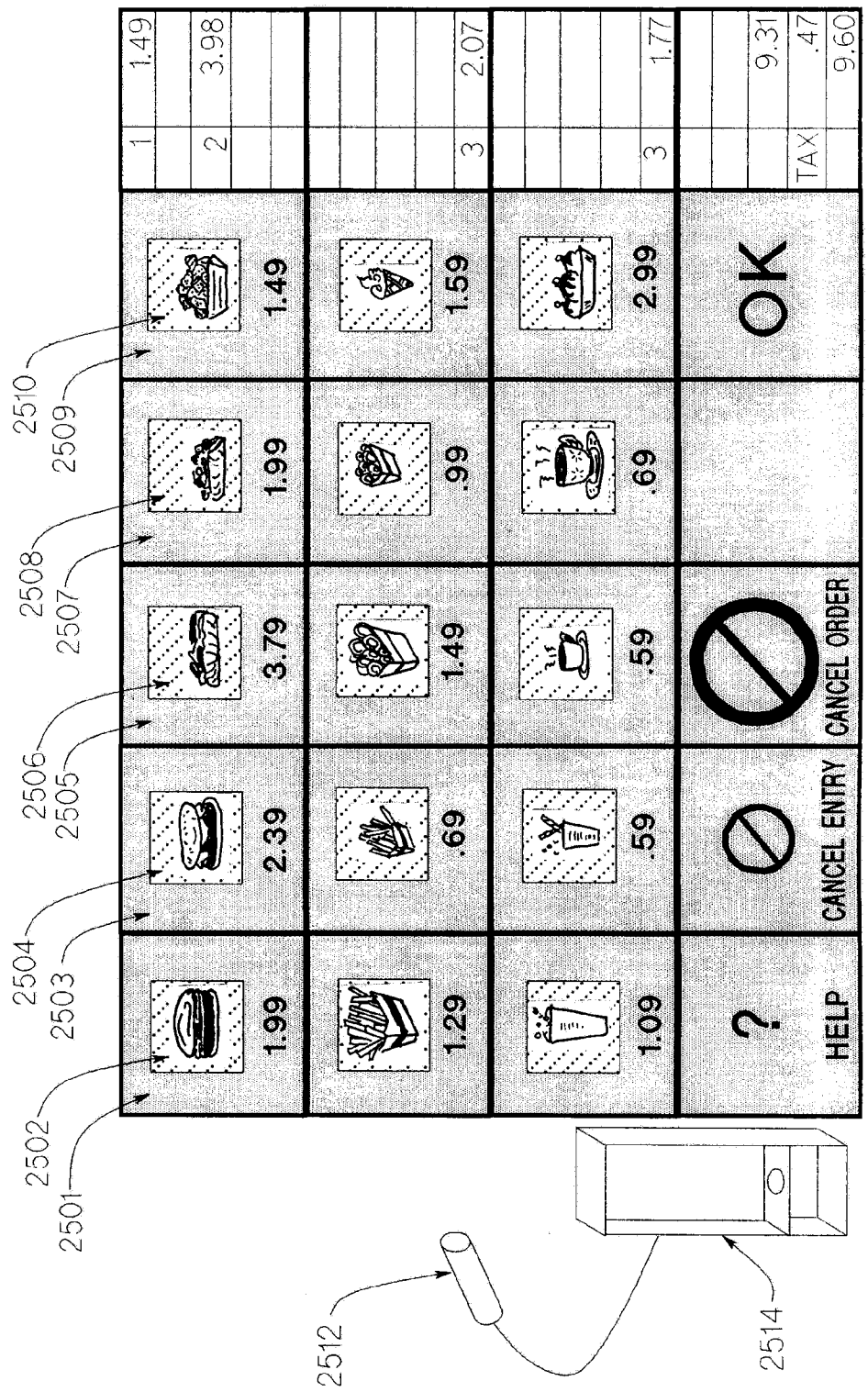
FIG. 38 is an illustration of another apparatus in accordance with the Dwell aspect of the disclosure.

FIG. 38 illustrates a display in accordance with of an embodiment of the Dwell aspect of the disclosure having a plurality of detectors, (2501), (2503), (2505), etc., arranged in a grid. Each detector is associated respectively with an indicator intersecting its associated detector, e.g. detector (2501) is associated with indicator (2502). Each detector is also associated respectively with an order entry item which may be selected by dwell. For example, detector (2501) is associated with a hamburger. Pointer (2512) (not drawn to scale) emits energy detectable by the detectors. Pointer (2512) may be housed in stationary housing (2514) (not drawn to scale).

Means for determining the difference between two data items or signals and means for totaling two or more data items or signals may each include a processing unit programmed to calculate this difference or total. Alternatively, the difference or total may be determined by electronic, mechanical, optical, or other suitable means.

The two step procedure described earlier for operating conventional menu-driven data entry and order entry systems incorporating pointing at intended selections may be simplified to a single step in accordance with the Dwell aspect of the disclosure. Referring now to FIG. 38, the operator points pointer (2512) at an order entry item. The item brightens responsive to the signals falling on the associated detector, indicating to the operator which order entry item he is dwelling on and his dwell time on that order entry item. When his dwell time equals or exceeds the selection threshold, the order entry item is selected. The operation of such a system is intuitive and may be learned or relearned by pointing and dwelling. No surface is required, unlike a standard mouse. Additionally, an operator seated in the driver's seat of a vehicle is probably right-handed and may be making selections with his left hand, the hand closest to the window in a left-hand drive vehicle. Pointing and maintaining a pointer in a steady position requires less coordination than pointing and clicking.

D. Path Directness

The Path Directness aspect of the disclosure includes several aspects, hereinafter "subaspects", called Facilitated Dwell, Direction and Intersection, Direction, Appraisal and Drift Attenuation. The preferred embodiment and certain alternative embodiments of each of these subaspects will now be described.

Figure 39:
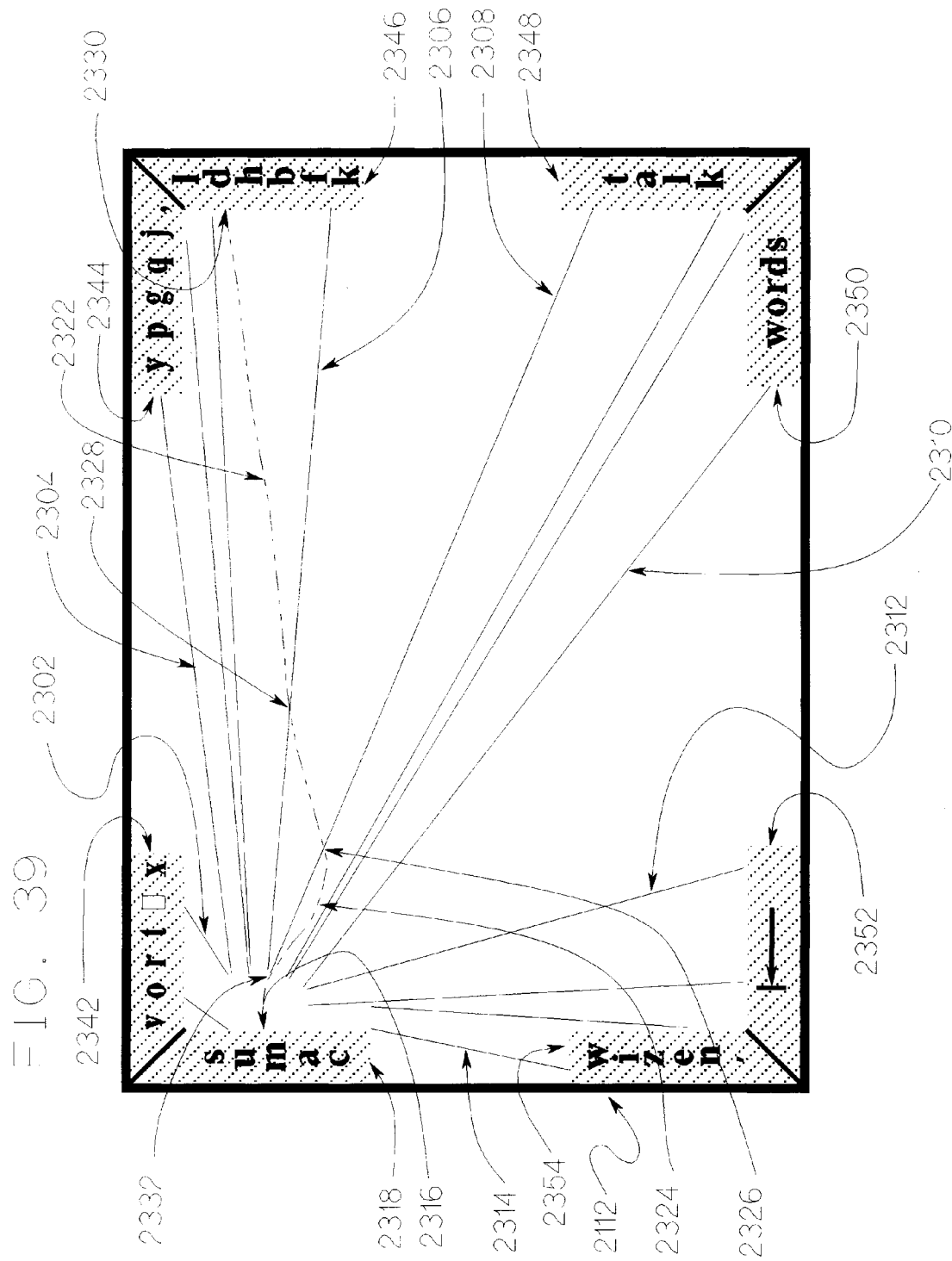
FIG. 39 is an illustration of a display and structures in accordance with the preferred embodiment of the Path Directness aspect of the disclosure.

According to the Facilitated Dwell subaspect of the disclosure, the duration of the dwell period required for selection ("selection threshold period") of a menu option associated with a selectable region varies with the directness of the cursor's path to that selectable region. The preferred embodiment of the Facilitated Dwell subaspect of the disclosure will now be described in detail from a functional perspective using an example illustrated in FIG. 39. In FIG. 39 on display (2112) are defined corridors (2302), (2304), (2306), (2308), (2310), (2312) and (2314) lying between the previously selected selectable region (2318) and, respectively, selectable regions (2342), (2344), (2346), (2348), (2350), (2352) and (2354). Each selectable region is associated respectively with a selection threshold period. Each cursor location in a cursor path, for example cursor path (2322), may slightly decrease one or more the selection threshold periods, except for the selection threshold period associated with the previously selected selectable region, selectable region (2318) in this example. The effect of a cursor location depends, in the preferred embodiment, on whether that cursor location intersects one of the corridors. If it does, as for example location (2324) intersects corridor (2308), then the selection threshold period associated with the selectable region to which the intersected corridor leads, (2348) in this example, is decreased, preferably to a limit of approximately 20% of the initial value of the selection threshold period so that some period of intersection of the cursor and the intended selectable region is still required for selection. A changed selection threshold period is preferably indicated by a change in the brightness of the selectable region associated with the changed selection threshold period. Thus, when the operator moves the cursor within a corridor, the selectable region associated with the corridor brightens, indicating both the target selectable region the system believes the cursor is headed toward and the changed selection threshold period. When the operator moves the cursor outside a corridor the cursor had previously intersected, the selectable region associated with the previously intersected corridor darkens in accord with the dynamic dwell aspect of the disclosure, indicating both that the system no longer believes the cursor is headed toward that selectable region and the changed selection threshold period. Reducing the selection threshold period facilitates selection of dwell-selectable regions without unduly increasing the likelihood of erroneous selections, since cursor locations within a corridor evidence the operator's intention to select the selectable region associated with the corridor.

Preferably, corridors are hidden from view, but they may be may be shown on the display or shown only at certain times or under certain conditions. Corridors may have fixed boundaries, depending on which selectable region has been selected, or their boundaries may be determined when a starting location, for example, cursor location (2316) in FIG. 39, is known. Corridor shape, size, number and position about the associated selectable region may vary, as illustrated by the alterative embodiments shown in FIGS. 40 and 41. Where corridors overlap, a cursor location intersecting two or more corridors may be defined to be in a cursor path toward zero, one or more selectable regions associated with the intersected corridors.

The intersection of a cursor location and a corridor is but one means of identifying which one of a plurality of selectable regions is most nearly along a cursor path. A cursor path may be indicated by an intersection of a cursor location and a predetermined region, e.g. a corridor, by a cursor location and a movement related signal from which may be derived a second location, or by two or more successive cursor locations. As used herein, successive locations include a plurality of locations distributed in time. Successive location may be, but need not be, consecutive. Given a location and a movement related signal or two locations, an intention to select a particular selectable region may be inferred, for example, by extrapolation, and the selection thresholds associated with either or both the intended or unintended selectable regions modified accordingly. As an example, assume successive cursor locations are periodically stored in a ring buffer and the magnitude of the angle between two line segments, the first between the oldest cursor location in the ring buffer and a predetermined point in the selectable region, and the second between the oldest cursor location in the ring buffer and the current cursor location, is determined. The selectable region associated with the smallest of these angles may be considered to be the selectable region most nearly along the cursor path indicated by the first line segment.

An alternative means of identifying which one of a plurality of selectable region is most nearly along a cursor path is to determine the ratio of the number cursor locations indicating a selectable region to the total cursor locations in the cursor path.

Figure 42:
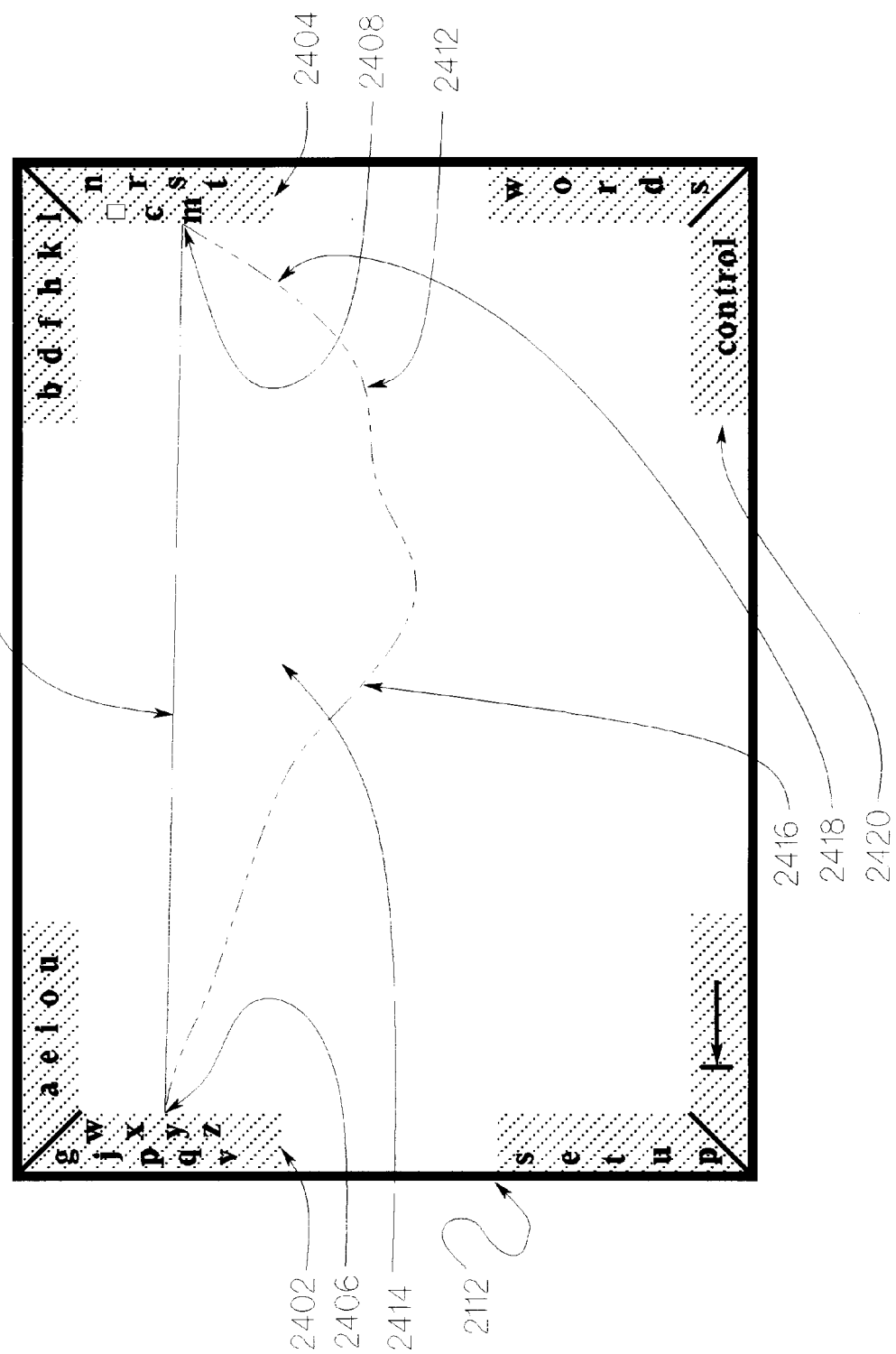
FIG. 42 is an illustration of a display and structures in accordance with another embodiment of the Path Directness aspect of the disclosure.

FIG. 42 illustrates still another alternative means for identifying which one of a plurality of selectable regions is most nearly along a cursor path. FIG. 42 shows line (2410) from starting cursor location (2406) to ending cursor location (2408) just within selectable region (2404). Line (2410) is the most direct path between these two points. In this example, the actual path traveled by the cursor between these two points is path (2412). The ending cursor location (2408) is known before the selection threshold period associated with selectable region (2404) is modified. Identification may be made by measuring or approximating the area within region (2414) bounded by line (2410) and cursor path (2412). The smaller the area, the more direct the cursor path. Alternatively, identification may be made by storing a sampling among successive cursor locations along a cursor path and, in response to the cursor intersecting a selectable region, the selectable region most nearly along the cursor path may be identified at one or more sampled points along the cursor path. The identification may be based upon a plurality of cursor locations or upon a single cursor location and a movement related signal. Alternatively, identification may be made by measuring and comparing the number of times a cursor path diverges from a predetermined path toward the intersected selectable region and/or the degree of divergence of a cursor path from a predetermined path toward the intersected selectable region.

Another apparatus in accord with the Path Directness aspect of the disclosure is illustrated in FIG. 34. In this Figure, selectable regions (3101), (3103), (3105), (3107), (3109), (3111), (3115), (3117), (3119), (3121), (3125), (3127), (3129), (3131), (3133), (3135), (3139), (3141), (3143) and (3145) circumscribe area (3151). Area (3151) and optionally the selectable regions include detectors for sensing radiant energy emitted from a pointer (2202) coupled to a body member of the operator. A computer coupled to the detectors determines which selectable region is most nearly along the path indicated by the body member of the operator. Responsive to the indicated path, the embodiment may facilitate the selection of one of the selectable regions by reducing a selection threshold, may select a selectable region upon intersection of the point indicated by the pointer (2202) and a selectable region, or may select a particular selectable region in advance of intersection of the point indicated by the pointer (2202) and the particular selectable region.

A move direction of a body member of an operator may be determined in any way that a cursor path may be determined, including sampling among data indicative of position of the body member. In determining move direction of a body member, data indicative of body member positions may serve the same function as cursor locations in indicating a path toward a selectable region. Position indicating means, used, for example, in indicating a position of the body member, includes each of the means for indicating that a selection event has occurred.

As an alternative to decreasing a selection threshold period, an embodiment may include a plurality of selection thresholds, each associated respectively with a selectable region. One or more of the selection thresholds may be increased when the direction of cursor movement does not indicate a path toward the associated selectable region.

Means for indicating which one of the plurality of selectable regions is most nearly along the cursor path includes each of the means for indicating an intersection of the location indicated by the movement related signal and a selectable region.

According to the Direction and Intersection subaspect of the disclosure, the selection threshold period is completely satisfied in response to a cursor path to a particular selectable region, so that when the cursor intersects the particular selectable region, that region is selected. Preferably, the selection threshold period is completely satisfied in response to a measure of directness of a cursor path to a particular selectable region equalling or exceeding a predetermined measure of directness. In circumstances where the measured directness is less than the predetermined measure, a dwell period is required for selection of the particular selectable region.

According to the Direction subaspect of the disclosure, a selectable region is selected in response to a cursor path to that selectable region, in advance of an intersection of the cursor and that selectable region. Preferably, the selectable region is selected in response to a measure of directness of a cursor path to a particular selectable region equalling or exceeding a predetermined measure of directness. In circumstances where the measured directness is less than the predetermined measure, a dwell period is required for selection of the particular selectable region.

According to the Appraisal subaspect of the disclosure, the directness of a cursor path to a selectable region is measured. Preferably, the means for measuring the directness of a cursor path includes each of the means for identifying which one of a plurality of selectable regions is most nearly along a cursor path. Thus, the particular means for identifying which one of a plurality of selectable regions is most nearly along a cursor path which best correlates with an operator's intended target selectable region may be identified.

As earlier described, some NMD operators have relatively unimpaired directional control, despite having other movement disorders. The Facilitated Dwell, Direction and Intersection, and Direction subaspects of the Path Directness aspect of the disclosure utilize that capability for computer access. Specifically, the ability of an operator to move a cursor in a direct path toward a selectable region is used to facilitate selection of that selectable region. The selectable region is selected more quickly than in conventional systems utilizing selection by dwell, increasing operator productivity. In addition, when selectable regions are located in accordance with the Perimeter Menu aspect of the disclosure, a cursor path toward a selectable region is often unambiguous, since usually there is only one selectable region along a cursor path, and a large rectangular area on the display is available for the output of an application program and is not obstructed by the menu. In certain embodiments in accordance with the Facilitated Dwell, Direction and Intersection, and Direction subaspects of the Path Directness aspect of the disclosure, the operator may receive an indication of which selectable region the system believes the operator is moving the cursor toward. The operator may adjust the cursor path in response to this feedback and thus move the pointer more accurately. Additionally, in embodiments in accordance with both the Facilitated Dwell subaspect of the Path Directness aspect of the disclosure and the Dwell aspect of the disclosure, the operator may receive an indication of the dwell time required to select the selectable region most nearly along the cursor path as the required dwell time changes in response to the cursor path.

Figure 43:
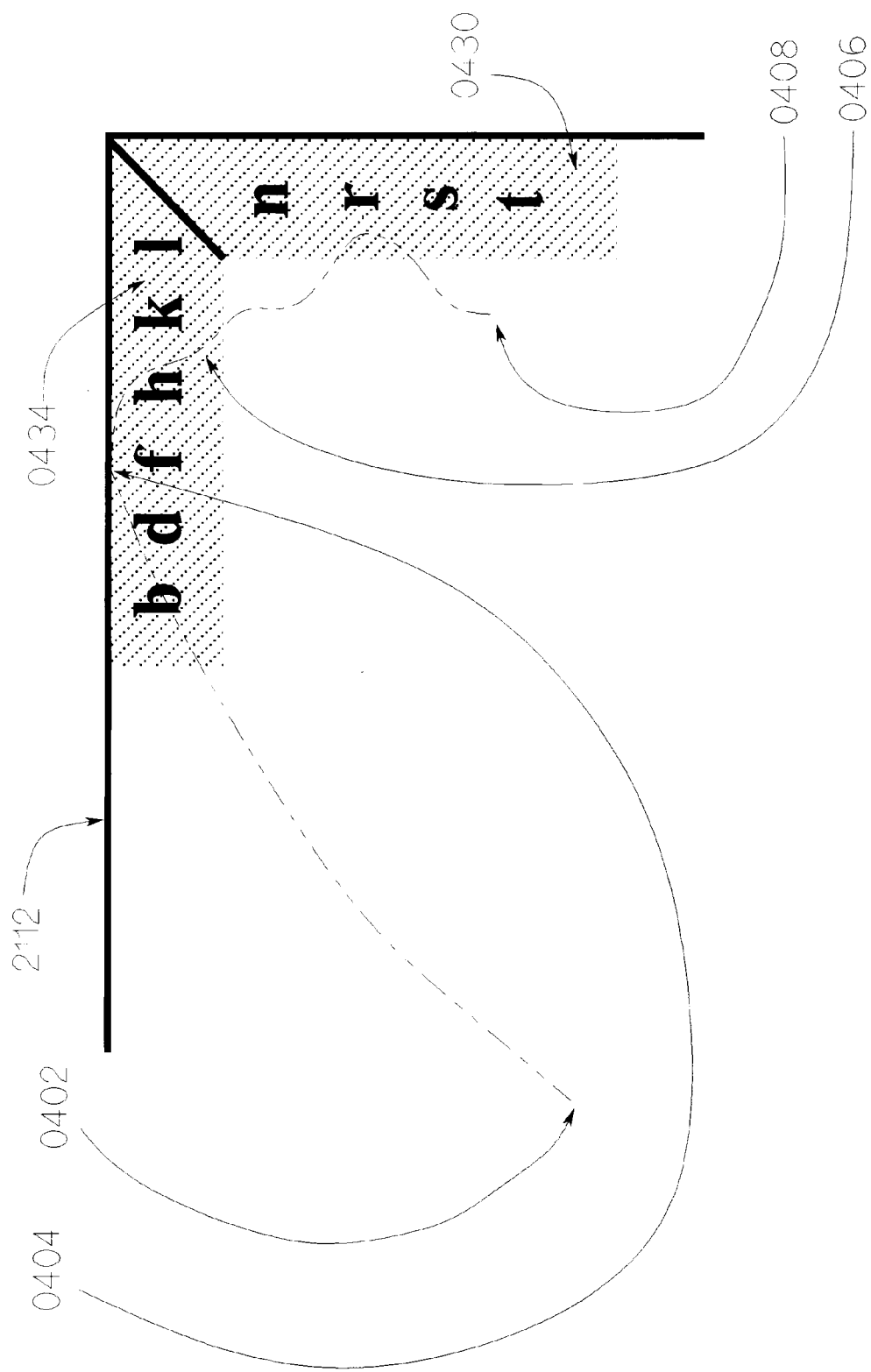
FIG. 43 is an illustration of a display and structures in accordance with another embodiment of the Path Directness aspect of the disclosure.

The preferred embodiment of the Drift Attenuation subaspect of the disclosure will now be described in detail from a functional perspective using an example illustrated in FIG. 43. FIG. 43 depicts the upper right corner of a display (2112) having two selectable regions (0434) and (0430) thereon. Assuming, for purposes of this example, that a movement related signal indicates the path shown from point (0402) to point (0404) ("first segment") at a relatively high velocity and from point (0404) to point (0408) ("second segment") at a relatively low velocity. The path of the first segment is relatively direct, the path of the second segment, relatively meandering. During receipt of the movement related signal for the first segment, the cursor preferably tracks the exact path indicated by the movement related signal. During receipt of the movement related signal for the second segment, the movement of the cursor is attenuated, preferably so that the cursor does not leave selectable region (0434) until it is selected.

Many NMD operators are unable to cleanly stop movement of a body member, resulting in a relatively slow or meandering path being indicated by the movement related signal. According to the Drift Attenuation subaspect of the disclosure, drift, that is, unintentional movement, indicated by the movement related signal following intentional movement is distinguished from the intentional movement, and cursor movement responsive to the drift is attenuated relative to cursor movement responsive to intentional movement. Thus unintentional movements of NMD operators are filtered so that the cursor is displayed closer to the location intended by the operator and drifting of the cursor into a nearby, but unintended, selectable region, is avoided, resulting in fewer errors due to unintended selections.

The preferred embodiment of each subaspect of the Path Directness aspect of the disclosure will now be described in detail from an implementation perspective. Preferably, the Facilitated Dwell subaspect is implemented by modifications to the access program (1206) described in the detailed description of the Perimeter Menu aspect of the disclosure. The modifications required are: (1) Additional state processing should be added to ST_SELECTED to create a Windows® region in the shape of a corridor starting a predetermined distance from the selected selectable region to each of the other selectable regions; (2) The event data structure should be expanded to accommodate an event for a selectable region along a cursor path; (3) The procedure CreateEvent should be changed so that, before setting an event to EV_DECAY or EV_MOVEMENT, a test is made for the intersection of the cursor hotspot and each corridor, and, on finding such an intersection, a new event, EV_CORRIDOR, is stored in the event data structure indicated by pEvent for the selectable region associated with the intersected corridor; (4) A column should be added to the state table so that each state which in the prototype may receive either EV_MOVEMENT or EV_DECAY will on receipt of EV_CORRIDOR drive that state machine to ST_CORRIDOR; (5) An additional variable, Corridorincrement, preferably having an initial value one half the value of Increment, should be added the set of data associated with each state machine; and (6) A new state, ST_CORRIDOR, should be added to the procedure PocketFsm. The pseudo-code for state processing in ST_CORRIDOR follows:

```
case ST_CORRIDOR:
                            /* set state to previous state   */
                            /* in preparation for the next   */
                            /* state transition              */
     set pPocket->State to pPocket->PreviousState
     increment pPocket->Color by
     pPocket->CorridorIncrement, but not above
     pPocket->InitialColor plus 80% of the difference
     between pPocket->CrestTide and
     pPocket->InitialColor
     if pPocket->Color was changed
         set pPocket->fPaint to TRUE
     set fInternalEvent to TRUE
     set Event to EV_NULL
     break
```

An example of the selection of selectable region (2346) in accord with the preferred embodiment of the Facilitated Dwell subaspect of the disclosure will now be described with reference to FIG. 39, assuming that the prototype has been modified as described, that the operator has just selected selectable region (2318), that all state machines are in state ST_RESET, and that the operator moves the cursor hotspot from a location inside selectable region (2318) to location (2316), a location just outside selectable region (2318). On receipt of the next WM_TIMER message, procedure PocketFsm is called with the indicator for the state machine associated with selectable region (2318) and with event EV_CROSS_OUT. Event EV_CROSS_OUT drives this state machine from its current state, ST_RESET, to ST_EBB_TIDE. The pseudo-code for ST_EBB_TIDE in procedure PocketFsm is a break statement, indicating that no state specific action is taken at this time, other than the transition to ST_EBB_TIDE. Control returns to Windows® (1204).

Shortly before or shortly after the state machine associated with selectable region (2318) receives EV_CROSS_OUT all other state machines each receive EV_MOVEMENT and each makes the transition from ST_RESET to ST_EBB_TIDE.

Assume that the operator moves the cursor hotspot along path (2322) toward location (2332), a location outside all corridors, and then the next WM_TIMER message is received. All state machines receive EV_MOVEMENT and are driven from ST_EBB_TIDE to ST_DECAY to ST_EBB_TIDE. The state processing associated with these states has been described in the description of the Perimeter Menu aspect of the disclosure.

Assuming that the operator moves the cursor hotspot along path (2322), the transition from ST_EBB_TIDE to ST_DECAY to ST_EBB_TIDE is repeated every 54 milliseconds for each state machine until the operator moves the cursor hotspot beyond location (2332). At this time the procedure CreateEvent determines that the cursor hotspot intersects corridor (2308) and that consequently EV_CORRIDOR should be sent to the state machine associated with selectable region (2348). EV_CORRIDOR drives this state machine from ST_EBB_TIDE to ST_CORRIDOR. Stepping through the pseudo-code for ST_CORRIDOR, the ST_CORRIDOR state sets pPocket→State to the value stored in pPocket→PreviousState, increments pPocket→Color by pPocket→Corridorincrement, but not above pPocket→InitialColor plus 80% of the difference between pPocket→CrestTide and pPocket→InitialColor, sets pPocket→fPaint to TRUE, sets fInternalEvent to TRUE, and sets Event to EV_NULL. Following the break statement, the while fInternalEvent condition is true and another state transition occurs. The new state is found at aPocketFsm [ST_EBB_TIDE][EV_NULL], which equals ST_EBB_TIDE. This path is unlike an ordinary state transition because the starting state is set by ST_CORRIDOR. All transitions from ST_CORRIDOR share this distinction. The state machine executes the code for the new state, ST_EBB_TIDE, which is simply a break statement. The procedure PocketFsm determines that fPaint is TRUE, invalidates the client rectangle and exits. As a result of invalidating the client rectangle, Windows® (1204) sends a WM_PAINT message to the access program (1206). On receipt of WM_PAINT, the access program (1204) checks the value of fPaint for each state machine, and if TRUE, sets fPaint to FALSE and redraws the visible subregion of the selectable region associated with that state machine and any menu option located thereon. The color of the redrawn visible subregion is determined by the value of the Color variable for that state machine. The incremented value of pPocket→Color results in a slight brightening of selectable region (2348) and reduces the difference between pPocket→Color and pPocket→CrestTide, corresponding to the dwell period required to select the associated selectable region. After redrawing, control returns to Windows® (1204).

Shortly before or shortly after the state machine associated with selectable region (2348) receives EV_CORRIDOR, all other state machines each receive EV_MOVEMENT and each makes the state transitions from ST_EBB_TIDE to ST_DECAY to ST_EBB_TIDE.

This scenario is repeated at 54 millisecond intervals while the cursor hotspot travels along path (2322) to location (2326), a location intersecting corridor (2308). Between this location (2326) and location (2328), a location intersecting corridor (2306), along path (2322), the procedure CreateEvent determines that all state machines should receive EV_MOVEMENT, driving each of them from their current state to ST_DECAY and back to their current state. As described in the example in the detailed description of the Perimeter Menu aspect of the disclosure, ST_DECAY state processing darkens the selectable region associated with the state machine, but not below a predetermined brightness represented by the variable InitialColor. Thus selectable region (2348) darkens when the cursor hotspot no longer intersects corridor (2308). From location (2328) to location (2330), the procedure CreateEvent determines that the state machine associated with selectable region (2346) should received EV_CORRIDOR and all other state machines EV_MOVEMENT. Consequently, selectable region (2346) gradually brightens up to a ceiling represented by pPocket→InitialColor plus 80% of the difference between pPocket→CrestTide and pPocket→InitialColor. The duration of dwell time required for selection of selectable region (2346) is thus reduced to approximately 20% of the dwell period required without Facilitated Dwell.

Preferably, the Direction and Intersection subaspect of the disclosure is implemented by making the changes to the prototype described for the Facilitated Dwell subaspect, except that, in incrementing pPocket→Color in ST_CORRIDOR, the upper limit for pPocket→Color in ST_CORRIDOR state processing is pPocket→CrestTide minus pPocket→Increment. Assuming these changes, a selectable region whose associated Color variable is at this upper limit is selected during processing of the WM_TIMER message immediately following the intersection of the cursor hotspot and the selectable region.

Figure 40:
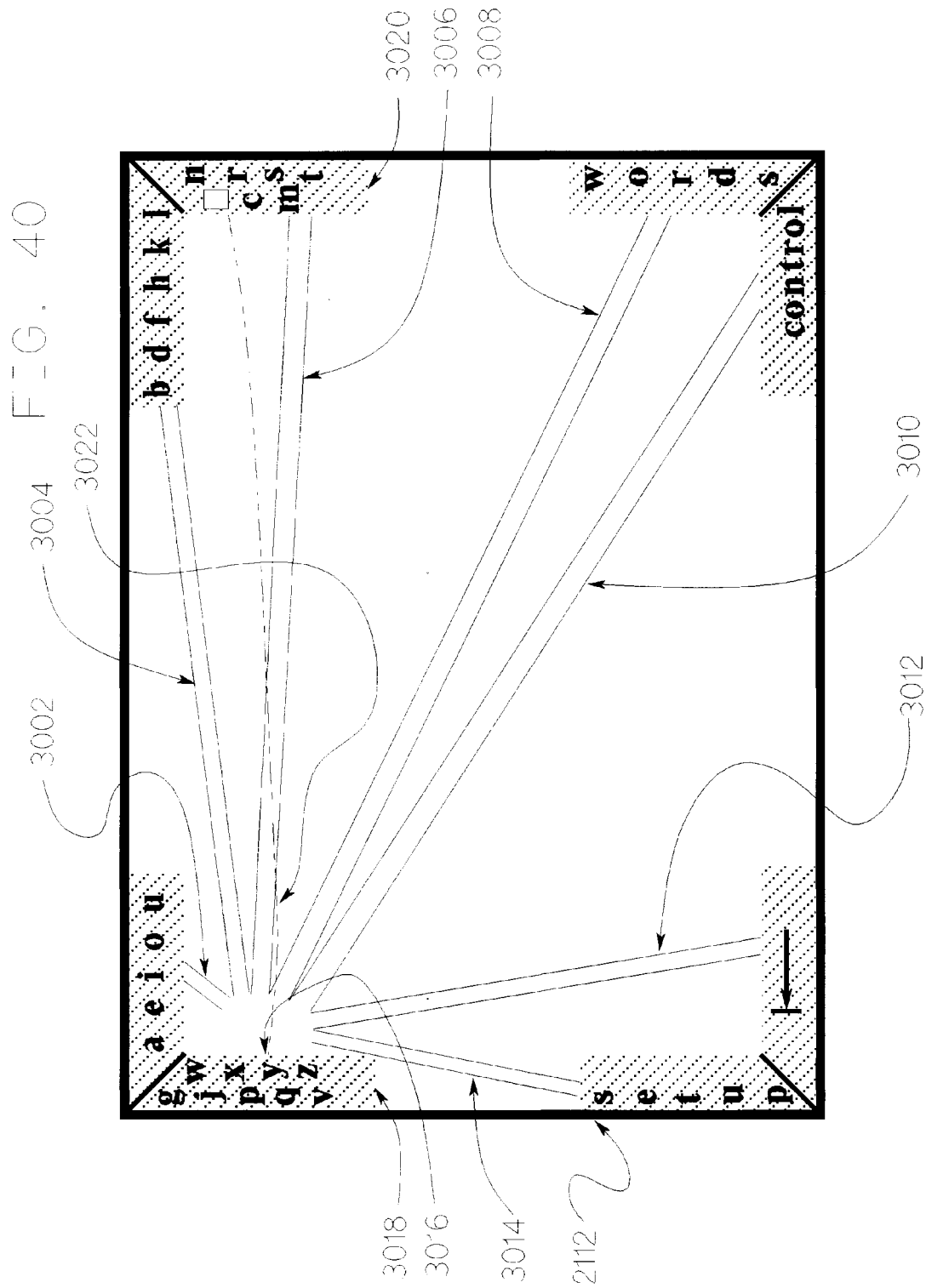
FIG. 40 is an illustration of a display and structures in accordance with an embodiment of the Path Directness aspect of the disclosure.
Figure 41:
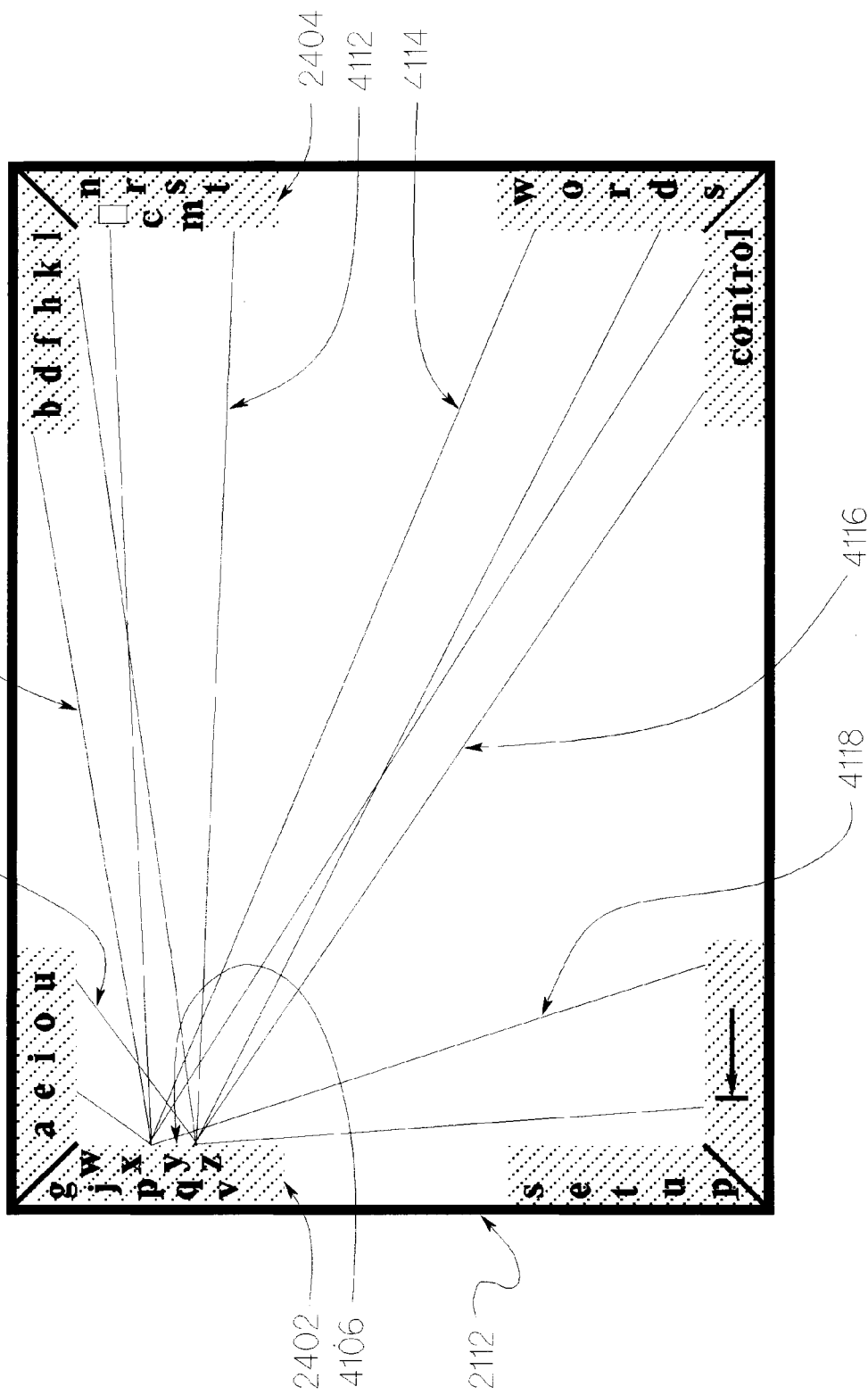
FIG. 41 is an illustration of a display and structures in accordance with another embodiment of the Path Directness aspect of the disclosure.

Preferably, the Direction subaspect of the disclosure is implemented by making the changes to the prototype described for the Direction and Intersection subaspect of the disclosure, except that (1) the corridors are narrow, as illustrated in FIG. 40; and (2) the pseudo-code for state processing in ST_CORRIDOR is as follows:

```
case ST_CORRIDOR:
                    /* set state to previous state  */
                    /* in preparation for the next  */
                    /* state transition             */
    set pPocket->State to pPocket->PreviousState
    increment pPocket->Color by
    pPocket->CorridorIncrement but not above
    pPocket->Ceiling
    if pPocket->Color was changed
        set pPocket->fPaint to TRUE
    set fInternalEvent to TRUE
    if pPocket->Color was changed from a value below
    pPocket->CrestTide to a value greater than or
    equal to
    pPocket->CrestTide
        set Event to EV_STEP_UP
    else
        set Event to EV_NULL
    break
```

State ST_CORRIDOR may now generate the internal event EV_STEP_UP, as state ST_DWELL does in the detailed description of the Perimeter Menu aspect of the disclosure. A state machine in state ST_EBB_TIDE having a Color variable equal to or exceeding the CrestTide variable, will transition via PocketFsm[ST_EBB_TIDE][EV_STEP_UP] to ST_SELECTED, and perform the ST_SELECTED state processing described in the detailed description of the Perimeter Menu aspect of the disclosure.

Preferably, the Appraisal subaspect of the disclosure is implemented by making the changes to the prototype described for the Facilitated Dwell subaspect, except that (1) the corridors are visible on the display (2112), (2) one of the selectable regions is designated to be the target selectable region and this is indicated to the operator, (3) cursor locations are stored in memory (2106), and (4) following an intersection of the cursor hotspot and the target or selection of a selectable region other than the target, path directness is measured in accordance with the stored cursor locations.

The preferred embodiment of the Drift Attenuation aspect of the disclosure will now be described in detail from an implementation perspective. Preferably, the Drift Attenuation aspect is implemented by modifications to the access program (1206) described in the detailed description of the Perimeter Menu aspect of the disclosure, modified as described above in the description of the implementation of the preferred embodiment of the Facilitated Dwell subaspect of the disclosure and further modified as follows: (1) add two booleans to the data set associated with each state machine, one called fDirectPath, the other fAttenuateDrift, and initialize each of them in all state machines to FALSE; (2) in both ST_DECAY and ST_CORRIDOR, set both pPocket→fDirectPath and pPocket→fAttenuateDrift to FALSE; (3) append to ST_ENTRY state processing corresponding to the following pseudo-code:

```
if pPocket->Color equals or exceeds
(pPocket->InitialColor + (0.5 * (pPocket->CrestTide -
pPocket->InitialColor)))
    set pPocket->fDirectPath to TRUE
```

(4) append to ST_DWELL state processing corresponding to the following pseudo-code:

```
if the present cursor position intersects the edge of the
Windows ® cursor clipping rectangle and
pPocket->fDirectPath is TRUE
    set pPocket->fAttentuateDrift to TRUE
if pPocket->fAttentuateDrift is TRUE
    store the difference in each of the x and y
    coordinates ("delta") between consecutive cursor
    locations in a circular buffer accommodating the
    last ten deltas, overwriting the oldest delta with
    the newest delta
    if ten deltas have been accumulated
        calculate the average acceleration indicated by
        the last ten deltas
        if the average acceleration is negative
            set the cursor at the location one half the
            distance between the current cursor location
            and the previous cursor location
            display the cursor at this new cursor
            location
```

E. Intersection

Figure 44:
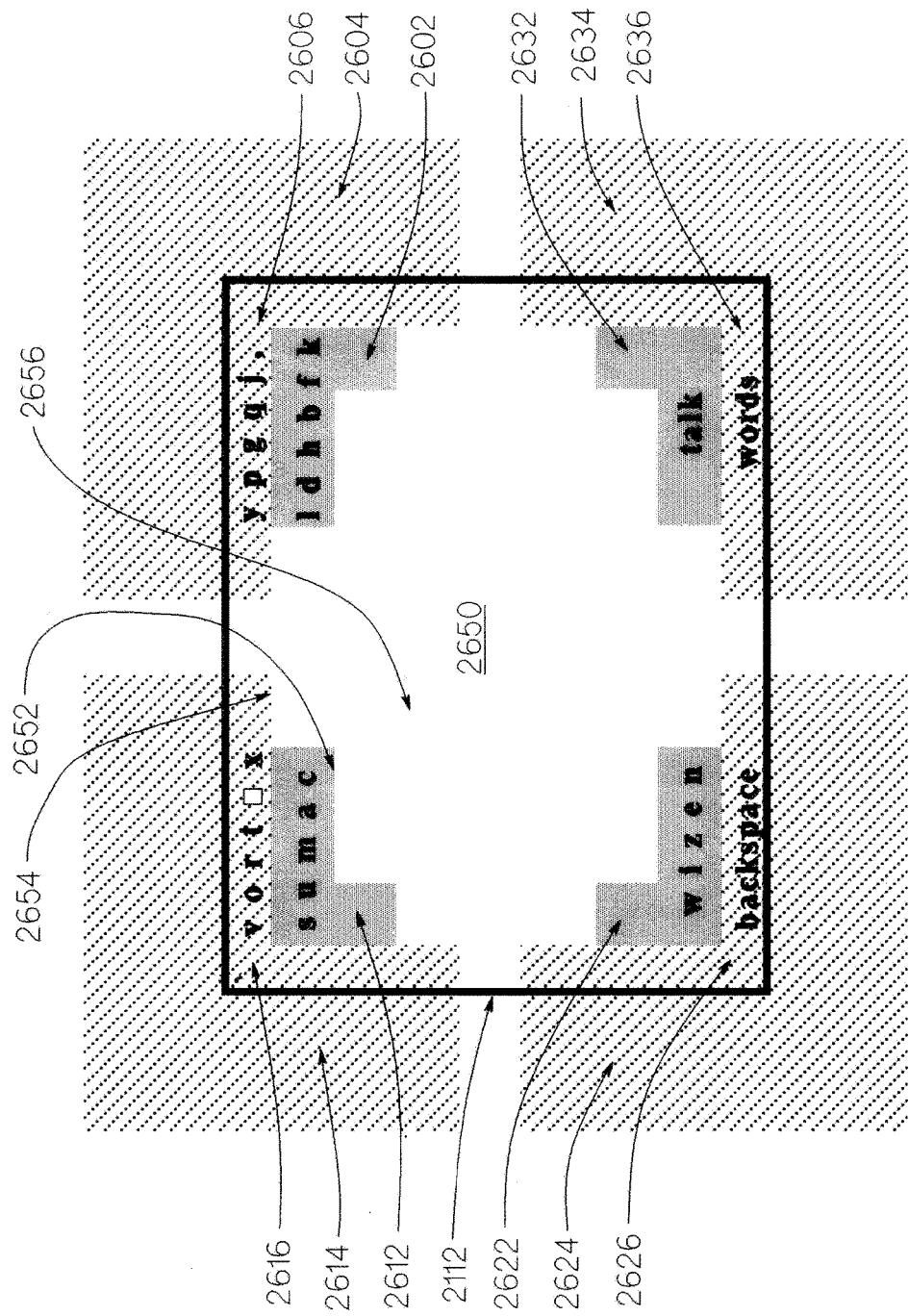
FIGS. 44, 45 and 46 are each illustrations of a display and structures in accordance with the preferred embodiment of the Intersection aspect of the disclosure.
Figure 45:
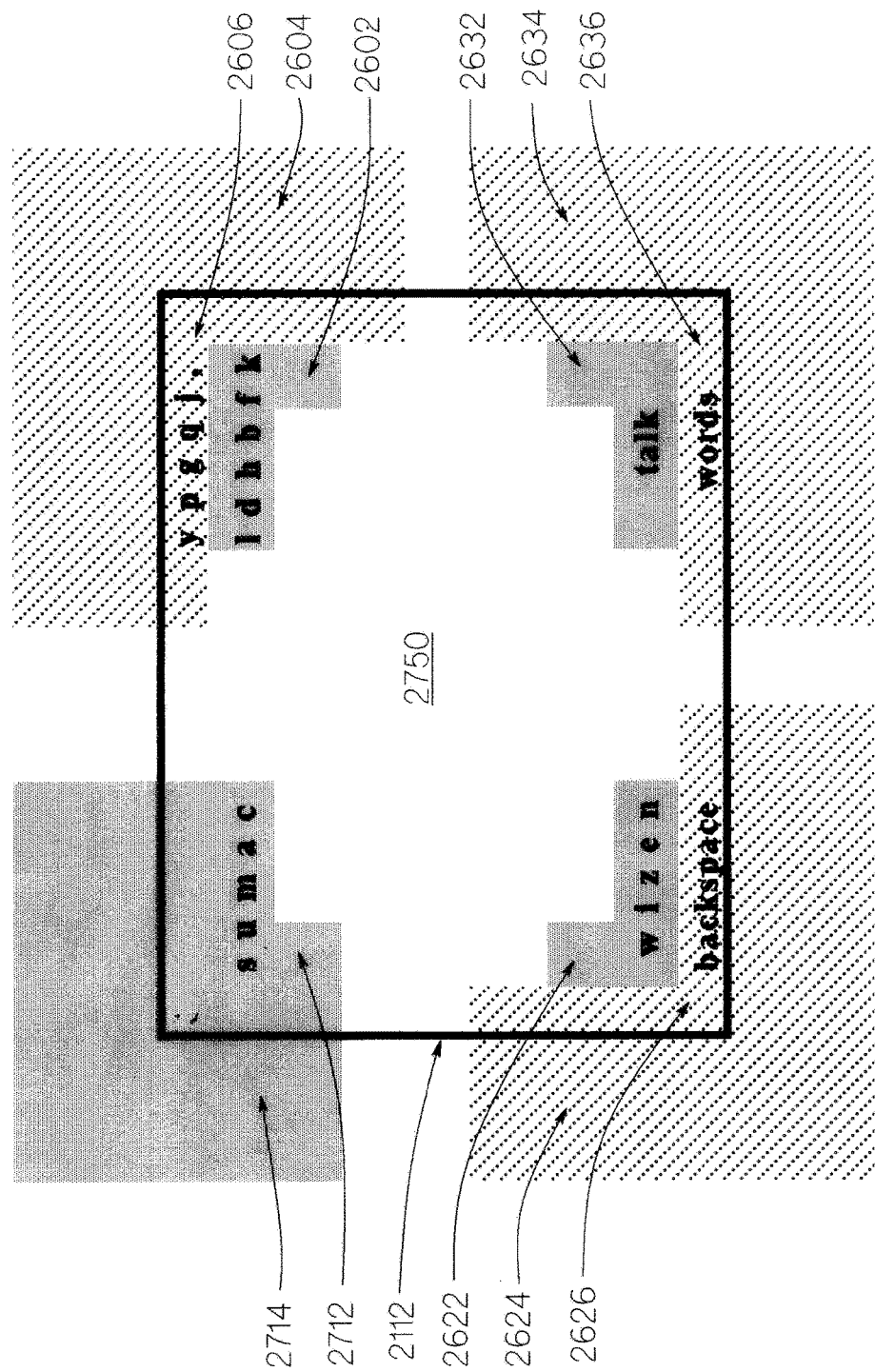
Figure 46:
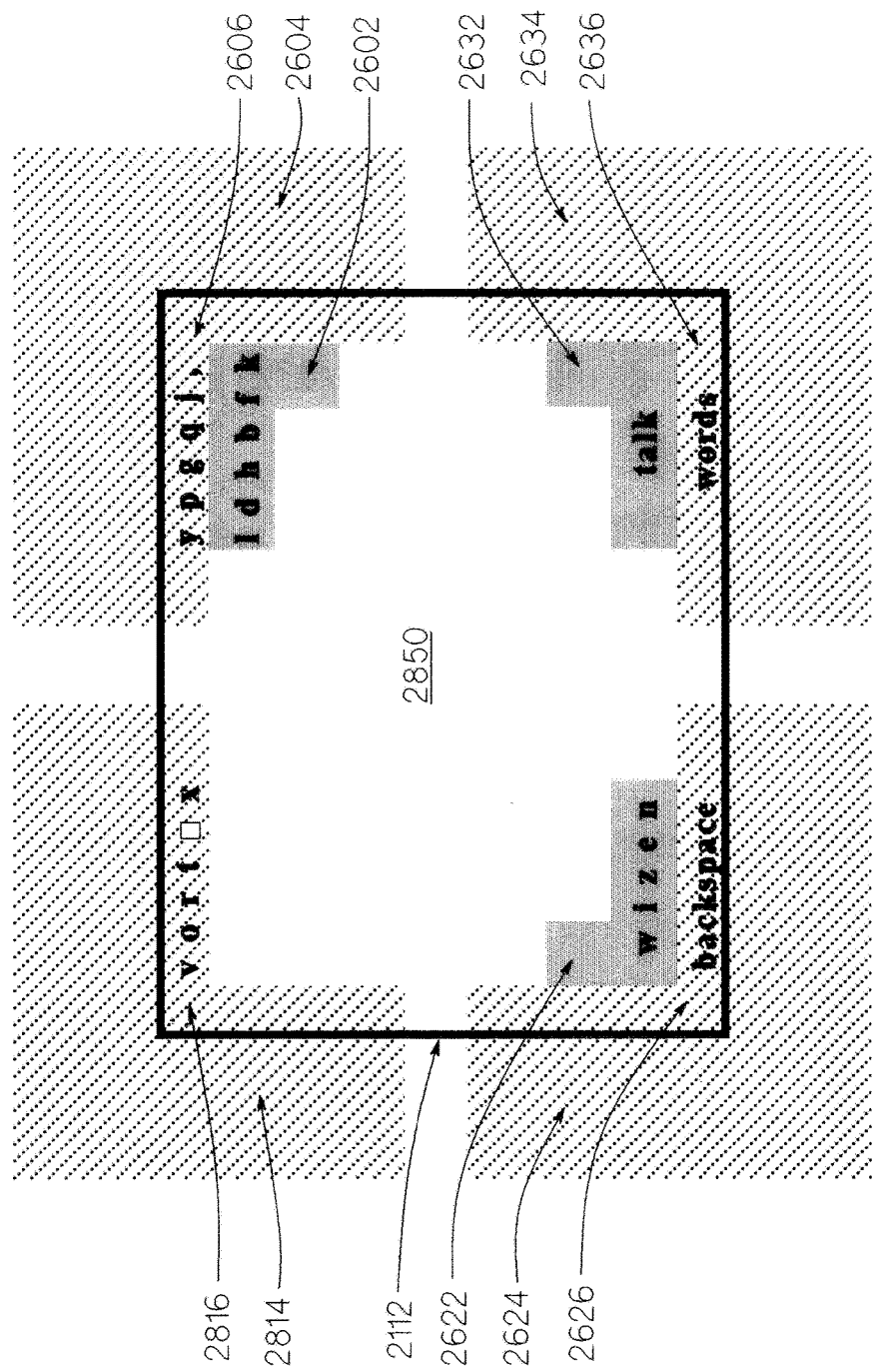

The preferred embodiment of the Intersection aspect of the disclosure will now be described in detail from a functional perspective using an example depicted in FIGS. 44, 45, 46. FIG. 44 shows the display (2112) of a general purpose computer system (2218 in FIG. 15) to which is coupled a pointer (2202). Eight regions are delimited with respect to the display (2112) and together circumscribe region (2650) on the display (2112). Four of these regions, (2602), (2612), (2622), and (2632), are entirely on the display (2112). Each of the other four regions respectively includes both a visible subregion ((2606), (2616), (2626), and (2636)) on the display (2112) and an invisible subregion ((2604), (2614), (2624), and (2634)) adjacent and outside the display (2112). Assume, for example, that the pointer is indicating location (2656) on the display (2112) and that the operator moves the pointer so that the location indicated by the pointer first intersects one of the regions at location (2652) in region (2612). Upon this intersection, the display changes to that shown in FIG. 45. FIG. 45 depicts a selectable region consisting of the union of invisible subregion (2714) and visible subregion (2716), hereinafter referred to as selectable region (2714/2716). Selectable region (2714/2712) is associated with menu option "sumac". In the preferred embodiment, the operator may select menu option "sumac" by dwelling on any part of the selectable region for the selection threshold period. Assuming, for example, that instead of moving the pointer from a position indicating location (2656) to location (2652), the operator instead moves the pointer so that the location indicated by the pointer first enters one of the regions at location (2654) in region (2614/2616). Upon this intersection, the display changes to that shown in FIG. 46. FIG. 46 depicts a selectable region consisting of the union of invisible subregion (2814) and visible subregion (2816), hereinafter referred to as selectable region (2814/2816). Selectable region (2814/2816) is associated with menu option "vort<space>x". In the preferred embodiment, the operator may select menu option "vort<space>x" by dwelling on any part of the selectable region for the selection threshold period.

In the preferred embodiment, each of the other seven regions shown in FIG. 44 is associated with a selectable region and each selectable region is associated with a menu option. The menu options shown in FIG. 44, in addition to "sumac" and "vort<space>x" are "wizen", "backspace", "words", "talk", "ldhbfk" and "ypgqj,". The operator may select the menu option associated with any one of the selectable regions by moving the location indicated by the pointer from circumscribed region (2650) into the region associated with the selectable region and then dwelling on the selectable region for the selection threshold period. Each selectable region preferably includes all the area of its associated region.

An operator having impaired ability to maintain a body member in a steady position but who can control the point at which the location indicated by a body member enters a region may, in accord with the Intersection aspect of the disclosure, use his relatively unimpaired motor capability to selectively enlarge a selectable region or determine which of two or more selectable regions will occupy a predetermined area, thus making it easier for him to select. If the general purpose computer system of the preferred embodiment is coupled to a speech synthesizer and the menu options are letters or words, an operator with impaired speech may select or spell words and speak them.

Figure 47:
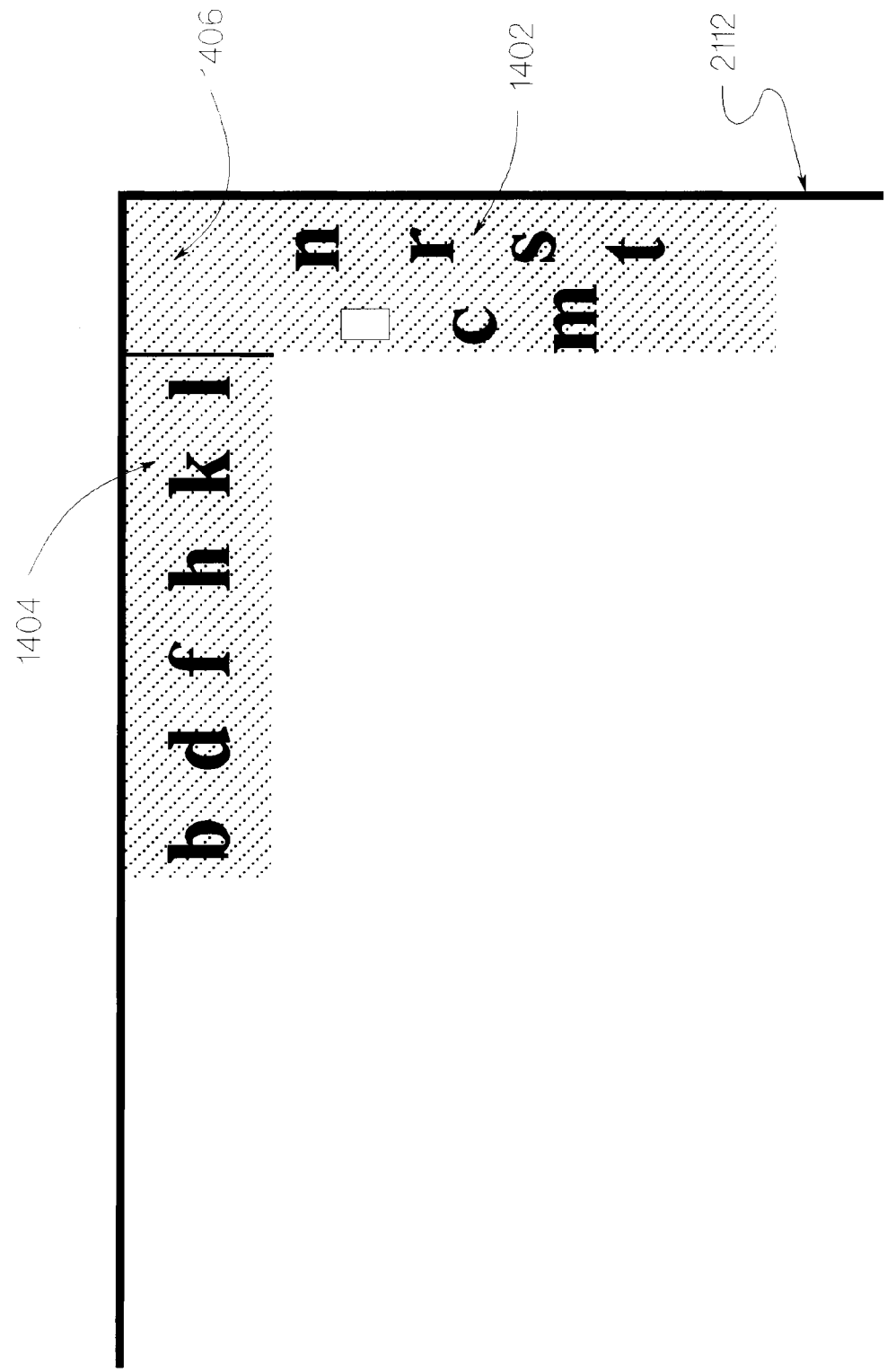
FIGS. 47 and 48 are each illustrations of a display and structures in accordance with another embodiment of the Intersection aspect of the disclosure.
Figure 48:
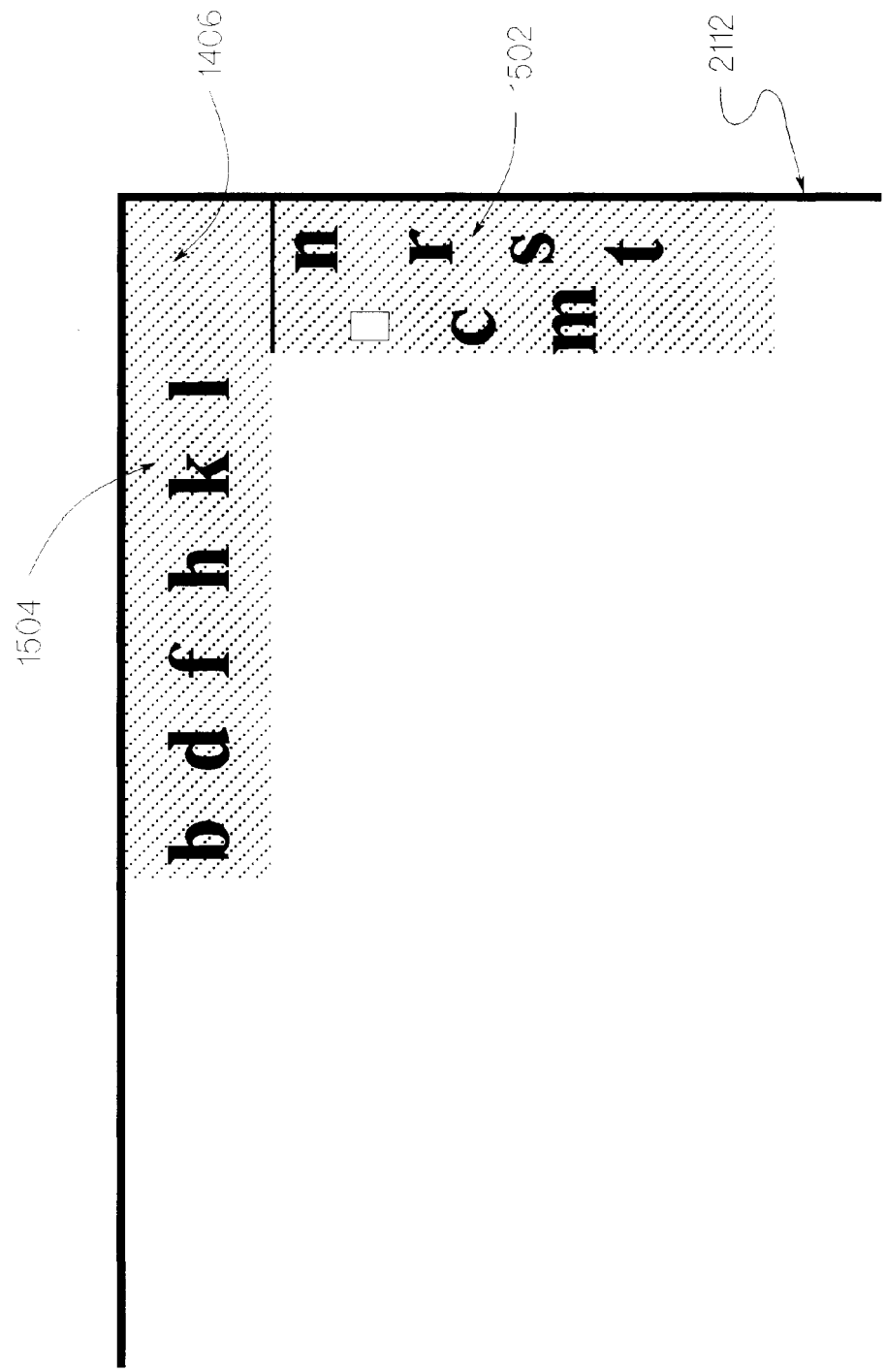

FIGS. 47 and 48 illustrate the upper right corner of a display in accordance with an alternative embodiment of the Intersection aspect of the disclosure. FIG. 47 depicts the upper right corner of a display (2112) of a computer system (2116) having thereon two regions, (1404) and (1402), each associated respectively with a selectable region, each selectable region associated respectively with menu options "bdfhkl" and "<space>cmnrst". The selectable region associated with region (1402) includes all of region (1402). The selectable region associated with region (1404) includes all of region (1404) plus area (1406) between region (1404) and the right edge of the display (2112). Assuming the operator uses a pointer to indicate a location on the display and that the location to first intersect the union of regions (1402) and (1404) intersects region (1402), the display remains as shown in FIG. 47. Dwelling in area (1406) operates to select the menu option "<space>cmnrst". If instead the location to first intersect the union of regions (1402) and (1404) intersects region (1404), the display changes to that shown in FIG. 48. Dwelling in area (1406) then operates to select the menu option "bdfhkl".

The preferred embodiment of the Intersection aspect will now be described in detail from an implementation perspective. The Intersection aspect is preferably implemented by modifications to the access program (1206) described above in the detailed description of the Perimeter Menu aspect of the disclosure. The modifications are: (1) add a row to the state table aPocketFsm at row index 18 for a new state, ST_EXIT and initialize the value of aPocketFsm[ST_EXIT][EV_NULL] to 4, the value of ST_LOW_TIDE; (2) at initialization time, change aPocketFsm[ST_LOW_TIDE][EV_CROSS_OUT] to 18, the value of ST_EXIT; (3) at initialization time for each state machine, (a) if the visible subregion associated with the state machine does not abut the edge of the display, set fInterior to TRUE, otherwise set fInterior to FALSE; (b) initialize iAdjacentPocket to the index of the state machine associated with the adjacent region. For example, assuming the index of the state machine associated with region (2614/2616) in FIG. 44 is 2 and the index of the state machine associated with region (2612) in FIG. 44 is 3, iAdjacentPocket in the data set associated with the state machine associated with region (2614/2616) is initialized to 3 and iAdjacentPocket in the data set associated with the state machine associated with region (2612) is initialized to 2; (c) initialize the second array of points to define the boundaries of the region associated with the selectable region associated with each state machine, for example, region (2612), and initialize the first array of points to define the boundaries of the visible subregion of the selectable region associated with the state machine, for example, visible subregion (2712); (4) remove creation of Windows® regions corresponding to visible subregions from the access program (1206) initialization; (5) append to ST_ENTRY state processing corresponding to the following pseudo-code:

```
if pPocket->fInterior equals TRUE
    if pPocket->hRegion is not NULL
        delete the Windows ® region having the handle
        pPocket->hRegion
    create a Windows ® region having the boundaries
    defined by the second array of points associated
    with this state machine and set pPocket->hRegion to
    the handle to this region
    set pPocket->fPaint to TRUE
send EV_RESET to all state machines except this one and
the state machine having the index
pPocket->iAdjacentPocket
set pAdjacentPocket to point to the data set associated
with the state machine having the index
pPocket->iAdjacentPocket
delete the Windows ® region having the handle
pAdjacentPocket->hRegion
set pAdjacentPocket->hRegion to NULL
set pAdjacentPocket->fPaint to TRUE
```

(4) append to ST_RESET state processing corresponding to the following pseudo-code:

```
if pPocket->hRegion is not NULL
    delete the Windows ® region having the handle
    pPocket->hRegion
create a Windows ® region having the boundaries defined by
the second array of points associated with this state
machine and set pPocket->hRegion to the handle to this
region
```

An example of the selection of selectable region in accord with the Intersection aspect of the disclosure will now be described with reference to FIGS. 44 and 45. Following initialization, assume that the operator moves the pointer (2202) from a position indicating location (2656) toward location (2652) in FIG. 44. At the next expiration of the cursor polling timer, the procedure CreateEvent sends an EV_MOVEMENT event to the state machine associated with the selectable region associated with the menu option "sumac". The event EV_MOVEMENT drives this state machine from its current state, ST_RESET, to ST_EBB_TIDE. The pseudo-code for ST_EBB_TIDE in procedure PocketFsm is a break statement, indicating that no state specific action is taken at this time, other than the transition to ST_EBB_TIDE. Control returns to Windows® (1204). At the expiration of the cursor polling timer after the location indicated by the pointer reaches location (2652), the procedure CreateEvent sends event EV_DWELL to the state machine associated with the selectable region associated with the menu option "sumac". EV_DWELL drives this state machine from ST_EBB_TIDE to ST_ENTRY. Following the pseudo-code for ST_ENTRY state processing shown above and in the Procedure PocketFsm, fInternalEvent is set to TRUE, Event is set to EV_NULL, the Windows® region corresponding to region (2612), ie. the Windows® region having the handle pPocket→hRegion, is deleted and a new Windows® region having the boundaries indicated in the first array of points, ie. visible subregion (2712) in FIG. 45, is created and the handle stored in pPocket→hRegion. pPocket→fPaint is set to TRUE, EV_RESET is sent to state machines associated with regions other than (2612) and (2614/2616). Data in the data set associated with the adjacent region (2614/2616) is now modified. The Windows® region corresponding to region (2614/2616) is deleted, hRegion for the state machine associated with that region is set to NULL and fPaint associated with that state machine is set to TRUE. The event EV_NULL drives the state machine associated with selectable region (2714/2712) to ST_LOW_TIDE. The pseudo-code for ST_LOW_TIDE is only a break statement, so there is no state specific action for ST_LOW_TIDE other than entry into this state. pPocket-fPaint is TRUE so the client rectangle is invalidated, resulting in the redrawing of Windows® regions associated with state machines having fPaint equal to TRUE so that the display (2112) appears as shown in FIG. 45. Control returns to Windows® (1204).

Dwelling at any location within selectable region (2714/2712) now causes the procedure CreateEvent to send EV_DWELL to the state machine associated with this selectable region. Selection of this selectable region proceeds as described above in the detailed description of the Perimeter Menu aspect of the disclosure.

Assuming the operator moves the location indicated by the pointer out of selectable region (2714/2712) prior to selection, the procedure CreateEvent sends the event EV_CROSS_OUT to the state machine associate with that selectable region, driving it to ST_EXIT. The state processing for ST_EXIT causes the display (2112) to change to that shown in FIG. 44.

F. Alignment

Figure 49:
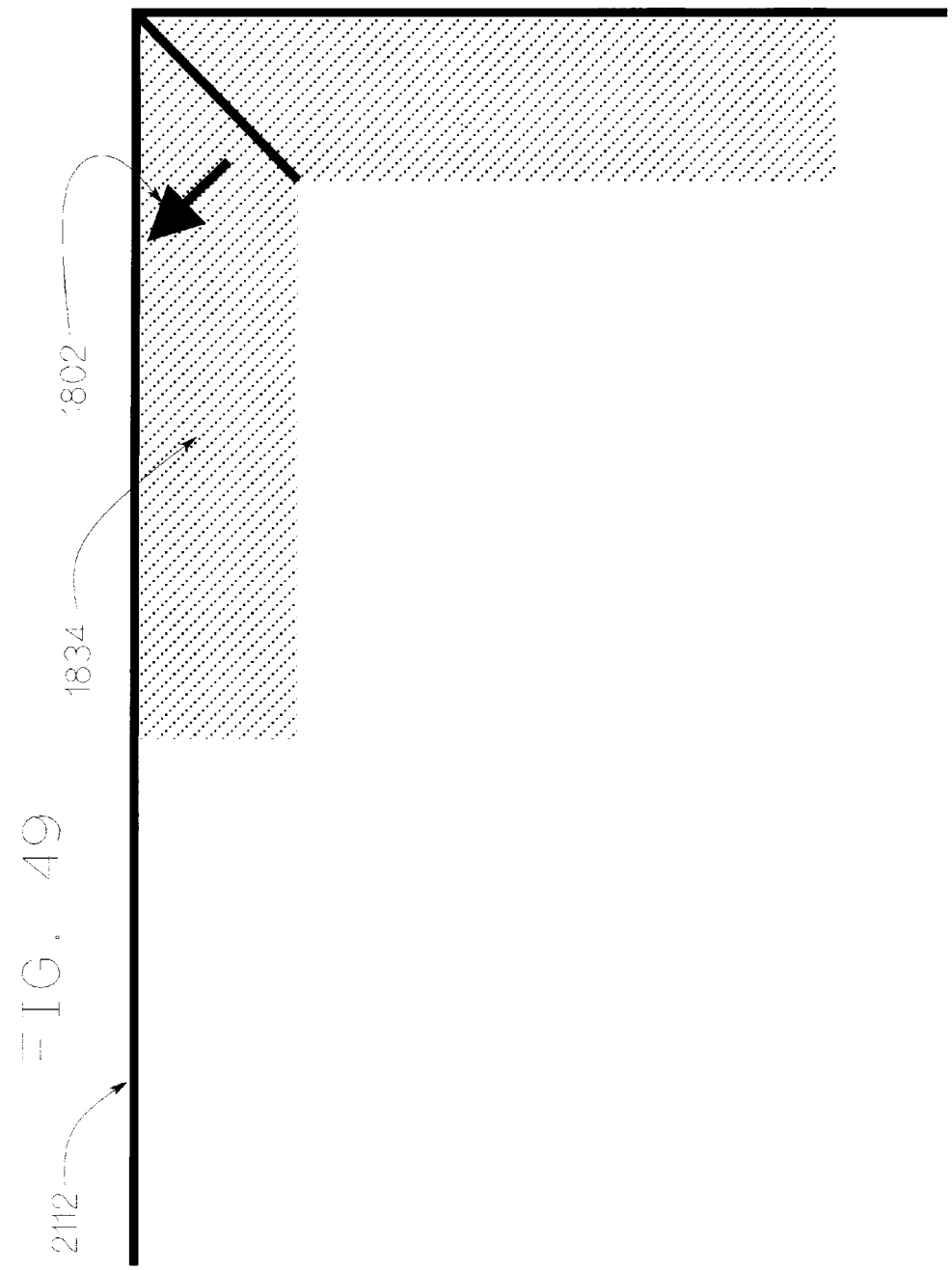
FIGS. 49, 50 and 51 are each illustrations of a display and structures in accordance with the preferred embodiment of the Alignment aspect of the disclosure.
Figure 50:
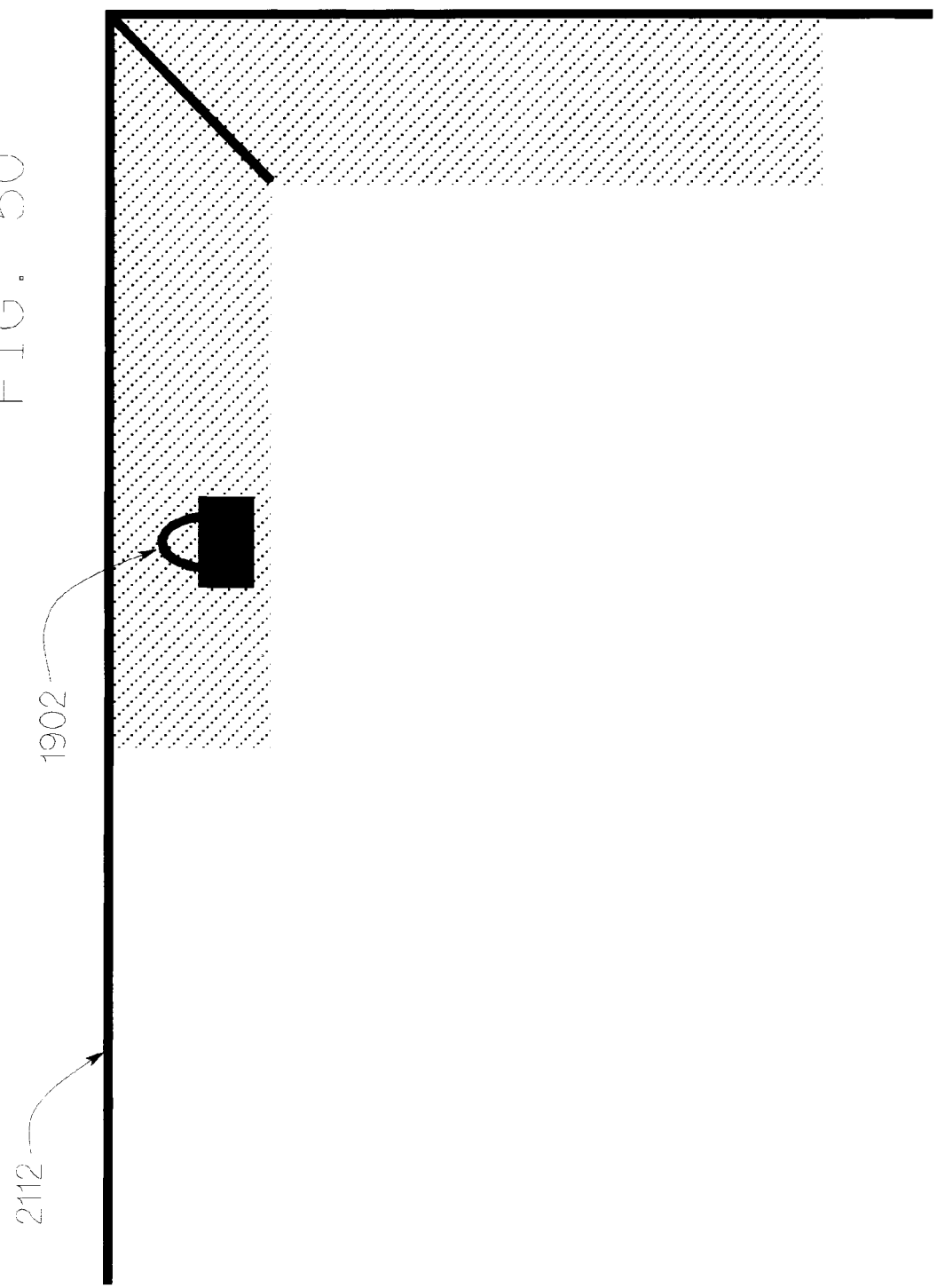
Figure 51:
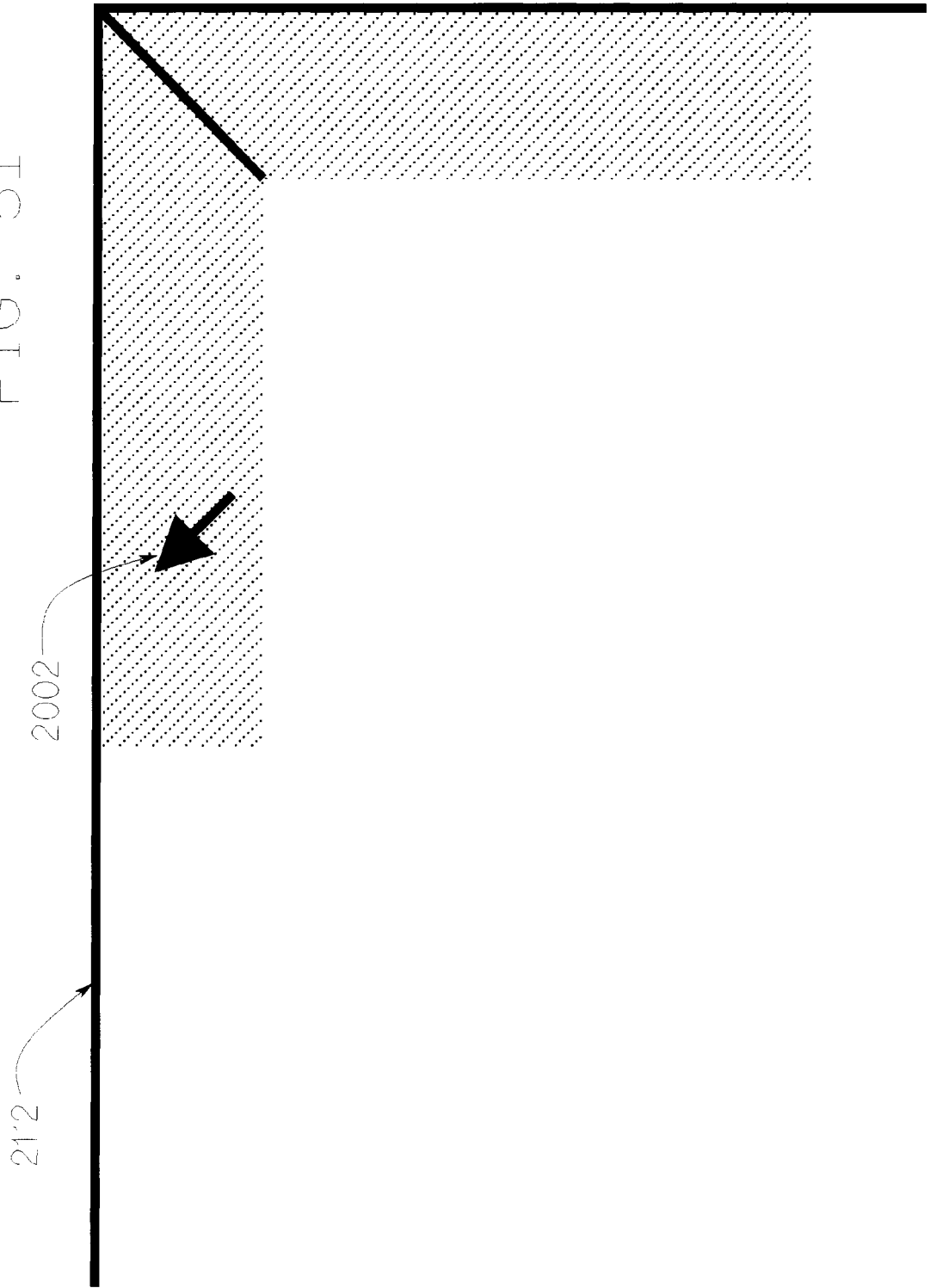

The embodiment of the Alignment aspect of the disclosure as implemented in the prototype will now be described in detail from a functional and implementation perspective using an example depicted in FIGS. 49, 50, and 51. Each of these Figures depicts the upper right corner of a display (2112) having two visible subregions on the display. In these Figures, no subregions outside the display (2112) are shown. Alignment is achieved in several steps and requires operator interaction with the apparatus. For purposes of this example, assume that FIG. 49 depicts the upper right corner of the display (2112), that an operator, fitted with a head pointer, desires to keep the cursor on the display directly in his line of sight and that the location indicated by the pointer is presently 15 degrees to the right of the location of the arrow cursor (1802). The operator now dwells on selectable region (1834) for a predetermined period ("the lock threshold") which preferably is significantly greater than the selection threshold period. The apparatus responds to this extended dwell period by changing the display to that shown in FIG. 49. The arrow cursor is removed from the display and the lock icon (1902) is displayed in a predetermined location of the intersected selectable region ("lockspot") on the display. The lock icon remains on the lockspot for a predetermined period ("the lock period"); it does not move responsive to the operator's head movement. While the lock icon is displayed, the operator turns his head, bringing his line of sight into alignment with the lockspot. At the expiration of the lock period, the apparatus changes the display to that shown in FIG. 51. The lock icon is erased and the arrow cursor appears in the lockspot, which is where the operator is now looking. The arrow cursor moves in response to the operator's head movement.

An operator who loses alignment between the location indicated by his pointer and the cursor may thus initiate an alignment sequence, and then, by moving his head or other body member when the prototype indicates he should do so by displaying the lock icon, regain alignment. That the lock icon is displayed indicates to the operator that he can align his head or other body member. The position of the lock icon indicates to the operator the location on the display with which he should align his head or other body member. This is the location where the arrow cursor will appear at the expiration of the lock period.

The Alignment aspect will now be described in detail from an implementation perspective as implemented in the prototype. The Alignment aspect of the disclosure is implemented as an integral part of the state machine described in the detailed description of the Perimeter Menu aspect of the disclosure, using the same state machines and initialization, with the exception that aPocketFsm[ST_CREST_TIDE][EV_CEILING] is changed from 9, the value of ST_DWELL, to 14, the value of ST_BEGIN_LOCK. The operator initiates the alignment process by moving the cursor so that the cursor hotspot intersects a selectable region. As an example, FIG. 49 shows the arrow cursor (1802) intersecting selectable region (1834). The operator then dwells on the selectable region for the lock threshold, preferably at least one second greater than the selection threshold period. This operator action causes the state machine associated with the intersected selectable region to reach state ST_CREST_TIDE. On receipt of the first WM_TIMER message following entry into state ST_CREST_TIDE, the procedure CreateEvent creates event EV_CEILING, which drives the state machine from state ST_CREST_TIDE to state ST_BEGIN_LOCK. The state processing within state ST_BEGIN_LOCK beeps, sets the system cursor location to the selectable region's lockspot, sets the system cursor to null erasing the arrow cursor, displays a the lock icon (1902 in FIG. 50) on the selectable region's lockspot and initializes the global variable iLockCursor to the number of expirations of the cursor polling timer corresponding to the period of time the cursor will be locked (the "lock period") configured by the operator, preferably two seconds, and control is returned to Windows® (1204). Following the next expiration of the cursor polling timer, the procedure CreateEvent may generate an event EV_DECAY, EV_DWELL, EV_CROSS_OUT, EV_MOVEMENT or EV_CEILING. Each of these events drives the state machine from state ST_BEGIN_LOCK to state ST_LOCK. Within state ST_LOCK the system cursor is moved to the selectable region's lockspot and iLockCursor is decremented. Then it is determined whether iLockCursor equals zero. If not, control returns to Windows® (1204) for another iteration through ST_LOCK. During the lock period, the system cursor is moved to the lockspot upon every expiration of the cursor polling timer, thus inhibiting movement of the cursor from the lockspot so that, during the lock period, the operator may move the location indicated by the pointer while the lock icon remains on or very close to the selectable region's lockspot. When, eventually, iLockCursor is decremented to zero, the global Event is set to EV_NULL and fInternalEvent is set to TRUE so that another state transition occurs immediately. This transition drives the state machine from state ST_LOCK to state ST_END_LOCK. Within state ST_END_LOCK, the lock icon is erased, Windows® (1204) is directed to display the arrow cursor (2002) at the lockspot, as shown in FIG. 51, the fPaint flag associated with the intersected selectable region is set to TRUE so that the selectable region will be drawn, restoring the background behind the erased lock icon. Assuming the cursor hotspot remains on the selectable region for another 54 milliseconds, CreateEvent generates EV_DWELL, which drives the state machine to ST_DISCARD. Referring to the pseudo-code in PocketFsm, ST_DISCARD state processing sets State to PreviousState, returning the state machine to ST_END_LOCK and in effect, discarding the last event. Following the expiration of the cursor polling timer after the operator moves the cursor out of the selectable region it presently intersects, the procedure CreateEvent generates an event EV_CROSS_OUT which drives the state machine from state ST_END_LOCK to state ST_SELECT_AND_OUT. The access program (1206) performs the state processing for state ST_SELECT_AND_OUT and subsequent states as previously described in the description of the Perimeter Menu aspect of the disclosure.

In the prototype, the operator may initiate alignment by depressing any character key on the keyboard. On receipt of a WM_CHAR message from Windows® (1204), the access program (1206) removes the arrow cursor from the display and displays the lock icon at a predetermined location on the display. In the prototype, the predetermined location is the center of the display (2112). After a predetermined period, two seconds in the prototype, the lock cursor icon is erased and the arrow cursor displayed at the predetermined location.

In the prototype, the cursor is automatically centered if the cursor hotspot does not move for two minutes. Lack of movement of the cursor hotspot is detected in the procedure CreateEvent, which generates the event EV_IDLE_TIMEOUT for all state machines. The state processing of each state machine on receipt of EV_IDLE_TIMEOUT depends upon its current state. State machines in states ST_INITIAL and ST_RESET stay in those states. State machines in all other states in which an external event can be received are driven to ST_IDLE. Referring to the pseudo-code in PocketFsm, ST_IDLE state processing moves the cursor to the center of the display, sets fInternalEvent to TRUE and sets Event to EV_NULL. PocketFsm[ST_IDLE][NULL] equals 3, the value of ST_RESET. The access program (1206) performs the state processing for the ST_RESET and subsequent states as described in the description of the Perimeter aspect of the disclosure.

G. Length Order

Figure 52:
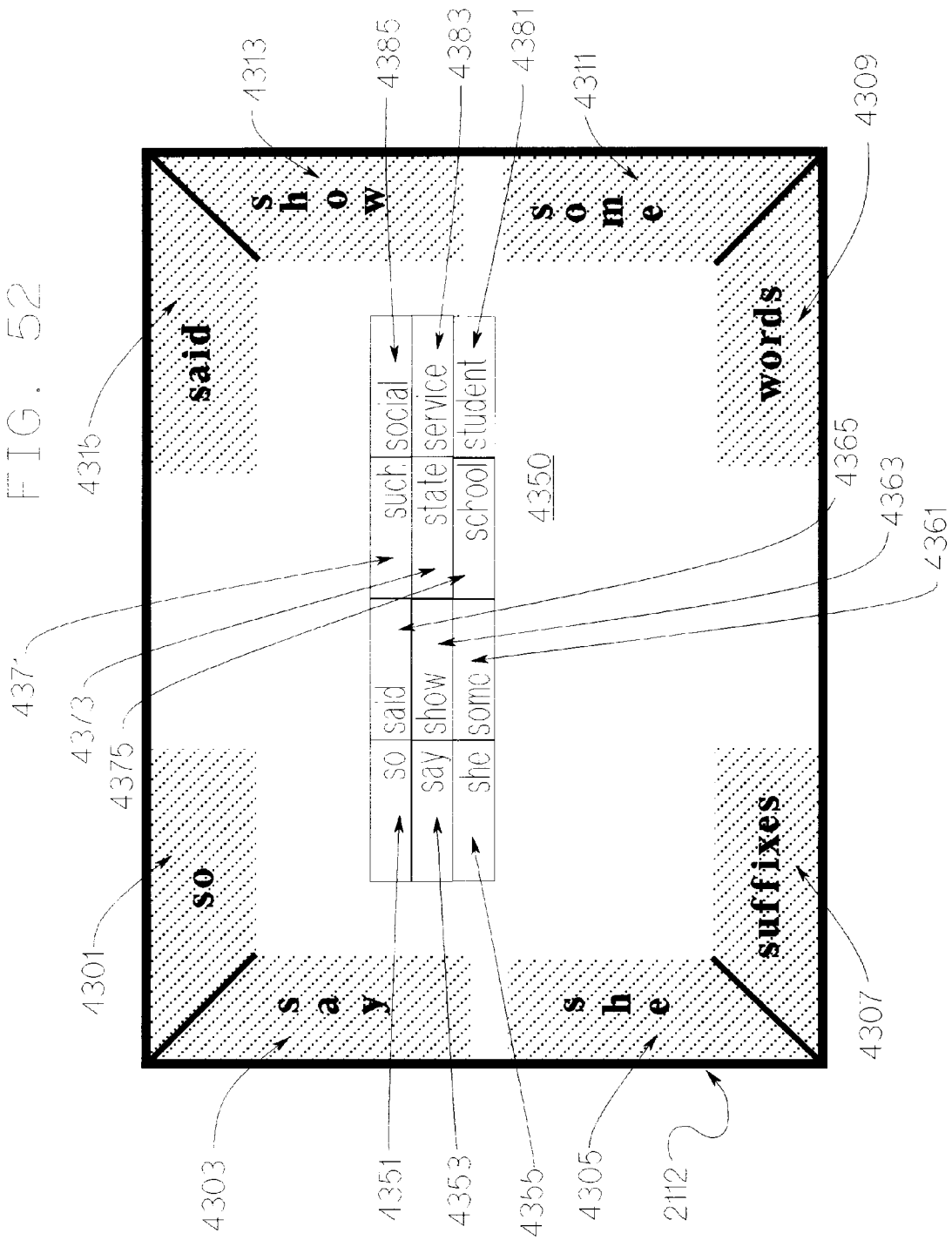
FIG. 52 is an illustration of a display and structures in accordance with the preferred embodiment of the Location Indication and the Length Order aspects of the disclosure.

The preferred embodiment of the Length Order aspect of the disclosure will now be described in detail from a functional and implementation perspective using an example depicted in FIG. 52 and described in the detailed description of the Location Indication aspect of the disclosure. Assume, for purposes of this example, that the operator has previously selected the letter "s". In the preferred embodiment, the string "s" is passed from the access program (1206 in FIG. 16) via the Windows® Dynamic Data Exchange ("DDE") interface to a database program (1210 in FIG. 16), preferably the FoxPro for Windows® version 2.6 program, available from Microsoft Corporation, Redmond, Wash., USA. The FoxPro program looks up the record having the index "s" in a database composed of 26 letters, one for each letter of the alphabet. Each record includes one field for a letter of the alphabet and 12 fields containing the 12 most frequently used English words beginning with that letter. The 12 words in the record are ordered primarily by length, determined by the number of letters in each word, and secondarily by alphabetic order. The FoxPro program returns these 12 words to the access program (1206) and these are displayed on the display (2112) as named menu options. The twelve named menu options, ordered as described and depicted in FIG. 52, are "so", "say", "she", "said", "show", "some", "such", "state", "school", "social", "service", and "student". Preferably, only the root form of inflected forms of words which can be created through available suffixes ("root word") may be displayed as named menu options, so that the limited number of available menu options in combination with the apparatus' capability to add suffixes offers a large number of inflected forms.

Words which may be named menu options in the same menu may be ordered by any suitable method. Preferably ordering is done by an ordering program operating on a corpus of text or speech including text or speech produced by individuals whose age, sex, geographic location and disability are the same as or similar to that of the operator. The ordering program determines the frequency of use of root words in the corpus, selects the twelve most common root words, beginning with every possible combination of one, two and three letters, and stores them in three FoxPro databases for one, two and three letter word beginnings respectively, the words in each record ordered as described above. Ordering the words prior to a request minimizes the delay between the operator's selection of a letter or letters and the display of the named menu options. Preferably, the ordering program also creates a database of records for root words beginning with four or more letters. Each record includes the words and its frequency of use in the corpus. When the operator selects four or more letters consecutively, the access program (1206) requests via DDE that the FoxPro program (1210) look up words starting with four or more letters in the database for words beginning with four or more letters, select the 12 most frequently used words matching the selected letters, order them as described above, and return them to the access program (1206).

An operator searching named menu options for a desired menu option may start his search in the area on the display most likely to contain the desired menu option. Upon comparison of the length of the desired menu option to a displayed menu option, the operator may determine whether to continue his search from the displayed menu option toward the front of the list or toward the rear of the list, or to jump to another displayed menu option in the list Further, he may make this determination more quickly than if the displayed menu options were sorted conventionally. The reduced menu option search time increases the operator's productivity with respect to conventional menu interfaces.

H. Location Indication

The preferred embodiment of the Location Indication aspect of the disclosure will now be described in detail from a functional perspective using an example depicted in FIG. 52. FIG. 52 shows the display (2112) of a general purpose computer system (2218 in FIG. 15) having thereon eight selectable regions, each associated respectively with a menu option. Each of the eight selectable regions consists of the union of a visible subregion on the display (2112) and an invisible subregion (not shown) located outside the display (2112) and adjacent the visible subregion. Selectable region (4301) is associated with menu option "so", selectable region (4303) with menu option "say", selectable region (4305) with menu option "she", selectable region (4307) with menu option "suffixes", selectable region (4309) with menu option "words", selectable region (4311) with menu option "some", selectable region (4313) with menu option "show" and selectable region (4315) with menu option "said". Also shown on the display (2112) are 12 indicating regions, each associated respectively with a menu option. Indicating region (4351) is associated with menu option "so", indicating region (4353) with menu option "say", indicating region (4355) with menu option "she", indicating region (4361) with menu option "some", indicating region (4363) with menu option "show", indicating region (4365) with menu option "said", indicating region (4371) is associated with menu option "such", indicating region (4373) with menu option "state", indicating region (4375) with menu option "school", indicating region (4381) with menu option "student", indicating region (4383) with menu option "service" and indicating region (4385) with menu option "social". Each indicating region is located on the display (2112) in the region (4350) circumscribed by the selectable regions. In accord with the Location Indication aspect of the disclosure, the location of each of the indicating regions (4351), (4353), (4355), (4361), (4363) and (4365) indicates the location of each of the selectable regions associated with the menu option associated with the indicating region. These selectable regions, respectively, are (4301), (4303), (4305), (4311), (4313) and (4315).

In the preferred embodiment, selection of menu option "words" causes selectable region (4301) to be associated with menu option "such" instead of menu option "so", selectable region (4303) to be associated with menu option "state" instead of menu option "say", selectable region (4305) to be associated with menu option "school" instead of menu option "she", selectable region (4311) to be associated with menu option "student" instead of menu option "some", selectable region (4313) to be associated with menu option "service" instead of menu option "show", and selectable region (4315) to be associated with menu option "social" instead of menu option "said". In the preferred embodiment, following the selection of menu option "words", the menu option newly associated with each selectable region is displayed on that selectable region (not shown). Following the selection of menu option "words", indicating regions (4371), (4373), (4375), (4381), (4383) and (4385) each indicate the location of each of the selectable regions associated with the menu option associated with the indicating region.

The indicating regions and the menu options displayed thereon in FIG. 52 are disproportionately large relative to the rest of FIG. 52. They are approximately 1.5 times their proportionate size. They are represented as shown in FIG. 52 in compliance with Patent Cooperation Treaty Rules requiring a minimum size for letters in figures.

In the preferred embodiment of the Perimeter Menu aspect of the disclosure, all the menu options displayed on the selectable regions cannot be seen in a glance by many operators. However, when the displayed menu options are displayed on the indicating regions, for example, as shown in FIG. 52, the displayed menu options can be seen in a glance, facilitating searching of the menu by the operator for his intended menu option. Since the location of each selectable region is indicated by the location of the associated indicating region, the operator may point to the intended selectable region without searching it out or pausing to verify that the menu option associated with a selectable region is the menu option he desires. The frequent operator of such a menu interface may habituate the process of selecting an intended menu option so he can focus his attention on another task while selecting the option, for example, planning his next interaction with the menu interface.

Figure 53:
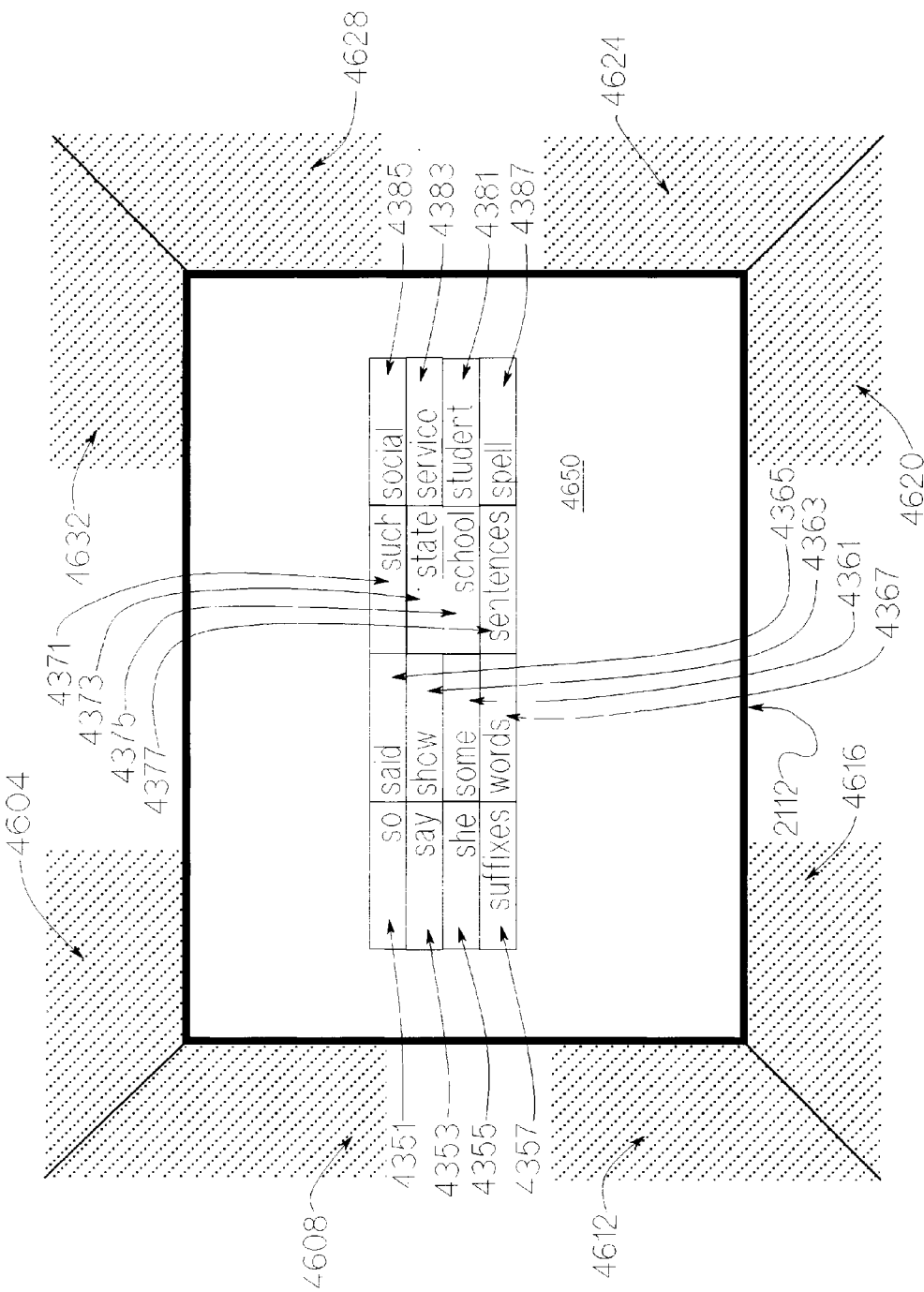
FIG. 53 is an illustration of a display and structures in accordance with an embodiment of the Location Indication aspect of the disclosure.

FIG. 53 depicts a display and structures in accord with an another embodiment of the Location Indication aspect of the disclosure. Selectable regions (4604), (4608), (4612), (4616), (4620), (4624), (4628) and (4632) are located adjacent the display (2112) and associated respectively with menu options "so", "say", "she", "suffixes", "said", "show", "some" and "words". Each selectable region is unbounded on the side furthest from and parallel to the edge of the display. Indicating regions (4351), (4353), (4355), (4357), (4367), (4361), (4363) and (4365) are associated respectively with menu options "so", "say", "she", "suffixes", "said", "show", "some" and "words". In accord with the Location Indication aspect of the disclosure, the location of an indicating region indicates the location of the selectable region associated with the menu option associated with the indicating region.

The large size of the selectable regions outside the display, for example, as shown in FIG. 53, facilitate selection by individuals with impaired fine motor control while the indicating regions indicate the location of each associated selectable region.

Figure 54:
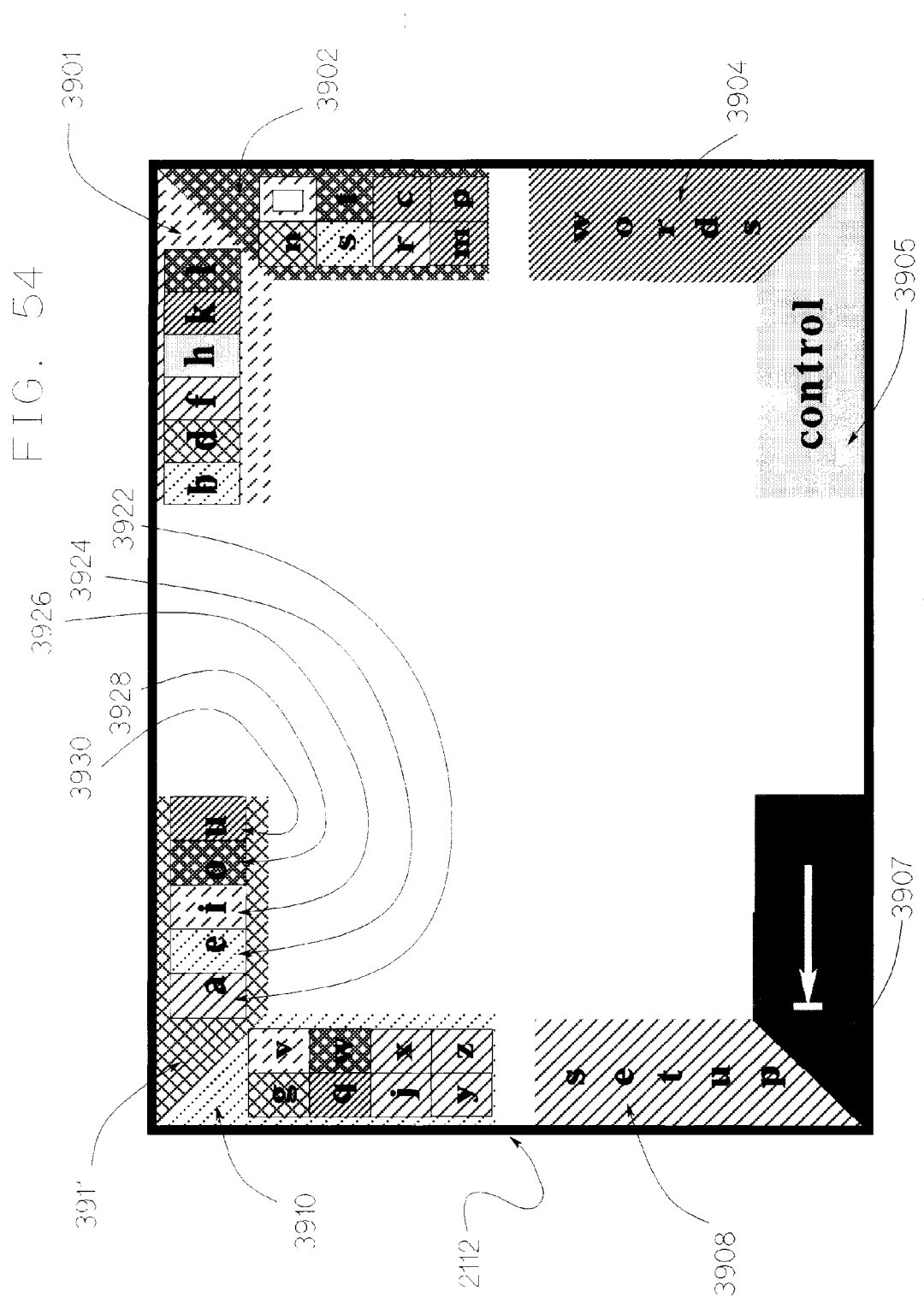
FIGS. 54 and 55 are each illustrations of a display and structures in accordance with another embodiment of the Location Indication aspect of the disclosure.
Figure 55:
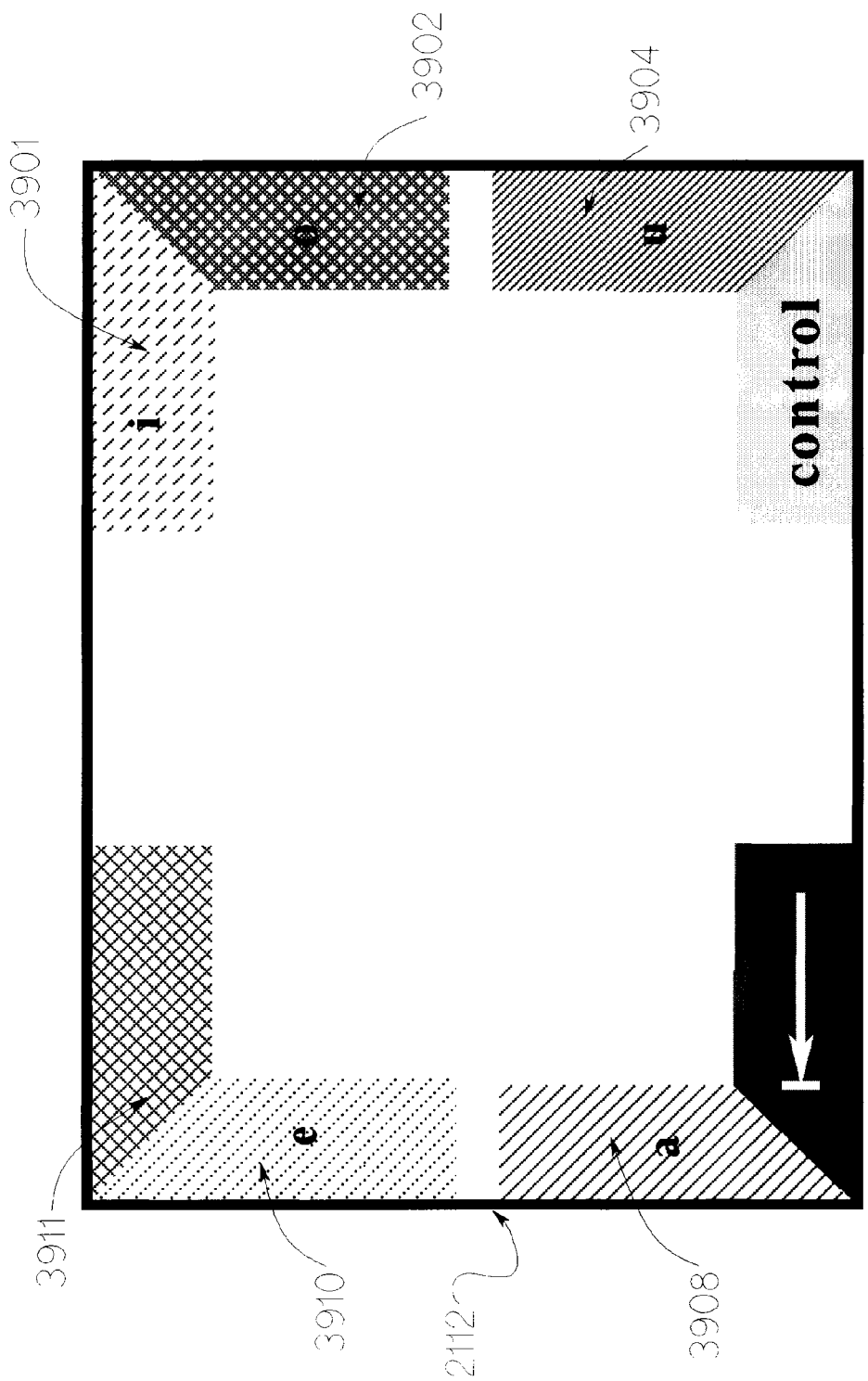

Yet another embodiment in accord with the Location Indication aspect of the disclosure is shown in FIGS. 54 and 55. FIG. 54 depicts a display (2112) having thereon eight selectable regions, each associated respectively with a menu option. As shown in the Figure, selectable region (3911) is associated with menu option "aeiou", selectable region (3910) with menu option "gqjyvwxz", selectable region (3908) with menu option "setup", selectable region (3907) with menu option undo, selectable region (3905) with menu option "control", selectable region (3904) with menu option "words", selectable region (3902) with menu option "nsrm<space>tcp" and selectable region (3901) with menu option "bdfhkl". Menu option "aeiou" is associated with a submenu which includes submenu options "a", "e", "i", "o" and "u", displayed on indicating regions (3922), (3924), (3926), (3928) and (3930) respectively. The background pattern of indicating region (3922) matches the background pattern of selectable region (3908), indicating that submenu option "a" will be associated with selectable region (3908) following selection of menu option "aeiou". Similarly, the background pattern of indicating region (3924) matches the background pattern of selectable region (3910), indicating that submenu option "e" will be associated with selectable region (3910) following selection of menu option "aeiou". Alternatively, the indication may be made by the size, shape, hue, brightness, contrast, dithering, fill, blinking, hatching or pattern of the indicating region or any part thereof, including either of the foreground and background of the indicating region.

When the operator selects selectable region (3911), the display (2112) changes to that shown in FIG. 55. Now, selectable region (3910) is associated with submenu option "e", selectable region (3908) with submenu option "a", selectable region (3904) with submenu option "u", selectable region (3902) with submenu option "o" and selectable region (3901) with submenu option "i". In accord with the Location Indication aspect of the disclosure, the appearance of an indicating region indicates the location of the selectable regions associated with the submenu option associated with the indicating region.

The embodiment shown in FIGS. 54 and 55 illustrates how the Location Indication aspect of the disclosure speeds selection of a submenu option of a menu hierarchy. The operator, by observing the background pattern of the submenu option within the displayed menu option, may determine which selectable region he should next dwell on. The operator may make this determination prior to selection of the menu option and need not wait for the submenu options to be displayed on their associated selectable regions. In accordance with the Location Indication aspect of the disclosure, the operator may select or spell out words more quickly than with conventional automated menu hierarchy. Assuming the display (2112) is part of computer system, these words may be input to an application program, and, if the computer system is coupled to a speech synthesizer, these words may be spoken.

Figure 56:
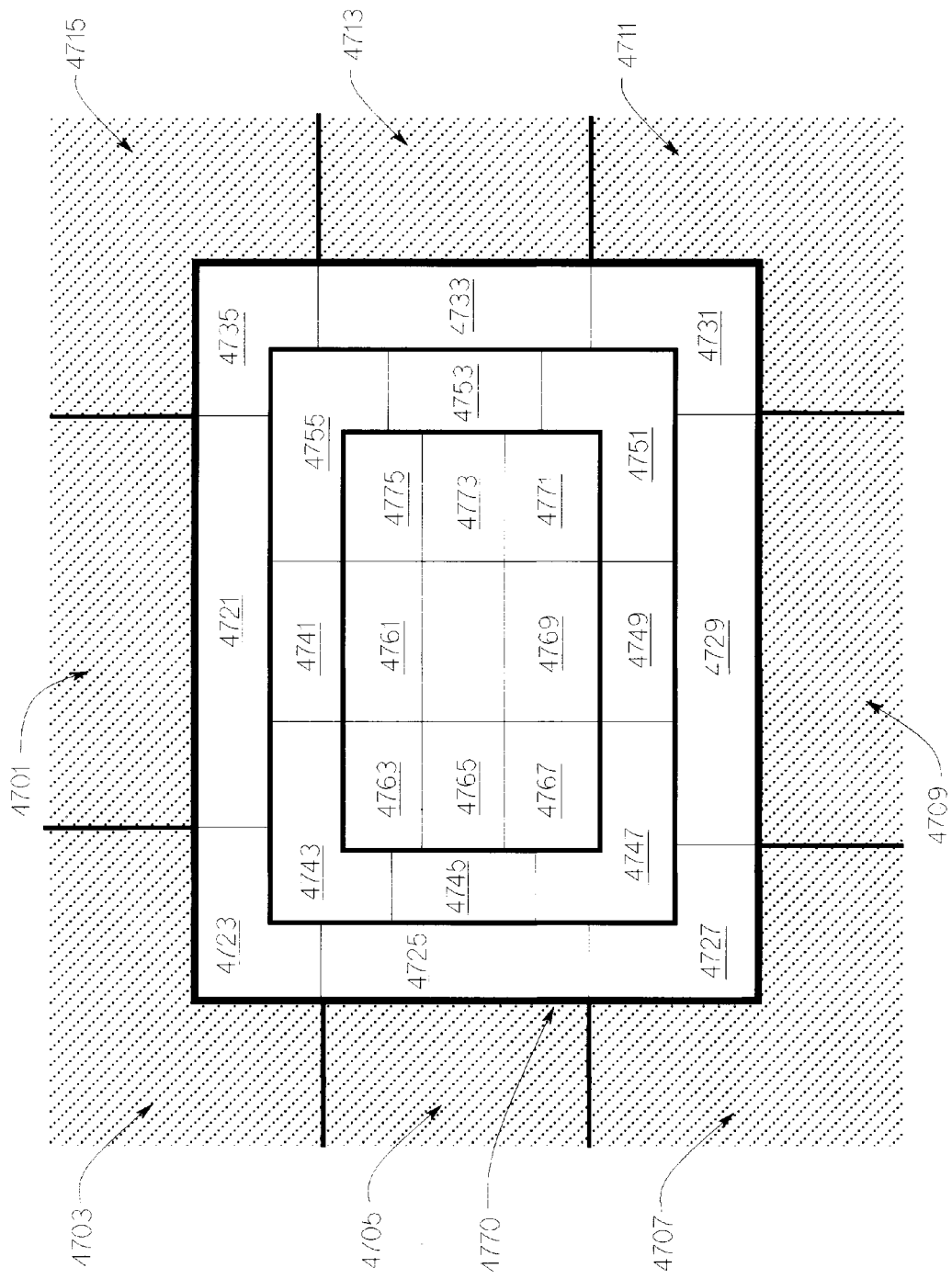
FIG. 56 is an illustration of a display and structures in accordance with a still further embodiment of the Location Indication aspect of the disclosure.

FIG. 56 depicts another apparatus in accord with the Location Indication aspect of the disclosure. An example of the operation of this apparatus will now be described. FIG. 56 depicts display area (4770) adjacent to which are located selectable regions (4701), (4703), (4705), (4707), (4709), (4711), (4713) and (4715). Not shown in the Figure are three sets of eight menu options. At different times during the operation of the apparatus shown in FIG. 56, for example at one second intervals, the plurality of selectable regions is associated with a different set of eight menu options such that, for a one second period, each selectable region is associated respectively with one menu option of the associated set of menu options. On the display area are 24 indicators, each associated respectively with one of the menu options. Each indicator indicates when a selectable region is associated with the menu option associated with the indicator. Thus, each of the indicators (4721), (4723), (4725), (4727), (4729), (4731), (4733) and (4735) is associated respectively with a menu option which may be in turn associated respectively, for example, during a first one second period, with one of the selectable regions. The operator may select a desired one of the 24 menu options by selecting the associated selectable region during the period when the desired menu option is associated with the associated selectable region.

Alternatively, the apparatus shown in FIG. 56 may require two successive selection events, the first selection event to select a set of eight menu options or to select a set of three menu options, the set being associated with one selectable region, and the second selection event to select one of the selected set. For example, the first selection event may select the set of menu options associated with indicators (4773), (4753) and (4733), and the second selection event may select one menu option from this set.

Figure 57:
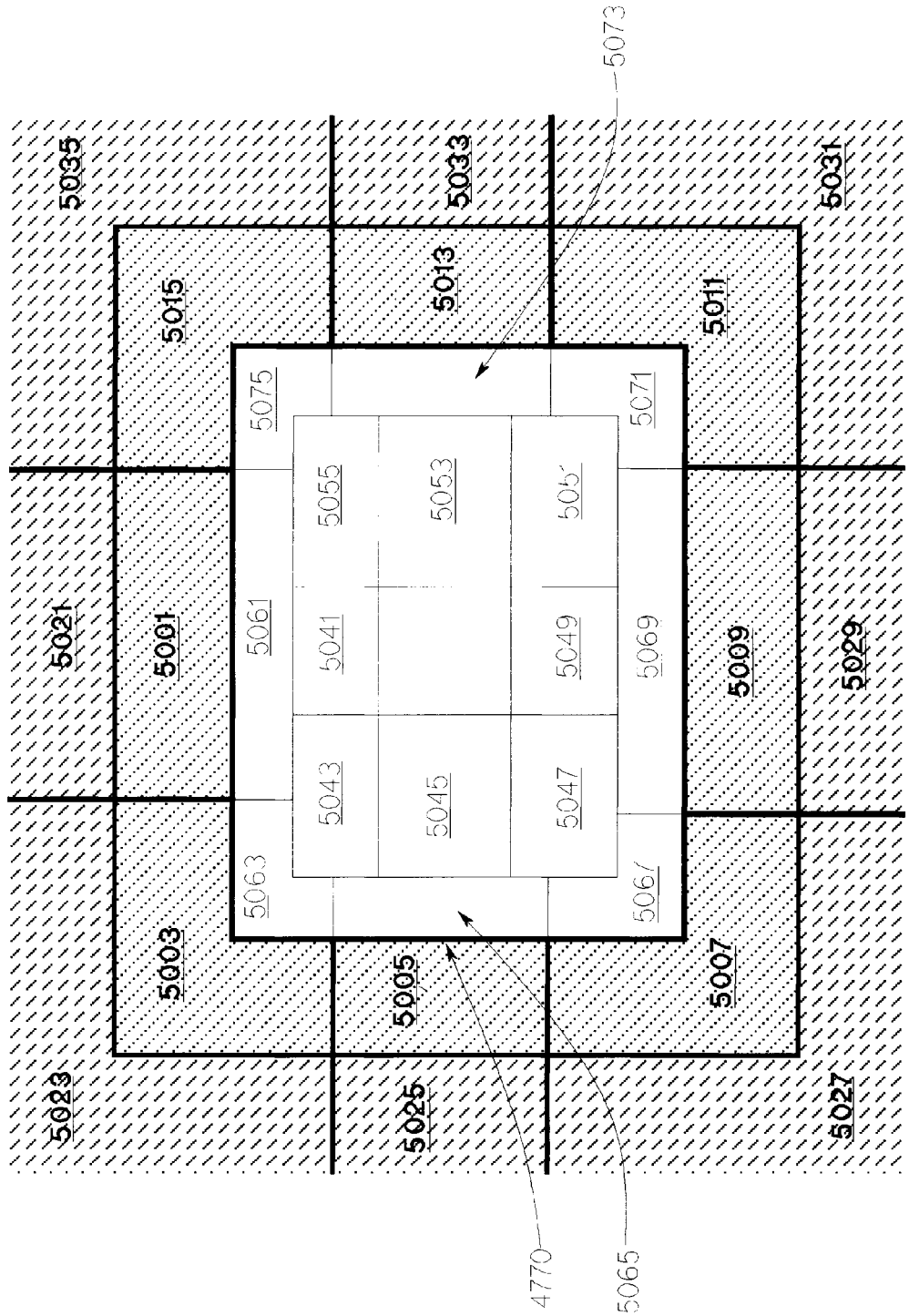
FIG. 57 is an illustration of a display and structures in accordance with a further embodiment of the Location Indication aspect of the disclosure.

Still another apparatus in accord with the Location Indication aspect of the disclosure is shown in FIG. 57. FIG. 57 depicts display area (4770) outside of which are located selectable regions (5001), (5003), (5005), (5007), (5009), (5011), (5013), (5015), (5021), (5023), (5025), (5027), (5029), (5031), (5033) and (5035). The location of each selectable region is indicated by an indicating region on the display area, (5041), (5043), (5045), (5047), (5049), (5051), (5053), (5055), (5061), (5063), (5065), (5067), (5069), (5071), (5073) and (5075), respectively.

The Location Indication aspect of the disclosure will now be described from an implementation perspective with reference to FIG. 52. Preferably, the Location Indication aspect is implemented by modifications to the access program (1206) described in the detailed description of the Perimeter Menu aspect of the disclosure. The modifications required for the Location Indication aspect of the disclosure are: (1) at initialization time: (a) create twelve child edit windows, each corresponding to one of the indicating regions shown in FIG. 52, each of the class "edit", each having the style (WS_CHILD WS_BORDER | WS_DISABLED | ES_MULTILINE | AlignmentStyle) where " " represents a logical OR operation and where AlignmentStyle equals ES_RIGHT for child windows having right justified text and ES_LEFT for child windows having left justified text, as shown in FIG. 52; (b) move the child edit windows so they are located in or near the center of the display; (c) display the child edit windows; and (d) initialize an array which maps each child edit window, for example, by an index between 0 and 11 inclusive, to an element of the aLabel array; and (2) modify the code implementing ST_SELECTED state processing, so that after changing the menu options associated with various selectable regions (by changing the pLabel element of the data set associated with each of the state machines to point to the menu option in the aLabel array to be associated with that state machine), the array mapping each child window to an element of the aLabel array is used to access the text of the menu option and the text of each child edit window is set accordingly. In the preferred embodiment, the six menu options displayed in indicating regions (4371), (4374), (4375), (4381), (4383) and (4385) are present in the aLabel array when FIG. 52 is shown, but are not associated with selectable regions until the operator selects menu option "words".

I. Sound Match

Figure 58:
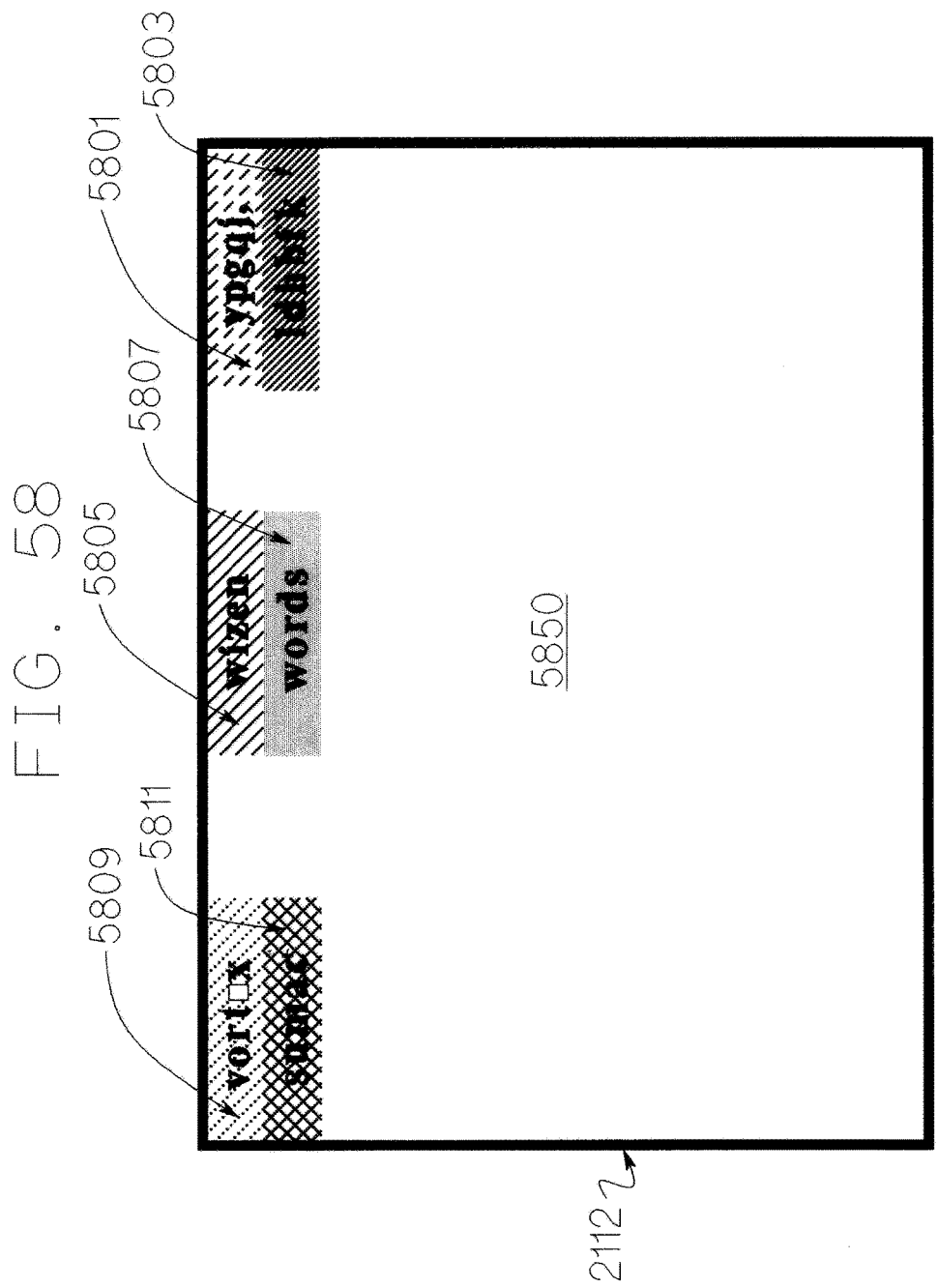
FIGS. 58 and 59 are illustrations of a display and structures in accordance with the preferred embodiment of the Sound Match aspect of the disclosure.
Figure 59:
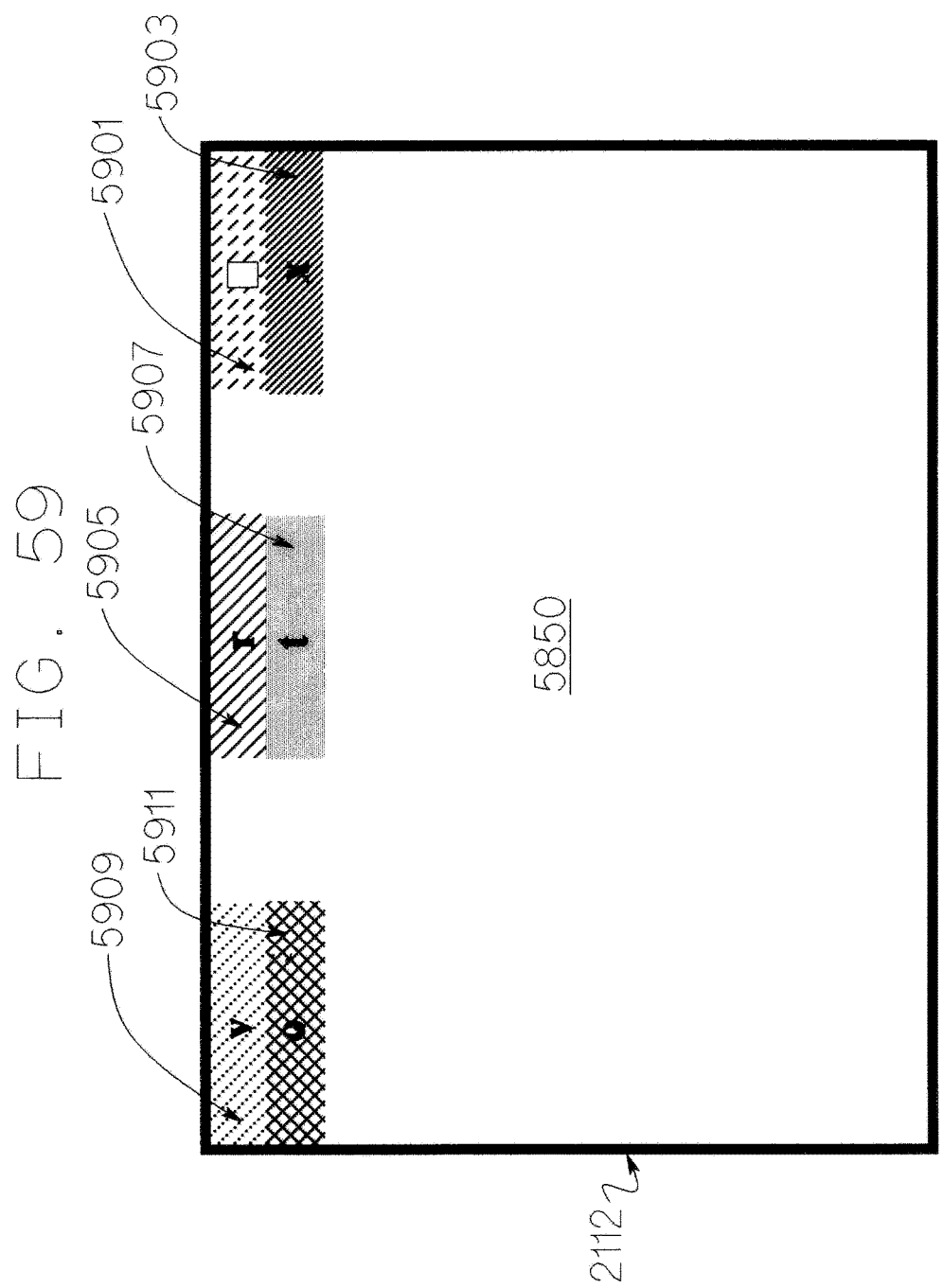

The preferred embodiment of the Sound Match aspect of the disclosure will now be described in detail from a functional perspective using an example depicted in FIG. 58. FIG. 58 shows a display (2112) of a computer system (2116) having thereon six regions or sound indicators, (5801), (5803), (5805), (5807), (5809), and (5811), each associated with a menu option, "ypgqj,", "ldhbfk", "wizen", "words", "vort x", and "sumac", respectively. Each menu option is displayed on its associated sound indicator. Each sound indicator has a distinct hue. For example, sound indicator (5801) may be green, (5803) white, (5805) blue, (5807) red, (5809) orange and (5811) grey. Each of these sound indicators indicates a sound the operator is able to consistently produce, for example, the vowel sound e as it sounds in green, i as it sounds in white, u as it sounds in blue, e as it sounds in red, o as it sounds in orange and e it sounds in grey. Assuming the operator says o as it sounds in orange, "vort x", the menu option associated with the orange sound indicator (5809) is selected and the display is changed to that shown in FIG. 59. In the preferred embodiment, submenu options space, "x", "r", "t", "v" and "o" are now associated with each of the sound indicators (5901), (5903), (5905), (5907), (5909), and (5911) respectively. Assuming the operator says e as in green, submenu option space is selected and a space is input to the application program (6107) whose output appears in region (5850).

Figure 60:
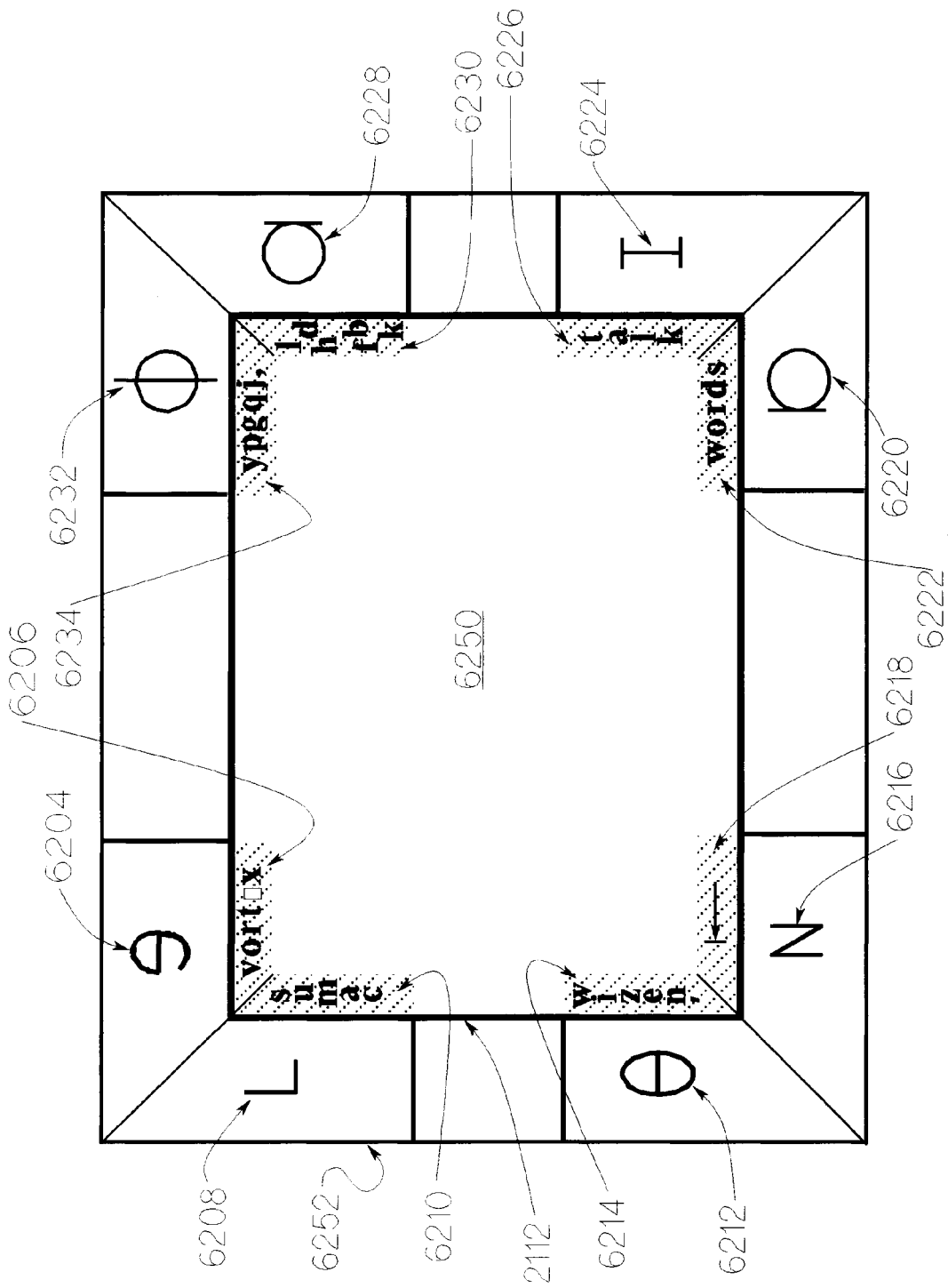
FIG. 60 is an illustration of a display and structures in accordance with another embodiment of the Sound Match aspect of the disclosure.

FIG. 60 illustrates a display and structures in accordance with an alternative embodiment of the Sound Match aspect of the disclosure. FIG. 60 depicts a display (2112) of a computer system (2116). Adjacent the display (2112) is a static display (6252) having thereon eight sound indicators (6204), (6208), (6212), (6216), (6220), (6224), (6228), and (6232). Each of the eight sound indicators is a symbol in a phonetic character set graphically representing a sound. Alternatively, the sound indicators may include a picture of an object, for example, a tree, a house, a boy, or a map of a country, or may include a shape, for example, a square, a circle, or a triangle, or may include a hue indicator, a pitch indicator, a volume indicator, a sound duration indicator, a change in pitch indicator, or a change in volume indicator. Eight menu options, "vort<space>x", "sumac", "wizen", undo, "words", "talk", "ldhbfk" and "ypgqj,", are displayed on the display (2112), each adjacent and associated respectively with one of the sound indicators, the eight menu options together circumscribing region (6250) on the display. The operator may select any one of the menu options by producing the sound indicated by the sound indicator associated with the menu option. In response to a menu selection, submenu options of the selected menu option may be displayed and associated respectively with a sound indicator.

An operator with impaired speech but who is able to consistently produce a relatively small number of sounds distinguishable by conventional speech recognition means may, in accord with the Sound Match aspect of the disclosure, select from among the small number of menu options by using the sounds he can produce. Assuming the display (2112) is part of computer system, the menu option may represent inputs to an application program, and, if the computer system is coupled to a speech synthesizer, the menu option may represent words to be spoken.

Figure 61:
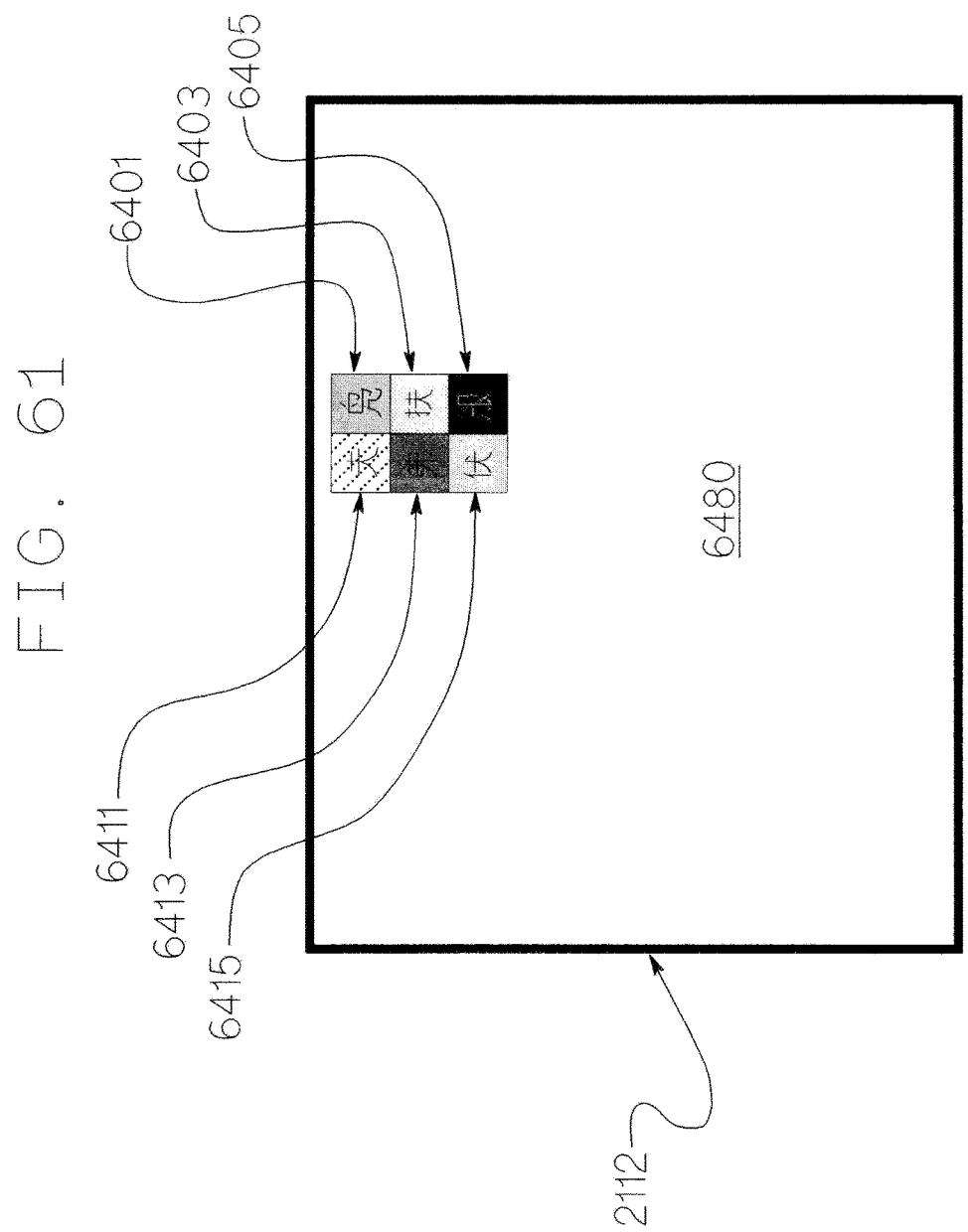
FIG. 61 is an illustration of a display and structures in accordance with another embodiment of the Sound Match aspect of the disclosure.

FIG. 61 illustrates a display and structures in accordance with an alternative embodiment of the Sound Match aspect of the disclosure. FIG. 61 depicts a display (2112) of a computer system (2116) having thereon six square sound indicators, (6401), (6403), (6405), (6411), (6413), and (6415) arranged in two columns of three sound indicators. Each sound indicator abuts a sound indicator in the other column, the sound indicator located above it, if any, and the sound indicator located below it, if any. Assume that the operator is entering Chinese, that he uses a keyboard to enter a phonetic unit and intonation according to the Pin Yin coding method for the Chinese language, and that he enters the distinct sound "fú", each of the sound indicators shown in FIG. 61 is associated respectively with a menu option, each of the plurality of menu options having a common characteristic. In this example, the menu options are homophones and the common characteristic is a phonetic unit and intonation but may be a phonetic unit alone, an intonation alone, a stroke used to draw an ideograph, a number of horizontal strokes, a number of vertical strokes, a number of total strokes, a stroke order, a radical, a part of speech, an ideograph, a kana, a diacritic, a classification of a part of an ideograph or other characteristic of a class of ideographs. Each of the sound indicators has a distinct hue. The operator may select any one of the displayed menu options, according to the Sound Match aspect of the disclosure, by speaking the sound associated with the sound indicator associated with the desired menu option. For example, assume the operator says, "blue" or a translation thereof, preferably a Chinese translation in this example. The ideograph located on the blue sound indicator is selected. In this example, this ideograph is input to a word processing program and appears on the display (2112).

The Sound Match aspect of the disclosure thus allows an operator to select from an option from a menu, using speech recognition means, whether or not the menu options are homophones. The operator does not need to use his hands to make this selection and so may keep both his hands on the home row of the keyboard, in preparation for entering the next common characteristic, or, if specifying the common characteristic by voice, may select a menu option without interrupting the manual activity he's engaged in.

Figure 62:
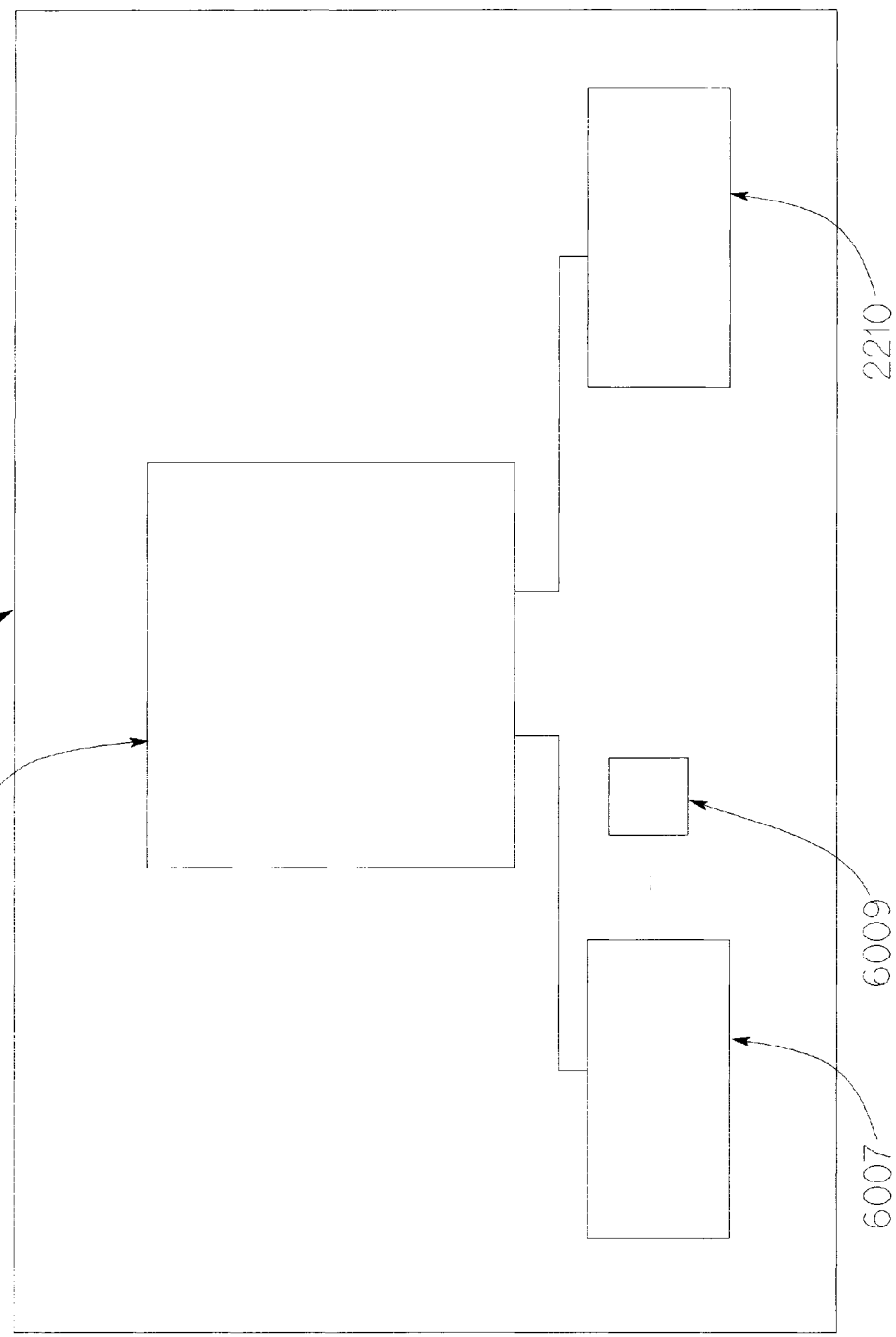
FIG. 62 is a block diagram of a speech recognition system which may be utilized in accordance with the Sound Match aspect of the disclosure.
Figure 63:
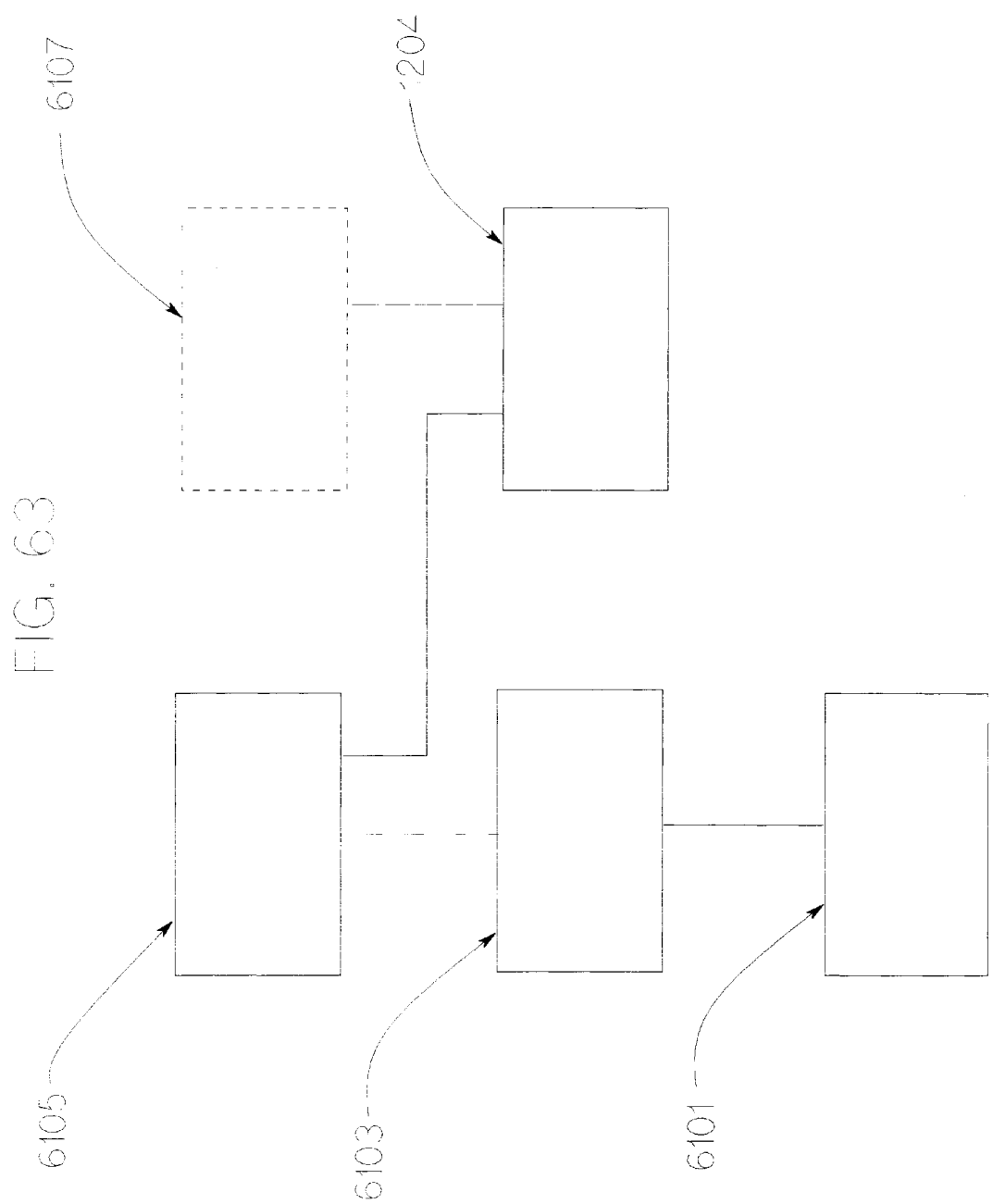
FIG. 63 is an illustration of software components of an apparatus in accordance with an embodiment of the Sound Match aspect of the disclosure.

The preferred embodiment of the Sound Match aspect of the disclosure will now be described in detail from an implementation perspective, beginning with the hardware and software operating environment which will now be described with reference to FIG. 62 which depicts a speech recognition system (6001) including a computer system (2116) and keyboard (2210), as earlier described, a sound board (6007) and a microphone (6009). The conventional computer system (2116) preferably includes an 80486 CPU running at 33 MHz or faster, and is provided with Dragon Dictate Power Edition software, available from Dragon Systems, Inc., Newton, Mass., USA. Preferably, the sound board is the Audio Capture Playback Adaptor and the microphone is the Shur Headset microphone, both available from Dragon Systems, Inc. FIG. 63 depicts the software environment of the preferred embodiment, which includes the earlier described Windows® version 3.1 operating system (1204), an optional Windows® application program (6107), the Windows® Dragon software driver (6101) included in the Dragon Dictate Power Edition software, the Dragon Application (6103) included in the Dragon Dictate Power Edition software, and a speech recognition access program (6105). The Dragon Application (6103) is configured to match a sample of each of six sounds distinguishable by the Dragon Application (6103) which the operator can consistently produce. Using the example described above, these are the vowel sounds produced by the operator of e as it sounds in green, i as it sounds in white, u as it sounds in blue, e as it sounds in red, o as it sounds in orange and e it sounds in grey. Each of these sounds is associated respectively with an identifier, for example, a number or a sequence of one or more characters. The speech recognition access program (6105) is preferably a Windows® application program developed using, in part, the Voice Tools Software Development Kit available from Dragon Systems, Inc. At initialization time, the speech recognition access program (6105) defines an array of data structures defining the menu and submenu options and the menu hierarchy. For example, one of the elements of this array determines that, on selection, certain actions are to be taken, for example, inputting text to an application program, and that certain submenu options and related data are to be associated with certain child edit windows. Also at initialization time, the speech recognition access program (6105) initializes callback procedures using the Dragon Application's Application Program Interface to receive notification from the Dragon Application when a sound has been matched. Also at initialization time, the main window of the speech recognition access program (6105) is preferably sized to just encompass the sound indicators shown in FIG. 58. Also at initialization time, the speech recognition access program (6105) creates six child edit controls, each corresponding to one of the sound indicators shown in FIG. 58. Each of the child edit controls has the background color described above and a text color of black or white depending upon which provides better contrast against the background color of the child edit control, and each is located on the display (2112) as shown in FIG. 58. Also at initialization time, the menu options of the initial menu are each associated respectively with one of the child edit controls. After initialization, the speech recognition access program (6105), upon notification from the Dragon Application that a sound has been received and a match attempted, sequentially searches the list of identifiers matched to the sound by the Dragon Application (6103), starting with the best match, until it finds an identifier corresponding to any one of the six sounds distinguishable by the Dragon Application (6103). Assuming the operator says o as it sounds in orange, the Dragon Application (6103) provides to the speech recognition access program (6105) a list of matches including, before any other identifier corresponding to any one of the six sounds distinguishable by the Dragon Application (6103), the identifier associated with child edit control (5809). This child edit control is currently associated with menu option "vort x", the matched menu option. The speech recognition access program (6105) then sets the text of each of the child edit controls to one of the submenu options associated with the matched menu option. In the example above, submenu options space, "x", "r", "t", "v" and "o" are associated with each of the child edit controls respectively and the text of the associated child edit control is set to the submenu option. Assuming the operator says e as in green, submenu option space is the matched submenu option and a space is input to the application program (6107) whose output appears in region (5850). Preferably the application program (6107) is an application program capable of executing a WM_SIZE command so that the speech recognition access program (6105) may size the windows of the application program (6107) to fit neatly in region (5850) and is capable of executing WM_CHAR messages so that the speech recognition access program (6105) may input characters to the application program (6107).

J. Ideographic Language

Figure 64:
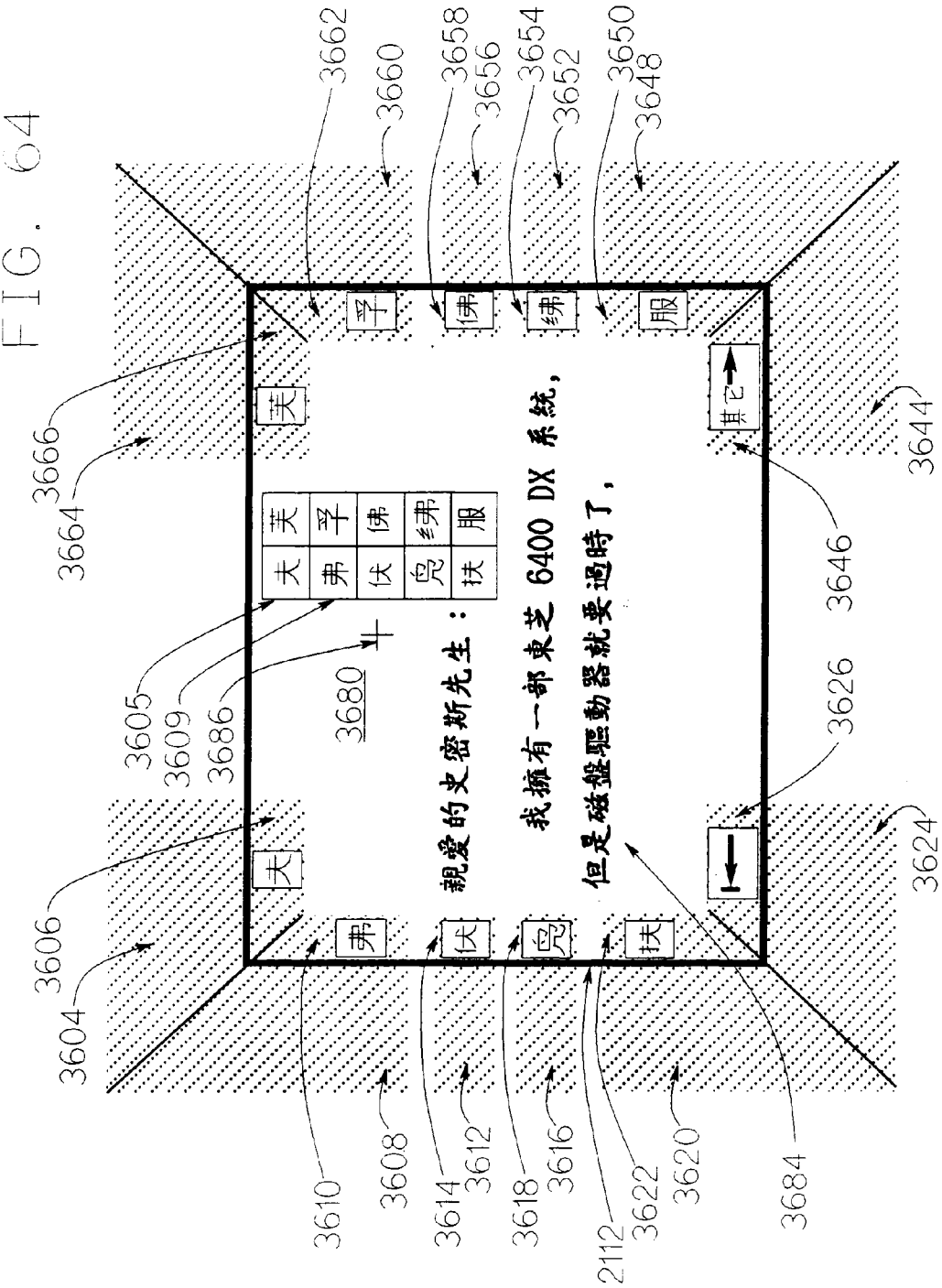
FIG. 64 is an illustration of a display and structures in accordance with the preferred embodiment of the Ideographic Language aspect of the disclosure.

The preferred embodiment of the Ideographic Language aspect of the disclosure will now be described in detail from a functional perspective using an example depicted in FIG. 64. FIG. 64 shows the display (2112) of a general purpose computer system (2218 in FIG. 15) and 12 selectable regions. Each of the 12 selectable regions consists of the union of a visible subregion on the display (2112) and an invisible subregion located outside the display (2112) and adjacent the visible subregion. For example, the selectable region in the upper left corner both above and below the top of the display (2112) in FIG. 64 consists of invisible subregion (3604) and visible subregion (3606), and hereinafter is referred to as selectable region (3604/3606). The other selectable regions shown in FIG. 64, proceeding counter clockwise from selectable region (3604/3606) are (3608/3610), (3612/3614), (3616/3618), (3620/3622), (3624/3626), (3644/3646), (3648/3650), (3652/3654), (3656/3658), (3660/3662) and (3664/3666). In FIG. 64 each of the visible subregions is adjacent an edge of the display (2112). The selectable regions together circumscribe region (3680) in the center of the display. Also shown on the display (2112) within region (3680) in FIG. 64 are ten square indicating regions arranged in two columns of five indicating regions. Each indicating region abuts an indicating region in the other column, the indicating region located above it, if any, and the indicating region located below it, if any. In the preferred embodiment, each indicating region indicates by its location the location of a respectively associated selectable region, in accord with the Location Indication aspect of the disclosure. For example, the uppermost indicating region in the left column of indicating regions (3605) is associated with the uppermost selectable region (3604/3606) on the left side of the display. Indicating region (3609) located immediately below indicating region (3605) is associated with selectable region (3608/3610) located immediately below selectable region (3604/3606).

The operation of the example of the preferred embodiment of the Ideographic Language aspect of the disclosure will now be described. Assuming that the operator is fitted with a head pointer coupled to the general purpose computer system (2218), that he uses a keyboard to enter a phonetic unit and intonation according to the Pin Yin coding method for the Chinese language, and that he enters the distinct sound "fú", each of the plurality of the selectable regions shown in FIG. 64 is associated with one of a plurality of menu options, each of the plurality of menu options having a common characteristic. In this example, the common characteristic is a phonetic unit and intonation but may be a phonetic unit alone, an intonation alone, a stroke used to draw an ideograph, a number of horizontal strokes, a number of vertical strokes, a number of total strokes, a stroke order, a radical, a part of speech, an ideograph, a kana, a diacritic, a classification of a part of an ideograph or other characteristic of a class of ideographs. The ten menu options shown in FIG. 64 are Chinese ideographs each starting with the distinct sound "fú". Alternatively, the menu options may be sequences of graphic symbols including one or more kanji. In FIG. 64 the Chinese ideographs are each displayed on the visible subregion of the associated selectable region and on the indicating region associated with the selectable region. The remaining two of the 12 selectable regions, (3624/3626) and (3644/3646), are associated with menu options for undo and for displaying more menu options, respectively. In the preferred embodiment, in response to the selection of the menu option for displaying more menu options, each of the selectable regions associated with a menu option starting with the distinct sound "fú" is associated with a menu option not previously displayed and the newly associated menu option replaces the old menu option on the display.

Resuming now with the description of the example of the preferred embodiment, a cross hair cursor (3686) is displayed in the circumscribed region (3680). Assuming the operator desires to select the menu option associated with selectable region (3608/3610), he turns his head to the left and the cross hair cursor (3686) moves to the left, responsive to the head movement, until the cross hair cursor hotspot intersects selectable region (3608/3610) and he maintains the location of the cross hair cursor hotspot on that selectable region for the selection threshold period. The menu option associated with selectable region (3608/3610) is selected and added to text (3684) displayed in the circumscribed region (3680), the general purpose computer system (2218) emits an audible beep indicating that selection has occurred and the displayed menu options, both on the indicating regions and the visible subregions, are removed from the display.

In the preferred embodiment, selection is made in accord with the Facilitated Dwell subaspect of the Dwell aspect of the disclosure, described above. Thus, the operator receives an indication of the progress of his selection by a change in appearance of the indicating region associated with the intersected selectable region. Alternatively, selection may be by intersection of a location indicated by the at least part of a cursor and a selectable region alone, by such an intersection accompanied by a switch operation, for example, a depression of a space bar on the keyboard, or by other suitable means.

In accord with the Location Indication aspect of the disclosure, the operator sees the entire menu in the compact indicating regions and may discover the location of the selectable region associated with each menu option without having to visually scan all the visible subregions. In the preferred embodiment, the plurality of indicating regions may be moved to a different location on the display to avoid obstructing the area of the display showing most recently added graphic symbols or the area of the display where graphic symbols will soon be added. In accord with the Ideographic Language aspect of the disclosure, an operator may select from among many sequences of one or more ideographs without lifting either hand from the keyboard, thus speeding entry of single ideographs or sequences of ideographs in word processing systems for the Chinese, Japanese and Korean languages. Since, in the preferred embodiment, the selectable regions are located adjacent the edge of the display, a large rectangular region remains available on the display for the output of an application program. Further, if the selectable regions are located entirely outside the display, the indicating regions obstruct only a relatively small portion of the circumscribed region (3680), permitting the display of a sequences of ideographs for selection simultaneous with the display of previously selected ideographs, neither obstructing the operator's view of the other. If the general purpose computer system is coupled to a speech synthesizer and the ideographs are symbols of a symbol set, for example, the Blissymbolics Symbol Set, an illiterate operator, for example, a school child having impaired speech, may select symbols associated with words and those words may be spoken via the speech synthesizer.

Figure 65:
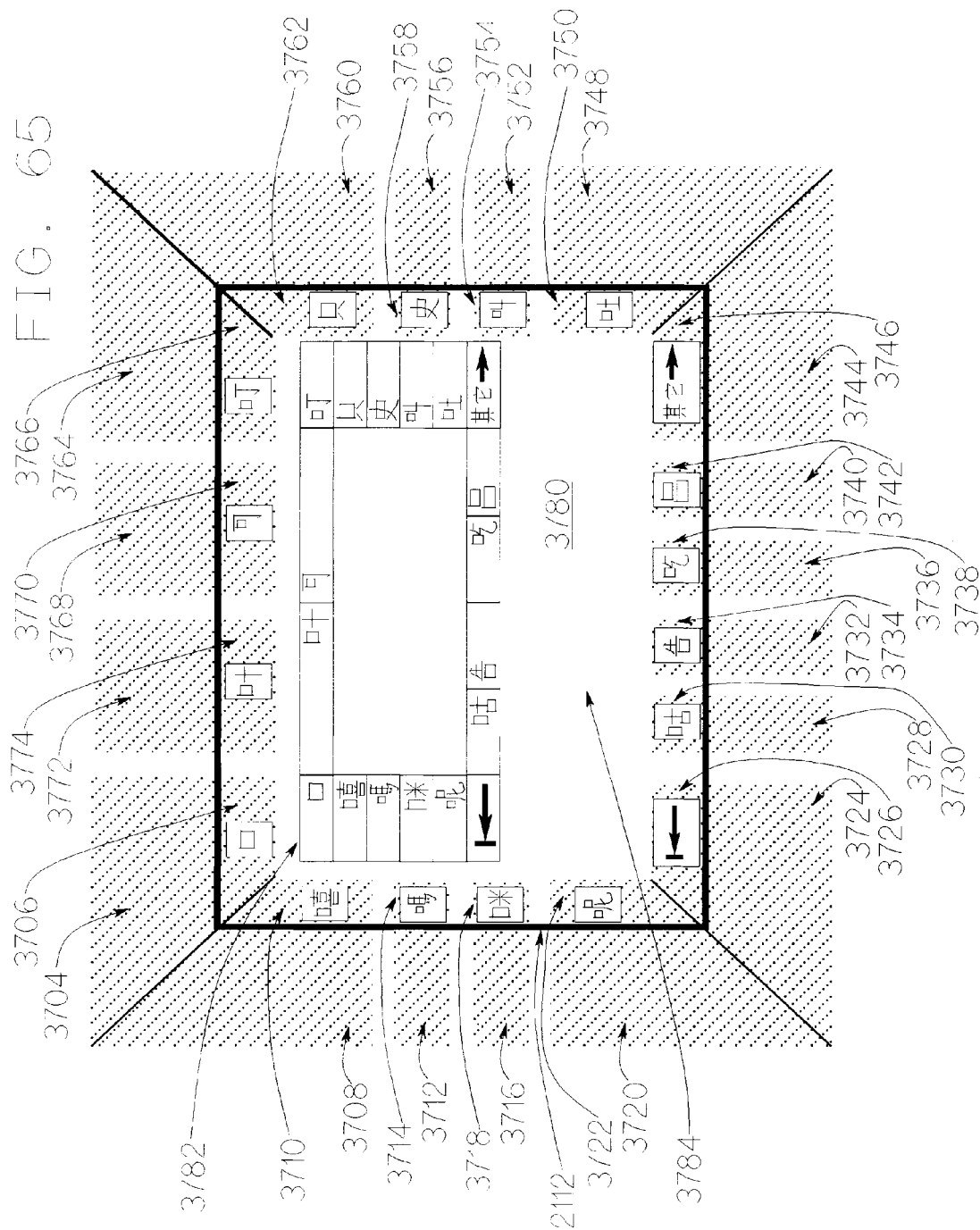
FIG. 65 is an illustration of a display and structures in accordance with another embodiment of the Ideographic Language aspect of the disclosure.

FIG. 65 illustrates a display and structures in accordance with an alternative embodiment of the Ideographic Language aspect of the disclosure. In this Figure, 18 selectable regions (3704/3706), (3708/3710), (3712/3714), (3716/3718), (3720/3722), (3724/3726), (3728/3730), (3732/3734), (3736/3738), (3740/3742), (3744/3746), (3748/3750), (3752/3754), (3756/3758), (3760/3762), (3764/3766), (3768/3770), (3772/3774) and (3776/3778) circumscribe region (3780) on the display (2112). The visible subregions of four of the 18 selectable regions abut each of the top, left and right edges of the display (2112). The visible subregions of six of the 18 selectable regions abut the bottom edge of the display (2112). The 18 indicating regions are located within the top half of region (3780). 12 of the 18 indicating regions are arranged in two columns of six indicating regions each. The column on the left is close to the visible subregions abutting the left edge of the display. The column on the right is close to the visible subregions abutting the right edge of the display. Two of the 18 indicating regions are located between the top indicating regions in each of the left and right columns. The remaining four of the 18 indicating regions are located between the bottom indicating regions in each of the left and right columns Each of the four indicating regions in the top row of indicating regions indicates the location of a respectively associated selectable region along the top edge of the display. Each of the six indicating regions in the bottom row of indicating regions indicates the location of a respectively associated selectable region along the bottom edge of the display. Each of the middle four indicating regions in each of the left and right columns of indicating regions indicates the location of a respectively associated selectable region along the left and right edge of the display. The 16 menu options shown in FIG. 65 are Chinese ideographs each of which includes the radical kŏu, a radical having the shape of a rectangle. Each ideograph is displayed on the visible subregion of the associated selectable region and on the indicating region associated with the selectable region. The remaining two of the 18 selectable regions, (3724/3726) and (3744/3746), are associated with menu options for undo and for displaying more menu options, respectively.

The indicating regions (3782) in FIG. 65 are disproportionately large relative to the rest of FIG. 65. They are approximately 1.5 times their proportionate size. They are represented as shown in FIG. 65 in compliance with Patent Cooperation Treaty Rules requiring a minimum size for letters in figures.

Figure 66:
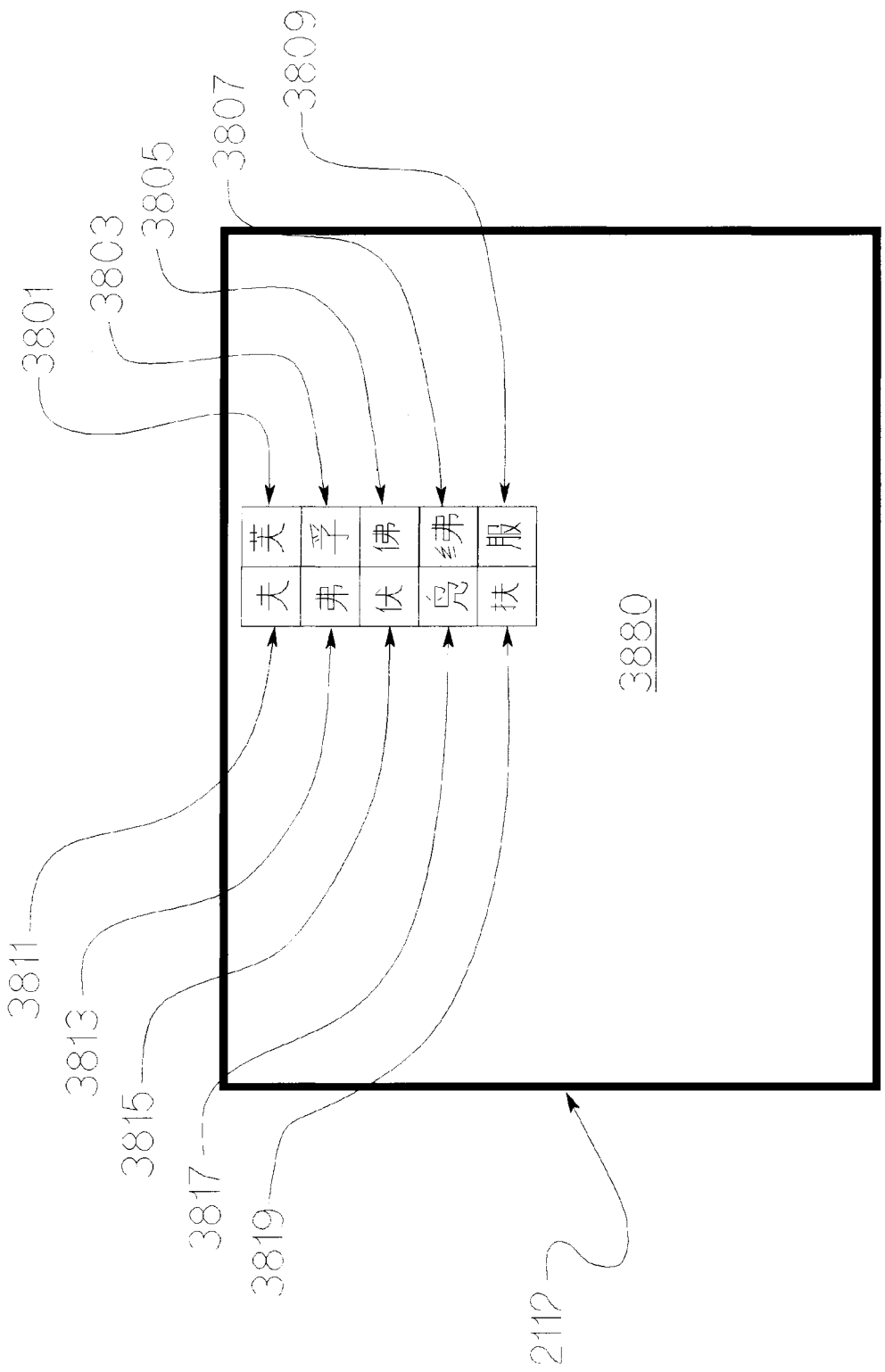
FIG. 66 is an illustration of a display and structures in accordance with still another embodiment of the Ideographic Language aspect of the disclosure.

FIG. 66 illustrates a display and structures in accordance with an alternative embodiment of the Ideographic Language aspect of the disclosure. FIG. 66 depicts a display (2112) of a computer system (2116) having thereon ten square indicating regions, (3801), (3803), (3805), (3807), (3809), (3811), (3813), (3815), (3817), and (3819), arranged in two columns of five indicating regions. Each indicating region abuts an indicating region in the other column, the indicating region located above it, if any, and the indicating region located below it, if any. Each indicating region indicates the location of a respectively associated selectable region (not shown) outside the display. Assume that the operator is entering Chinese and uses a keyboard coupled to the computer system (2116) to enter the distinct sound "fú". On each of the indicating regions is then displayed an ideograph having with the distinct sound "fú". The operator, using a pointer coupled to the computer system (2116), points to the selectable region associated with the indicating region on which is displayed the desired ideograph. The selectable region is selected in response to a selection event, and, in this example, the associated menu option is input to a word processing program and appears on the display (2112).

FIG. 67 illustrates a display and structures in accordance with an alternative embodiment of the Ideographic Language aspect of the disclosure. FIG. 67 depicts a display (2112) of a computer system (2116) having thereon eight selectable regions (6701), (6703), (6705), (6707), (6709), (6711), (6713), and (6715), each located on the display (2112) adjacent the edge of the display (2112) and associated respectively with a menu option. Together the eight selectable region circumscribe region (6750) on the display. In FIG. 67 each of eight menu options is displayed on its associated selectable region. Six of the eight menu options, associated with selectable regions (6703), (6705), (6707), (6701), (6715), and (6713) each represent a sequence of graphic symbols in the Japanese language. These sequences, in Romanized Japanese are respectively "hoka", "hoka ni", "hoka no", "hoka kara", "nanika hoka nomono", and "hoka demo nai ga". Each sequence includes the kanji "hoka" shown alone on selectable region (6703). The sequences are ordered by length, the shorter sequences on selectable regions on the left side of the display (2112) ordered by length from the top to the bottom of the display (2112), the longer sequences along the right side of the display (2112) ordered by length from the top to the bottom of the display (2112). The remaining two of the eight selectable regions, (6709) and (6711), are associated with menu options for displaying the previous and the next display of menu options, respectively. The menu option associated with a selectable region may be selected by a selection event.

The preferred embodiment of the Ideographic Language aspect of the disclosure will now be described in detail from an implementation perspective. Preferably, the Ideographic Language aspect of the disclosure is implemented by modifications to the access program (1206) described in the detailed description of the Perimeter Menu aspect of the disclosure, modified as described in the descriptions of the Facilitated Dwell subaspect and the Location Indication aspects of the disclosure. The modifications required for the Ideographic Language aspect of the disclosure are: (1) install on the general purpose computer system a font for the ideographic language of the embodiment; (2) at initialization time: (a) set the text of all labels for display on the selectable regions to null; (b) do not enable the cursor polling timer; and (c) hide the Windows® (1204) system cursor; (3) include in the main window processing procedure of the access program (1206) code to process WM_CHAR messages and, when a sequence of one or more WM_CHAR messages indicates a common characteristic: (a) lookup sequences or representations of sequences of one or more ideographs (hereinafter "sequences") having the common characteristic; (b) copy ten of the sequences to the labels; (c) set the Windows® (1204) system cursor to the cross hair cursor, set the cursor location to a predetermined location near an indicating region and show the Windows® (1204) system cursor; (d) set fPaint to TRUE for every state machine; (e) send EV_RESET to every state machine; (f) display each sequence at the appropriate location in the indicating region; and (g) enable the cursor polling timer; and (4) add state processing to ST_SELECTED to: (a) set the text of all labels for display to null; (b) hide the Windows® (1204) system cursor; (c) erase all sequences from the indicating region; (d) disable the cursor polling timer; (e) set fPaint to TRUE for every state machine; (f) send EV_RESET to every state machine; and (g) insert the selected sequence into the work space.

APPENDIX I

```
Procedure: PocketFsm
/************************************************************/
/*                                                          */
/* Procedure:   PocketFsm                                   */
/*                                                          */
/* Description: State Machine for processing events to      */
/*              selectable regions.                         */
/*                                                          */
/* Input Parameters:                                        */
/*              pPocket    pointer to selectable region data*/
/*                         set                              */
/*              Event      event to process                 */
/*                                                          */
/************************************************************/
PocketFsm (pPocket, Event)
{
    BOOL      fInternalEvent       /* declaration of local
                                      boolean variable */
    set fInternalEvent to TRUE
    while (fInternalEvent is TRUE)
    {
        set fInternalEvent to FALSE
        set pPocket->PreviousState to pPocket->State
        set pPocket->State to aPocketFsm[pPocket->State][Event]
        switch (pPocket->State)
        {
            case ST_ILLEGAL_STATE:
            case ST_ERROR:
                turn off all timers
                log the error
                display an error message to the operator
                break
            case ST_INITIAL:
                break
            case ST_RESET:
                set time of selection to the current time
                if pPocket->Color is not equal to
                pPocket->InitialColor
                    set pPocket->Color to pPocket->InitialColor
                    set pPocket->fPaint to TRUE
                set pPocket->fInvert to FALSE
                break
            case ST_LOW_TIDE:
                break
            case ST_CREST_TIDE:
                break
            case ST_BEGIN_LOCK:
                emit an audible beep
                set the system cursor location to the visible
                subregion's lockspot
```

APPENDIX I-continued

```
            set the system cursor to null
            display the lock icon on the visible subregion's
            lockspot
                                    /*   initialize counter
                                         for locking */
            set iLockCursor to cLockCursor
            break
        case ST_LOCK:
            set the system cursor location to the visible
            subregion's lockspot
                                    /*   on lock counter
                                         expiration, */
                                    /*   transfer to the next
                                         state */
            decrement iLockCursor by 1
            if iLockCursor equals 0
                set Event to EV_NULL
                set fInternalEvent to TRUE
            break
        case ST_END_LOCK:
            erase the lock icon with white
            set the system cursor to the arrow cursor
            display the system cursor on the visible subregion'
            lockspot
            emit an audible beep
                                    /*   paint selectable
                                         region so that */
                                    /*   the white erasure
                                         of the lock */
                                    /*   cursor icon is
                                         overwritten */
            set pPocket->fPaint to TRUE
            break
        case ST_SELECTED:
            emit an audible beep
            take the action appropriate upon selection of this
            selectable region, for example, sending data to an
            application program, sending a control sequence to
            a device coupled to the computer, or displaying the
            selection
            set pPocket->fInvert to TRUE
            if appropriate, change the menu options associated
            with various selectable regions and set fPaint to
            TRUE for the state machines associated with those
            selectable regions
            set Event to EV_NULL
            set fInternalEvent to TRUE
            break
        case ST_SELECT_AND_OUT:
            send EV_RESET then EV_MOVEMENT to all state
            machines, resetting them and indicating that the
            operator is moving the cursor
            break
        case ST_DECAY:
                                    /*   set state to
                                         previous state */
                                    /*   in preparation for
                                         the next */
                                    /*   state transition */
            set pPocket->State to pPocket->PreviousState
            decrement pPocket->Color by pPocket->Decrement,
            but not below pPocket->InitialColor
            if pPocket->Color was changed
                set pPocket->fPaint to TRUE
                set fInternalEvent to TRUE
            if pPocket->Color was changed from a value greater
            than or equal to pPocket->CrestTide to a value below
            pPocket->CrestTide
                set Event to EV_STEP_DOWN
            else
                set Event to EV_NULL
            break
        case ST_DWELL:
                                    /*   set state to
                                         previous state */
                                    /*   in preparation for
                                         the next */
                                    /*   state transition */
            set pPocket->State to pPocket->PreviousState
            increment pPocket->Color by pPocket->Increment, but
            not above pPocket->Ceiling
            if pPocket->Color was changed
                set pPocket->fPaint to TRUE
                set fInternalEvent to TRUE
            if pPocket->Color was changed from a value below
            pPocket->CrestTide to a value greater than or equal
            to pPocket->CrestTide
                set Event to EV_STEP_UP
            else
                set Event to EV_NULL
            break
        case ST_IDLE:
            set the system cursor location to the center of the
            display
            set fInternalEvent to TRUE
            set Event to EV_NULL
            break
        case ST_EBB_TIDE:
            break
        case ST_ENTRY:
            set fInternalEvent to TRUE
            set Event to EV_NULL
            break
        case ST_DISCARD:
                                    /*   set state to
                                         previous state */
                                    /*   for the next
                                         transition*/
            set pPocket->State to pPocket->PreviousState
            break
        case ST_EXIT:
            set Event to EV_NULL
            set fInternalEvent to TRUE
            if pPocket->fInterior equals TRUE
                change the boundaries of the Windows ® region
                having the handle pPocket->hRegion to those
                defined by the second array of points associated
                with this state machine
            set pPocket->fPaint to TRUE
            send EV_RESET to the state machine having the
            index pPocket->iAdjacentPocket
            break
        default:
            display error message
            break
    }
    /* end switch */
}
/* end while */
if pPocket->fPaint is equal to TRUE
    invalidate the entire client area
}
/* end PocketFsm */
                            Procedure: CreateEvent
/**************************************************************/
/*                                                            */
/*  Procedure:    CreateEvent                                 */
/*                                                            */
/*  Description:  Examines movement of cursor and determines  */
/*                what events have occurred.                  */
/*                                                            */
/*  Input Parameters:                                         */
/*                pEvent      pointer to an event data structure */
/*                            for output                      */
/*  Output:       A completed event data structure            */
/*                indicated by pEvent including:              */
/*                (1)  an indication of whether the cursor hotspot */
/*                     intersects a selectable region         */
/*                (2)  the index of the intersected selectable */
/*                     region, if any                         */
/*                (3)  the event for the intersected selectable */
/*                     region, if any                         */
/*                (4)  the event for all non-intersected      */
/*                     selectable regions                     */
/*                                                            */
/*                Updated variables indicate:                 */
/*                (1)  the previous location of the cursor hotspot */
/*                (2)  the approximate time of the sampling of the */
/*                     previous location of the cursor hotspot */
/*                                                            */
```

APPENDIX I-continued

```
/*************************************************************/
CreateEvent (pEvent)
{
    get current cursor hotspot location
    if there has been cursor hotspot movement since the last cursor
    location sampling
        set time of previous cursor movement to time latest received
        WM_TIMER message was generated
        if cursor hotspot has crossed out of a selectable region
            set event to EV_CROSS_OUT for the intersected
            selectable region and to EV_MOVEMENT for all other
            selectable regions
        else
            if cursor hotspot intersects a selectable region
                if intersected selectable region's Color equals
                Ceiling
                    set event to EV_CEILING for the intersected
                    selectable region and to EV_DECAY for all
                    other selectable regions
                else
                    set event to EV_DWELL for the intersected
                    selectable region and to EV_DECAY for all
                    other selectable regions
            else
                set event to EV_MOVEMENT for all selectable
                regions
    else
        if cursor hotspot intersects a selectable region
            if idle time exceeded
                set event to EV_IDLE_TIMEOUT for all selectable
                regions
            else
                if intersected selectable region's Color equals
                Ceiling
                    set event to EV_CEILING for the intersected
                    selectable region and to EV_DECAY for all
                    other selectable regions
                else
                    set event to EV_DWELL for the intersected
                    selectable region and to EV_DECAY for all
                    other selectable regions
        else
            set event to EV_DECAY for all selectable regions
    set the previous cursor hotspot location to the current hotspot
    location
}
/* end CreateEvent */
```

I claim:

1. For use with a display, an apparatus comprising:
(a) a receiver for receiving a movement related signal indicating successive locations on the display, the successive locations including a first location and a second location, the second location occurring before the time the first location occurs, the successive locations responsive to movement of a body member of an operator, the body member selected from the group consisting of each of the operator's arms, each of the operator's shoulders, each of the operator's elbows, each of the operator's wrists, each of the operator's hands, each of the operator's fingers, each of the operator's thumbs, each of the operator's legs, each of the operator's hips, each of the operator's knees, each of the operator's ankles, each of the operator's feet, each of the operator's toes, and the operator's head; and
(b) a processor, coupled to the receiver and to the display, for:
(i) simultaneously displaying each of a plurality of first selectable regions on the display, the plurality of first selectable regions at least partially circumscribing a first region on the display; and
(ii) selecting a particular one of the first selectable regions responsive to a first dwell event, the first dwell event including:
(a) the first location intersecting the particular selectable region;
(b) the second location intersecting the particular selectable region; and
(c) a first quantity equalling or exceeding a first predetermined quantity, the first quantity being a function of the duration of a first period of intersection starting at the time the second location occurs and ending at the time the first location occurs.

2. The apparatus of claim 1 further comprising a touch screen including the display, the touch screen coupled to the receiver; and wherein the touch screen, responsive to movement of either one of: (a) a finger of the operator, and (b) a thumb of the operator, generates the movement related signal.

3. The apparatus of claim 1 further comprising a plurality of menu options; wherein the processor is further operative to associate each menu option respectively with one of the first selectable regions; and wherein the processor is further operative, responsive to the first dwell event, to select the particular menu option associated with the particular first selectable region.

4. The apparatus of claim 3 wherein the processor is further capable of coupling to a communications network; wherein the particular menu option represents a send command; and wherein the processor, responsive to the first dwell event, is further operative to send a message over the communications network.

5. The apparatus of claim 3 wherein the processor is further capable of coupling to a communications network capable of storing a message for the operator; wherein the particular menu option represents a retrieve command; and wherein the processor, responsive to the first dwell event, is further operative to retrieve the message from the communications network.

6. The apparatus of claim 3 further comprising a program for execution on the processor, the program for managing a calendar; and wherein the processor is further operative to display at least part of the calendar in the first region.

7. The apparatus of claim 6 wherein the particular menu option represents an add event function; and wherein the processor, responsive to the first dwell event, is further operative to add an event to the calendar.

8. The apparatus of claim 3 further comprising a program for execution on the processor, the program for displaying pages of a book; and wherein the processor is further operative to display a page of the book in the first region.

9. The apparatus of claim 8 wherein the particular menu option represents a next page function; and wherein the processor, responsive to the first dwell event, is further operative to display in the first region the page of the book following the displayed page.

10. The apparatus of claim 3 wherein the processor is further capable of coupling to a device; wherein the particular menu option represents a control function for the device; and wherein the processor is further operative, responsive to the first dwell event, to initiate the control function for the device.

11. The apparatus of claim 10 wherein the device is a telephone.

12. The apparatus of claim 11 further comprising the telephone.

13. The apparatus of claim 10 wherein the device is a radio.

14. The apparatus of claim 10 wherein the device is capable of playing either one of: (a) previously recorded music, and (b) previously recorded video.

15. The apparatus of claim 10 wherein the device is a computer peripheral.

16. The apparatus of claim 15 further comprising the computer peripheral.

17. The apparatus of claim 10 wherein the device is a television, the television including the display.

18. The apparatus of claim 17 further comprising the television.

19. The apparatus of claim 3 wherein the processor is further operative, responsive to the first dwell event, to display the particular menu option in the first region on the display.

20. The apparatus of claim 3 wherein the processor is further operative, prior to the time the first dwell event occurs, to display on the display each of the menu options on its associated first selectable region.

21. The apparatus of claim 3 wherein the processor is further operative, prior to the time the first dwell event occurs, to simultaneously display the menu options in the first region; wherein the menu options include an undesired menu option associated with an undesired one of the first selectable regions; and wherein the relation of the location on the display of the particular menu option to the location on the display of the undesired menu option prior to the time the first dwell event occurs indicates the relation of the location of the particular first selectable region to the location of the undesired first selectable region.

22. The apparatus of claim 3 further comprising a plurality of submenu options; and wherein the processor is further operative to:
   (a) associate the plurality of submenu options with the particular menu option;
   (b) display a plurality of second selectable regions on the display, each of the second selectable regions associated respectively with one of the submenu options, the plurality of second selectable regions together at least partially circumscribing a second region on the display; and
   (c) select, in response to a second dwell event, the submenu option associated with the specific one of the second selectable regions intersected by a third one of the successive locations, the third location being a location other than either one of the first location and the second location.

23. The apparatus of claim 22 wherein:
   (a) the processor is further operative to, prior to the time the first dwell event occurs and prior to the time the second dwell event occurs, simultaneously display the submenu options on the particular selectable region; and
   (b) the processor, in response to the first dwell event, is further operative to display each of the submenu options on the second selectable region associated with the submenu option.

24. The apparatus of claim 22 wherein each of the second selectable regions has a characteristic appearance different from the characteristic appearance of each of the other second selectable regions; and wherein the processor is further operative, prior to the time the first dwell event occurs, to display:
   (a) a plurality of indicating regions intersecting the particular first selectable region, each of the indicating regions associated respectively with one of the second selectable regions, and each of the indicating regions having an appearance similar to the characteristic appearance of the associated second selectable region; and
   (b) each of the submenu options on the indicating region associated with the second selectable region associated with the submenu option.

25. The apparatus of claim 24 wherein the appearance is selected from the group consisting of:
   (a) a size;
   (b) a shape;
   (c) a hue;
   (d) a brightness;
   (e) a contrast;
   (f) a dithering;
   (g) a fill;
   (h) a blinking;
   (i) a hatching; and
   (j) a pattern.

26. The apparatus of claim 3 wherein each of the menu options is associated with a sequence of one or more graphic symbols, one or more of the sequences including one or more ideographs, each of the sequences of one or more graphic symbols having a common characteristic.

27. The apparatus of claim 26 wherein each of the sequences of one or more graphic symbols belongs to any one of the Chinese language, Japanese language, and Korean language.

28. The apparatus of claim 26 wherein each of the sequences of one or more graphic symbols belongs to any one of the Picture Communication Symbols symbol set, Rebus symbol set, Picsyms symbol set, Pictogram Ideogram Communication Symbols symbol set, Yerkish symbol set, Blissymbolics symbol set, and a set of depictions of the signs of a manual sign language.

29. The apparatus of claim 3 wherein each of the menu options has in common a part of speech.

30. The apparatus of claim 3 wherein each of the menu options has in common a meaning.

31. The apparatus of claim 3 wherein each of the menu options has in common a meaning class.

32. The apparatus of claim 3 further comprising an application program for execution on the processor, the application program operative to display at least part of its output in the first region on the display; wherein the particular menu option represents an input to the application program; and wherein the processor is further operative, responsive to the first dwell event, to provide the input to the application program.

33. The apparatus of claim 3 wherein the processor is further operative to, prior to the time the first dwell event occurs, display the menu options physically grouped together on the display; wherein the location of each of the displayed menu options on the display indicates the location of the first selectable region associated with the displayed menu option; and wherein the displayed particular menu option associated with the particular first selectable region does not intersect the particular first selectable region.

34. The apparatus of claim 1 wherein the processor is further operative, responsive to an intersection of one of the successive locations and one of the first selectable regions, to modify the appearance of the intersected first selectable region.

35. The apparatus of claim 1 wherein the apparatus further comprises a circuit coupled to the receiver; wherein the operator may close the circuit; and wherein the receiver, responsive to circuit closure, receives the movement related signal.

36. The apparatus of claim 1 wherein the processor is further operative to display on the display each of two of the first selectable regions adjacent each of two different sides of the first region, respectively.

37. The apparatus of claim 1 wherein the processor is further operative to display on the display each of three of the first selectable regions adjacent each of three different sides of the first region, respectively.

38. The apparatus of claim 1 wherein the processor is further operative to display on the display the particular first selectable region not adjacent any other first selectable region.

39. The apparatus of claim 1 wherein the processor is further operative to display on the display each of the first selectable regions not adjacent any other first selectable region.

40. The apparatus of claim 1 wherein the processor is further operative to display on the display the particular first selectable region adjacent another of the first selectable regions.

41. The apparatus of claim 1 wherein the processor is further operative to display on the display the particular first selectable region adjacent the first region.

42. The apparatus of claim 1 wherein the movement related signal includes an image of the body member of the operator, the image indicating the first location on the display.

43. The apparatus of claim 1 further comprising a confiner for confining the successive locations indicated by the movement related signal within the boundary of the particular first selectable region furthest from the first region.

44. The apparatus of claim 43 wherein the confiner is further operative to confine the successive locations indicated by the movement related signal within the boundary of each of the first selectable regions furthest from the first region.

45. The apparatus of claim 1 wherein the processor is further operative to disable selection of one or more of the first selectable regions responsive to the first dwell event, while a supply of power is maintained to the apparatus.

46. The apparatus of claim 45 wherein one of the first selectable regions is not disabled; and wherein the processor is further operative, after disabling the one or more of the first selectable regions and responsive to a second dwell event associated with the non-disabled first selectable region, to enable selection of the one or more disabled first selectable regions.

47. The apparatus of claim 1 wherein the movement related signal includes a difference between two relative positions of the body member of the operator.

48. The apparatus of claim 47 wherein the processor is further operative to derive a movement of the body member of the operator from the difference.

49. The apparatus of claim 1 wherein the movement related signal includes a difference between two absolute positions of the body member of the operator.

50. The apparatus of claim 49 wherein the processor is further operative to derive a movement of the body member of the operator from the difference.

51. The apparatus of claim 1 wherein the processor is further operative to indicate to the operator, responsive to the first dwell event, that the first dwell event has occurred.

52. The apparatus of claim 1 wherein the movement related signal indicates a path of movement of the body member of the operator; and wherein the processor is further responsive to the path of movement for selecting the particular first selectable region.

53. The apparatus of claim 1 wherein the successive locations further include a third location intersecting the particular first selectable region, the third location occurring at a time after the time the second location occurs and before the time the first location occurs; and wherein the processor is further operative to indicate to the operator the duration of a second period, the second period starting at the time the second location occurs and ending at the time the third location occurs.

54. The apparatus of claim 53 wherein the indication includes an indicating region on the display for providing the indication to the operator, the indicating region intersecting the particular first selectable region.

55. The apparatus of claim 1 wherein the successive locations further include:
  (a) a third location intersecting the particular first selectable region, the third location occurring before the time the second location occurs; and
  (b) at a time before the time the third location occurs, a fourth location intersecting the particular first selectable region; and
  wherein the first quantity is further a function of the duration of a second period of intersection, the second period starting at the time the fourth location occurs and ending at the time the third location occurs.

56. The apparatus of claim 55 wherein the processor is further operative to indicate to the operator the duration of the second period of intersection.

57. The apparatus of claim 55 wherein the successive locations further include:
  (c) an intermediate starting location not intersecting the particular first selectable region, the intermediate starting location occurring after the time the third location occurs; and
  (d) an intermediate ending location not intersecting the particular first selectable region, the intermediate ending occurring after the time the intermediate starting location occurs and before the time the second location occurs; and wherein the first quantity decreases responsive to the duration of an intermediate period of non-intersection, the intermediate period of non-intersection starting at the time the intermediate starting location occurs and ending at the time the intermediate ending location occurs.

58. The apparatus of claim 57 wherein the processor is further operative to indicate to the operator the non-intersection of the intermediate starting location and the particular first selectable region.

59. The apparatus of claim 57 wherein the processor is further operative to indicate to the operator the duration of the intermediate period of non-intersection.

60. The apparatus of claim 1 wherein the processor is further operative to detect operator fatigue; and wherein the first quantity is further a function of detected operator fatigue.

61. For use with a display, an apparatus comprising:
  (a) a receiver for receiving a movement related signal indicating successive locations on the display, the successive locations including a first location and a second location, the second location occurring before the time the first location occurs, the successive locations responsive to movement of a body member of an operator, the body member selected from the group consisting of each of the operator's arms, each of the operator's shoulders, each of the operator's elbows, each of the operator's wrists, each of the operator's hands, each of the operator's fingers, each of the operator's thumbs, each of the operator's legs, each of the operator's hips, each of the operator's knees, each of the operator's ankles, each of the operator's feet, each of the operator's toes, and the operator's head; and
(b) a processor, coupled to the receiver and to the display, for:
(i) simultaneously displaying each of a plurality of first selectable regions on the display, the plurality of first selectable regions at least partially circumscribing a first region on the display; and
(ii) selecting a particular one of the first selectable regions responsive to a first dwell event, the first dwell event including:
(a) the first location intersecting the particular selectable region;
(b) the second location intersecting the particular selectable region; and
(c) the duration of the period between the time the second location occurs and the time the first location occurs equalling or exceeding a predetermined period.

62. The apparatus of claim 61 wherein the processor is further operative to indicate to the operator, prior to the time the first location occurs, the intersection of the second location and the particular first selectable region.

63. An apparatus comprising:
(a) a nontransitory computer-readable medium; and
(b) program instructions, stored on the medium, that, when executed by a processor, cause the processor to perform the operations of:
displaying a plurality of selectable regions on a display, the plurality of selectable regions together at least partially circumscribing a first region on the display;
receiving a movement related signal indicating successive locations on the display, the successive locations including a first location and a second location, the first location occurring before the time the second location occurs, the successive locations responsive to movement of a body member of an operator, the body member selected from the group consisting of each of the operator's arms, each of the operator's shoulders, each of the operator's elbows, each of the operator's wrists, each of the operator's hands, each of the operator's fingers, each of the operator's thumbs, each of the operator's legs, each of the operator's hips, each of the operator's knees, each of the operator's ankles, each of the operator's feet, each of the operator's toes, and the operator's head; and
selecting, in response to a dwell event, a particular one of the selectable regions, the dwell event including:
(i) an intersection of the first location and the particular selectable region;
(ii) an intersection of the second location and the particular selectable region; and
(iii) a first quantity equalling or exceeding a first predetermined quantity, the first quantity being a function of the duration of a first period of intersection starting at the time the second location occurs and ending at the time the first location occurs.

64. The apparatus of claim 63 wherein the program instructions, when executed by the processor, further perform the operation of associating each of a plurality of menu options respectively with one of the selectable regions; and wherein the selecting operation further includes, responsive to the dwell event, selecting the particular menu option associated with the particular selectable region.

65. The apparatus of claim 63 further comprising a computer system including the processor and the display.

66. The apparatus of claim 63 wherein the medium is selected from the group consisting of:
(1) a random access memory;
(2) a magnetic store; and
(3) an optical store.

67. The apparatus of claim 63 wherein the displaying operation includes displaying each of two of the selectable regions adjacent each of two different sides of the first region, respectively.

68. A user interface for selecting a menu option from a plurality of menu options, the user interface comprising:
(a) a touch screen for:
(1) displaying a plurality of menu options, each of the menu options associated respectively with, and capable of being displayed on, a first selectable region on the touch screen, the plurality of first selectable regions at least partially circumscribing a first region on the touch screen; and
(2) receiving a first location on the touch screen indicated by a user and a second location on the touch screen indicated by the user, each of the first location and the second location intersecting one of the first selectable regions, the second location occurring after the time the first location occurs; and
(b) selection means, coupled to the touch screen, for selecting the menu option associated with the intersected first selectable region responsive to a first quantity equalling or exceeding a first predetermined quantity, the first quantity being a function of the duration of a first period starting at the time the first location occurs and ending at the time the second location occurs.

69. The user interface of claim 68 wherein the selection means is further capable of coupling to a device; wherein the selected menu option represents a control function for the device; and wherein the selection means is further operative, responsive to the selection of the selected menu option, to initiate the control function for the device.

70. The user interface of claim 69 wherein the device is a telephone.

71. The user interface of claim 68 wherein the touch screen is further operative, responsive to the first quantity equalling or exceeding the first predetermined quantity, to display a plurality of submenu options, each of the submenu options associated with the selected menu option, each of the submenu options associated respectively with, and capable of being displayed on, a second selectable region on the touch screen, the plurality of second selectable regions at least partially circumscribing a second region on the touch screen; wherein the touch screen is further operative to receive each of a third location on the touch screen indicated by the user and a fourth location on the touch screen indicated by the user, each of the third location and the fourth location intersecting one of the second selectable regions, the fourth location occurring after the time the third location occurs; and wherein the selection means is further operative to select the submenu option associated with the intersected second selectable region responsive to a second quantity equalling or exceeding a second predetermined quantity, the second quantity being a function of the duration of a second period starting at the time the third location occurs and ending at the time the fourth location occurs.

72. The user interface of claim 68 wherein the selection means is further operative, responsive to the selection of the selected menu option, to display the selected menu option in the first region on the touch screen.

73. The user interface of claim 68 wherein the touch screen is further operative to display the plurality of menu options on at least three sides of the first region.

74. The user interface of claim 68 wherein the touch screen is further operative to display the plurality of first selectable regions on at least three sides of the first region.

75. An apparatus comprising:
(a) a touch screen operative to receive a movement related signal responsive to movement of either one of: (i) a finger of the operator, and (ii) a thumb of the operator, the movement related signal indicating successive locations on a display, the successive locations including a first location and a second location, the second location occurring after the time the first location occurs; and
(b) a processor, coupled to the touch screen and to the display, for:
  (i) simultaneously displaying each of a plurality of first selectable regions on the display, the plurality of first selectable regions at least partially circumscribing a first region on the display;
  (ii) responsive to a first intersection of a third one of the successive locations and a particular one of the first selectable regions, indicating the first intersection to the operator by modifying the appearance of the particular first selectable region prior to the time the second location occurs; and
  (iii) selecting the particular first selectable region responsive to the first location intersecting the particular first selectable region, the second location intersecting the particular first selectable region, and the duration of the period between the time the first location occurs and the time the second location occurs equalling or exceeding a predetermined period.

76. The apparatus of claim 75 wherein the processor is further operative to display on the display each of the first selectable regions not adjacent any other first selectable region.

77. The apparatus of claim 75 further comprising a plurality of first menu options; wherein the processor is further operative to associate each first menu option respectively with one of the first selectable regions; and wherein the processor is further operative, responsive to the selection of the particular first selectable region, to select the particular first menu option associated with the particular first selectable region.

78. The apparatus of claim 77 wherein the successive locations further include a fourth location and a fifth location, the fourth location occurring after the time the second location occurs, the fifth location occurring after the time the fourth location occurs; further comprising a plurality of submenu options; and wherein the processor is further operative to:
(a) associate the plurality of submenu options with the particular first menu option;
(b) display a plurality of second selectable regions on the display, each of the second selectable regions associated respectively with one of the submenu options, the plurality of second selectable regions together at least partially circumscribing the first region on the display;
(c) responsive to a second intersection of a sixth one of the successive locations and a specific one of the second selectable regions, indicate the second intersection to the operator by modifying the appearance of the specific selectable region prior to the time the fifth location occurs; and
(d) select the specific menu option responsive to the fourth location intersecting the specific selectable region, the fifth location intersecting the specific selectable region, and the duration of the period between the time the fourth location occurs and the time the fifth location occurs equalling or exceeding the predetermined period.

79. The apparatus of claim 77 wherein the processor is further capable of coupling to a telephone; wherein the particular first menu option represents a control function for the telephone; and wherein the processor is further operative, responsive to the selection of the particular first menu option, to initiate the control function for the telephone.

80. The apparatus of claim 79 further comprising the telephone.

81. The apparatus of claim 79 wherein the successive locations further include a fourth location and a fifth location, the fifth location occurring after the time the fourth location occurs; and wherein the processor is further operative to:
(a) couple to a communications network;
(b) simultaneously display each of a plurality of second selectable regions on the display, the plurality of second selectable regions at least partially circumscribing a second region on the display, each of the second selectable regions associated respectively with one of a plurality of second menu options, a particular one of the second menu options representing a send function, the particular second menu option associated with a particular one of the second selectable regions;
(c) responsive to a second intersection of a sixth one of the successive locations and the particular second selectable region, indicate the second intersection to the operator by modifying the appearance of the particular second selectable region prior to the time the fifth location occurs; and
(d) select the particular second menu option and send a message over the communications network responsive to the fourth location intersecting the particular second selectable region, the fifth location intersecting the particular second selectable region, and the duration of the period between the time the fourth location occurs and the time the fifth location occurs equalling or exceeding the predetermined period.

82. The apparatus of claim 81 wherein the successive locations further include a seventh location and an eighth location, the eighth location occurring after the time the seventh location occurs; and wherein the processor is further operative to:
(a) simultaneously display each of a plurality of third selectable regions on the display, the plurality of third selectable regions at least partially circumscribing a third region on the display, each of the third selectable regions associated respectively with one of a plurality of third menu options, a particular one of the third menu options representing a next page function, the particular third menu option associated with a particular one of the third selectable regions;
(b) display a page of a book in the third region on the display;
(c) responsive to a third intersection of a ninth one of the successive locations and the particular third selectable region, indicate the third intersection to the operator by modifying the appearance of the particular third selectable region prior to the time the eighth location occurs; and (d) select the particular third menu option and display in the third region on the display the page of the book following the displayed page responsive to the seventh location intersecting the particular third selectable region, the eighth location intersecting the particular third selectable region, and the duration of the period between the time the seventh location occurs and the time the eighth location occurs equalling or exceeding the predetermined period.

83. The apparatus of claim 82 wherein the successive locations further include a tenth location and an eleventh location, the eleventh location occurring after the time the tenth location occurs; and wherein the processor is further operative to:
(a) simultaneously display each of a plurality of fourth selectable regions on the display, the plurality of fourth selectable regions at least partially circumscribing a fourth region on the display, each of the fourth selectable regions associated respectively with one of a plurality of fourth menu options, a particular one of the fourth menu options representing an add event function, the particular fourth menu option associated with a particular one of the fourth selectable regions;
(b) display a calendar in the fourth region on the display;
(c) responsive to a fourth intersection of a twelfth one of the successive locations and the particular fourth selectable region, indicate the fourth intersection to the operator by modifying the appearance of the particular fourth selectable region prior to the time the eleventh location occurs; and
(d) select the particular fourth menu option and add an event to the calendar responsive to the tenth location intersecting the particular fourth selectable region, the eleventh location intersecting the particular fourth selectable region, and the duration of the period between the time the tenth location occurs and the time the eleventh location occurs equalling or exceeding the predetermined period.

84. For use with a display, a method of selecting a selectable region from a plurality of selectable regions, the method comprising:
receiving a movement related signal responsive to movement of a body member of an operator, the body member selected from the group consisting of each of the operator's arms, each of the operator's shoulders, each of the operator's elbows, each of the operator's wrists, each of the operator's hands, each of the operator's fingers, each of the operator's thumbs, each of the operator's legs, each of the operator's hips, each of the operator's knees, each of the operator's ankles, each of the operator's feet, each of the operator's toes, and the operator's head, the movement related signal indicating successive locations on the display, the successive locations including a first location and a second location, the first location occurring before the time the second location occurs;
displaying a plurality of selectable regions on the display, the plurality of selectable regions together at least partially circumscribing a first region on the display; and
selecting a particular one of the first selectable regions responsive to a dwell event, the dwell event including:
(a) the first location intersecting the particular selectable region;
(b) the second location intersecting the particular selectable region; and
(c) a first quantity equalling or exceeding a first predetermined quantity, the first quantity being a function of the duration of a first period of intersection starting at the time the first location occurs and ending at the time the second location occurs.

85. A method comprising transmitting a program that, when executed by a processor, causes the processor to perform the operations of:
simultaneously displaying each of a plurality of selectable regions on a display, the plurality of selectable regions together at least partially circumscribing a first region on the display;
receiving a movement related signal indicating successive locations on the display, the successive locations including a first location and a second location, the first location occurring before the time the second location occurs, the successive locations responsive to movement of a body member of an operator, the body member selected from the group consisting of each of the operator's fingers and each of the operator's thumbs; and
selecting a particular one of the first selectable regions responsive to a dwell event, the dwell event including:
(a) the first location intersecting the particular selectable region;
(b) the second location intersecting the particular selectable region; and
(c) the duration of the period between the time the first location occurs and the time the second location occurs equalling or exceeding a predetermined period.

86. The method of claim 85 further comprising reading the program from a computer-readable medium.

87. The method of claim 85 wherein the transmitting act transmits the program over an electronic network.

88. A method for use with a program that, when executed by a processor, causes the processor to perform the operations of:
simultaneously displaying each of a plurality of selectable regions on a display, the plurality of selectable regions together at least partially circumscribing a first region on the display;
receiving a movement related signal indicating a first location on the display and a second location on the display, each of the first location and the second location intersecting one of the selectable regions, the second location occurring after the time the first location occurs, each of the first location and the second location responsive to movement of a body member of an operator, the body member selected from the group consisting of each of the operator's fingers and each of the operator's thumbs; and
selecting the intersected selectable region responsive to a first quantity equalling or exceeding a first predetermined quantity, the first quantity being a function of the duration of a first period starting at the time the first location occurs and ending at the time the second location occurs,
the method comprising transmitting the program.

89. The method of claim 88 further comprising reading the program from a computer-readable medium.

90. The method of claim 88 wherein the transmitting act transmits the program over an electronic network.

91. A method for use with a program that, when executed by a processor, causes the processor to perform the operations of:

simultaneously displaying each of a plurality of selectable regions on a display, the plurality of selectable regions together at least partially circumscribing a first region on the display;

receiving a movement related signal indicating successive locations on the display, the successive locations including a first location and a second location, the second location occurring after the time the first location occurs, the successive locations responsive to movement of a body member of an operator, the body member selected from the group consisting of each of the operator's fingers and each of the operator's thumbs; and selecting a particular one of the first selectable regions responsive to a dwell event, the dwell event including:

(a) the first location intersecting the particular selectable region;

(b) the second location intersecting the particular selectable region; and (c) the duration of the period between the time the first location occurs and the time the second location occurs equalling or exceeding a predetermined period, the method comprising transmitting the program.

92. The method of claim 91 further comprising reading the program from a computer-readable medium.

93. The method of claim 91 wherein the transmitting act transmits the program over an electronic network.

* * * * *

UNITED STATES PATENT AND TRADEMARK OFFICE
CERTIFICATE OF CORRECTION

| | | |
|---|---|---|
| PATENT NO. | : 9,535,494 B2 | Page 1 of 1 |
| APPLICATION NO. | : 13/827216 | |
| DATED | : January 3, 2017 | |
| INVENTOR(S) | : Donald K. Forest | |

It is certified that error appears in the above-identified patent and that said Letters Patent is hereby corrected as shown below:

On the Title Page
On page 2, under item (56) References Cited, under U.S. PATENT DOCUMENTS, add
--3,541,521 A    11/1970        Koster
4,109,145 A    8/1978        Graf--
On page 3, under item (56) References Cited, under FOREIGN PATENT DOCUMENTS, add
--DE    U 93 00 231    8/1993--
On page 4, under item (56) References Cited, under OTHER PUBLICATIONS, add
--Barnett, C.J.; Dynche, M.P.; Golding, V.G.; Ng, Y.H.; Taylor, G.D.; "Speech Output Display Terminal," IBM Technical Disclosure Bulletin, vol. 26, no. 10A, March 1984, pages 4950-4951.--

In the Specification
At Column 13, Line 42, replace "Japanese kava" with --Japanese kana--
At Column 30, Line 55, insert a space between the "→" and the word "indicates"
At Column 31, Line 45, replace "invention" with --disclosure--
At Column 31, Line 49, replace "invention" with --disclosure--
At Column 31, Line 54, replace "invention" with --disclosure--
At Column 31, Line 59, replace "invention" with --disclosure--
At Column 46, Line 17, replace "Corridorincrement" with --CorridorIncrement--
At Column 47, Line 17, replace "Corridorincrement" with --CorridorIncrement--
At Column 59, Line 9, insert a --|-- between "WS_CHILD" and "WS_BORDER"
At Column 59, Line 10, replace the space between the """ and the """ with a --|--

In the Claims
In Claim 63, at Column 75, Line 59, replace "second location" with --first location--
In Claim 63, at Column 75, Line 60, replace "first location"' with --second location--

Signed and Sealed this
Fourteenth Day of March, 2017

Michelle K. Lee
*Director of the United States Patent and Trademark Office*